US012588996B2

(12) United States Patent
Miyashiro et al.

(10) Patent No.: US 12,588,996 B2
(45) Date of Patent: Mar. 31, 2026

(54) CARDIAC VALVE REPAIR DEVICES AND ASSOCIATED SYSTEMS AND METHODS

(71) Applicant: Medtronic, Inc., Minneapolis, MN (US)

(72) Inventors: Katherine Miyashiro, Menlo Park, CA (US); Hanson S. Gifford, III, Woodside, CA (US); James I. Fann, Portola Valley, CA (US); Ben F. Brian, III, Menlo Park, CA (US); Gaurav Krishnamurthy, Mountain View, CA (US); Jose Gonzalez, Fremont, CA (US); Paul Gunning, San Francisco, CA (US); Matthew McLean, San Francisco, CA (US); Neil Zimmerman, Menlo Park, CA (US); Robert O'Grady, San Francisco, CA (US); Douglas S. Sutton, Pacifica, CA (US); Jean-Pierre Dueri, San Mateo, CA (US); Ryan Helmuth, Woodside, CA (US); Marine De Gouy, Redwood City, CA (US)

(73) Assignee: MEDTRONIC, INC., Minneapolis, MN (US)

( * ) Notice: Subject to any disclaimer, the term of this patent is extended or adjusted under 35 U.S.C. 154(b) by 283 days.

(21) Appl. No.: 17/456,150

(22) Filed: Nov. 22, 2021

(65) Prior Publication Data

US 2022/0160508 A1     May 26, 2022

Related U.S. Application Data

(60) Provisional application No. 63/223,923, filed on Jul. 20, 2021, provisional application No. 63/116,724, filed on Nov. 20, 2020.

(51) Int. Cl.
A61F 2/24          (2006.01)

(52) U.S. Cl.
CPC .......... A61F 2/2445 (2013.01); A61F 2/2433 (2013.01); A61F 2/2454 (2013.01); A61F 2/2466 (2013.01)

(58) Field of Classification Search
CPC .............. A61F 2/246; A61F 2230/0026; A61F 2230/0019; A61F 2230/0056;
(Continued)

(56) References Cited

U.S. PATENT DOCUMENTS 11,173,032  B2 *  11/2021  Zeng ........................ A61F 2/246
2006/0058871  A1     3/2006   Zakay
(Continued)

FOREIGN PATENT DOCUMENTS

DE        102013017993  A1 *  6/2015   ............. A61F 2/246
WO    WO-2012035279  A1 *  3/2012   ........... A61F 2/2418
(Continued)

OTHER PUBLICATIONS

ISA, PCT Application No. PCT/US2021/072560, International Search Report and Written Opinion mailed Mar. 10, 2022, 18 pages.
(Continued)

*Primary Examiner* — Suzette J Gherbi
(74) *Attorney, Agent, or Firm* — Wentsler LLC

(57)          ABSTRACT

Cardiac valve repair devices and associated systems and methods are disclosed herein. A cardiac valve repair device configured in accordance with embodiments of the present technology can include, for example, a coaptation member configured to be positioned between one or more native leaflets of the cardiac valve to at least partially fill a space between the native leaflets. The cardiac valve repair device can further include one or more fixation mechanisms for securing the coaptation member in position between the
(Continued)

leaflets. A cardiac valve repair device configured in accordance with additional embodiments of the present technology can include an atrial member and a ventricular member configured to sandwich one or more the native leaflets therebetween.

16 Claims, 117 Drawing Sheets

(58) Field of Classification Search
CPC .... A61F 2/2445; A61F 2/2433; A61F 2/2454; A61F 2/2466
See application file for complete search history.

(56) References Cited

U.S. PATENT DOCUMENTS

| | | | | |
|---|---|---|---|---|
| 2014/0067054 | A1* | 3/2014 | Chau | A61F 2/2466 623/2.36 |
| 2016/0166382 | A1* | 6/2016 | Nguyen | A61F 2/246 623/2.17 |
| 2016/0199181 | A1* | 7/2016 | Kramer | A61F 2/2418 623/2.17 |
| 2017/0112618 | A1* | 4/2017 | Li | A61F 2/2445 |
| 2017/0231759 | A1 | 8/2017 | Geist et al. | |
| 2019/0076247 | A1* | 3/2019 | Zeng | A61F 2/2466 |
| 2019/0209324 | A1* | 7/2019 | Metchik | A61F 2/2463 |
| 2020/0138569 | A1* | 5/2020 | Basude | A61F 2/246 |
| 2021/0353418 | A1* | 11/2021 | Mohl | A61F 2/2463 |

FOREIGN PATENT DOCUMENTS

| | | |
|---|---|---|
| WO | WO2019010370 | 1/2019 |
| WO | WO2020146548 | 7/2020 |
| WO | WO2020163112 | 8/2020 |
| WO | WO2020167677 | 8/2020 |
| WO | WO2022109620 | 5/2022 |
| WO | WO2022109621 | 5/2022 |

OTHER PUBLICATIONS

ISA, PCT Application No. PCT/US2021/072559, International Search Report and Written Opinion mailed Apr. 14, 2022, 18 pages.

* cited by examiner

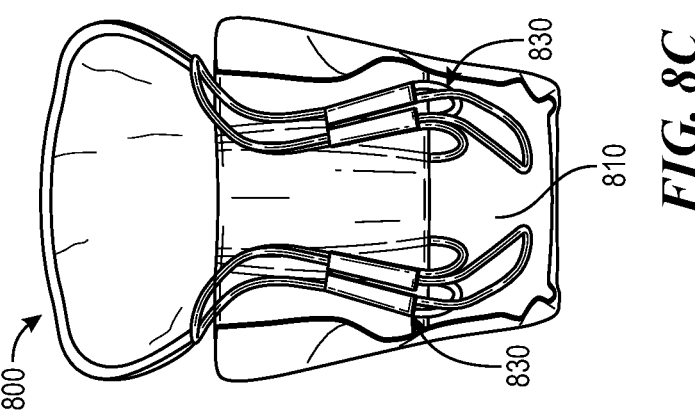
*FIG. 8C*
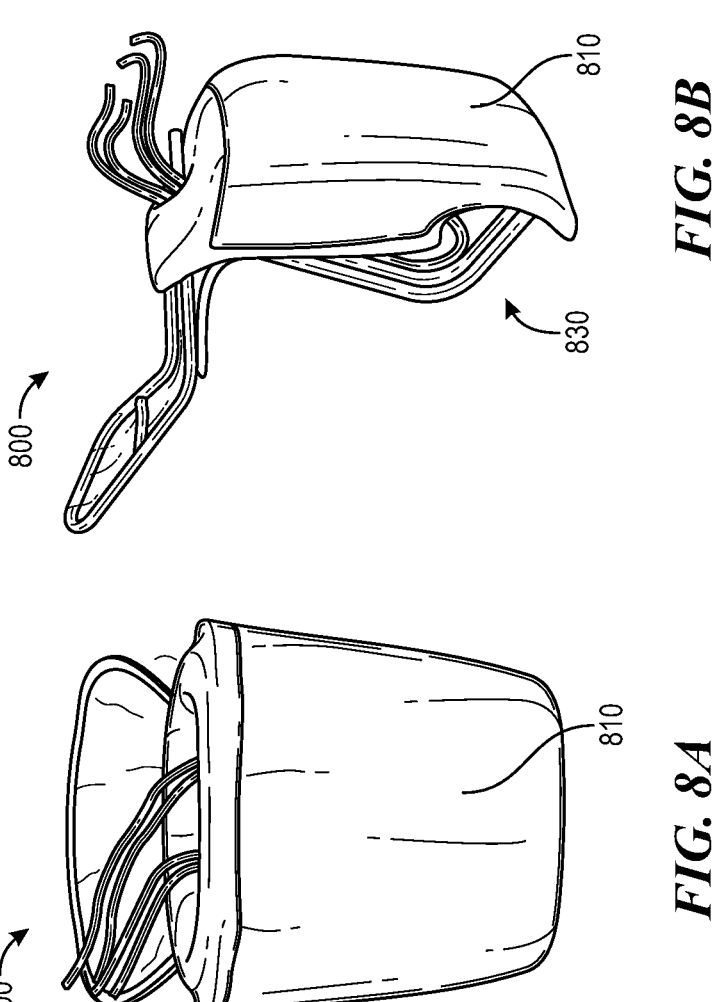
*FIG. 8B*
*FIG. 8A*

910

910

910

910

910

910

910

910

1010

1010

1010

1010

1010

1010

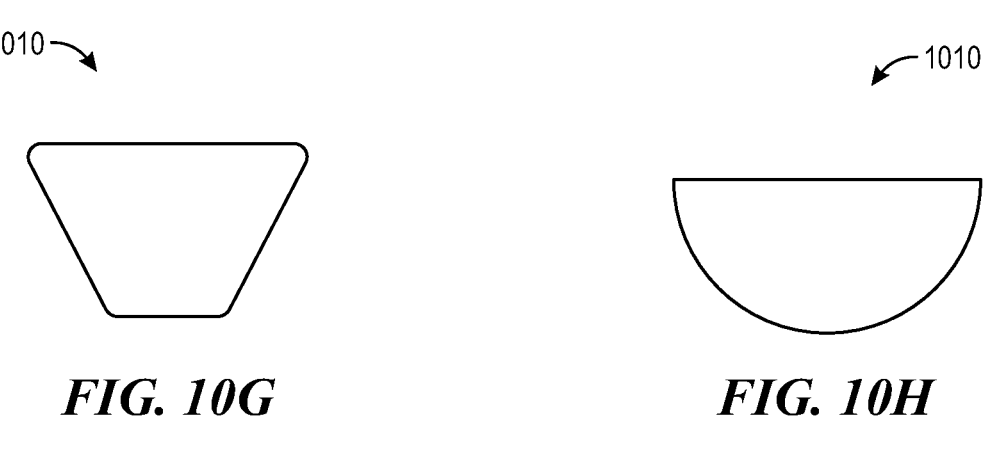
FIG. 10G           FIG. 10H
FIG. 10I           FIG. 10J
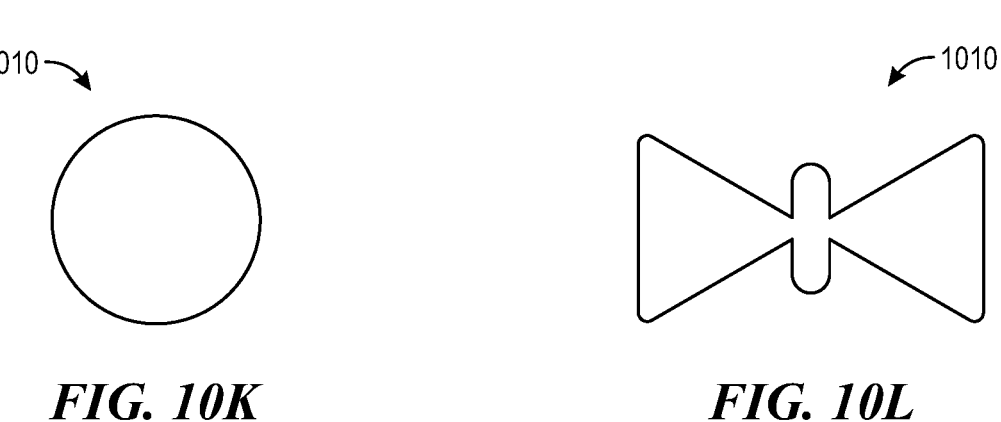
FIG. 10K           FIG. 10L

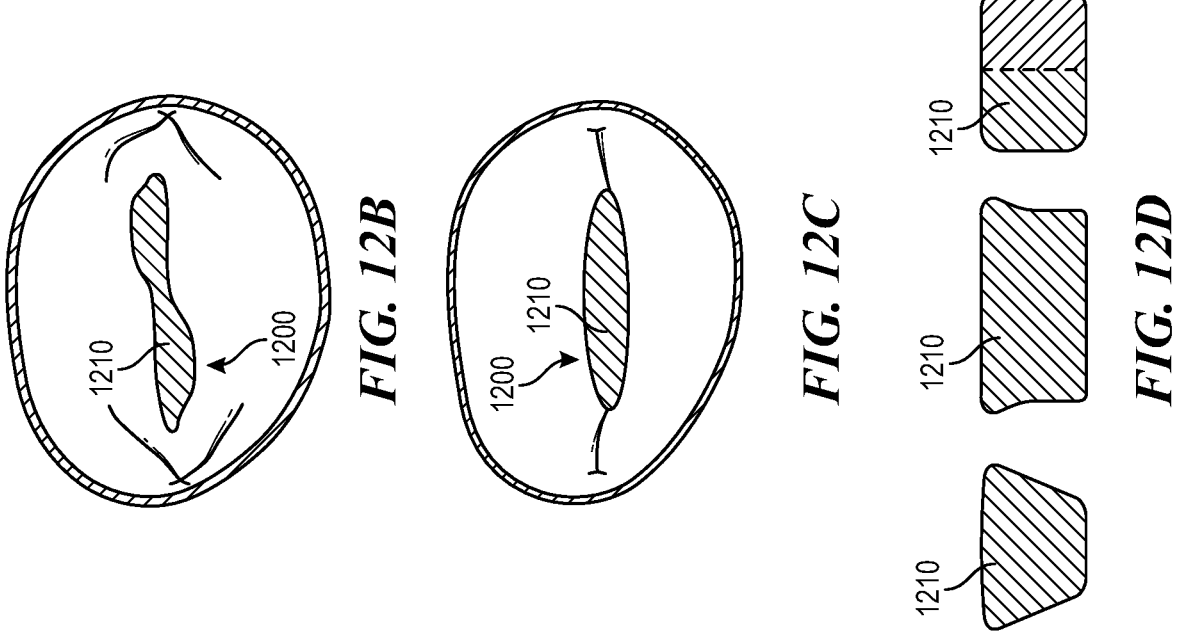
*FIG. 12B*
*FIG. 12C*
*FIG. 12D*
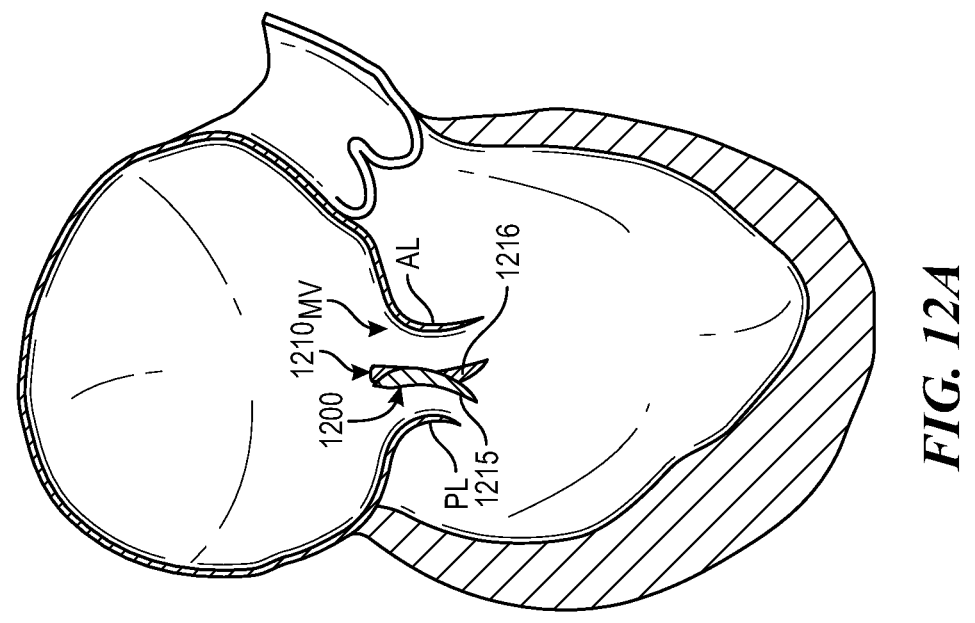
*FIG. 12A*

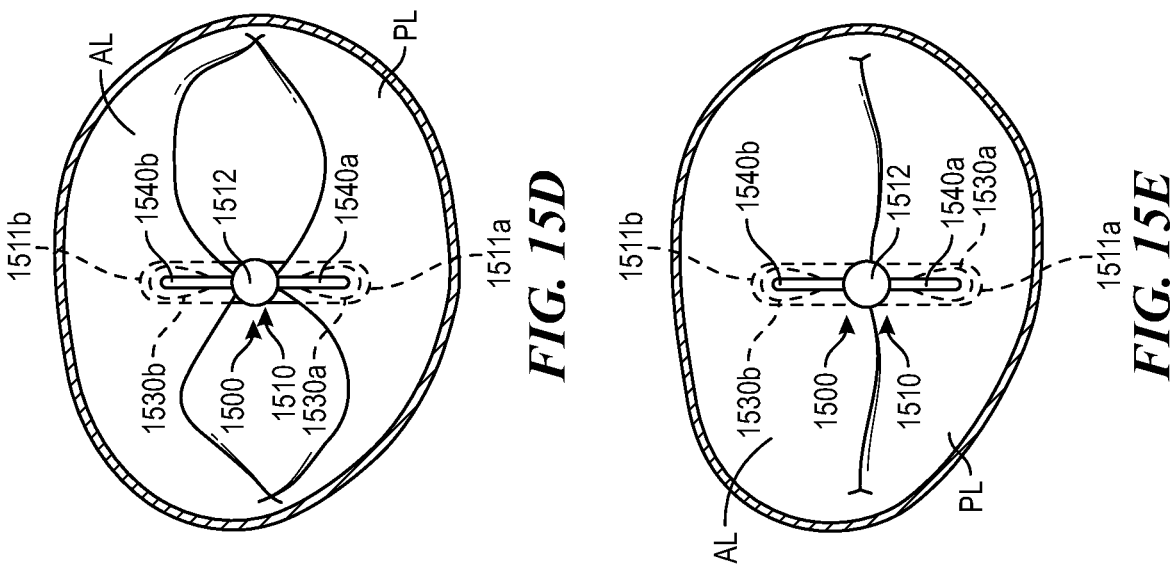
*FIG. 15D*
*FIG. 15E*
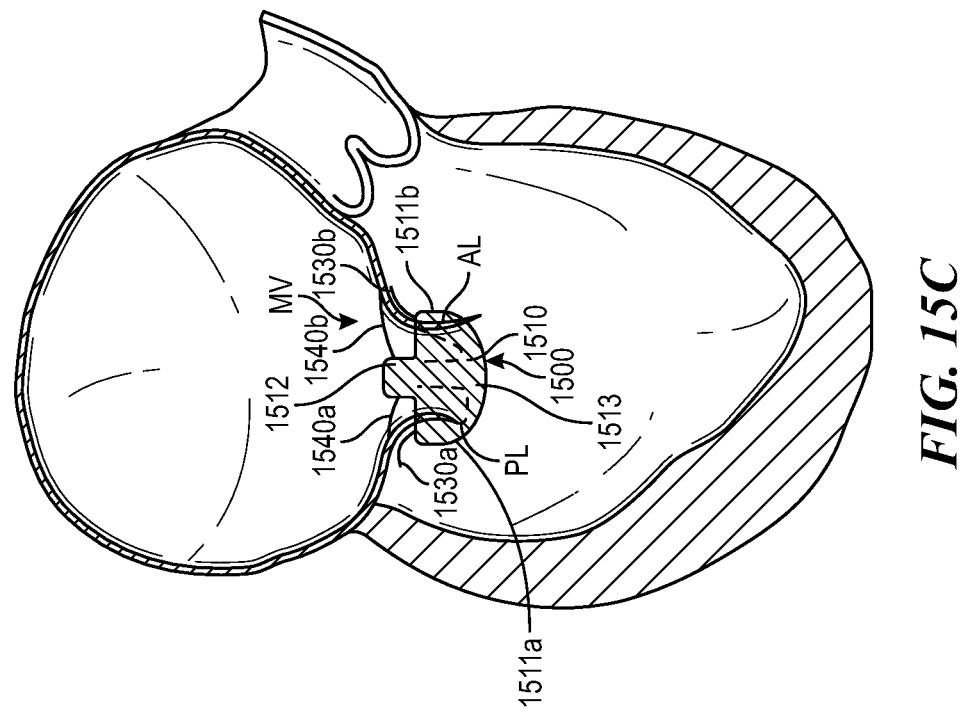
*FIG. 15C*

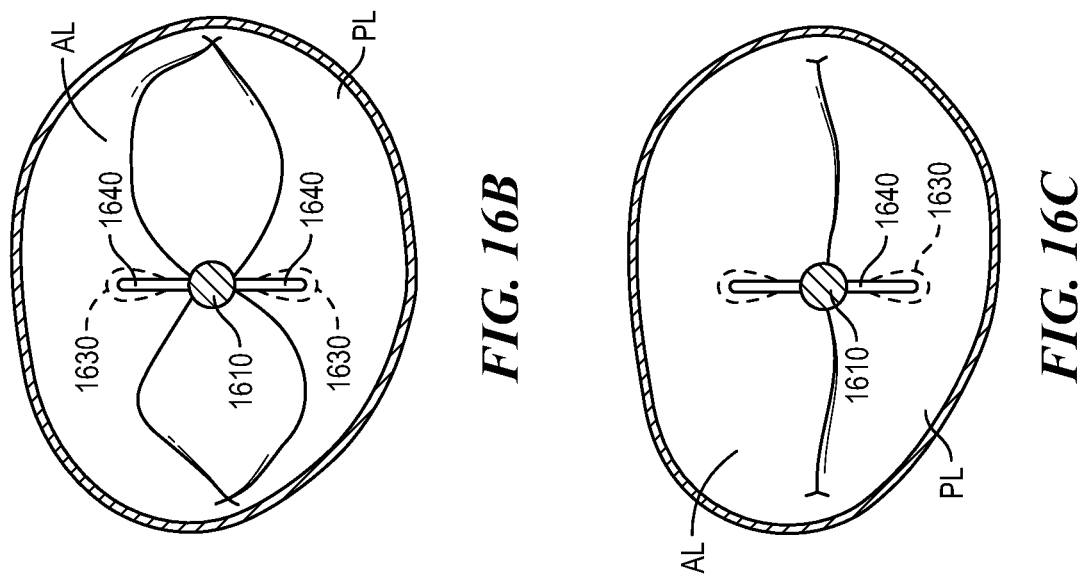
*FIG. 16B*
*FIG. 16C*
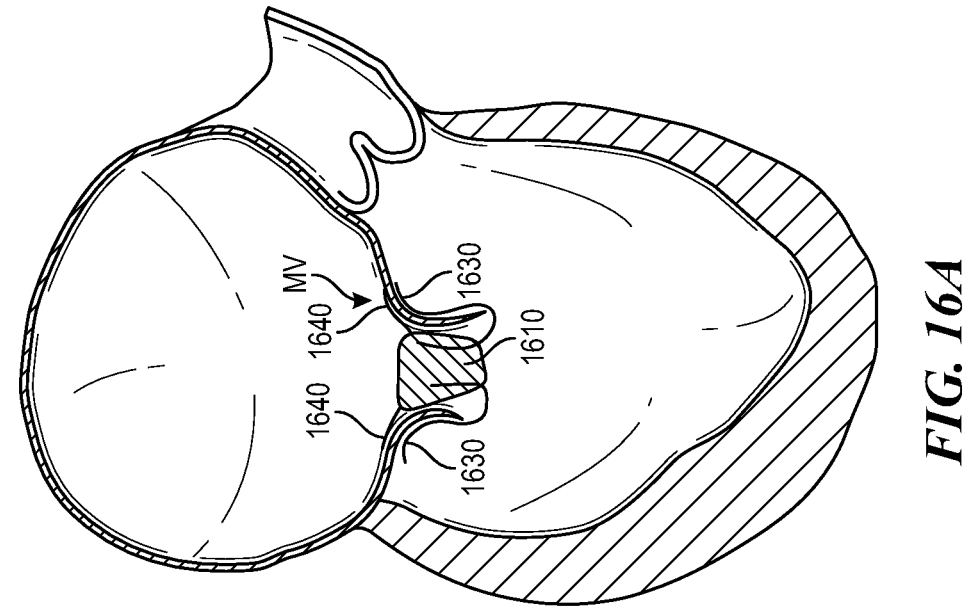
*FIG. 16A*

2000

2010

2030     2030

2011     2011     L

2100

2110

2111

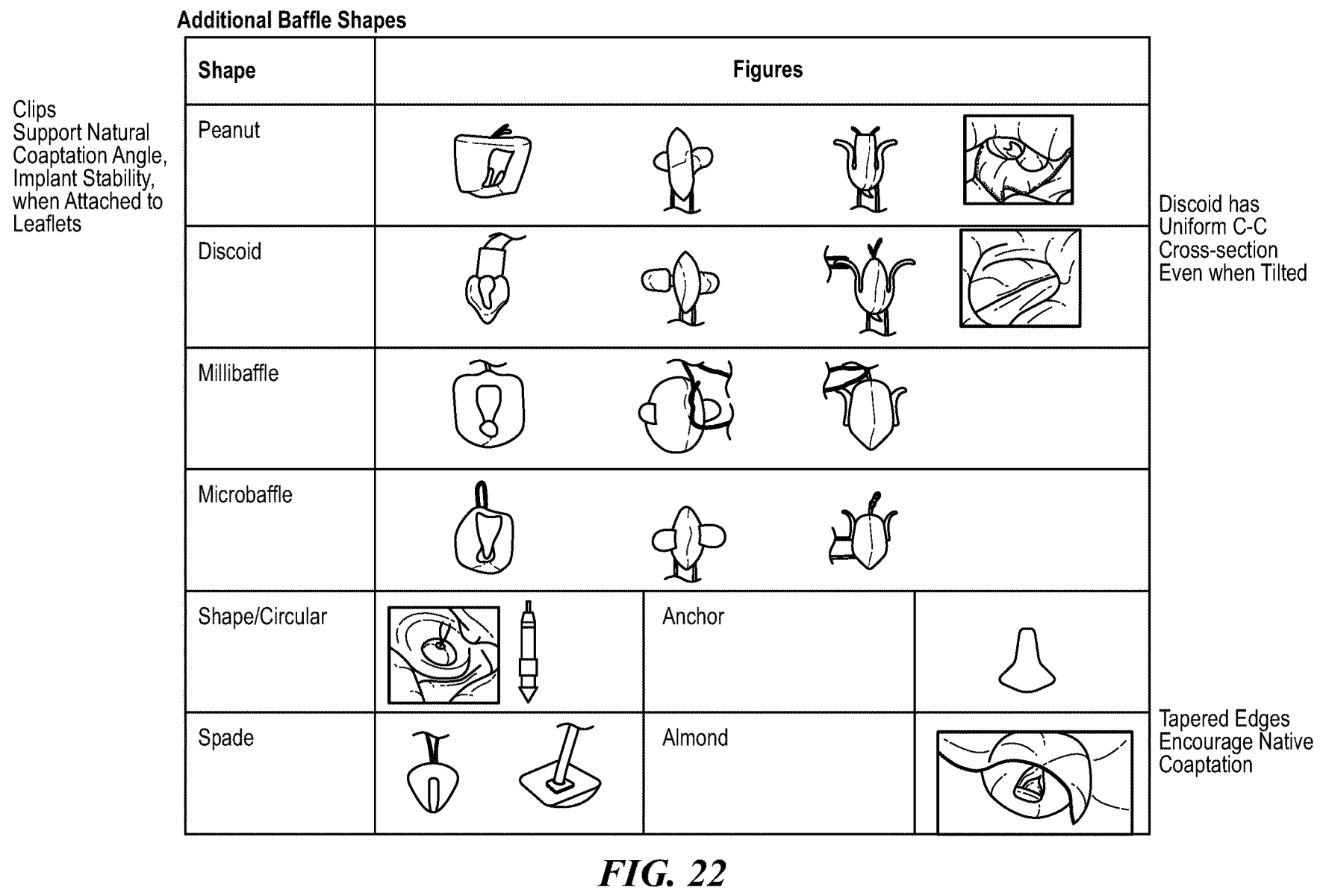

Additional Baffle Shapes

| Shape | Figures | | | |
|---|---|---|---|---|
| Peanut | | | | Clips Support Natural Coaptation Angle, Implant Stability, when Attached to Leaflets |
| Discoid | | | | Discoid has Uniform C-C Cross-section Even when Tilted |
| Millibaffle | | | | |
| Microbaffle | | | | |
| Shape/Circular | Anchor | | | |
| Spade | Almond | | | Tapered Edges Encourage Native Coaptation |

*FIG. 22*

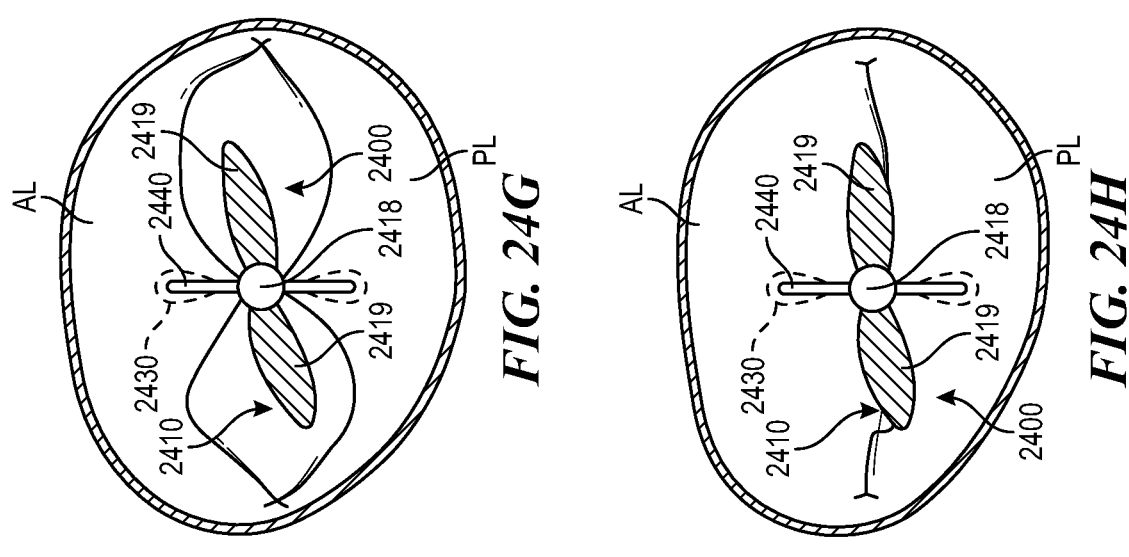
*FIG. 24G*
*FIG. 24H*
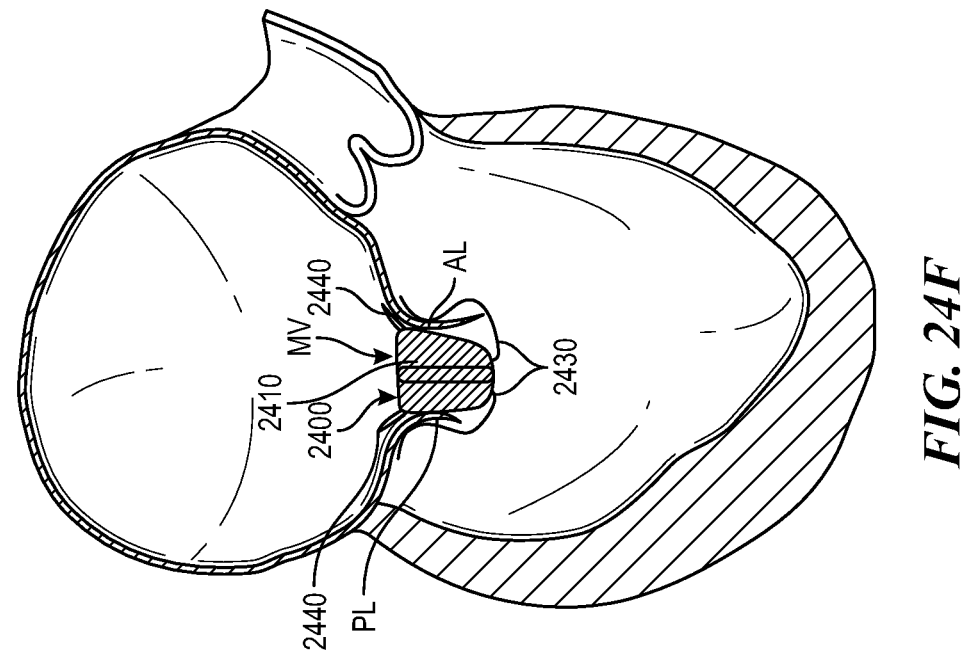
*FIG. 24F*

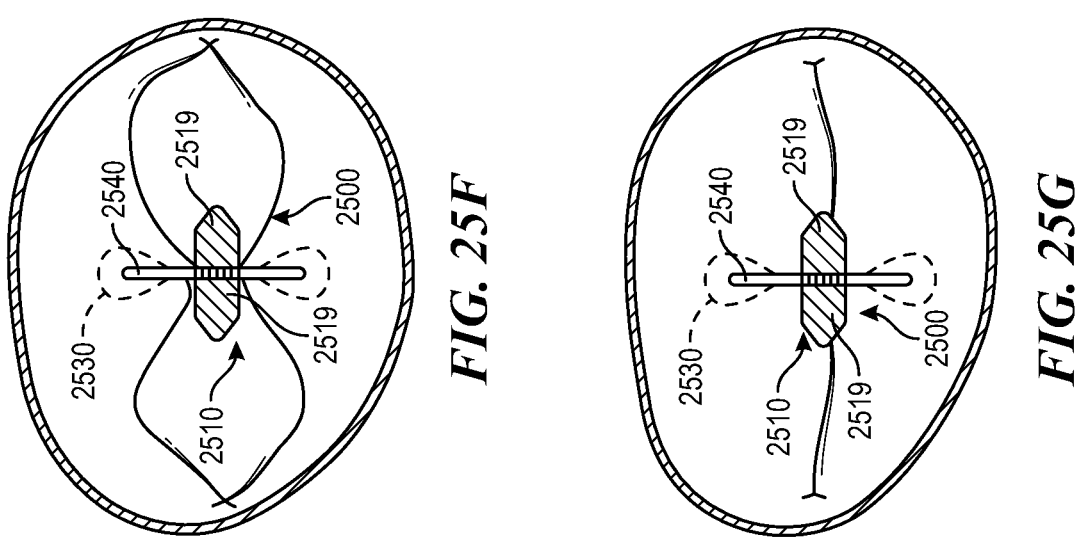
*FIG. 25F*
*FIG. 25G*
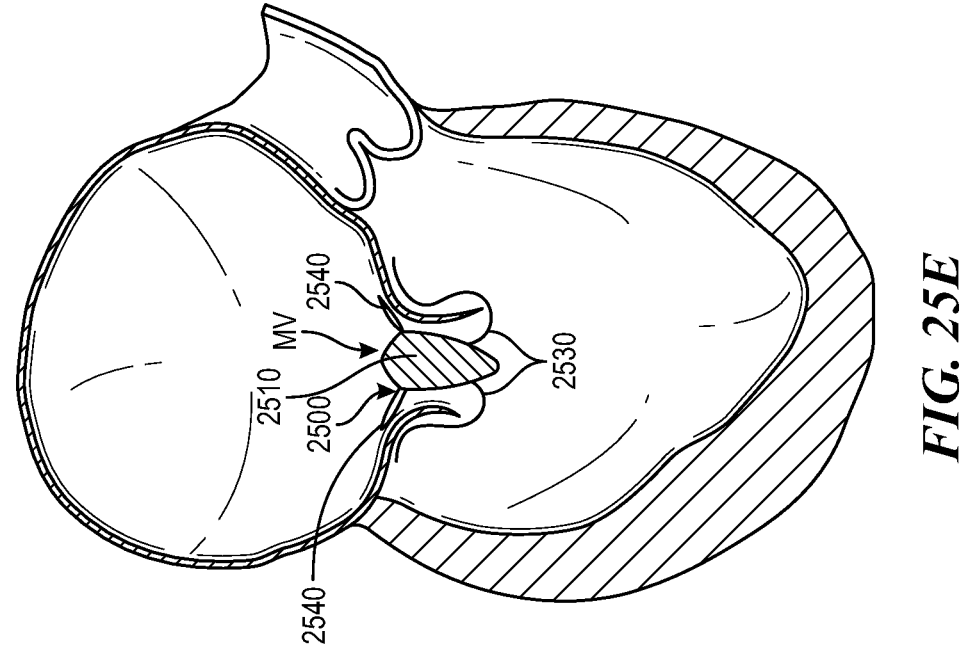
*FIG. 25E*

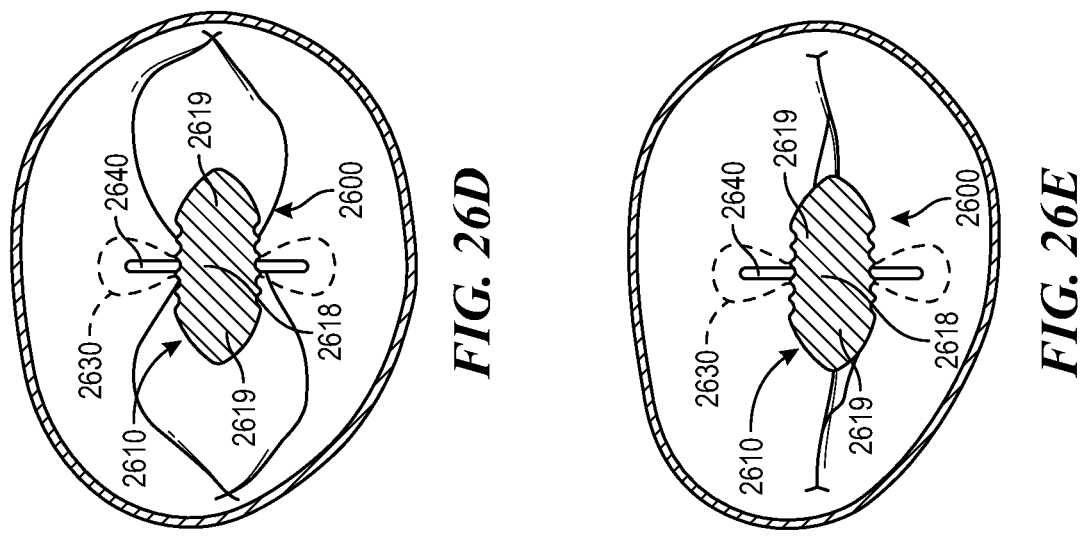
*FIG. 26D*
*FIG. 26E*
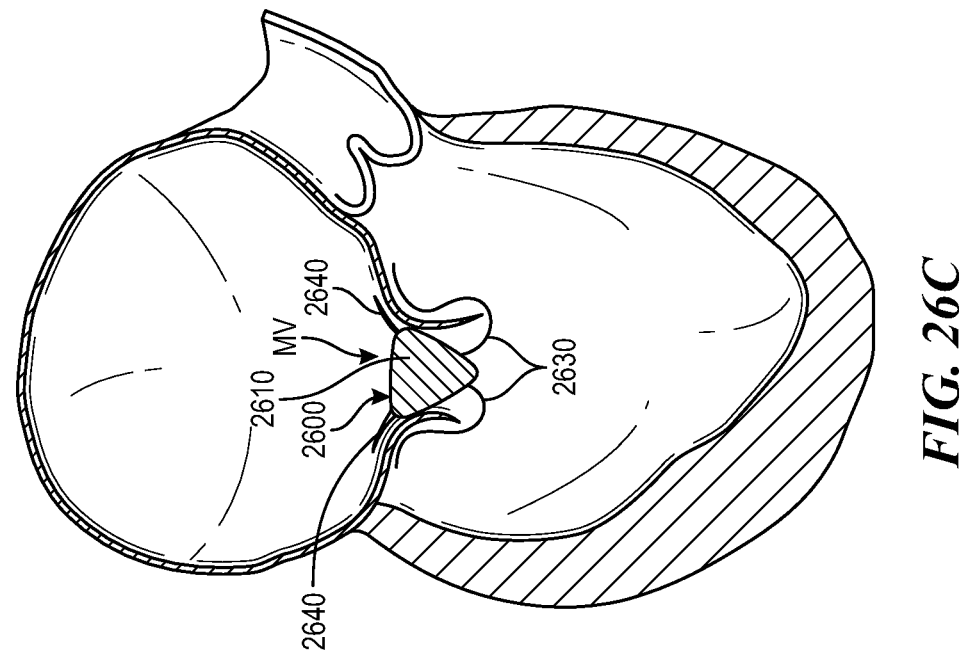
*FIG. 26C*

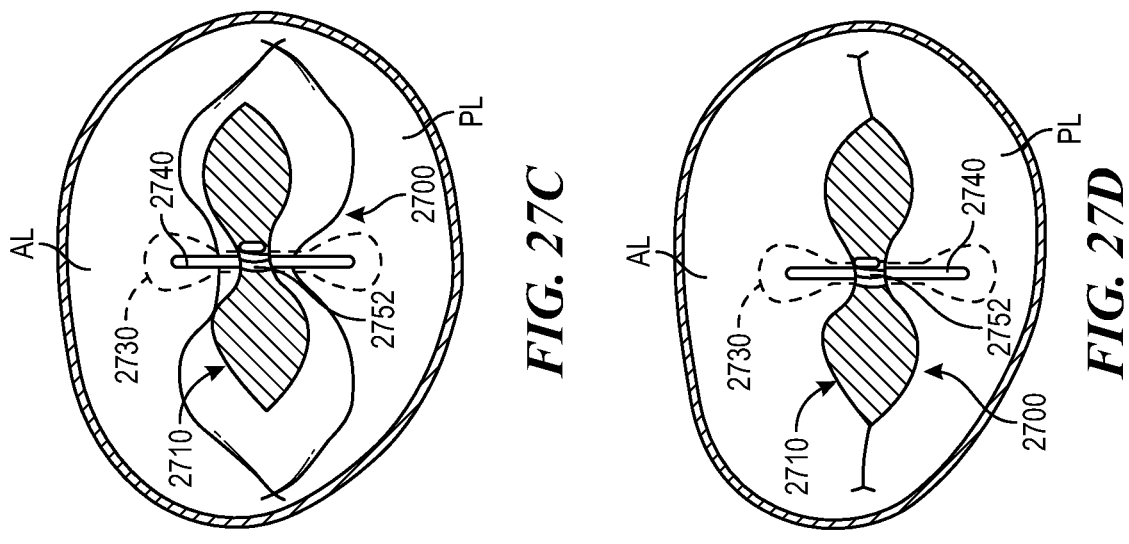
*FIG. 27C*
*FIG. 27D*
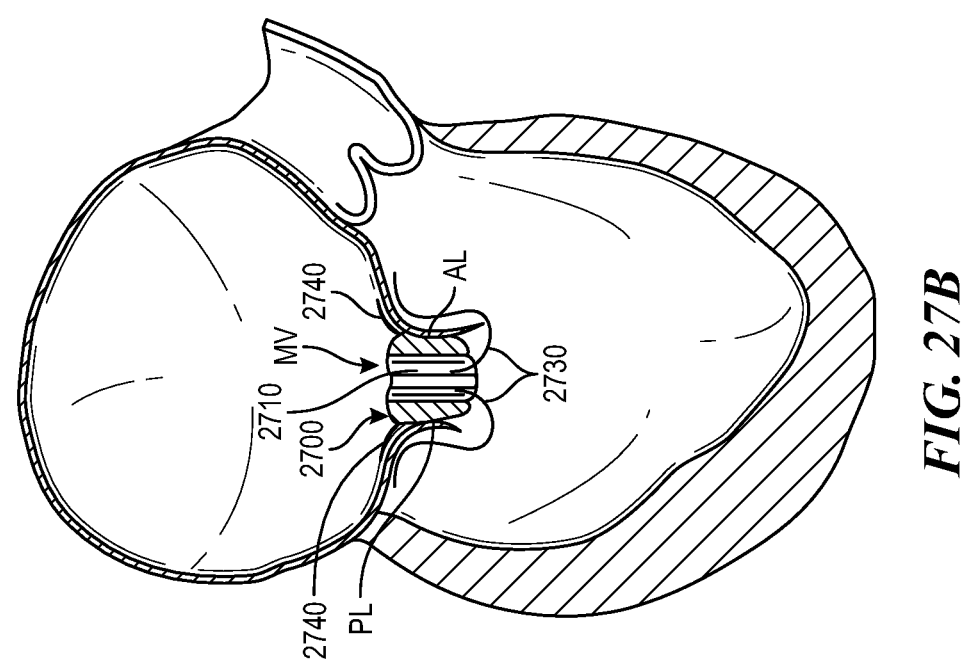
*FIG. 27B*

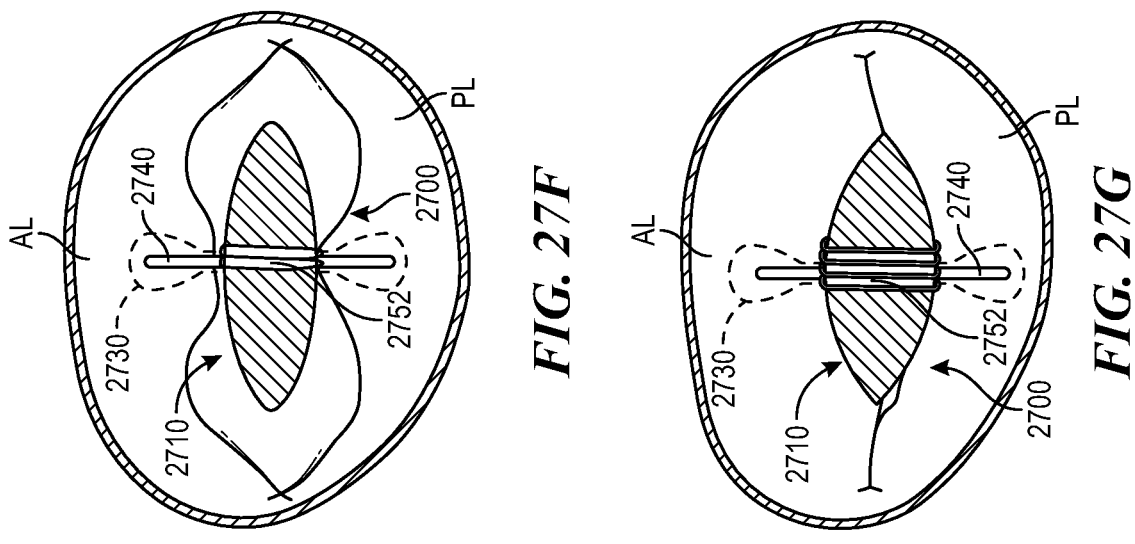
FIG. 27F
FIG. 27G
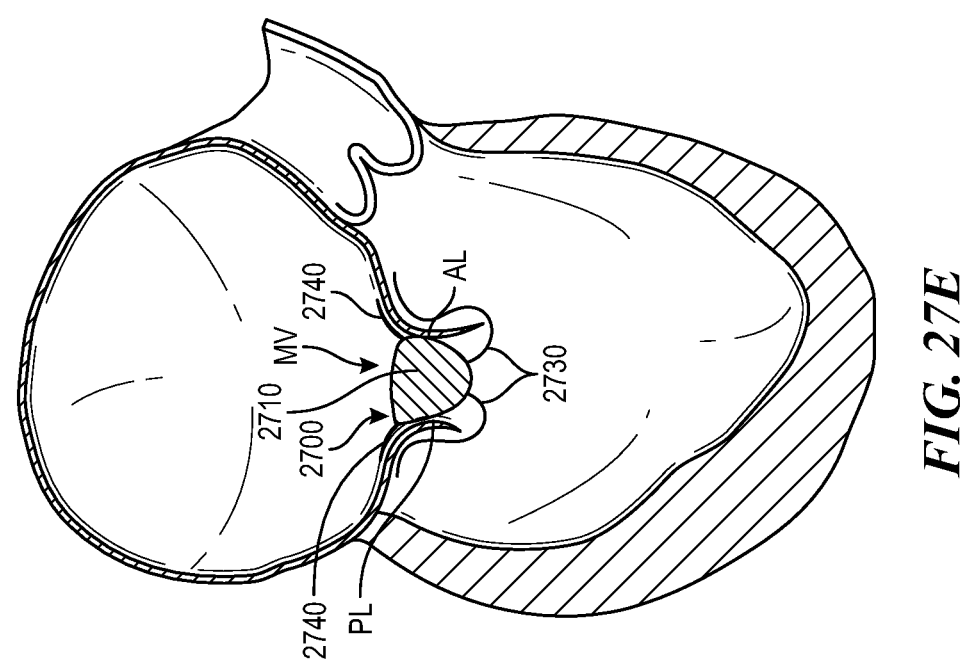
FIG. 27E

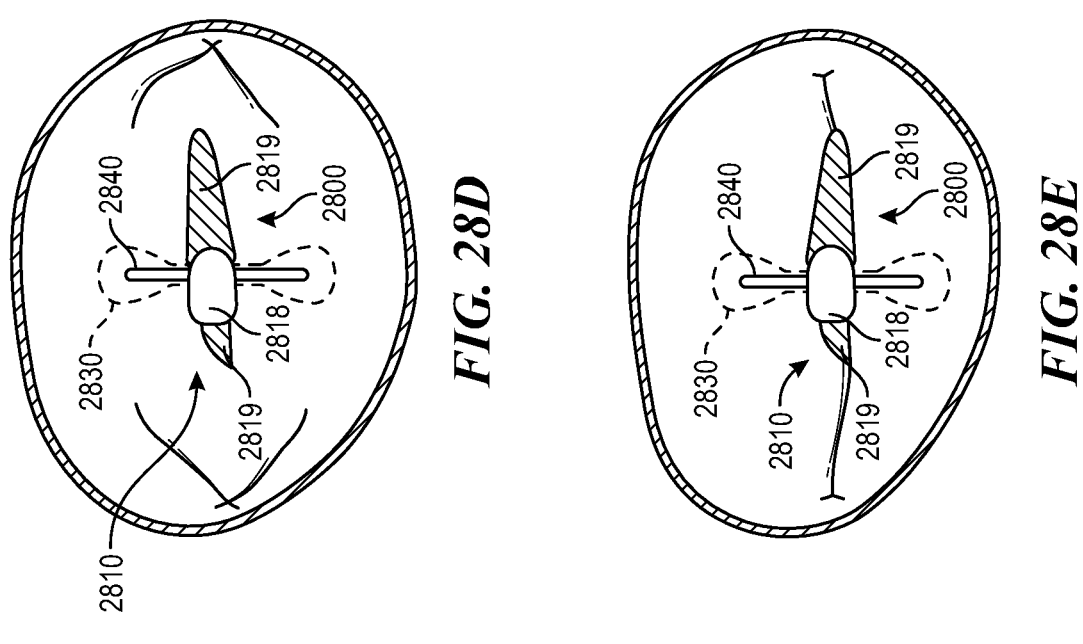
*FIG. 28D*
*FIG. 28E*
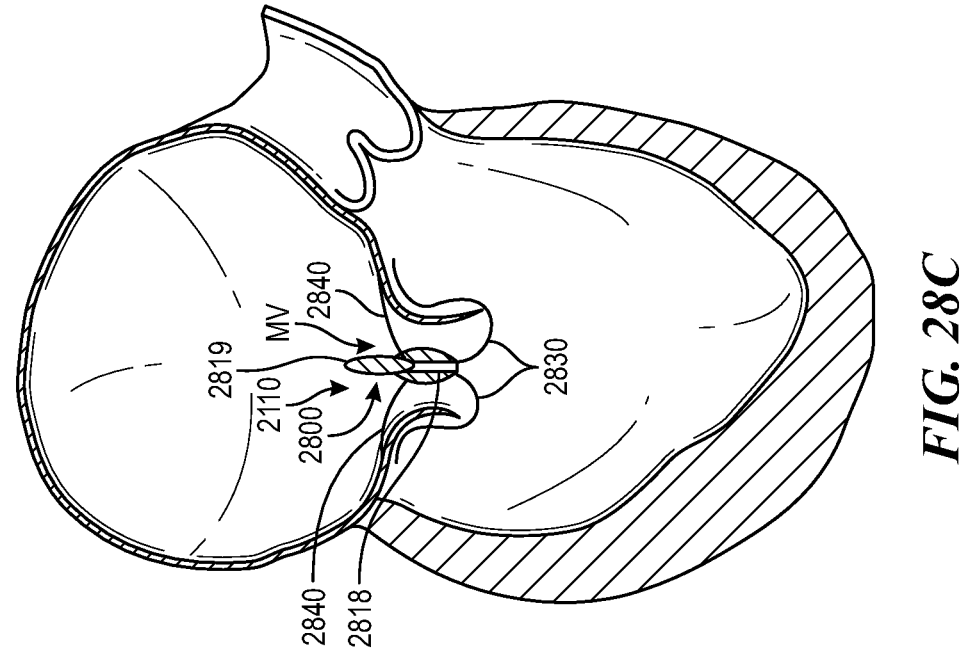
*FIG. 28C*

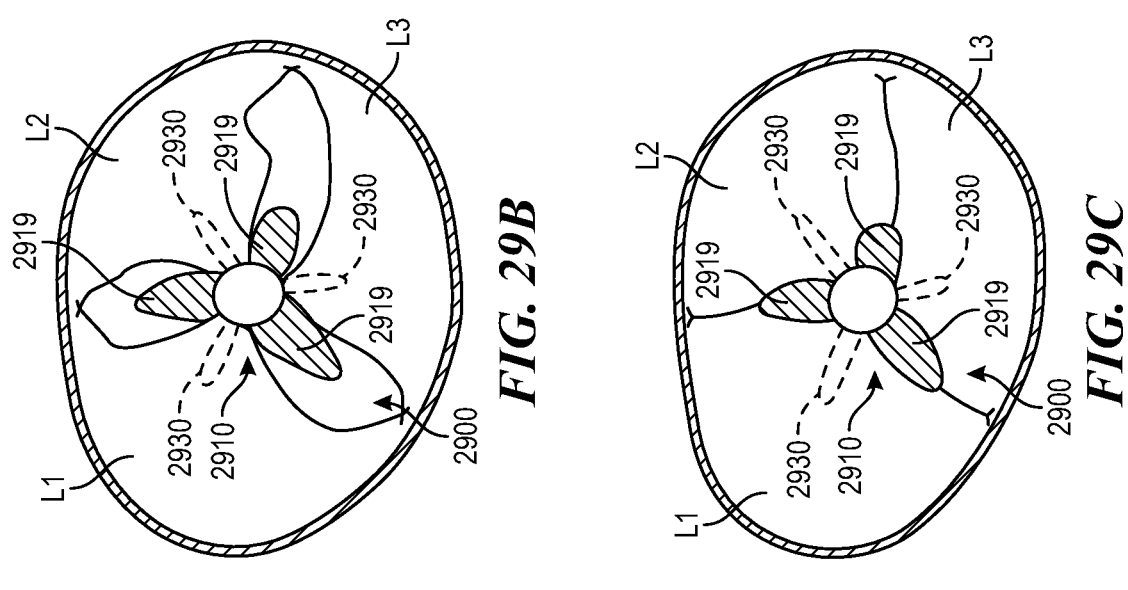
*FIG. 29B*
*FIG. 29C*
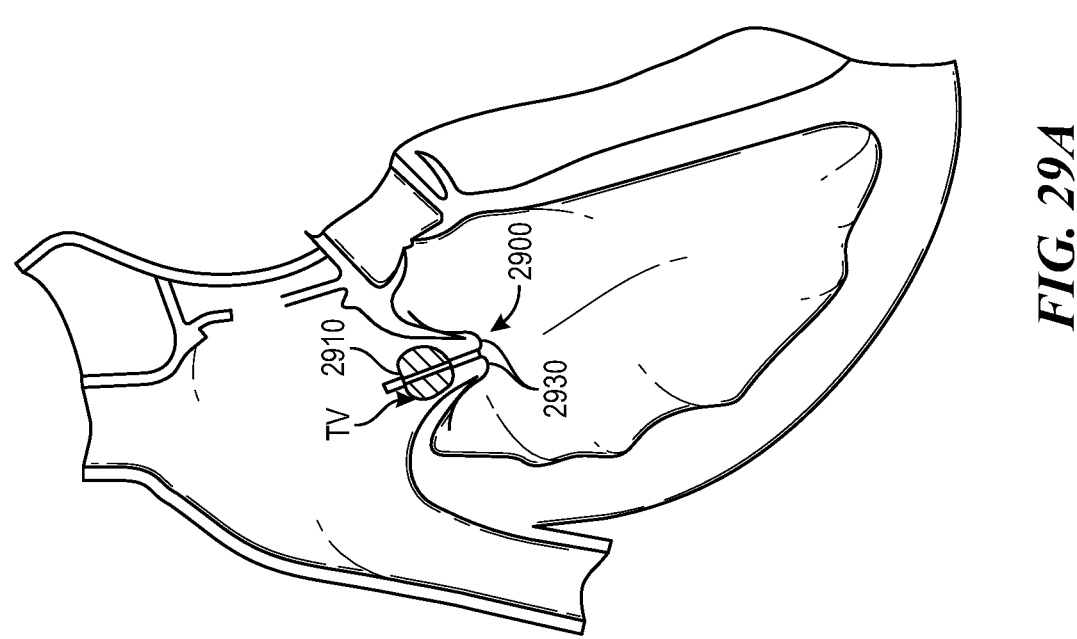
*FIG. 29A*

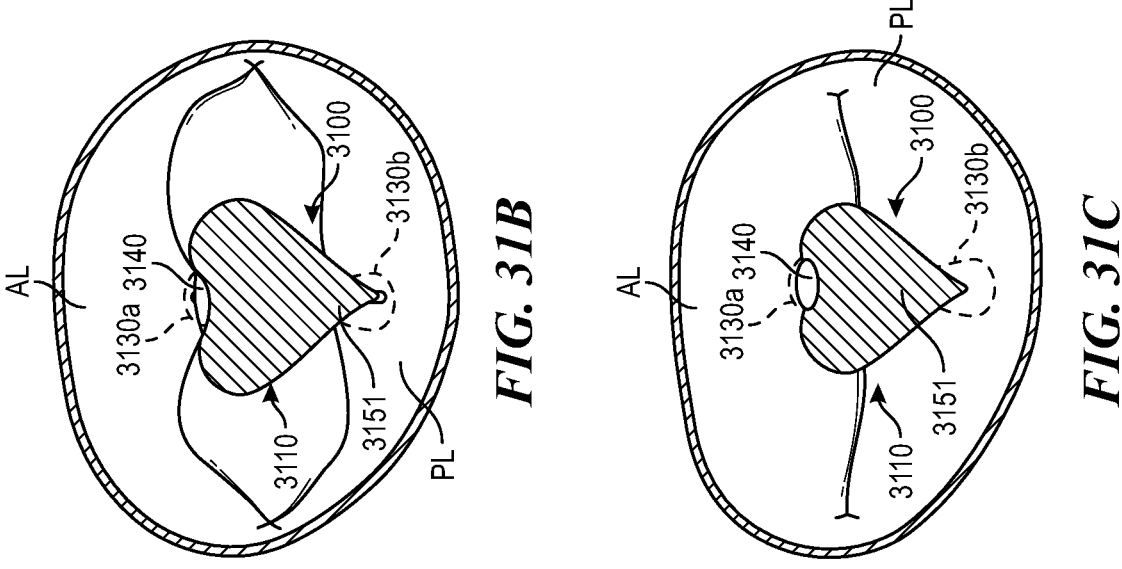
FIG. 31B
FIG. 31C
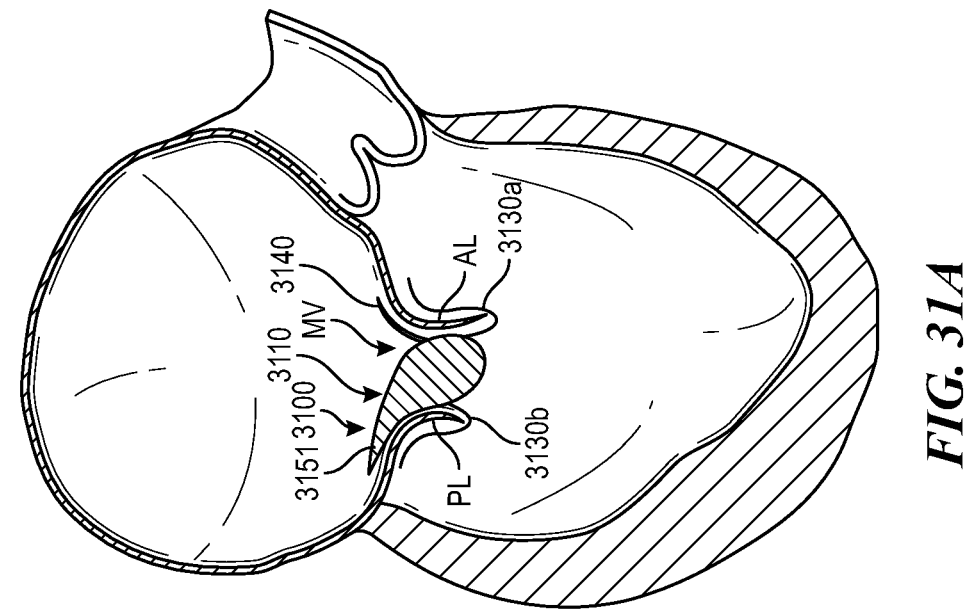
FIG. 31A

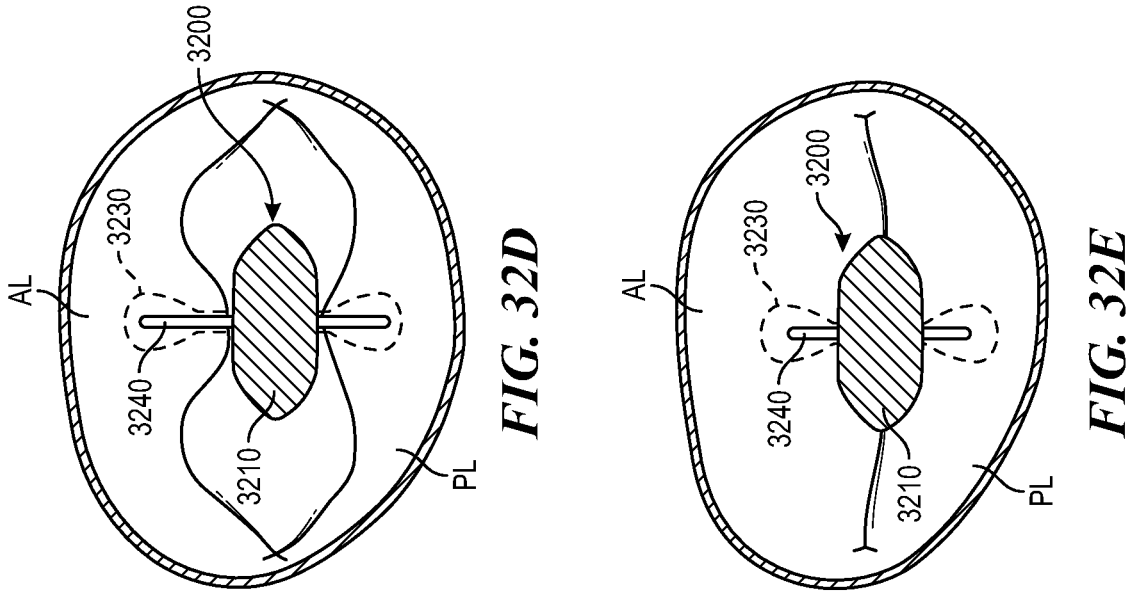
FIG. 32D
FIG. 32E
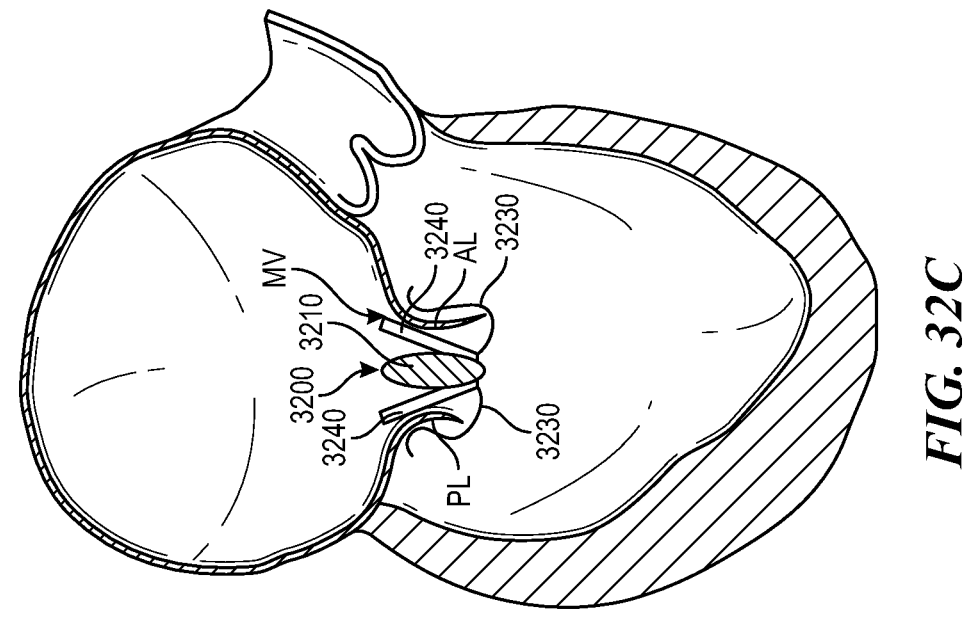
FIG. 32C

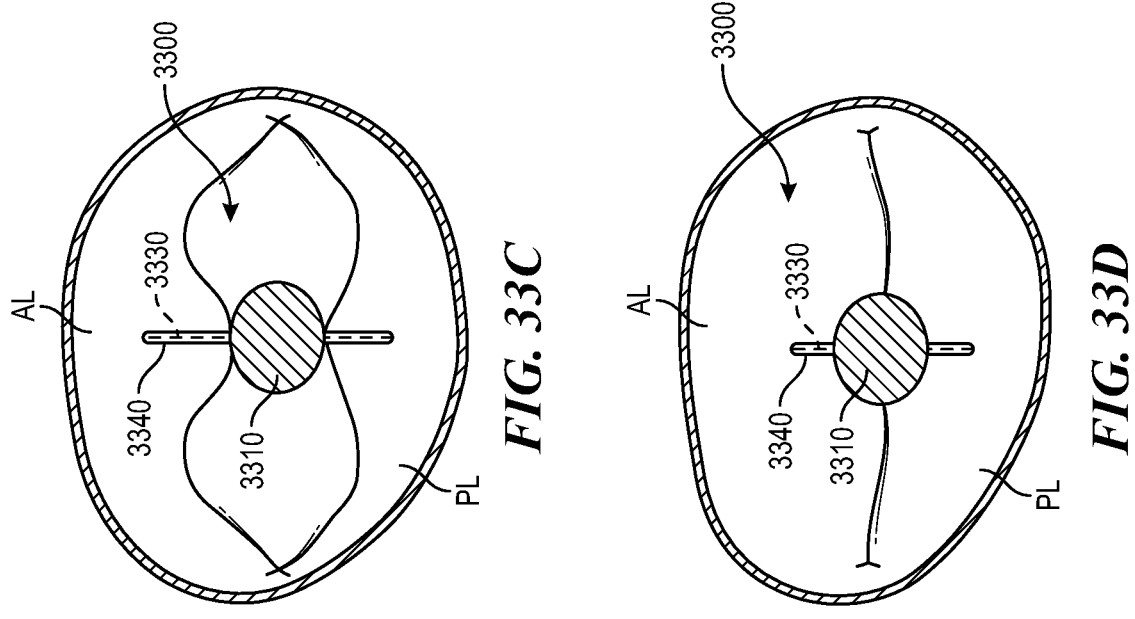
*FIG. 33C*
*FIG. 33D*
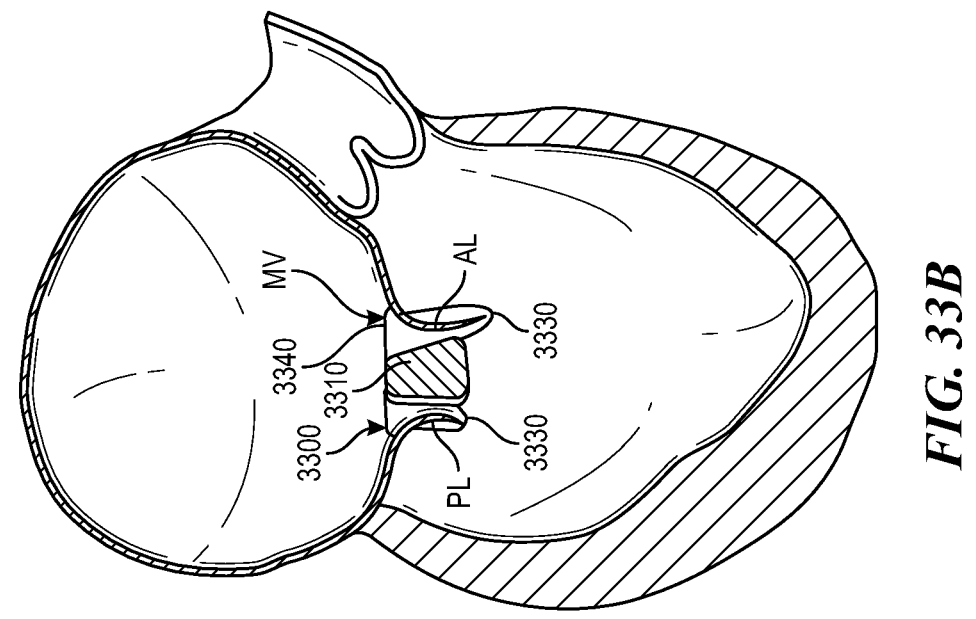
*FIG. 33B*

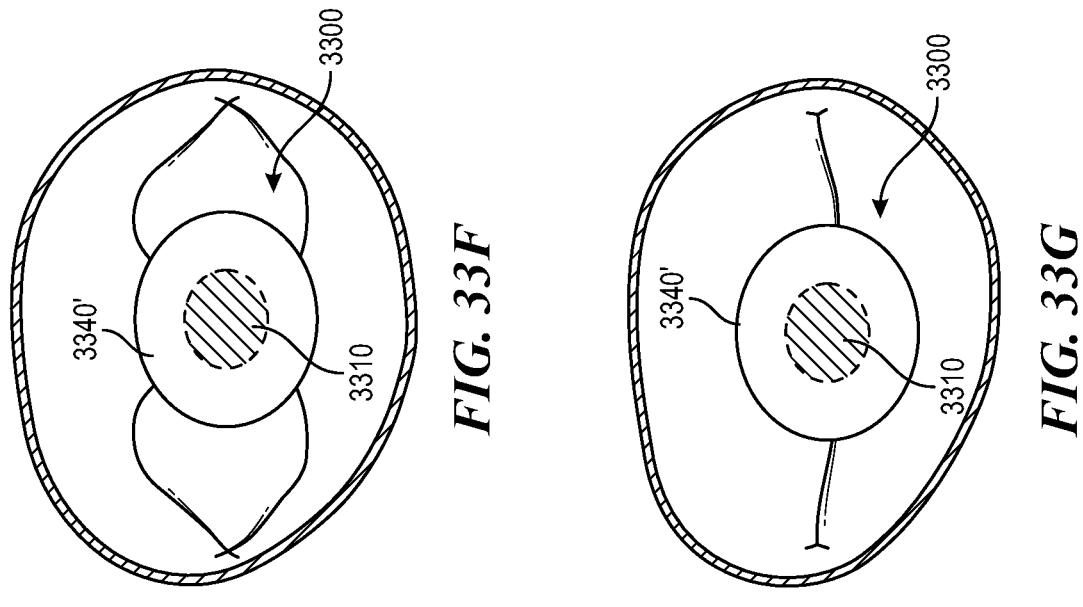
*FIG. 33F*
*FIG. 33G*
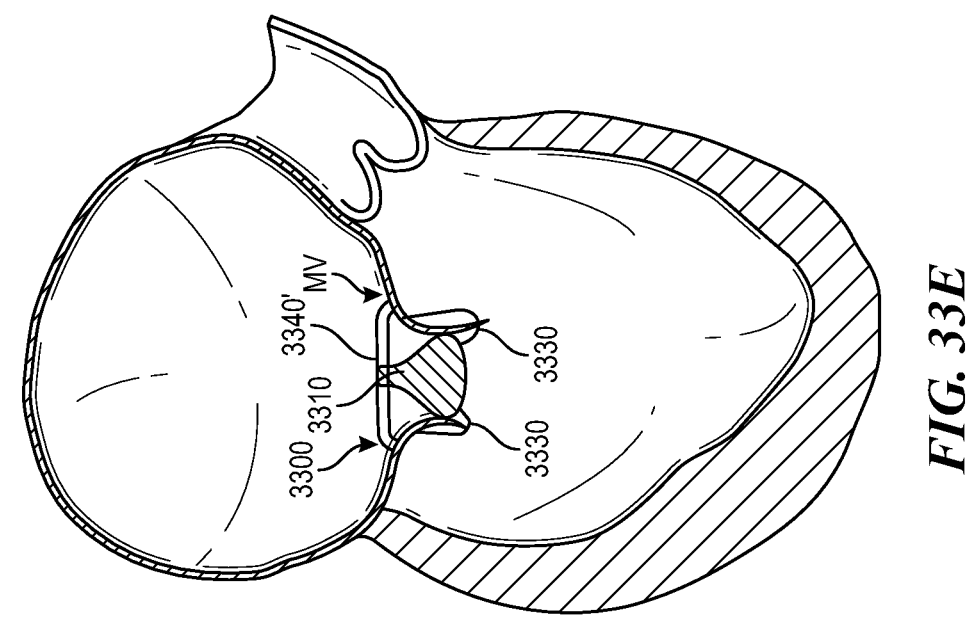
*FIG. 33E*

3400

3440

AL

PL

3410

3440

3400

3430

AL

3410

PL

3430

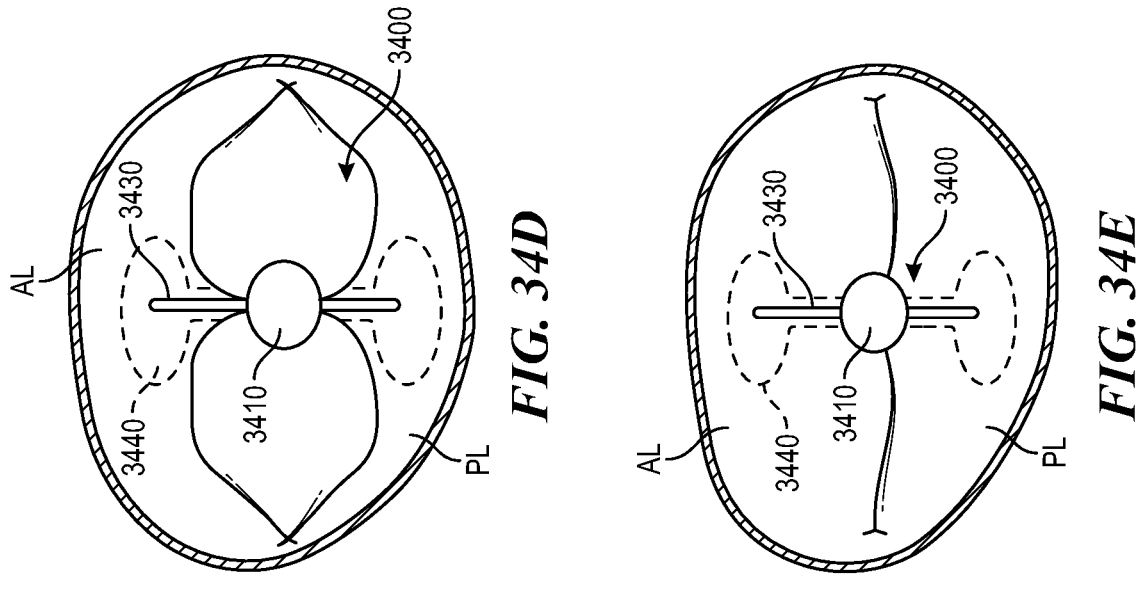
*FIG. 34D*
*FIG. 34E*
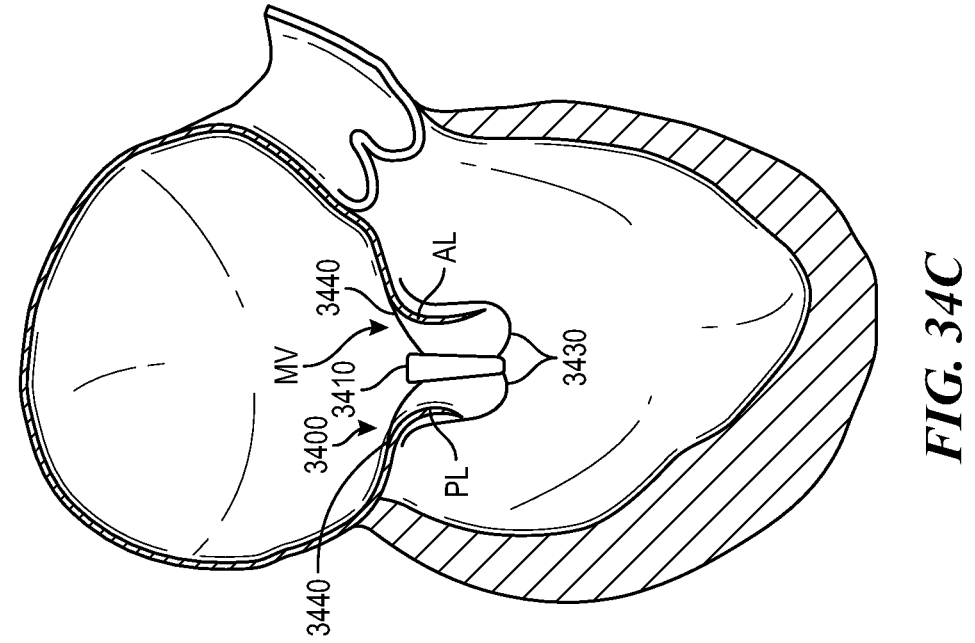
*FIG. 34C*

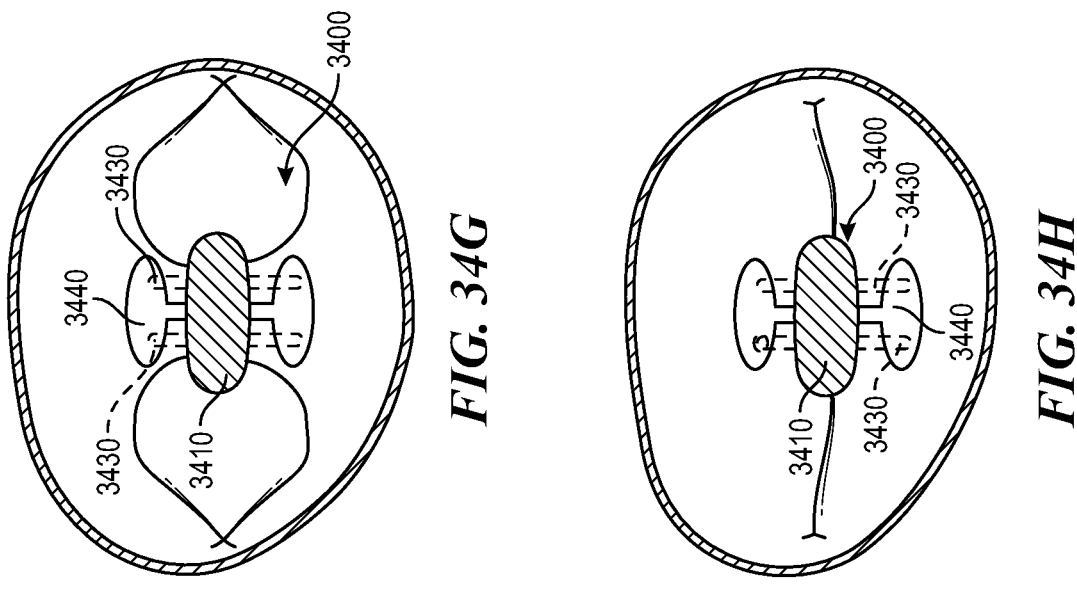
*FIG. 34G*
*FIG. 34H*
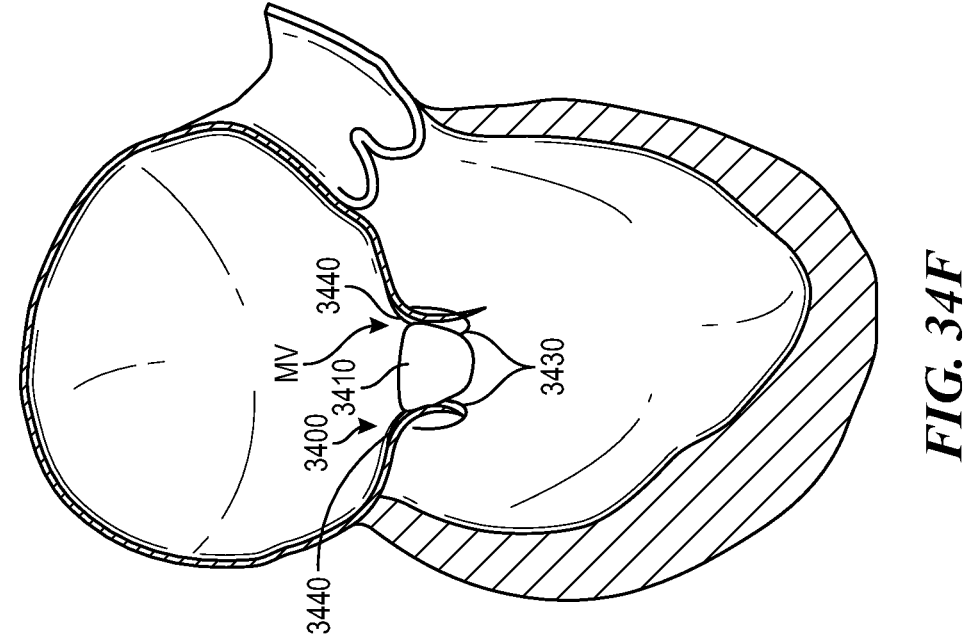
*FIG. 34F*

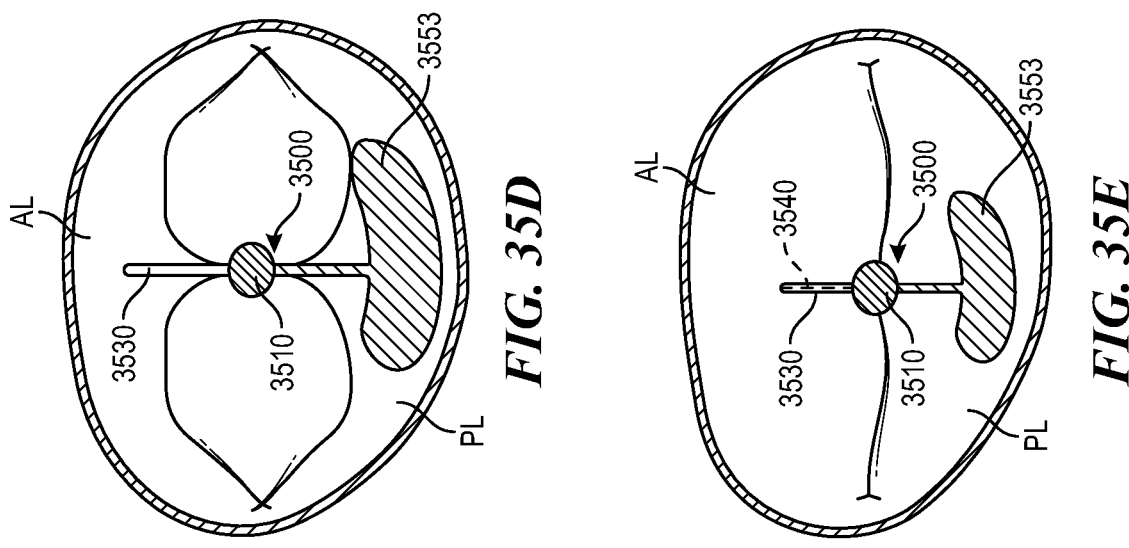
*FIG. 35D*
*FIG. 35E*
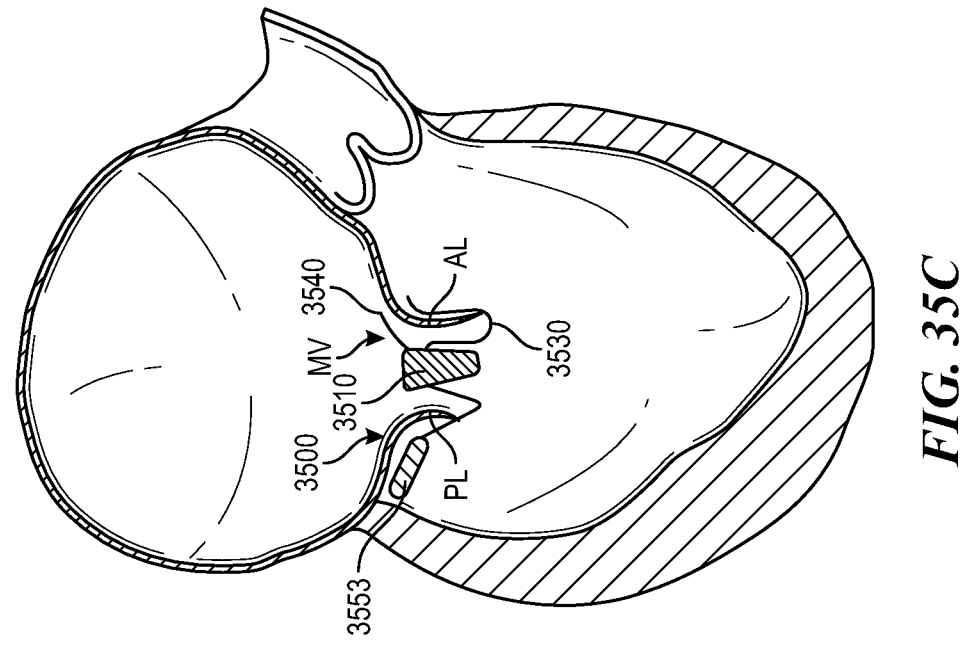
*FIG. 35C*

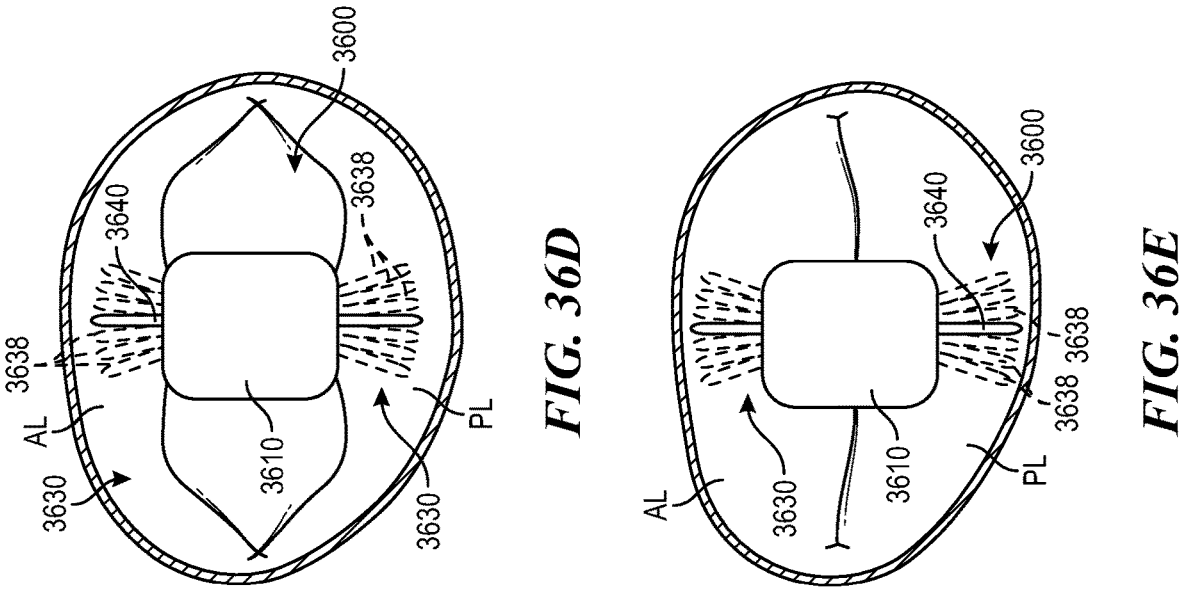
FIG. 36D
FIG. 36E
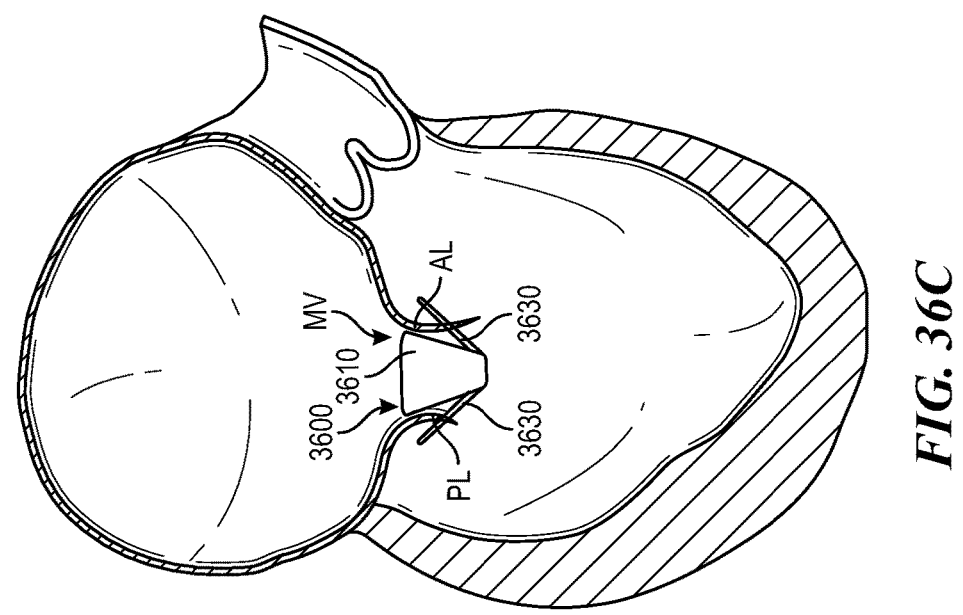
FIG. 36C

3700

3717

3710

3712

3730

3720

3700

3717

3712

3730

3710

4300

4390

4272

4370

4380

4282

4300

4391

4391

4392

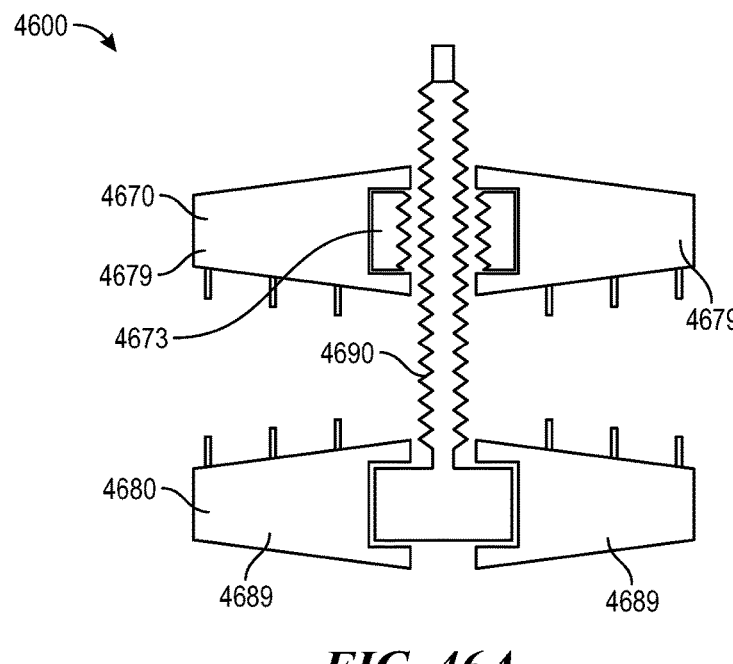
FIG. 46A
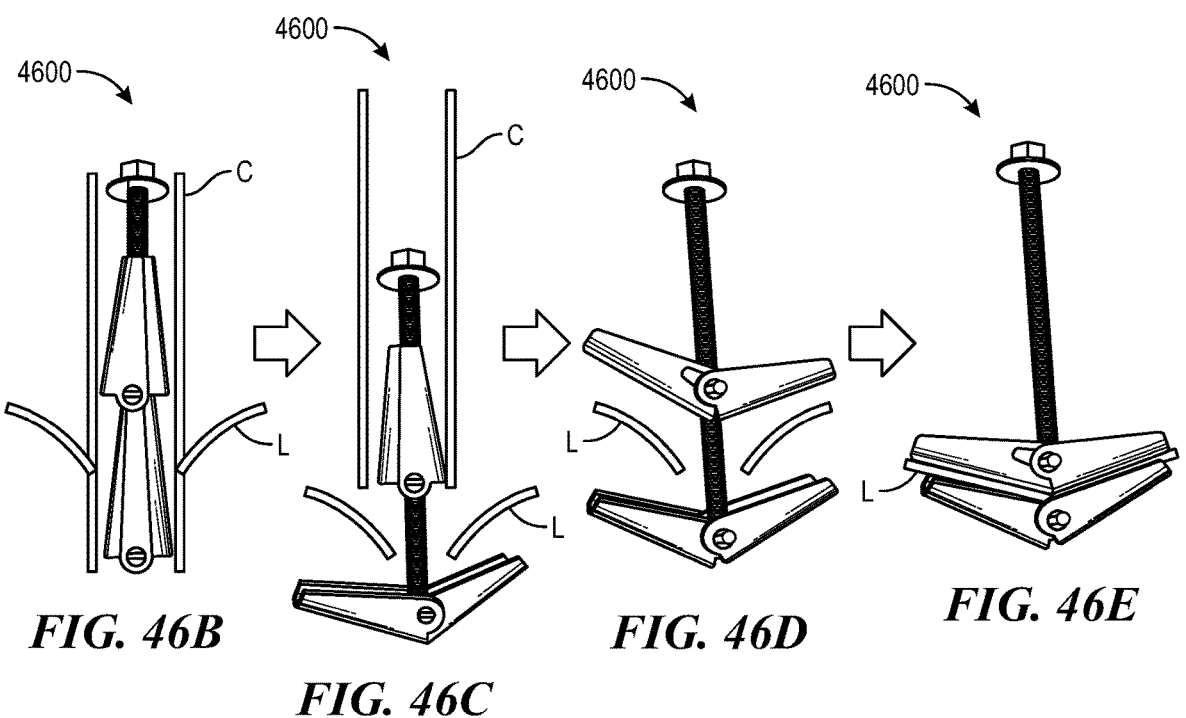
FIG. 46B
FIG. 46C
FIG. 46D
FIG. 46E

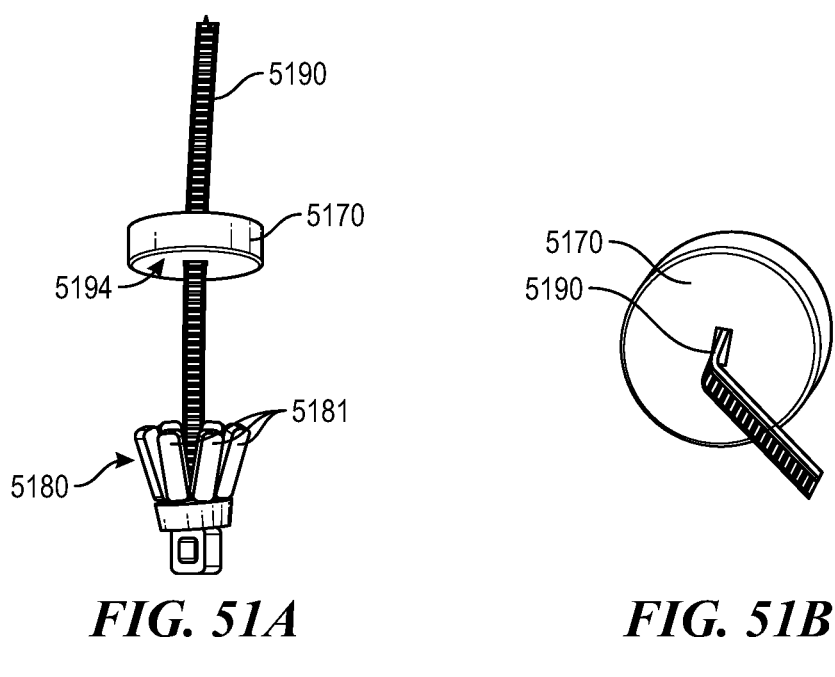
FIG. 51A            FIG. 51B
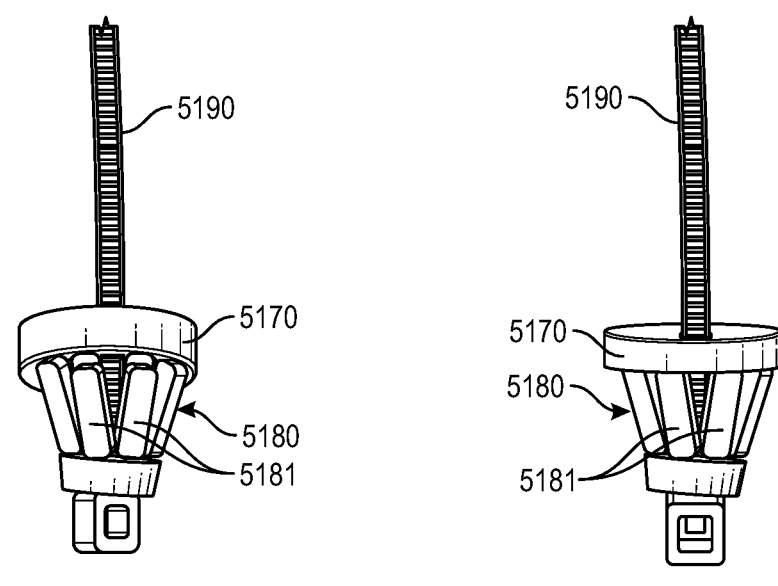
FIG. 51C            FIG. 51D

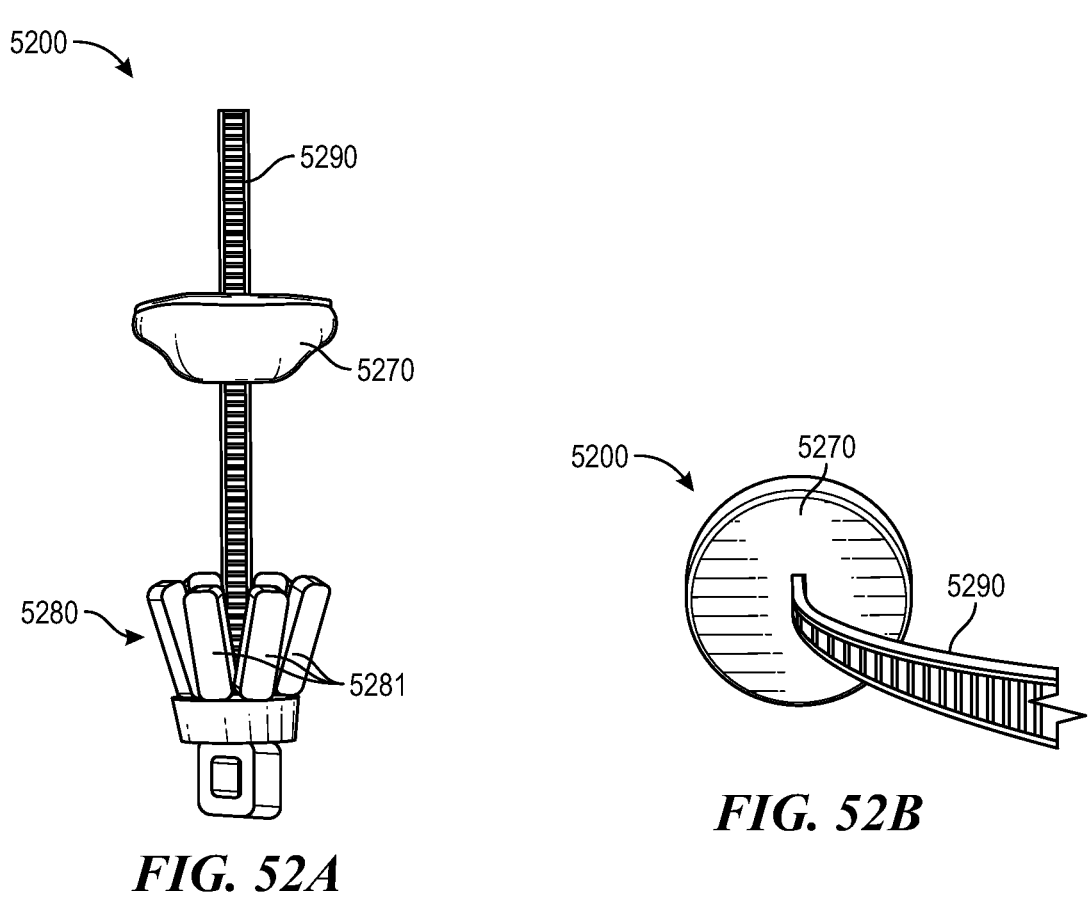
*FIG. 52A*
*FIG. 52B*
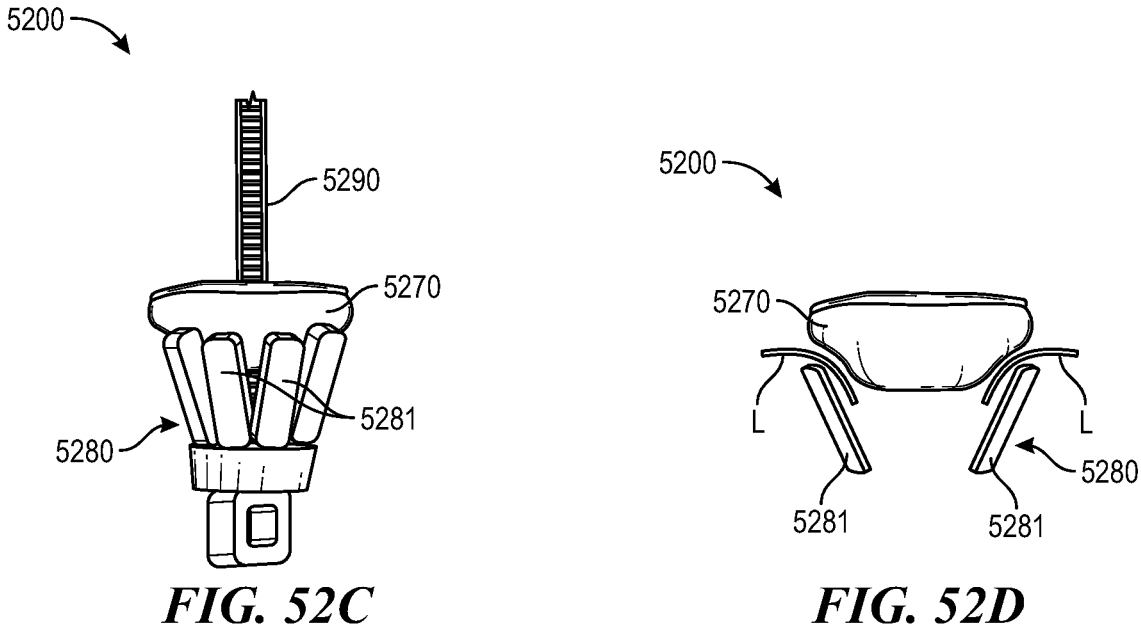
*FIG. 52C*
*FIG. 52D*

5300b

5300e

5300a

5300d

5300a

5300c

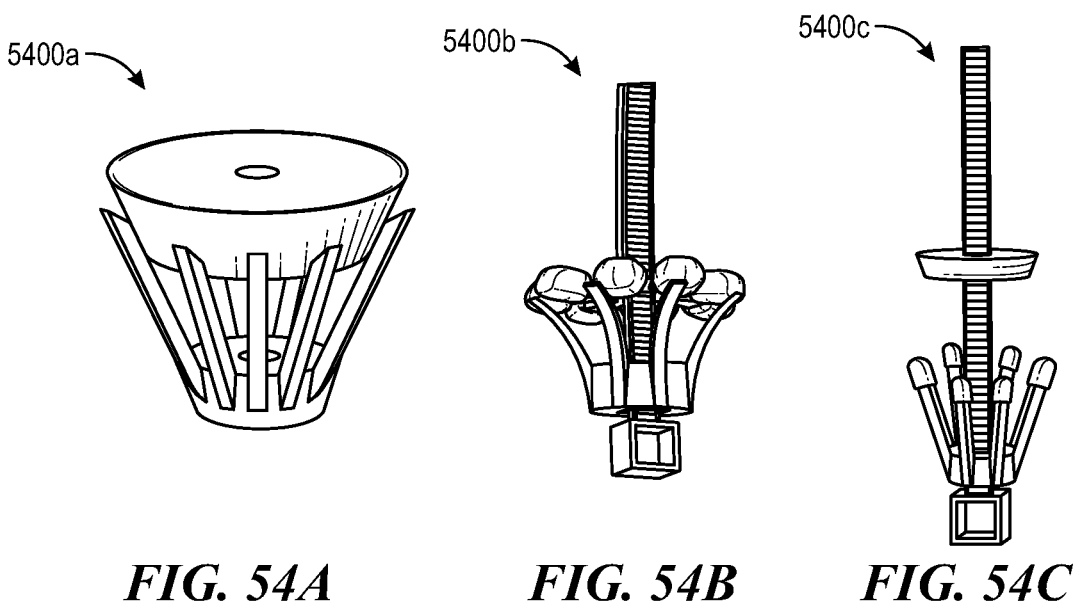
*FIG. 54A*          *FIG. 54B*          *FIG. 54C*
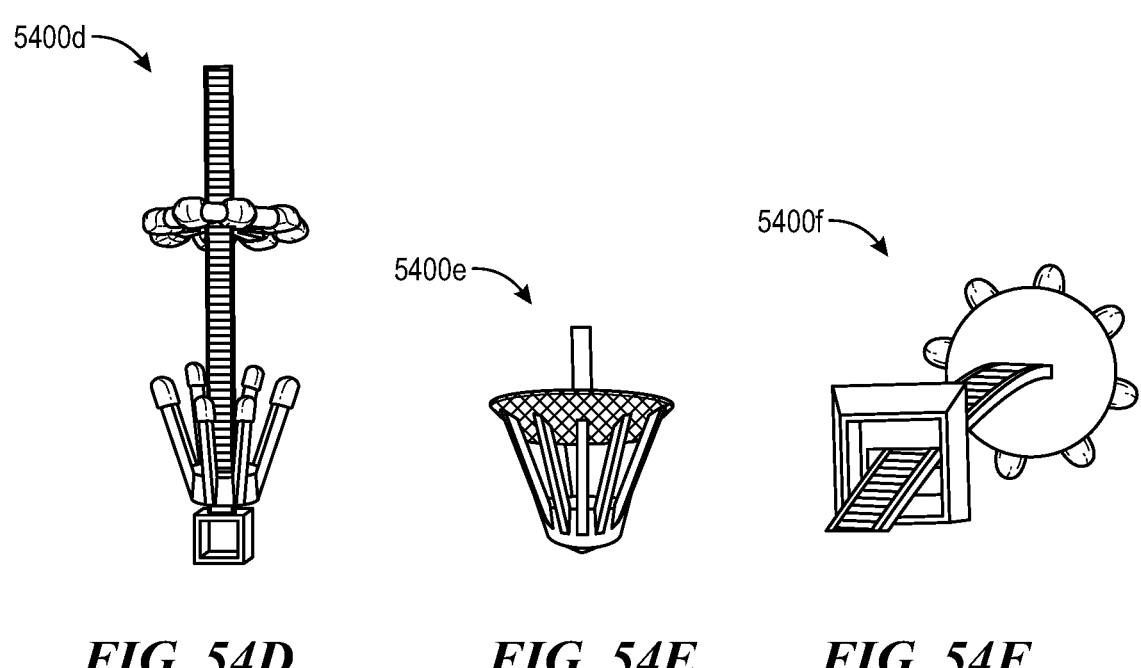
*FIG. 54D*          *FIG. 54E*          *FIG. 54F*

5500a

5500b

5500c

5500d

5500e

5500f

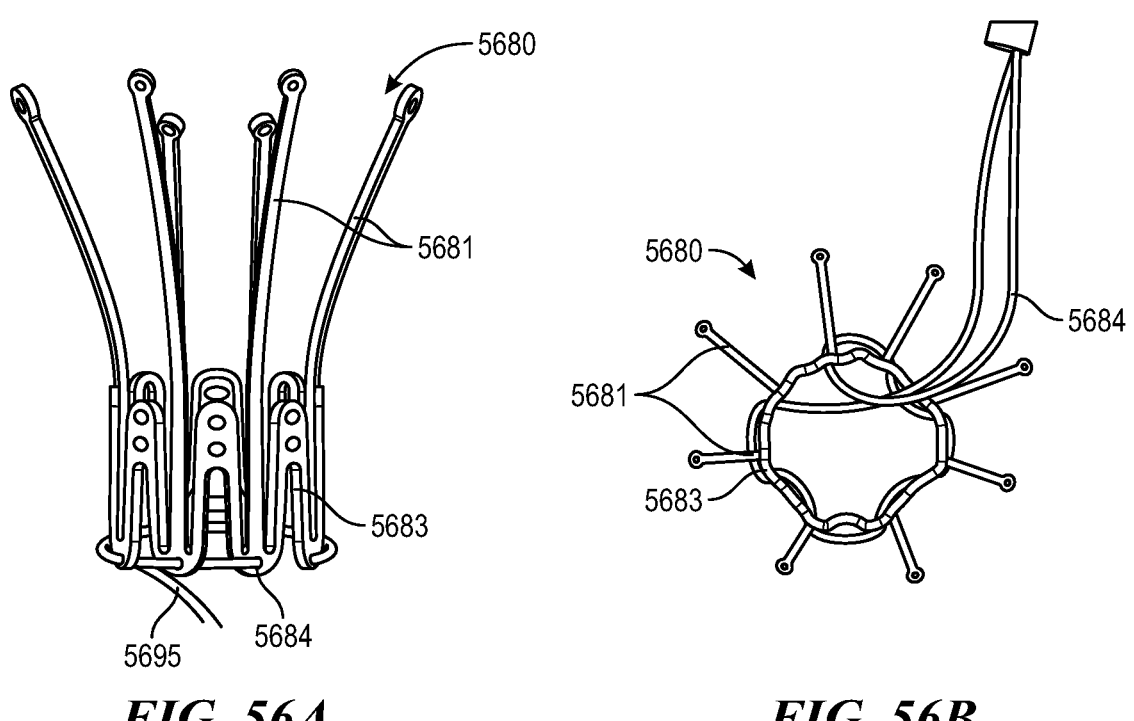
FIG. 56A
FIG. 56B
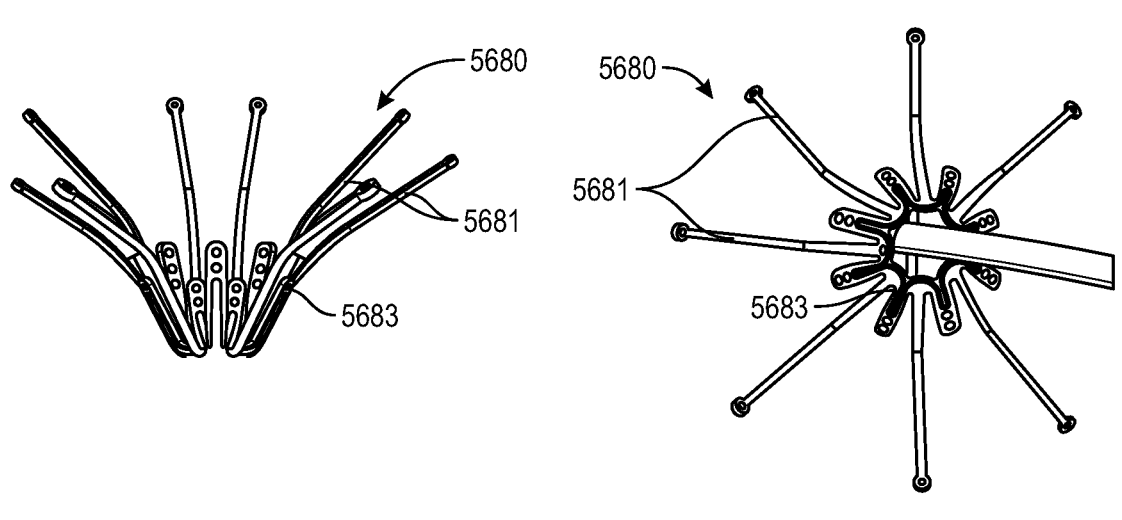
FIG. 56C
FIG. 56D

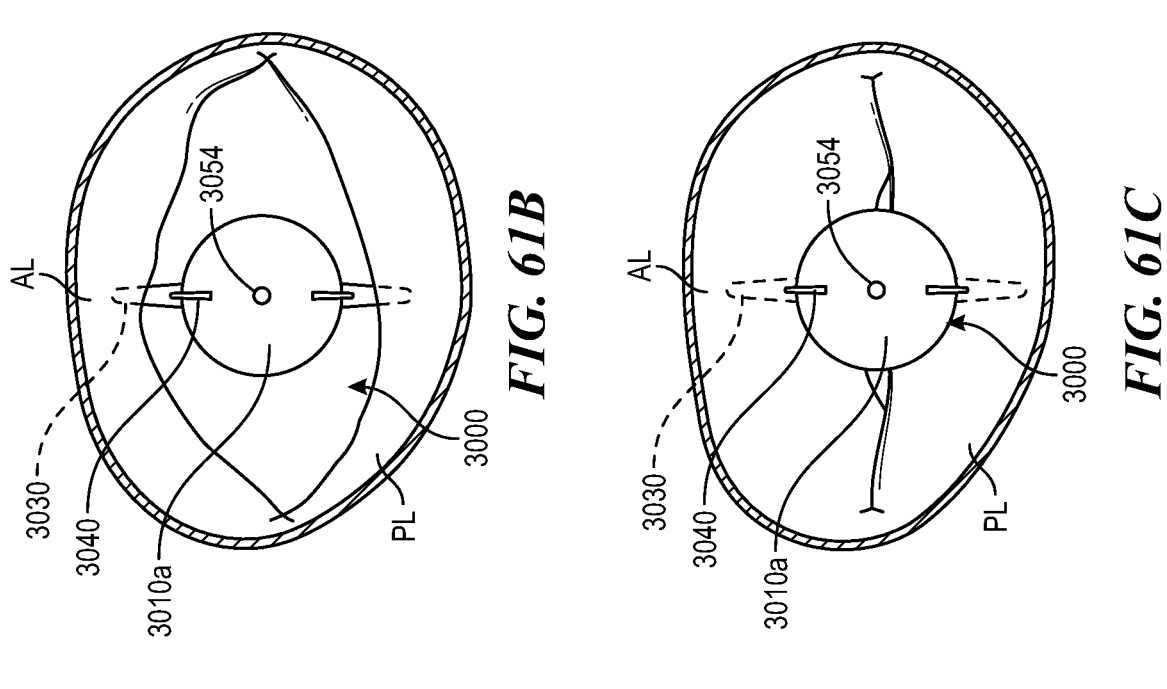
*FIG. 61B*
*FIG. 61C*
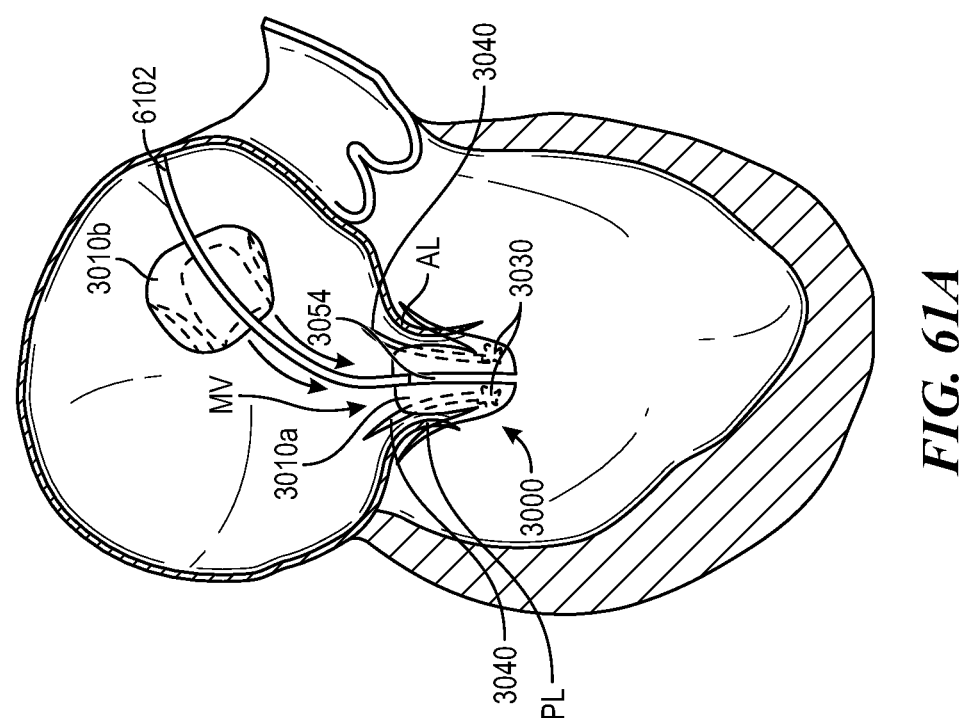
*FIG. 61A*

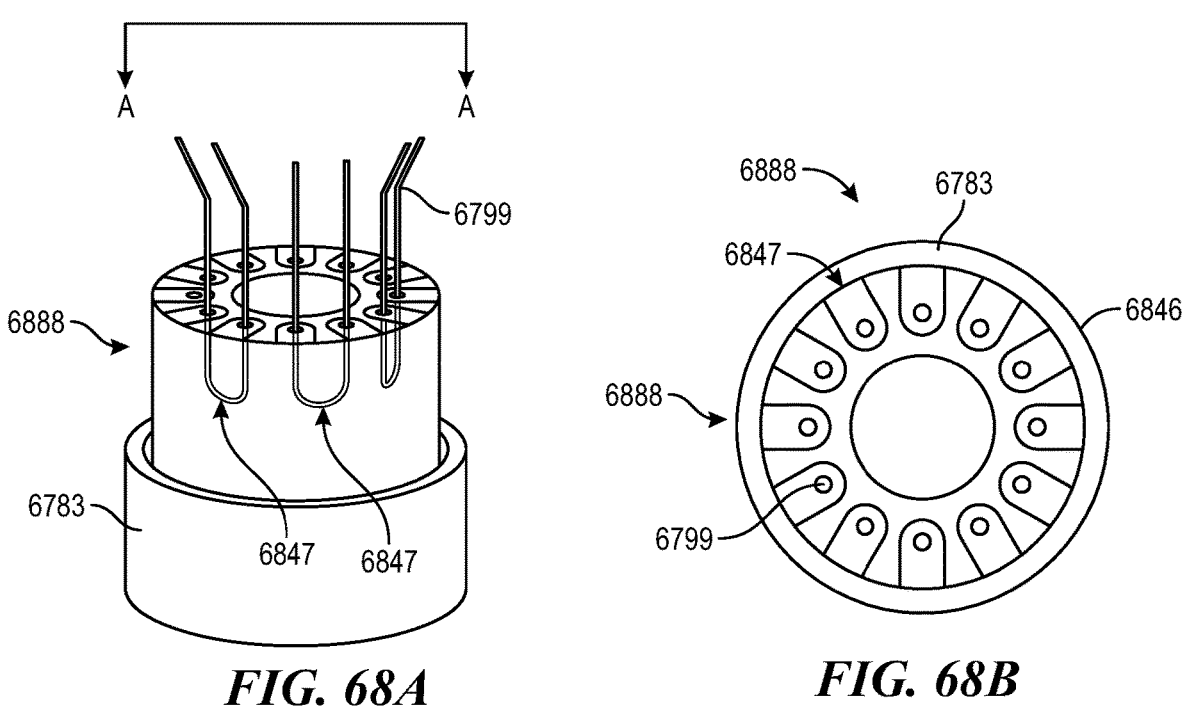
FIG. 68A
FIG. 68B
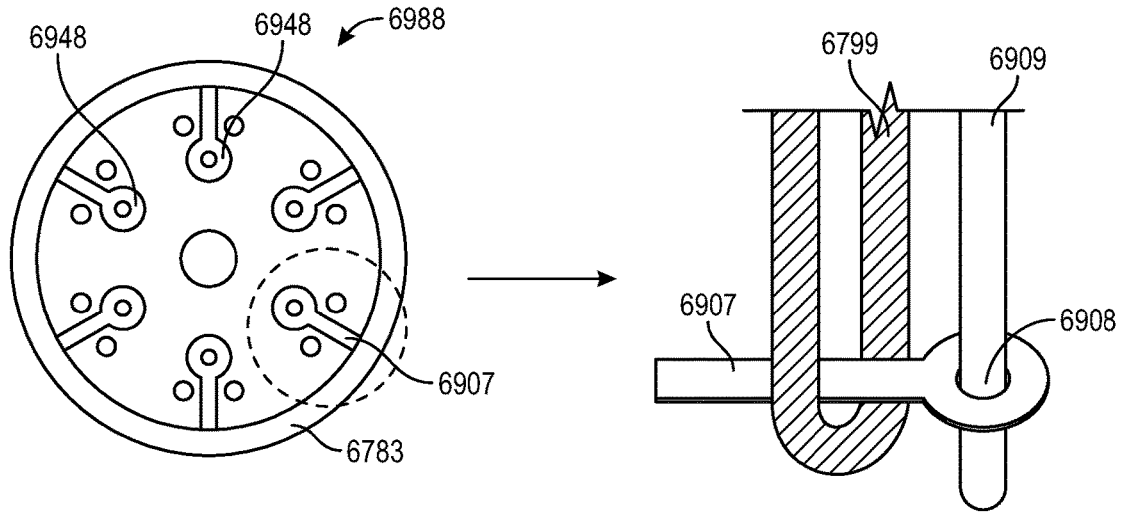
FIG. 69A
FIG. 69B

CARDIAC VALVE REPAIR DEVICES AND ASSOCIATED SYSTEMS AND METHODS

CROSS-REFERENCE TO RELATED APPLICATIONS

This application claims priority to and the benefit of (i) U.S. Provisional Patent Application No. 63/116,724, titled "CARDIAC VALVE REPAIR DEVICES AND ASSOCIATED SYSTEMS AND METHODS," and filed Nov. 20, 2020, and (ii) U.S. Provisional Patent Application No. 63/223,923, titled "CARDIAC VALVE REPAIR DEVICES AND ASSOCIATED SYSTEMS AND METHODS," and filed Jul. 20, 2021, both of which are incorporated herein by reference in their entirety.

TECHNICAL FIELD

The present technology is directed to devices, systems, and methods for cardiac valve repair, and more particularly to cardiac valve repair devices configured to be implanted at a cardiac valve, such as the mitral valve or the tricuspid valve of a human patient.

BACKGROUND

Proper functioning of cardiac valves, such as the mitral valve or the tricuspid valve of a human patient, can be affected by valve regurgitation, valve prolapse, valve stenosis, and/or other adverse conditions. Valve regurgitation can occur when the leaflets of the valve fail to coapt into apposition at peak contraction pressures such that blood leaks past the valve (e.g., from the left ventricle past the mitral valve and into the left atrium or from the right ventricle past the tricuspid valve and into the right atrium). Several structural factors may affect the proper closure of the valve leaflets. For example, an enlarged valve annulus caused by dilation of heart muscle may prevent proper coaptation of the leaflets during systole. Other conditions involve a stretch or tear in the chordae tendineae—the tendons connecting the papillary muscles to the mitral valve leaflets and the tricuspid valve leaflets—which may also affect proper closure of the valve leaflets. A ruptured chordae tendineae, for example, may cause a valve leaflet to prolapse (e.g., abnormally bulge up) into the left or right atrium due to inadequate tension on the leaflet, which can also lead to valve regurgitation. Abnormal backflow can also occur when the papillary muscles are compromised (e.g., due to ischemia) such that the affected papillary muscles do not contract sufficiently to effect proper closure during systole. Normal cardiac valve functioning can also be affected by valve stenosis (e.g., a narrowing of the valve orifice) which, for example, can impede filling of the right or left ventricle during diastole.

Valve regurgitation is often treated using diuretics and/or vasodilators to reduce the amount of blood flowing back into the left or right atrium. Other treatment methods, such as surgical approaches (open and intravascular), have also been used to either repair or replace native cardiac valves. For example, cinching or resecting portions of the dilated annulus are typical repair approaches. Cinching of the annulus has been accomplished by implanting annular or peri-annular rings which are generally secured to the annulus or surrounding tissue. Other repair procedures have also involved suturing or clipping of the valve leaflets into partial apposition with one another. Alternatively, more invasive procedures replace the entire valve with mechanical valves or biological tissue. These invasive procedures are conventionally done through large open thoracotomies and are thus very painful, have significant morbidity, and require long recovery periods.

However, with many repair and replacement procedures, the durability of the devices or improper sizing of annuloplasty rings or replacement valves may cause complications. Moreover, many of the repair procedures depend upon the skill of the cardiac surgeon since poorly or inaccurately placed sutures may affect the success of procedures.

BRIEF DESCRIPTION OF THE DRAWINGS

Many aspects of the present disclosure can be better understood with reference to the following drawings. The components in the drawings are not necessarily to scale. Instead, emphasis is placed on clearly illustrating the principles of the present disclosure.

FIGS. 8A-8C are a front view, a side view, and a rear view, respectively, of a valve repair device in accordance with embodiments of the present technology.

FIG. 12A is a side cross-sectional view of a valve repair device implanted at the mitral valve in accordance with embodiments of the present technology.

FIGS. 12B and 12C are transverse cross-sectional views of the valve repair device of FIG. 12A during diastole and systole, respectively, in accordance with embodiments of the present technology.

FIG. 12D illustrates various representative side views of the coaptation member shown in FIGS. 12B and 12C as viewed from a commissure-to-commissure perspective in accordance with embodiments of the present technology.

FIG. 15C is a side cross-sectional view of the valve repair device of FIGS. 15A and 15B implanted at the mitral valve in accordance with embodiments of the present technology.

FIGS. 15D and 15E are transverse cross-sectional views of the valve repair device of FIGS. 15A-15C during diastole and systole, respectively, in accordance with embodiments of the present technology.

FIG. 16A is a side cross-sectional view of a valve repair device implanted at the mitral valve in accordance with embodiments of the present technology.

FIGS. 16B and 16C are transverse cross-sectional views of the valve repair device of FIG. 16A during diastole and systole, respectively, in accordance with embodiments of the present technology.

FIG. 22 is a table including images of a valve repair devices having coaptation members of various shapes in accordance with embodiments of the present technology.

FIGS. 24C and 24F are side cross-sectional views of the valve repair device of FIGS. 24A and 24B implanted at the tricuspid valve and the mitral valve, respectively, in accordance with embodiments of the present technology.

FIGS. 24D and 24E are transverse cross-sectional views of the valve repair device of FIGS. 24A and 24B implanted at the tricuspid valve during diastole and systole, respectively, in accordance with embodiments of the present technology.

FIGS. 24G and 24H are transverse cross-sectional views of the valve repair device of FIGS. 24A and 24B implanted at the mitral valve MV during diastole and systole, respectively, in accordance with embodiments of the present technology.

FIGS. 25E and 25H are side cross-sectional views of the valve repair device of FIGS. 25A-25D implanted at the mitral valve in the unexpanded position and the expanded position, respectively, in accordance with embodiments of the present technology.

FIGS. 25F and 25G are transverse cross-sectional views of the valve repair device of FIGS. 25A-25D implanted at the mitral valve in the unexpanded position during diastole and systole, respectively, in accordance with embodiments of the present technology.

FIGS. 25I and 25J are transverse cross-sectional views of the valve repair device of FIGS. 25A-25D implanted at the mitral valve in the expanded position during diastole and systole, respectively, in accordance with embodiments of the present technology.

FIGS. 26C and 26F are side cross-sectional views of the valve repair device of FIGS. 26A and 26B implanted at the mitral valve in the unexpanded position and the expanded position, respectively, in accordance with embodiments of the present technology.

FIGS. 26D and 26E are transverse cross-sectional views of the valve repair device of FIGS. 26A and 26B implanted at the mitral valve in the unexpanded position during diastole and systole, respectively, in accordance with embodiments of the present technology.

FIGS. 26G and 26H are transverse cross-sectional views of the valve repair device of FIGS. 26A and 26B implanted at the mitral valve in the expanded position during diastole and systole, respectively, in accordance with embodiments of the present technology.

FIGS. 27B and 27E are side cross-sectional views of the valve repair device of FIG. 27A implanted at the mitral valve in the unexpanded position and an expanded position, respectively, in accordance with embodiments of the present technology.

FIGS. 27C and 27D are transverse cross-sectional views of the valve repair device of FIG. 27A implanted at the mitral valve in the unexpanded position during diastole and systole, respectively, in accordance with embodiments of the present technology.

FIGS. 27F and 27G are transverse cross-sectional views of the valve repair device of FIG. 27A implanted at the mitral valve in the expanded position during diastole and systole respectively, in accordance with embodiments of the present technology.

FIG. 28C is a side cross-sectional view of the valve repair device of FIGS. 28A and 28B implanted at the mitral valve in accordance with embodiments of the present technology.

FIGS. 28D and 28E are transverse cross-sectional views of the valve repair device of FIGS. 28A-28C during diastole and systole, respectively, in accordance with embodiments of the present technology.

FIG. 29A is a side cross-sectional view of a valve repair device with an expandable coaptation member implanted at the tricuspid valve in accordance with embodiments of the present technology.

FIGS. 29B and 29C are transverse cross-sectional views of the valve repair device of FIG. 29A during diastole and systole, respectively, in accordance with embodiments of the present technology.

FIG. 31A is a side cross-sectional view of a valve repair device implanted at the mitral valve in accordance with embodiments of the present technology.

FIGS. 31B and 31C are transverse cross-sectional views of the valve repair device of FIG. 31A during diastole and systole, respectively, in accordance with embodiments of the present technology.

FIG. 32C is a side cross-sectional view of the valve repair device of FIGS. 32A and 32B implanted at the mitral valve in the first position accordance with embodiments of the present technology.

FIGS. 32D and 32E are transverse cross-sectional views of the valve repair device of FIGS. 32A and 32B during diastole and systole, respectively, in accordance with embodiments of the present technology.

FIG. 33B is a side cross-sectional view of the valve repair device of FIG. 33A implanted at the mitral valve in accordance with embodiments of the present technology.

FIGS. 33C and 33D are transverse cross-sectional views of the valve repair device of FIGS. 33A and 33B during diastole and systole, respectively, in accordance with embodiments of the present technology.

FIG. 33E is a side cross-sectional view of the valve repair device of FIG. 33A implanted at the mitral valve and having a central lock mechanism having a generally circular shape in accordance with additional embodiments of the present technology.

FIGS. 33F and 33G are transverse cross-sectional views of the valve repair device of FIG. 33E during diastole and systole, respectively, in accordance with embodiments of the present technology.

FIG. 34C is a side cross-sectional view of the valve repair device of FIGS. 34A and 34B implanted at the mitral valve in accordance with embodiments of the present technology.

FIGS. 34D and 34E are transverse cross-sectional views of the valve repair device of FIGS. 34A-34C during diastole and systole, respectively, in accordance with embodiments of the present technology.

FIG. 34F is a side cross-sectional view of another embodiment of the valve repair device of FIGS. 34A and 34B implanted at the mitral valve in accordance with embodiments of the present technology.

FIGS. 34G and 34H are transverse cross-sectional views of the valve repair device of FIG. 34F during diastole and systole, respectively, in accordance with embodiments of the present technology.

FIG. 35C is a side cross-sectional view of the valve repair device of FIGS. 35A and 35B implanted at the mitral valve in accordance with embodiments of the present technology.

FIGS. 35D and 35E are transverse cross-sectional views of the valve repair device of FIGS. 35A-35C during diastole and systole, respectively, in accordance with embodiments of the present technology.

FIG. 36C is a side cross-sectional view of the valve repair device of FIGS. 36A and 36B implanted at the mitral valve in accordance with embodiments of the present technology.

FIGS. 36D and 36E are transverse cross-sectional views of the valve repair device of FIGS. 36A-36C implanted at the mitral valve in the expanded position during diastole and systole, respectively, in accordance with embodiments of the present technology.

FIG. 46A is a side cross-sectional view of a valve repair device in accordance with embodiments of the present technology.

FIGS. 46B-46E are side views of the valve repair device during delivery and deployment in accordance with embodiments of the present technology.

FIG. 51A is a perspective side view of a valve repair device in a first position in accordance with embodiments of the present technology.

FIGS. 51B-51D are a perspective top view, perspective side view, and an enlarged perspective side view of the valve repair device of FIG. 51A in a second position in accordance with embodiments of the present technology.

FIG. 52A is a perspective side view of a valve repair device in a first position in accordance with embodiments of the present technology.

FIGS. 52B and 52C are a perspective top view and a perspective side view of the valve repair device of FIG. 52A in a second position in accordance with embodiments of the present technology.

FIG. 52D is an enlarged cross-sectional view of the valve repair device of FIGS. 52A-52C secured to a pair of valve leaflets in accordance with embodiments of the present technology.

FIGS. 54A-54E are perspective side views, and

FIG. 54F is a perspective top view of various valve repair devices including an atrial member and a ventricular member configured to sandwich together in accordance with additional embodiments of the present technology.

FIGS. 55A-55H are perspective side views of various valve repair devices including an atrial member and a ventricular member configured to sandwich together in accordance with embodiments of the present technology.

FIGS. 56A and 56B are perspective side and bottom views, respectively, of a ventricular member of a valve repair device in a relaxed position in accordance with embodiments of the present technology.

FIGS. 56C and 56D are perspective side and bottom views, respectively, of the ventricular member of FIGS. 56A and 56B in an expanded position with a compressed ventricular-most end in accordance with embodiments of the present technology.

FIGS. 57A and 57B are side views of a ventricular member of a valve repair device in a compressed position and an expanded position, respectively, in accordance with embodiments of the present technology.

FIG. 58A is a side cross-sectional view of a valve repair device implanted at the tricuspid valve in accordance with embodiments of the present technology.

FIGS. 58B and 58C are transverse cross-sectional views of the valve repair device of FIG. 58A during diastole and systole, respectively, in accordance with embodiments of the present technology.

FIG. 59A is a side cross-sectional view of a valve repair device implanted at the tricuspid valve in accordance with embodiments of the present technology.

FIGS. 59B and 59C are transverse cross-sectional views of the valve repair device of FIG. 59A during diastole and systole, respectively, in accordance with embodiments of the present technology.

FIGS. 60A and 60B are an isometric view and a side view, respectively, of a valve repair device configured in accordance with embodiments of the present technology.

FIGS. 61A and 61D are side views of the valve repair device of FIG. 30 during a first delivery stage (e.g., an initial stage) and a second delivery stage (e.g., a subsequent stage) to the mitral valve MV, respectively, in accordance with embodiments of the present technology.

FIGS. 61B and 61C are transverse cross-sectional views of the valve repair device during the first delivery stage of FIG. 61A and during diastole and systole, respectively, in accordance with embodiments of the present technology.

FIGS. 61E and 61F are transverse cross-sectional views of the valve repair device during the second delivery stage of FIG. 61D and during diastole and systole, respectively, in accordance with embodiments of the present technology.

Figure 62A:
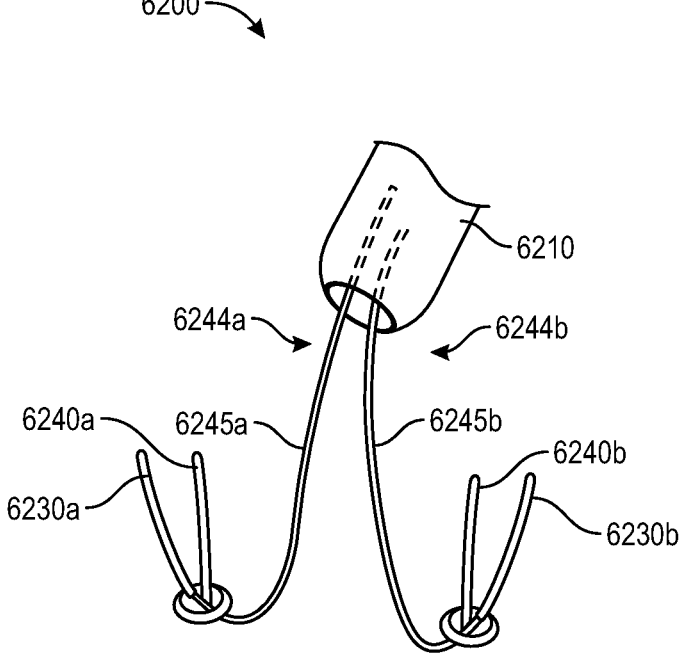

FIG. 62A is a side view of a valve repair device that can be sequentially delivered to a cardiac valve in accordance with embodiments of the present technology.

Figures 62B, 62C, 62D:
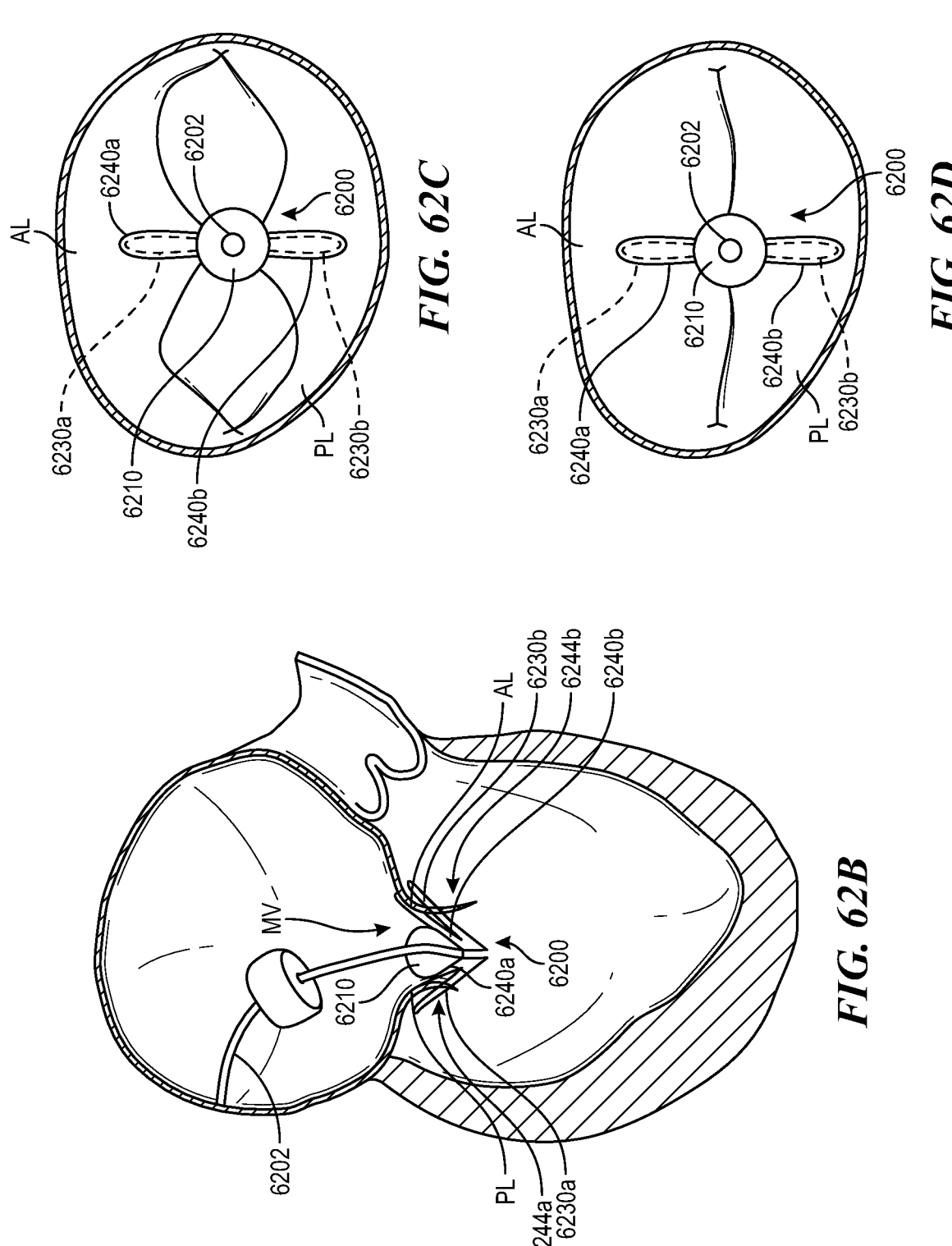

FIG. 62B is a side view of the valve repair device of FIG. 62A at the mitral valve with an optional additional coaptation member on a central delivery rail in accordance with embodiments of the present technology.

FIGS. 62C and 62D are side views of the valve repair device of FIG. 62B with the optional additional coaptation member added during diastole and systole, respectively, in accordance with embodiments of the present technology.

FIGS. 62E, 62H, 62K, and 62N are side views of the valve repair device of FIG. 62A during first through fourth delivery stages to the tricuspid valve, respectively, in accordance with embodiments of the present technology.

Figures 62E, 62F, 62G:
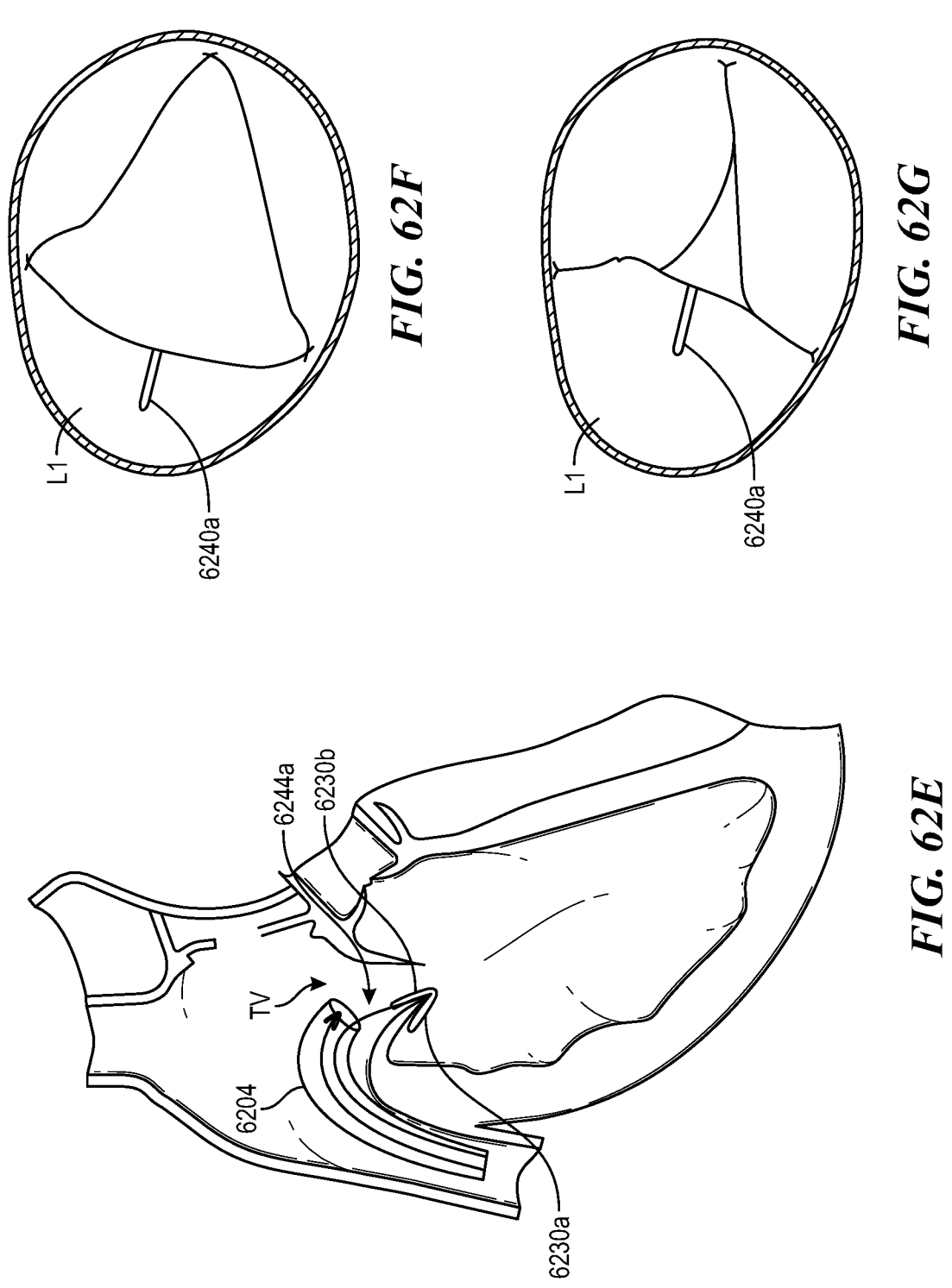

FIGS. 62F and 62G are transverse cross-sectional views of the valve repair device during the first delivery stage of FIG. 62E and during diastole and systole, respectively, in accordance with embodiments of the present technology.

Figures 62H, 62I, 62J:
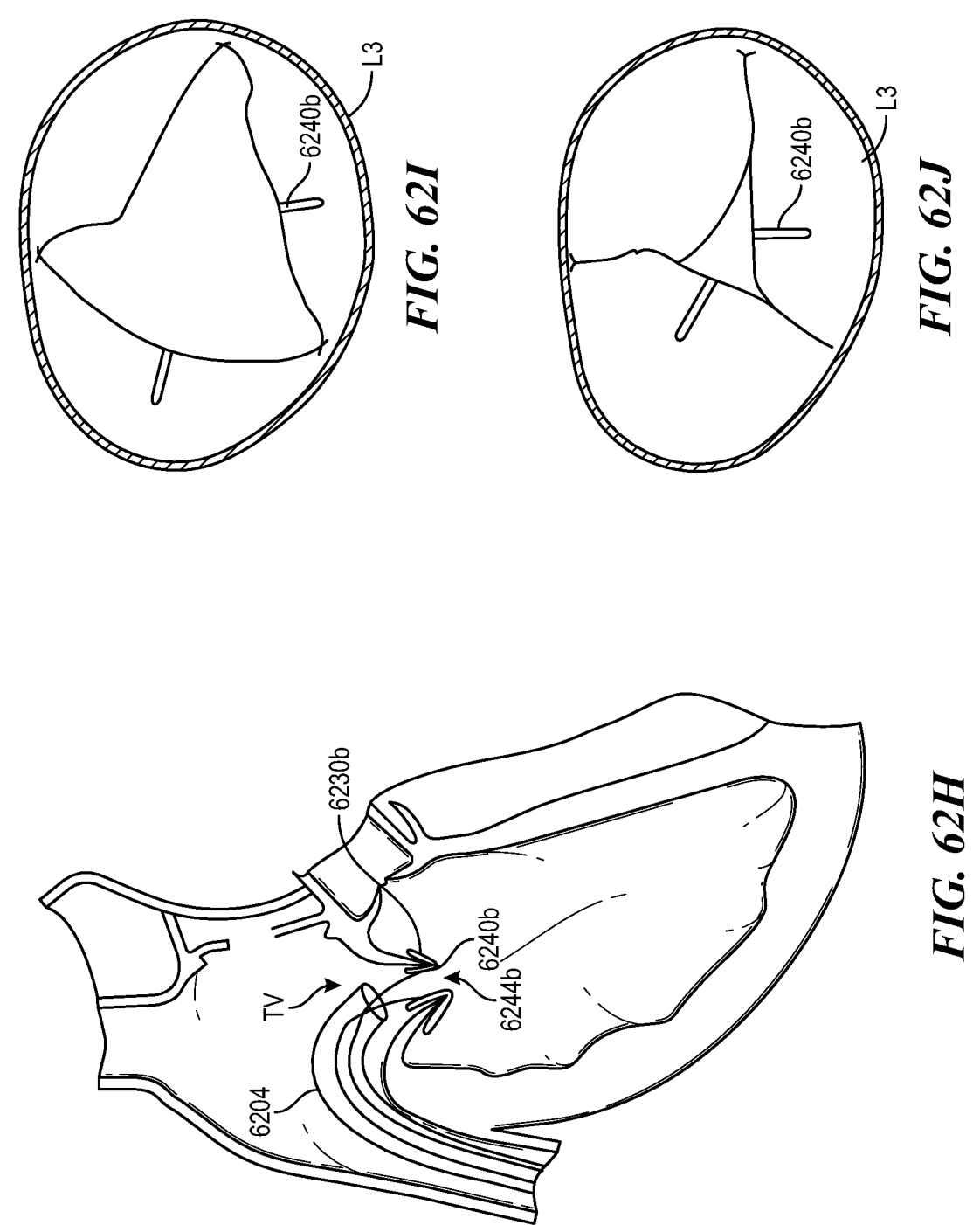

FIGS. 62I and 62J are transverse cross-sectional views of the valve repair device during the second delivery stage of FIG. 62H and during diastole and systole, respectively, in accordance with embodiments of the present technology.

Figures 62K, 62L, 62M:
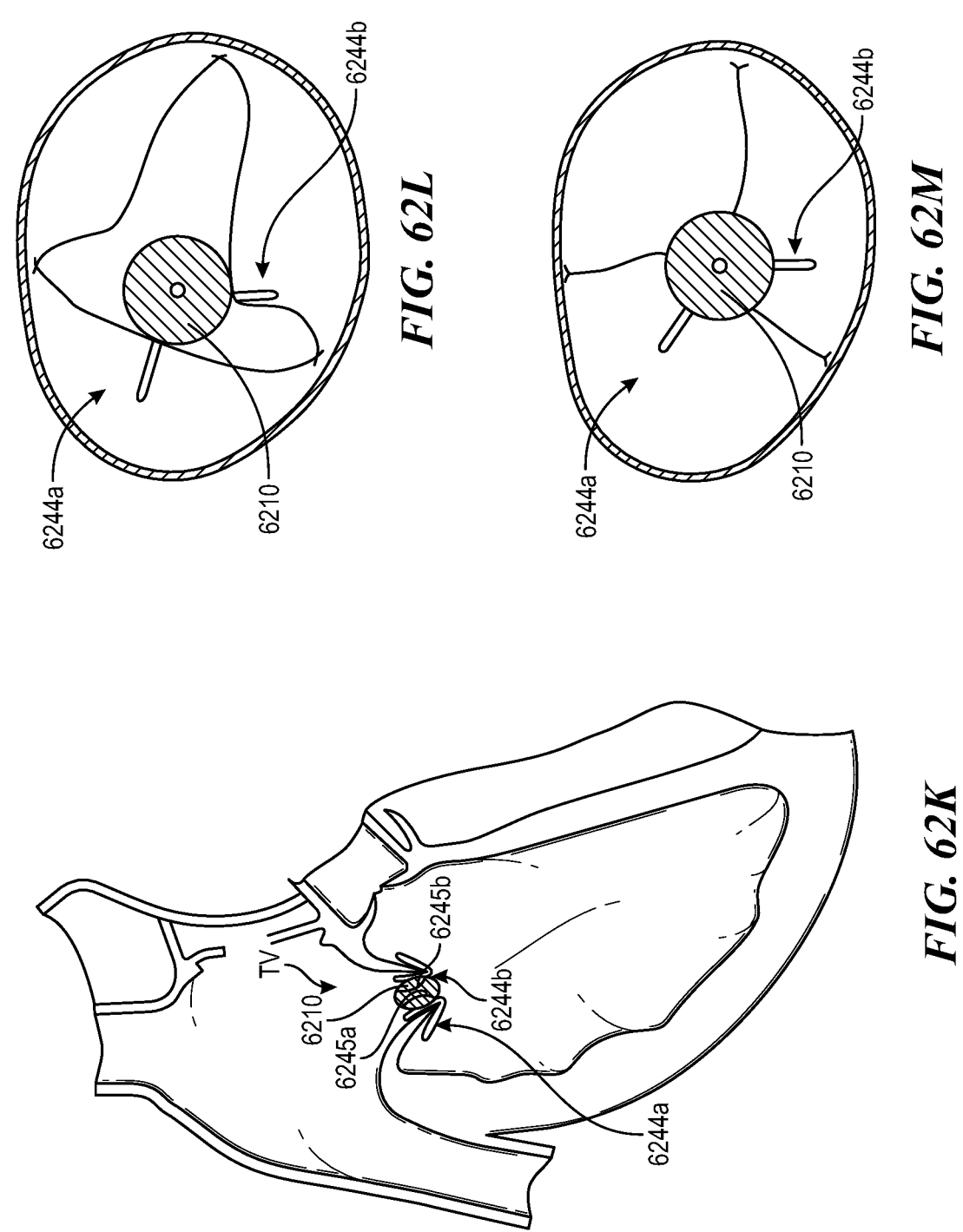

FIGS. 62L and 62M are transverse cross-sectional views of the valve repair device during a third delivery stage of FIG. 62L and during diastole and systole, respectively, in accordance with embodiments of the present technology.

Figures 62N, 62O, 62P:
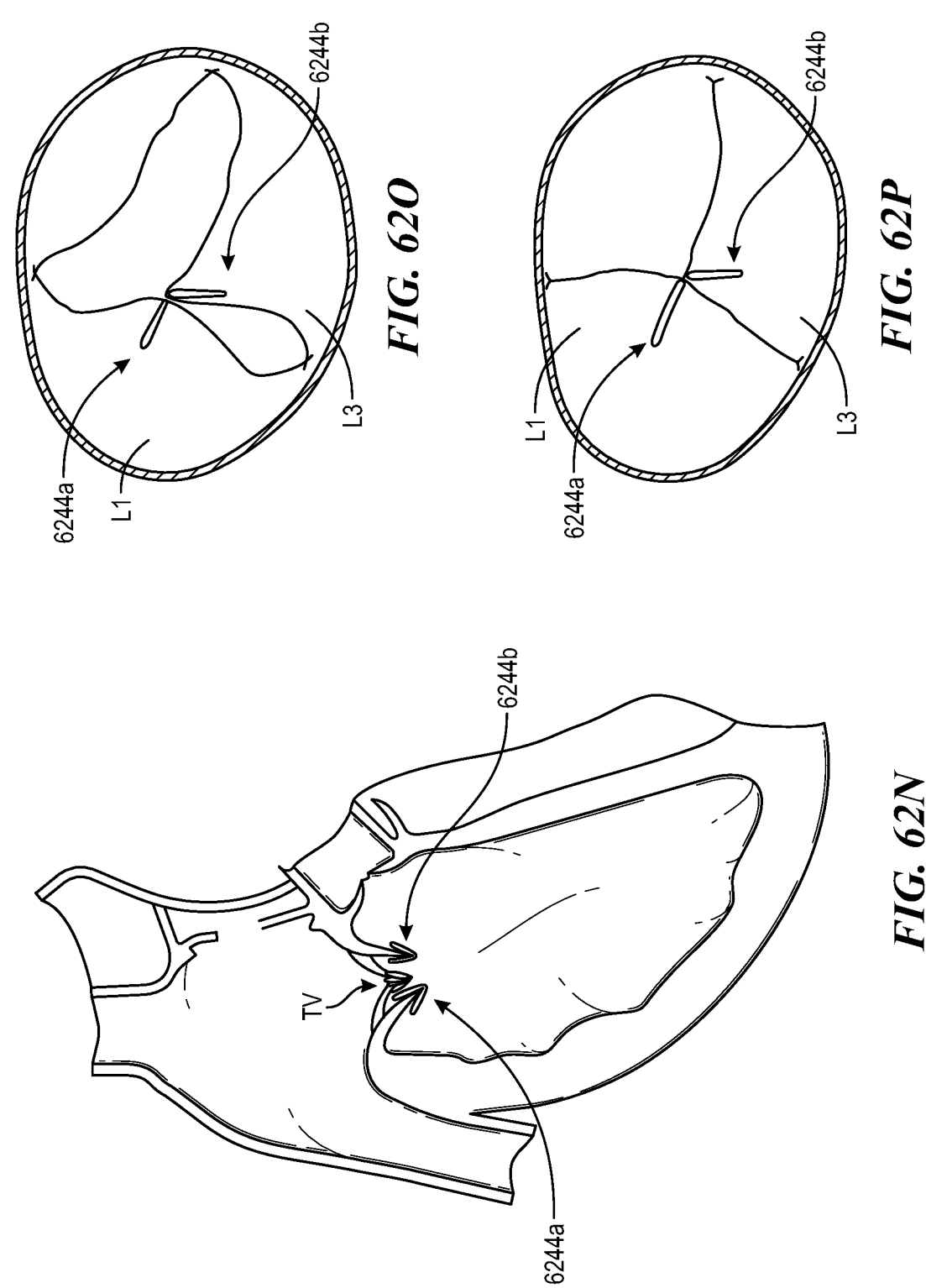

FIGS. 62O and 62P are transverse cross-sectional views of the valve repair device during an alternate third delivery stage of FIG. 62N and during diastole and systole, respectively, in accordance with embodiments of the present technology.

Figures 63A, 63B, 63C:
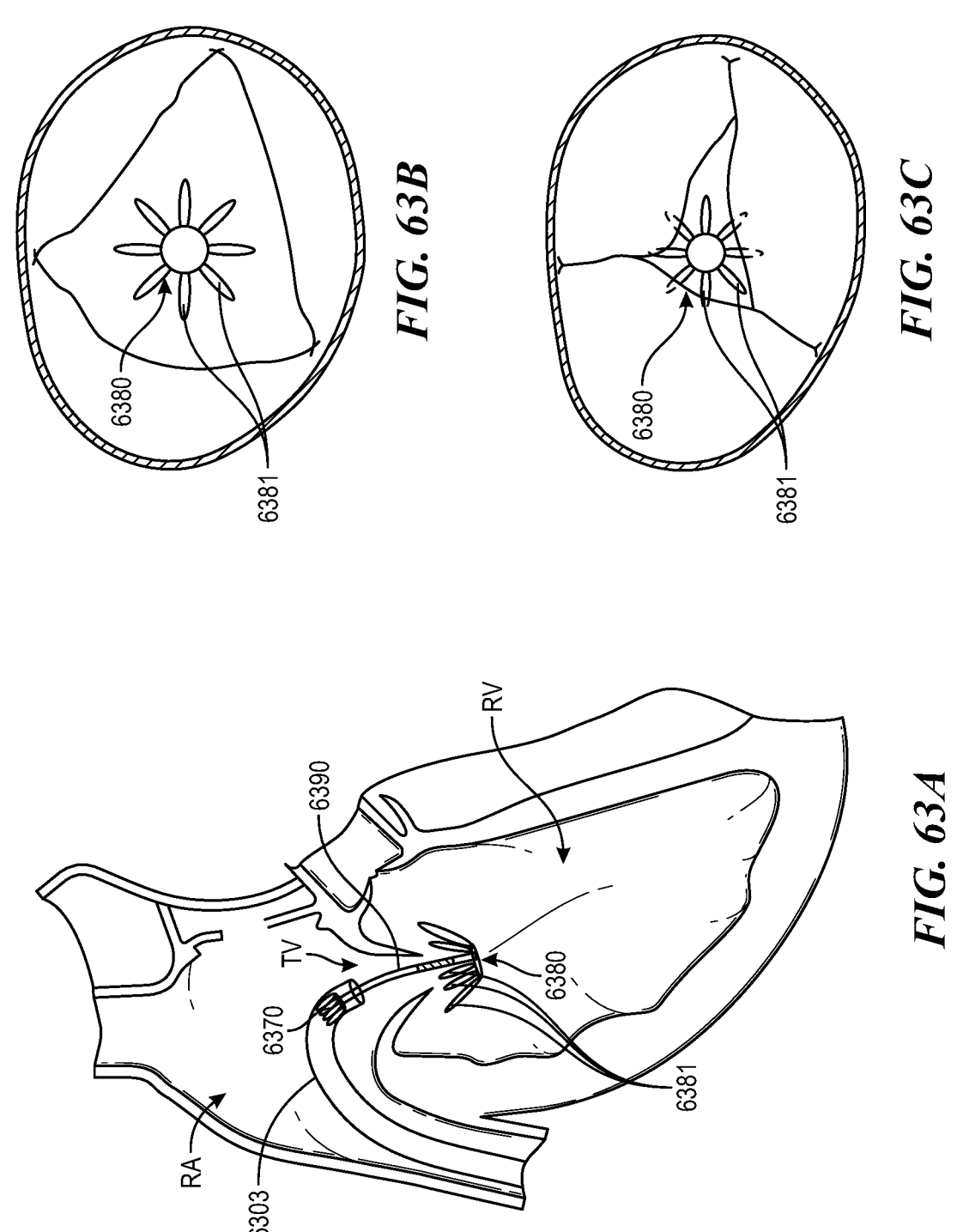
Figures 63D, 63E, 63F:
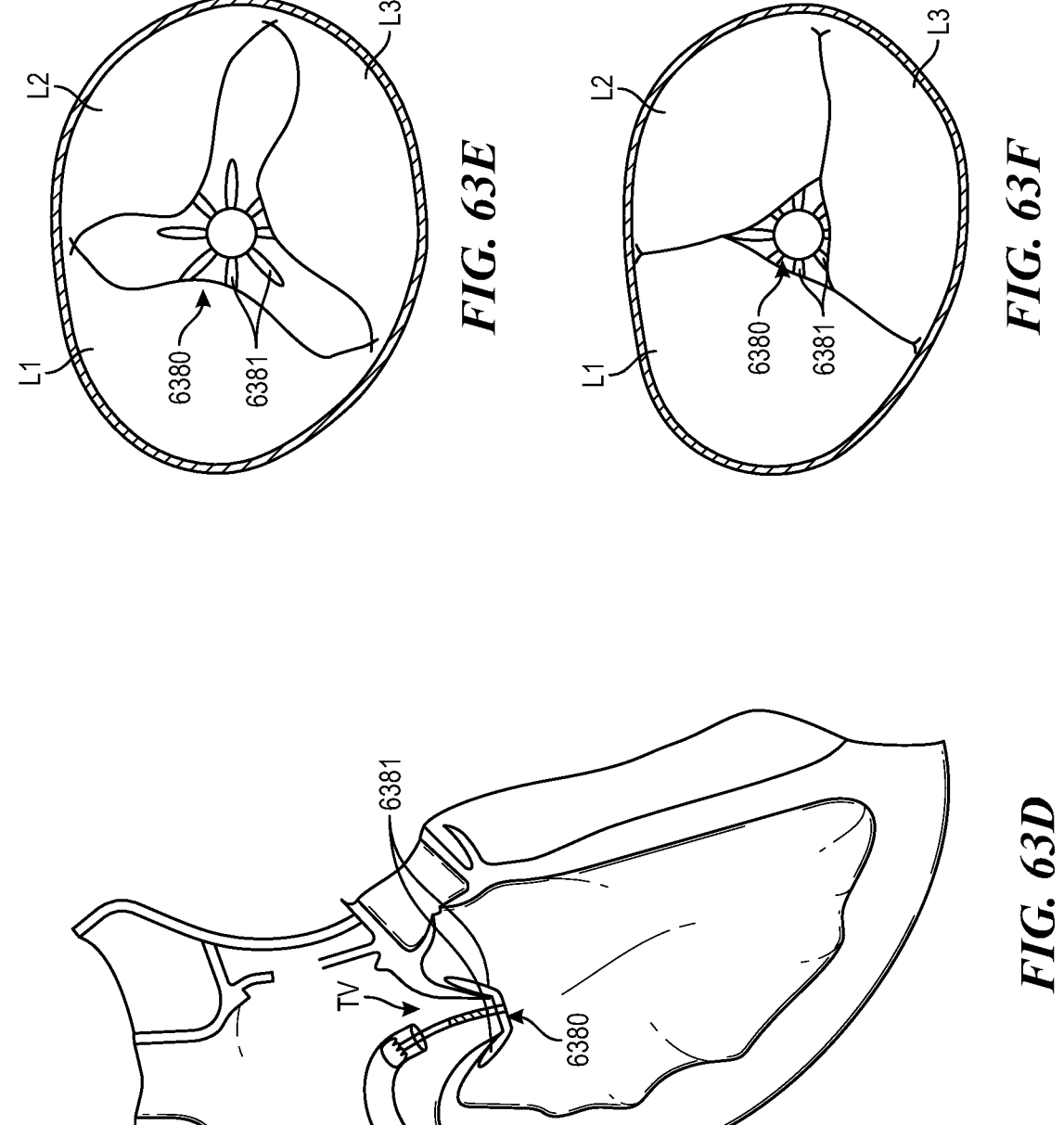
Figures 63G, 63H, 63I:
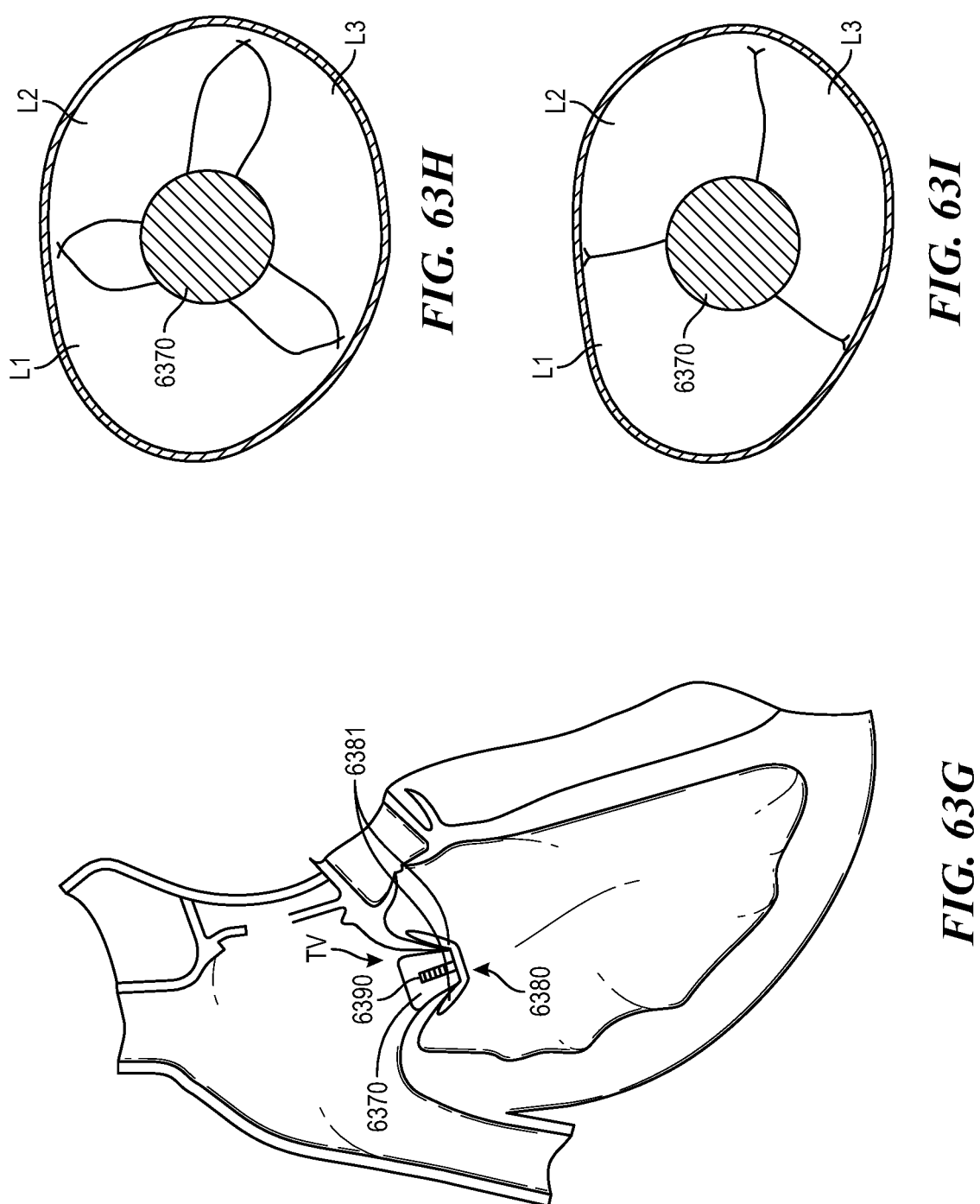

FIGS. 63A, 63D, and 63G are side views of a valve repair device of any of, for example, FIGS. 42A-45D or 52A-54F during first through third delivery stages to the tricuspid valve, respectively, in accordance with embodiments of the present technology.

FIGS. 63B and 63C are transverse cross-sectional views of the valve repair device during the first delivery stage of FIG. 63A and during diastole and systole, respectively, in accordance with embodiments of the present technology.

FIGS. 63E and 63F are transverse cross-sectional views of the valve repair device during the second delivery stage of FIG. 63D and during diastole and systole, respectively, in accordance with embodiments of the present technology.

FIGS. 63H and 63I are transverse cross-sectional views of the valve repair device during the third delivery stage of FIG. 63G and during diastole and systole, respectively, in accordance with embodiments of the present technology.

FIGS. 64A, 64D, 64G, and 64J are side views of a valve repair device of any of, for example, FIGS. 42A-45D or 52A-54F during first through fourth delivery stages to the tricuspid valve, respectively, in accordance with embodiments of the present technology.

Figures 64A, 64B, 64C:
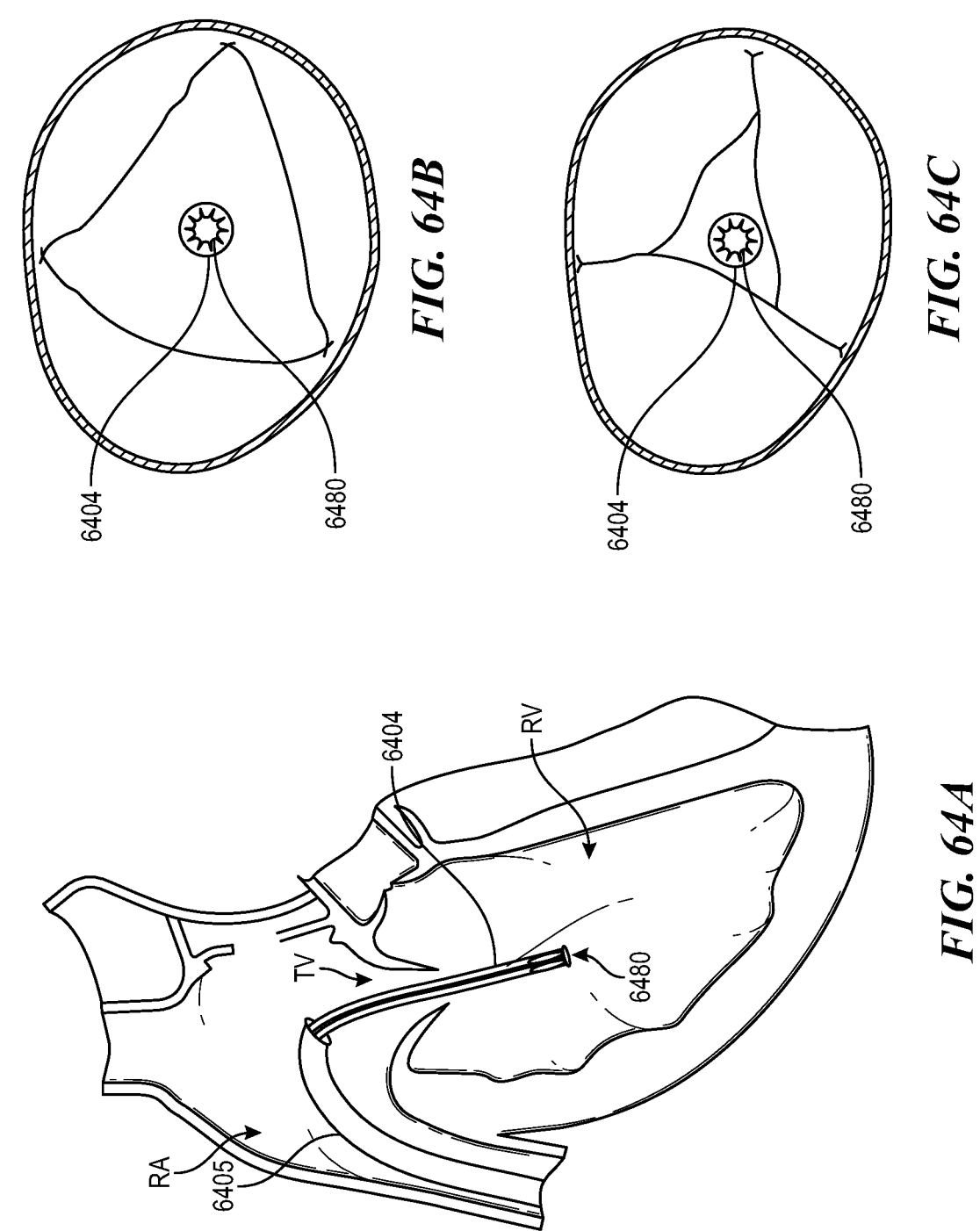

FIGS. 64B and 64C are transverse cross-sectional views of the valve repair device during the first delivery stage of FIG. 64A and during diastole and systole, respectively, in accordance with embodiments of the present technology.

Figures 64D, 64E, 64F:
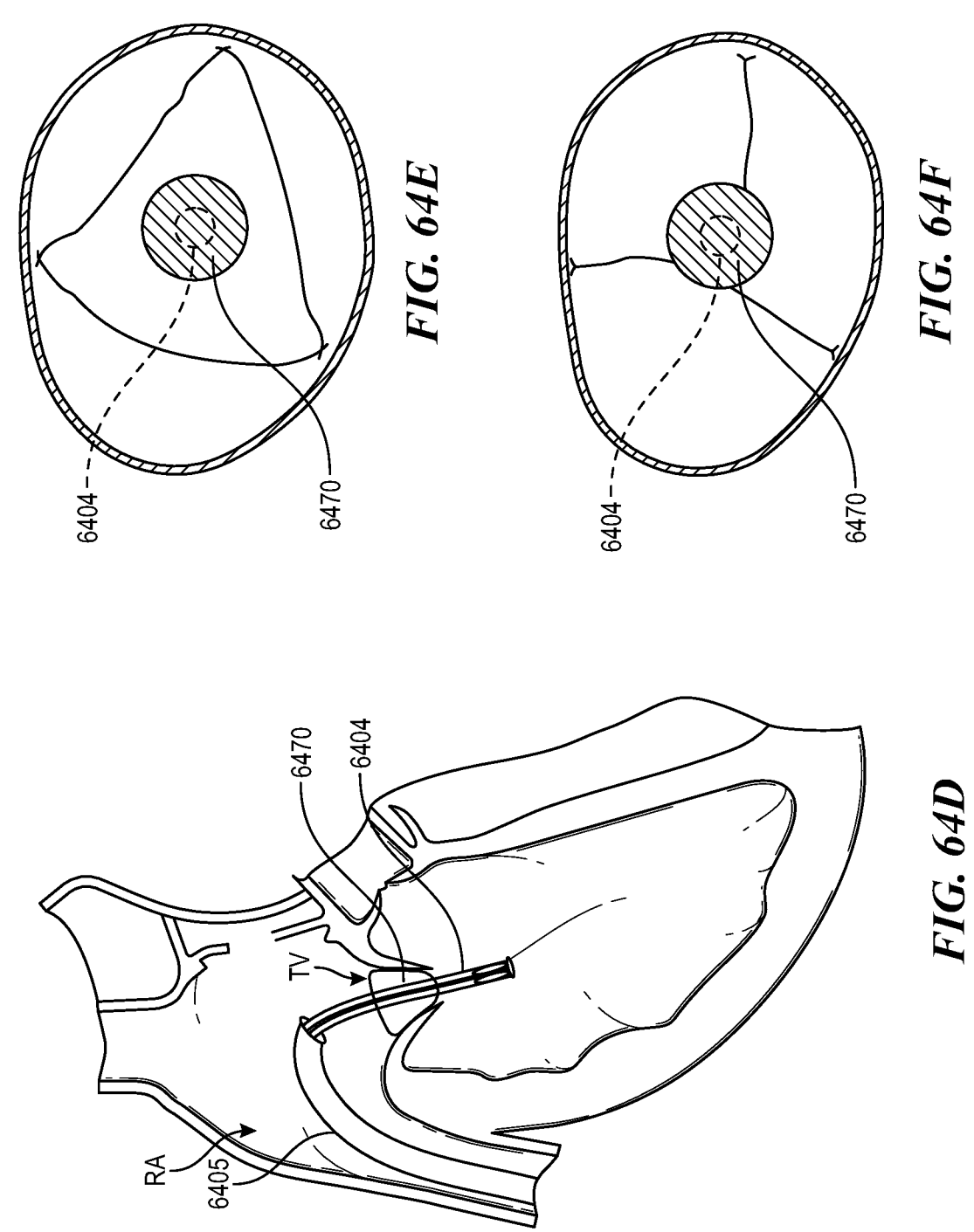

FIGS. 64E and 64F are transverse cross-sectional views of the valve repair device during the second delivery stage of FIG. 64D and during diastole and systole, respectively, in accordance with embodiments of the present technology.

Figures 64G, 64H, 64I:
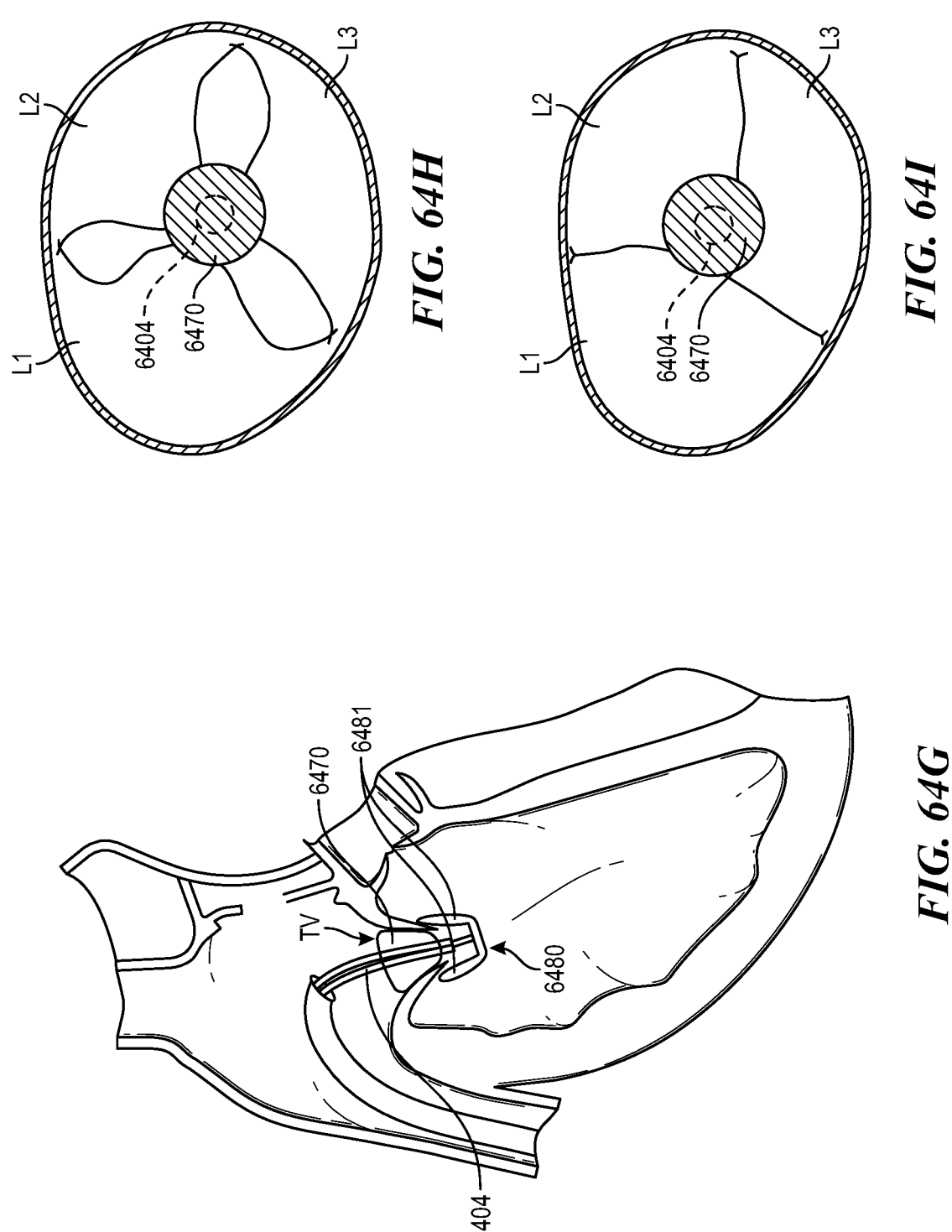

FIGS. 64H and 64I are transverse cross-sectional views of the valve repair device during the third delivery stage of FIG. 64G and during diastole and systole, respectively, in accordance with embodiments of the present technology.

Figures 64J, 64K, 64L:
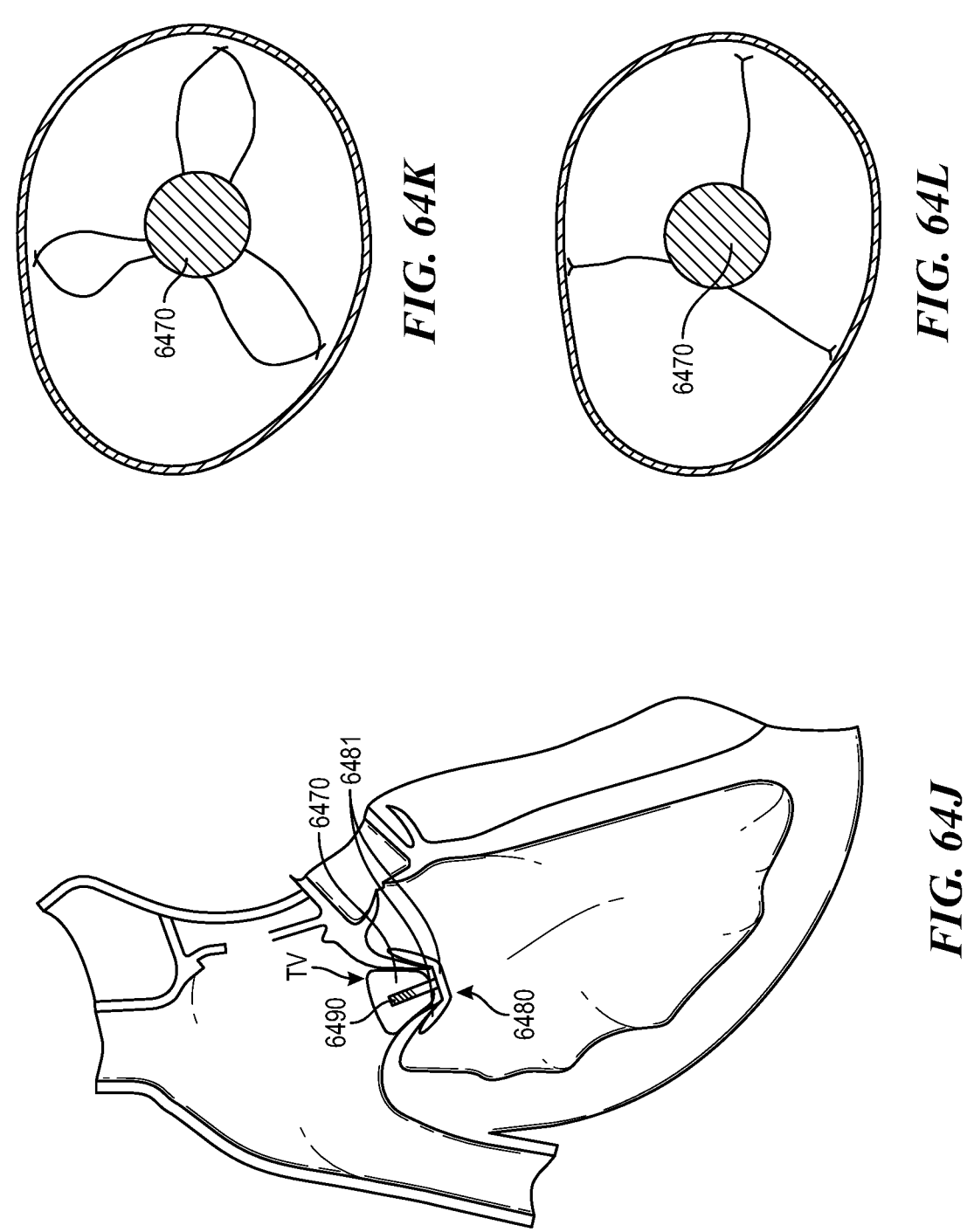

FIGS. 64K and 64L are transverse cross-sectional views of the valve repair device during the fourth delivery stage of FIG. 64J and during diastole and systole, respectively, in accordance with embodiments of the present technology.

Figure 60A:
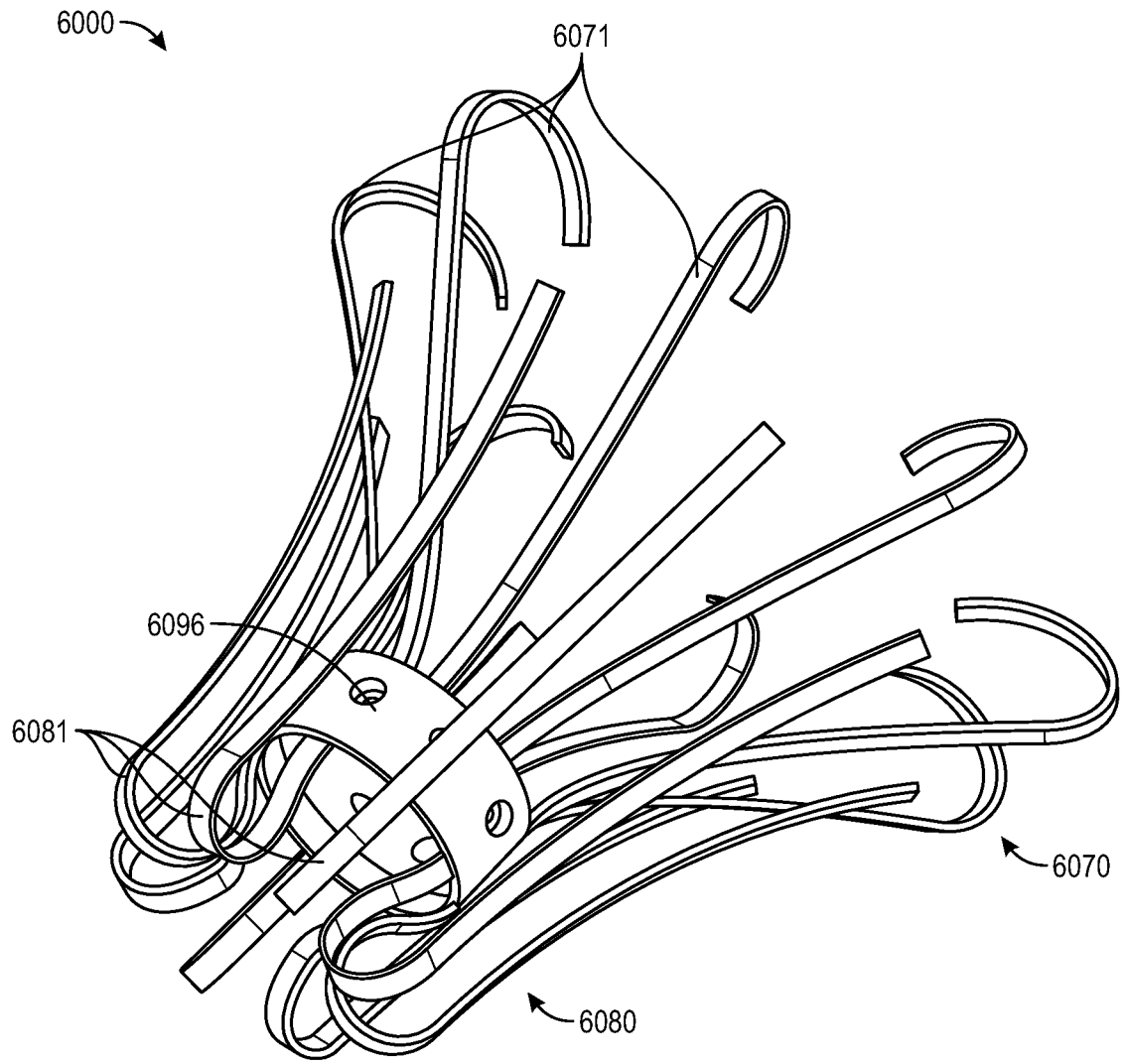
Figure 60B:
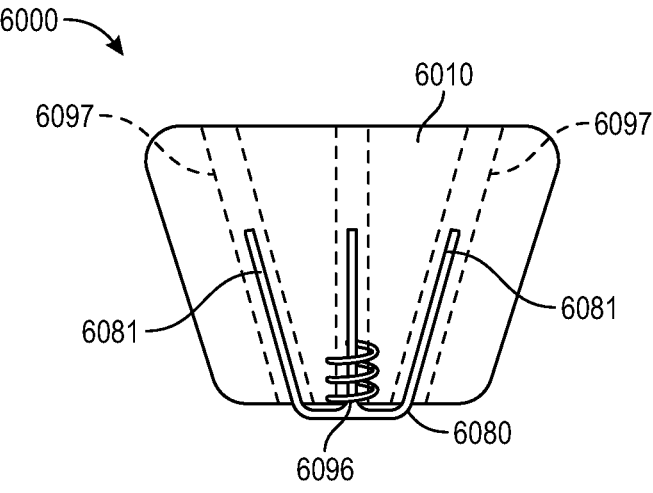

FIGS. 65A, 65D, 65G, 65J, and 65M are side views of a valve repair device of, for example, FIGS. 60A and 60B, during first through fifth delivery stages to the tricuspid valve, respectively, in accordance with embodiments of the present technology.

Figures 65A, 65B, 65C:
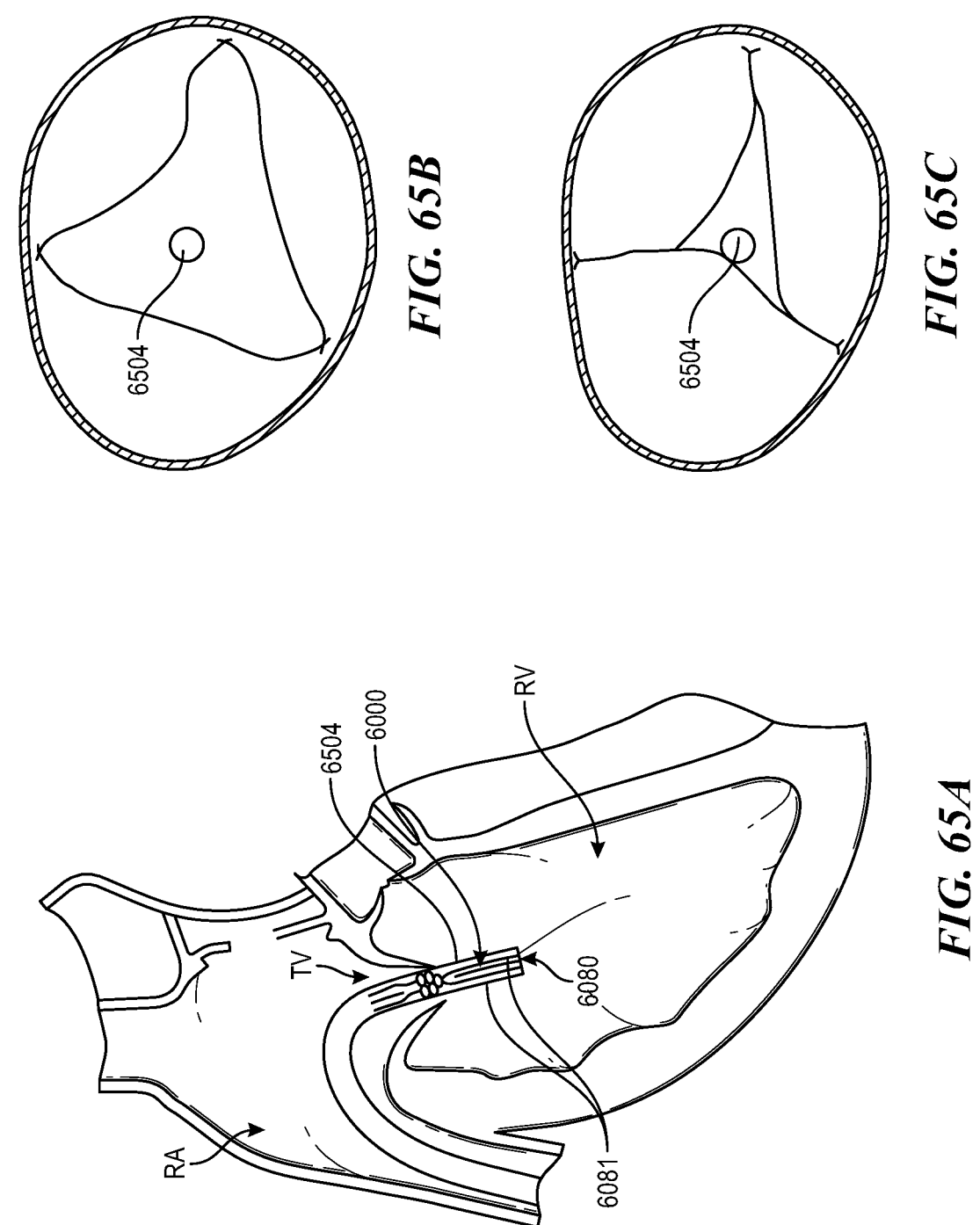

FIGS. 65B and 65C are transverse cross-sectional views of the valve repair device during the first delivery stage of FIG. 65A during diastole and systole, respectively, in accordance with embodiments of the present technology.

Figures 65D, 65E, 65F:
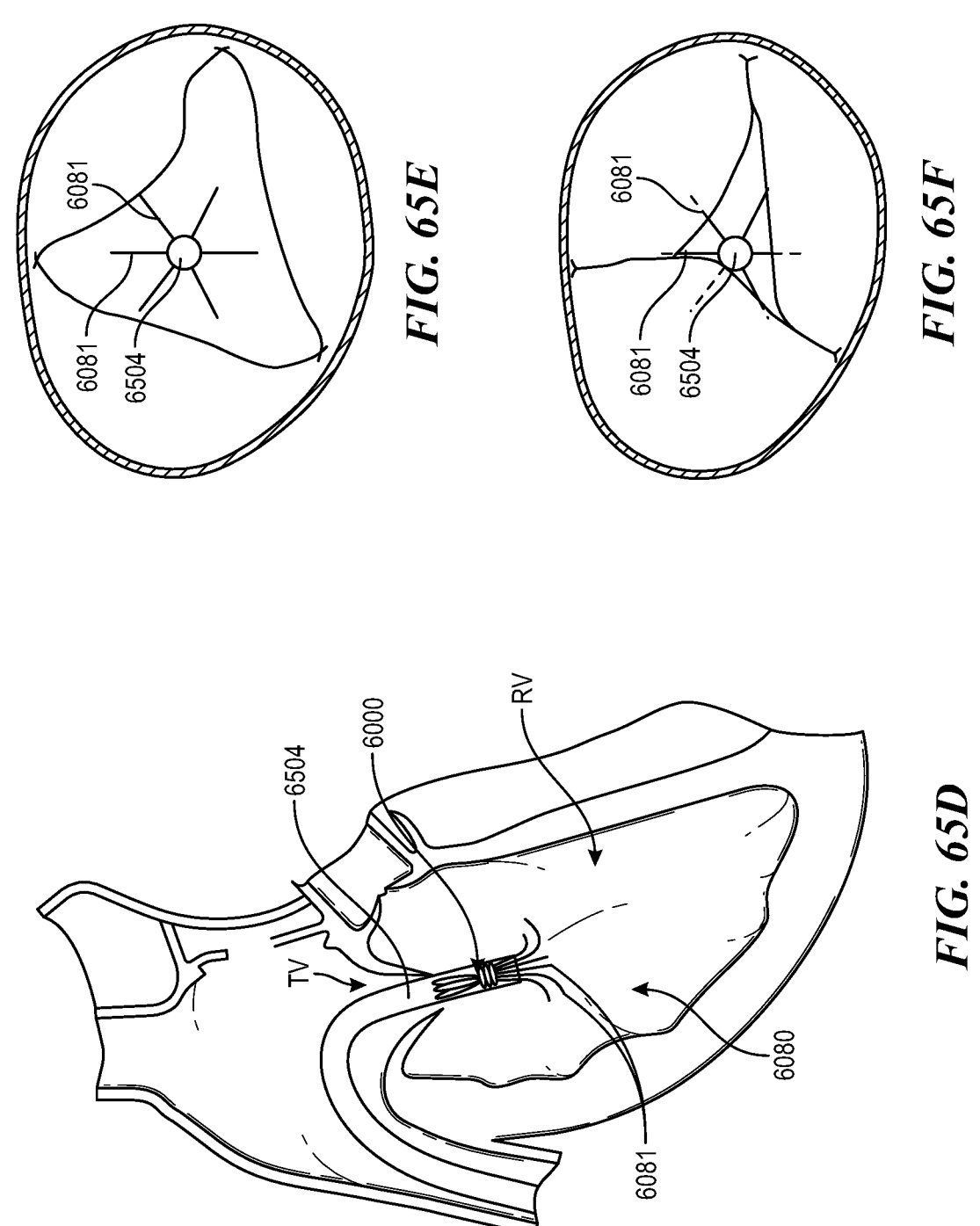

FIGS. 65E and 65F are transverse cross-sectional views of the valve repair device during the second delivery stage of FIG. 65D during diastole and systole, respectively, in accordance with embodiments of the present technology.

Figures 65G, 65H, 65I:
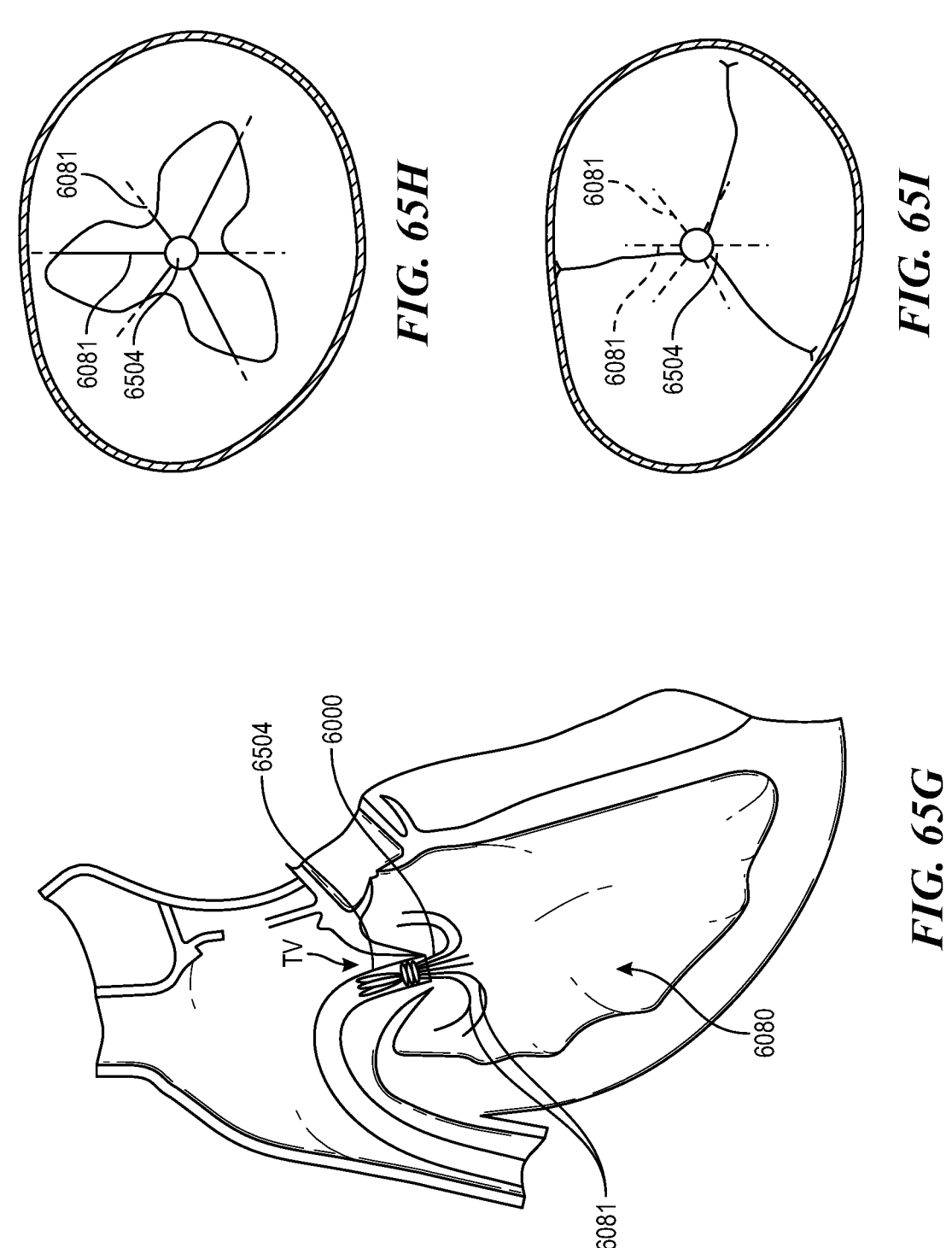

FIGS. 65H and 65I are transverse cross-sectional views of the valve repair device during the third delivery stage of FIG. 65G during diastole and systole, respectively, in accordance with embodiments of the present technology.

Figures 65J, 65K, 65L:
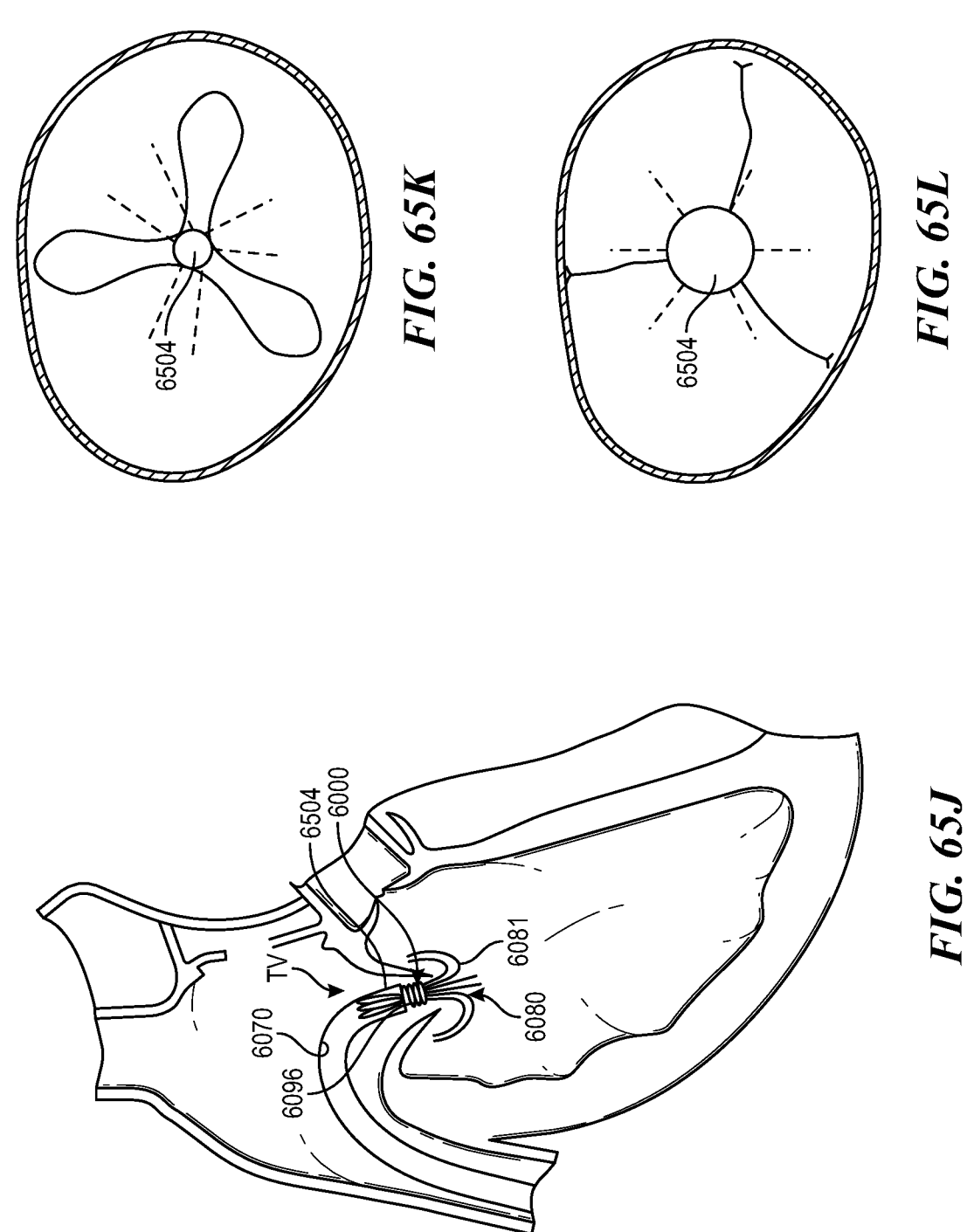

FIGS. 65K and 65L are transverse cross-sectional views of the valve repair device during the fourth delivery stage of FIG. 65J during diastole and systole, respectively, in accordance with embodiments of the present technology.

Figures 65M, 65N, 65O:
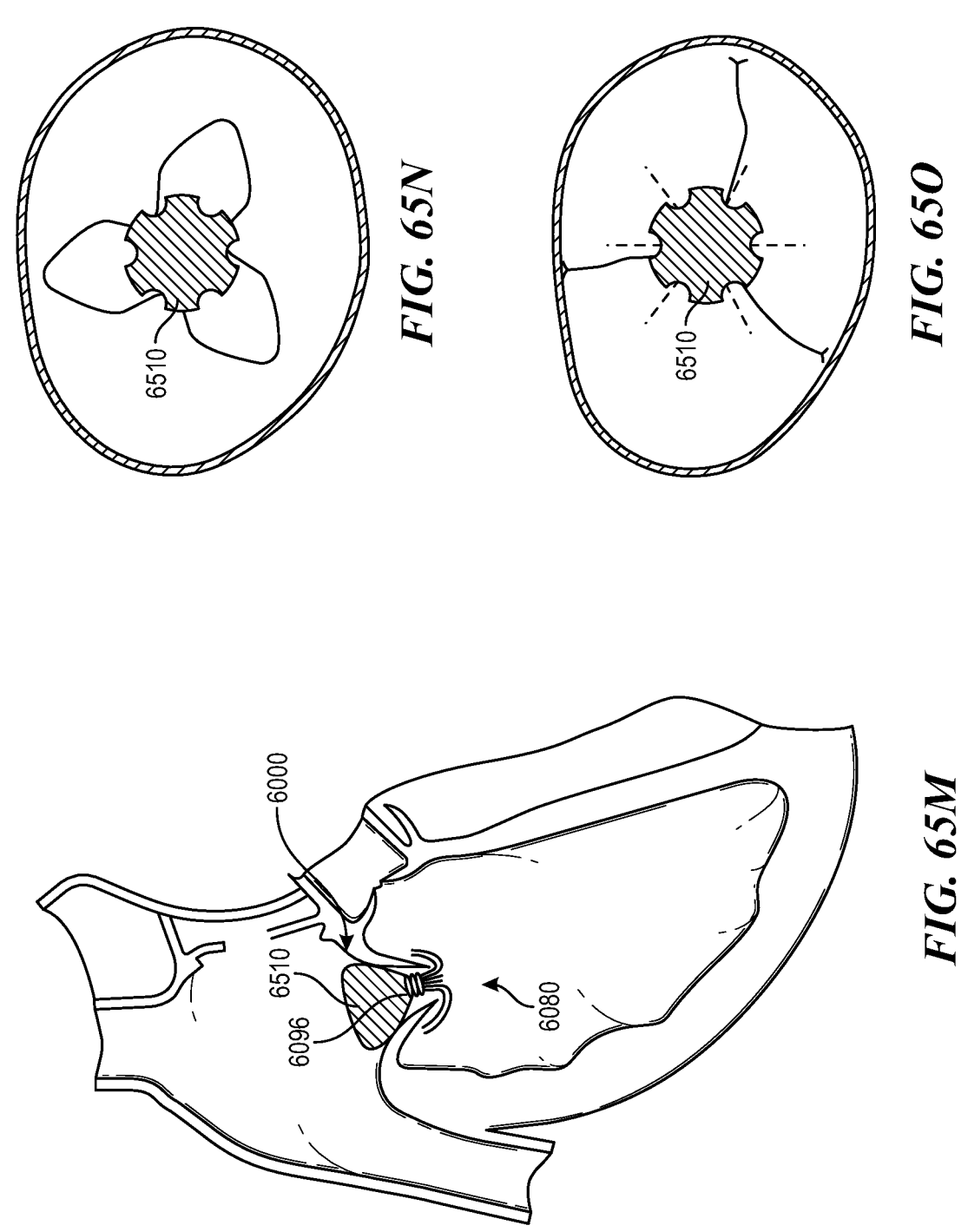

FIGS. 65N and 65O are transverse cross-sectional views of the valve repair device during the fifth delivery stage of FIG. 65M during diastole and systole, respectively, in accordance with embodiments of the present technology.

Figure 66A:
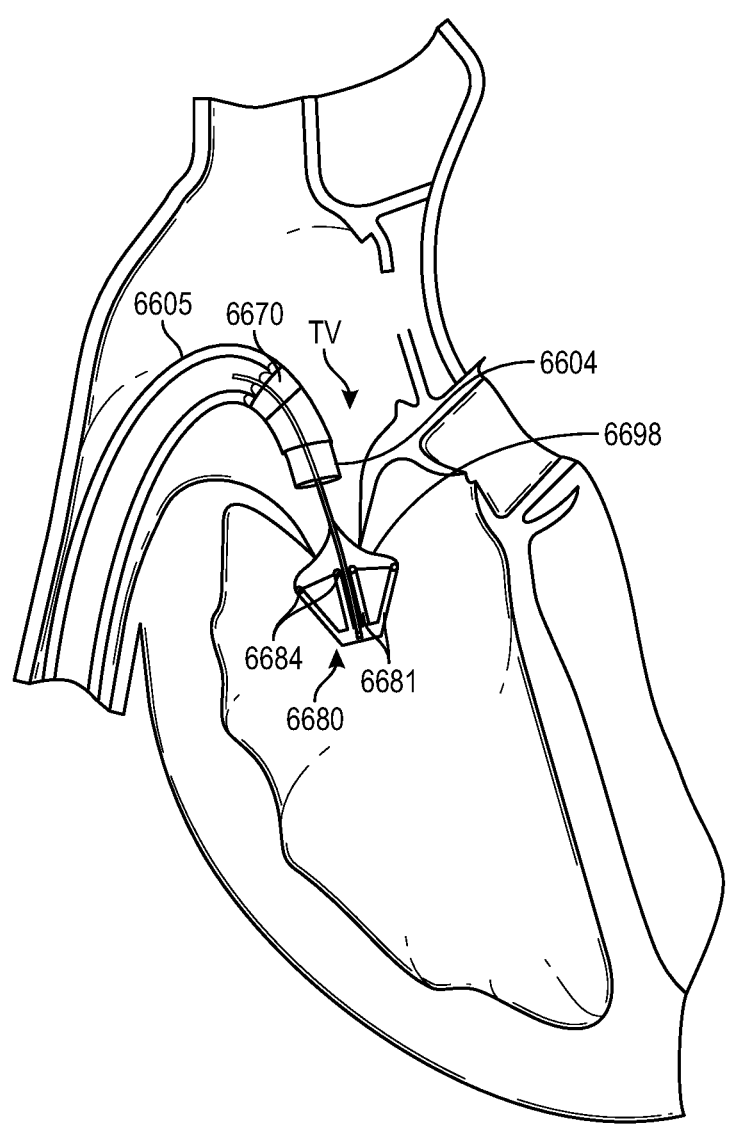
Figure 66B:
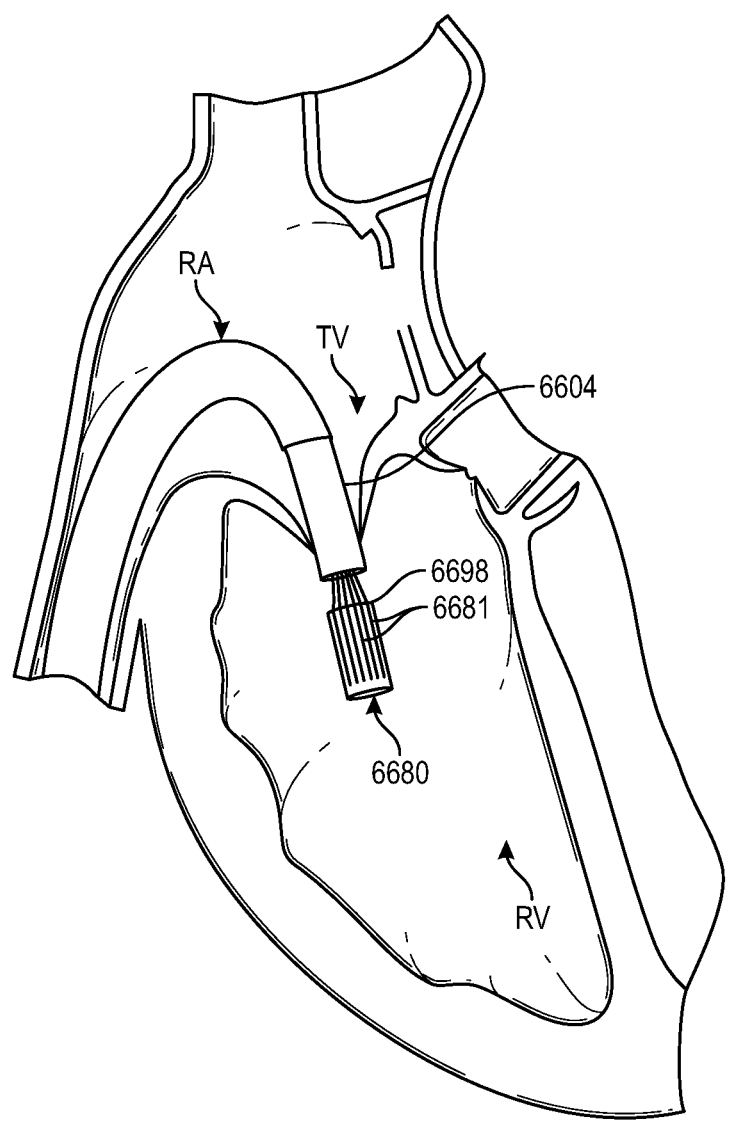
Figure 66C:
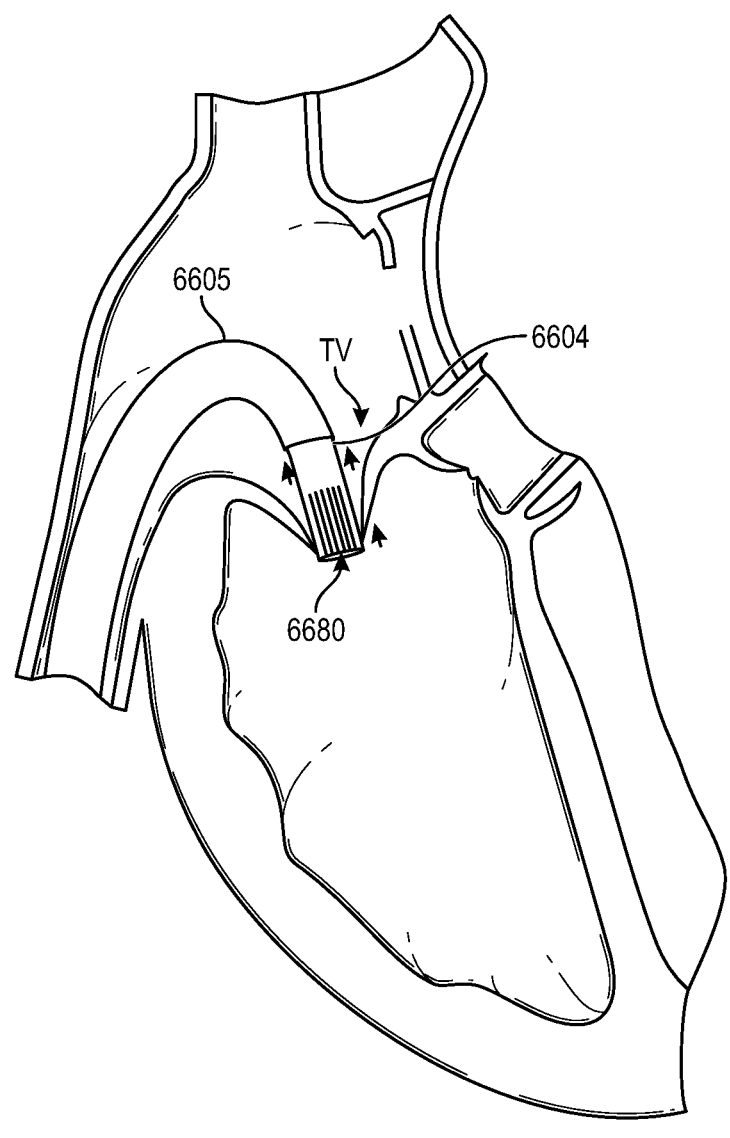

FIGS. 66A-66C are side views of a valve repair device of any of, for example, FIGS. 42A-45D or 52A-54F during first through third recovery stages of recovering the valve repair device from an implantation procedure at the tricuspid valve, respectively, in accordance with embodiments of the present technology.

Figure 67A:
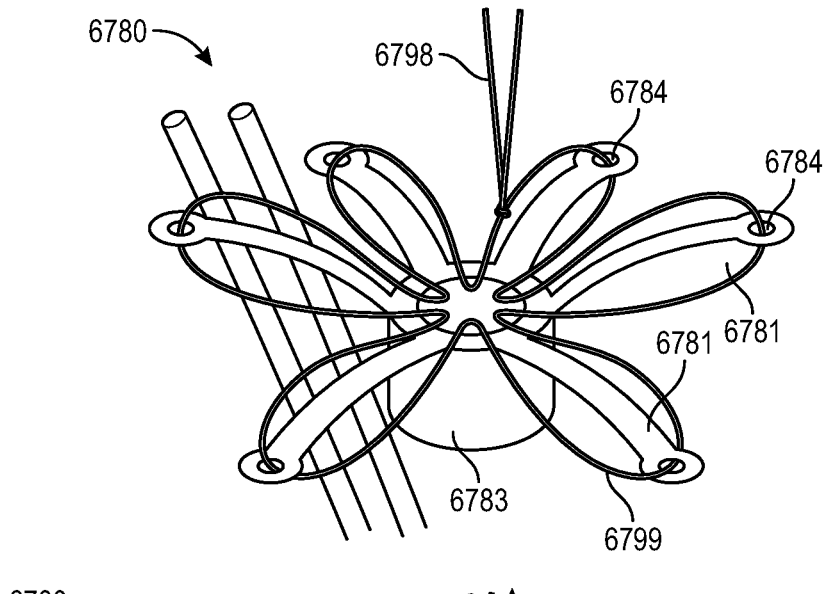
Figure 67B:
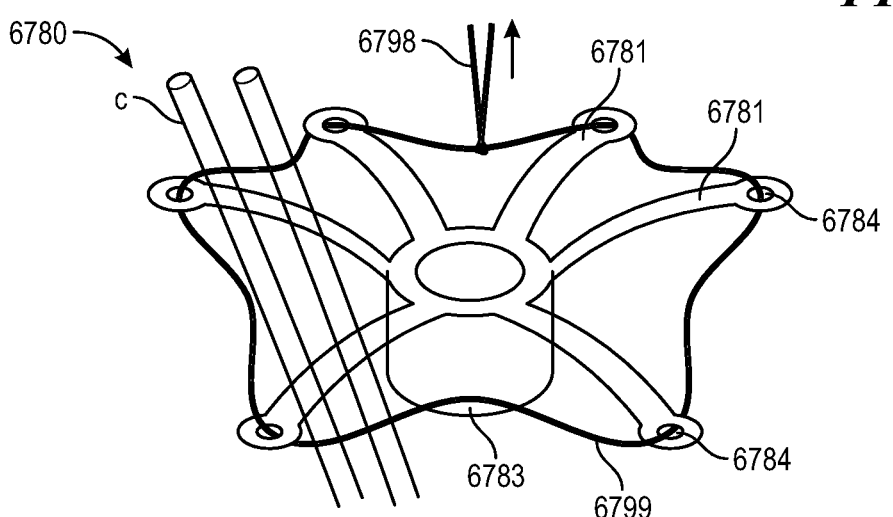
Figure 67C:
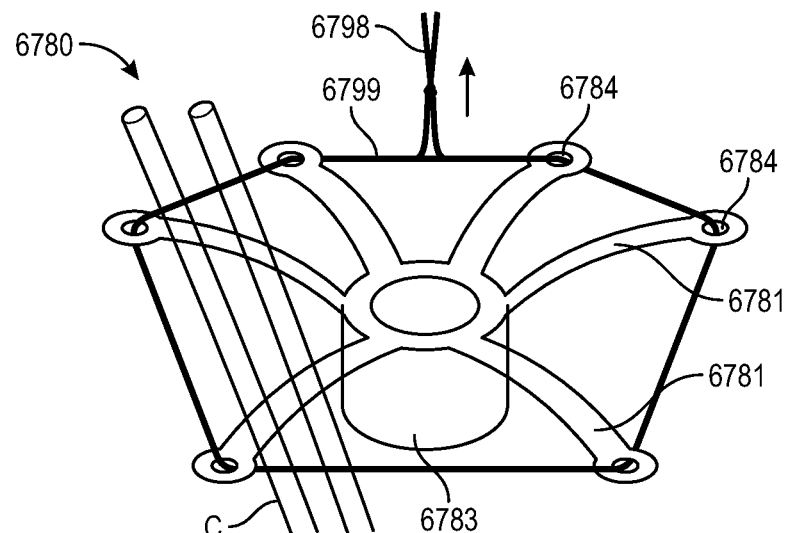

FIGS. 67A-67C are perspective side views of a ventricular member of a valve repair device positioned at a cardiac valve in a first position, a second position, and a third position, respectively, in accordance with embodiments of the present technology.

Figures 67D, 67E, 67F:
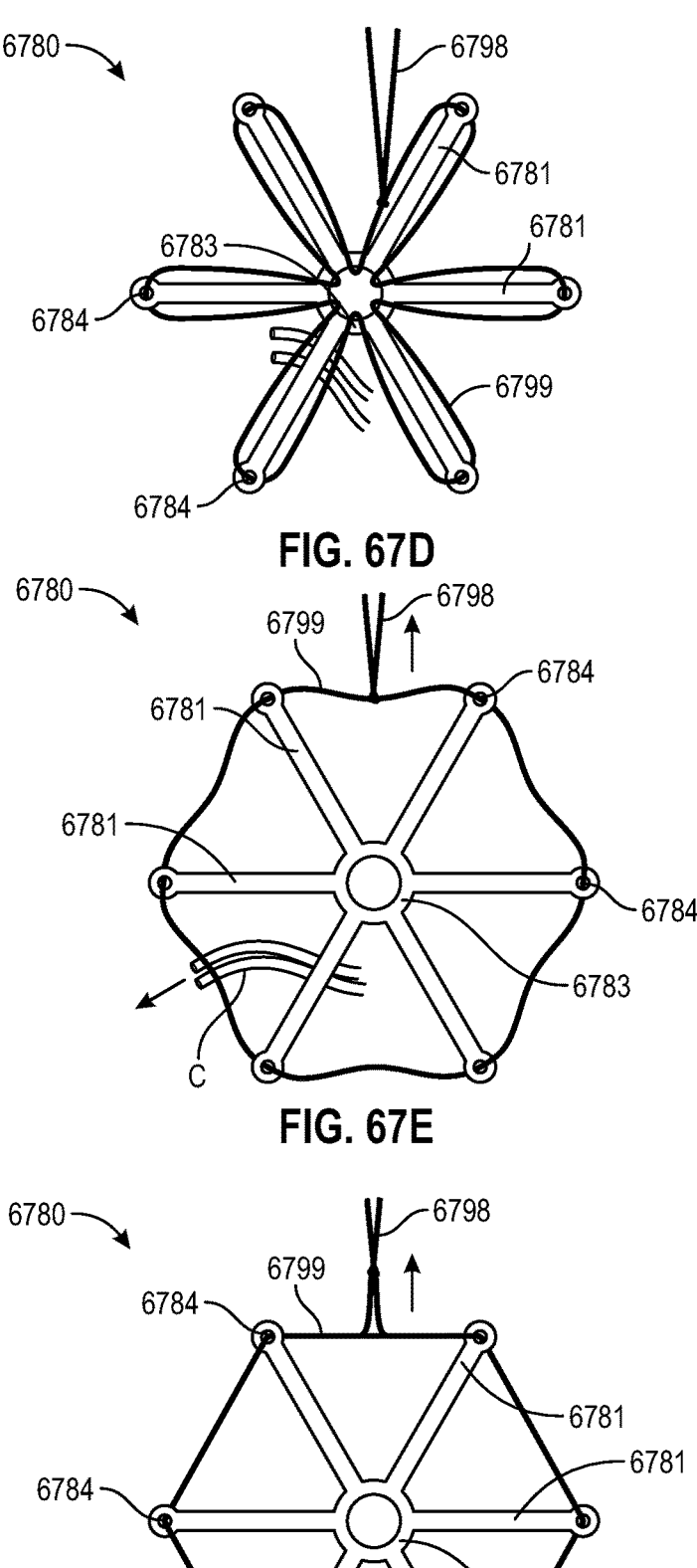

FIGS. 67D-67F are top views of the ventricular member of FIGS. 67A-67C positioned at the cardiac valve in the first position, the second position, and the third position, respectively, in accordance with embodiments of the present technology.

FIGS. 68A and 68B are a side view and a top view, respectively, of the base of the ventricular member of FIGS. 67A-67F including a securement mechanism in accordance with embodiments of the present technology.

FIG. 69A is a side view of the base of the ventricular member of FIGS. 67A-67F including a securement mechanism in accordance with additional embodiments of the present technology.

FIG. 69B is an enlarged side view of a portion of the securement mechanism of FIG. 69A in accordance with embodiments of the present technology.

Figure 70A:
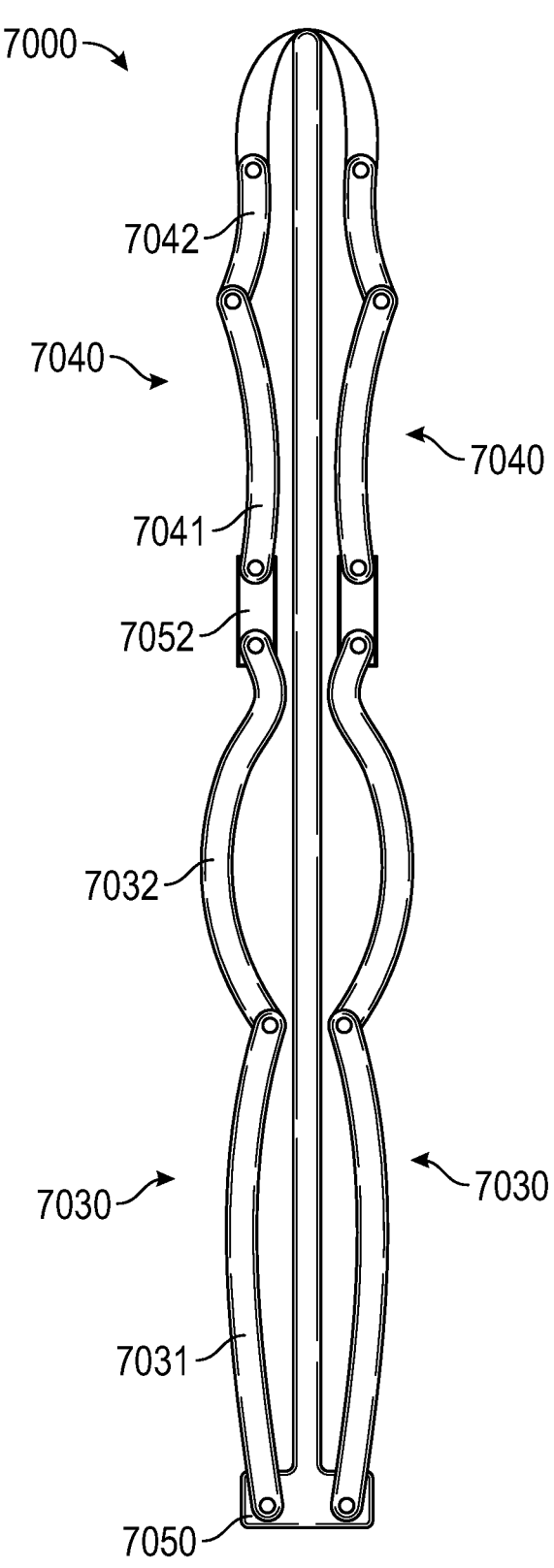

FIG. 70A is a side view of a valve repair device in a delivery configuration in accordance with embodiments of the present technology.

Figure 70B:
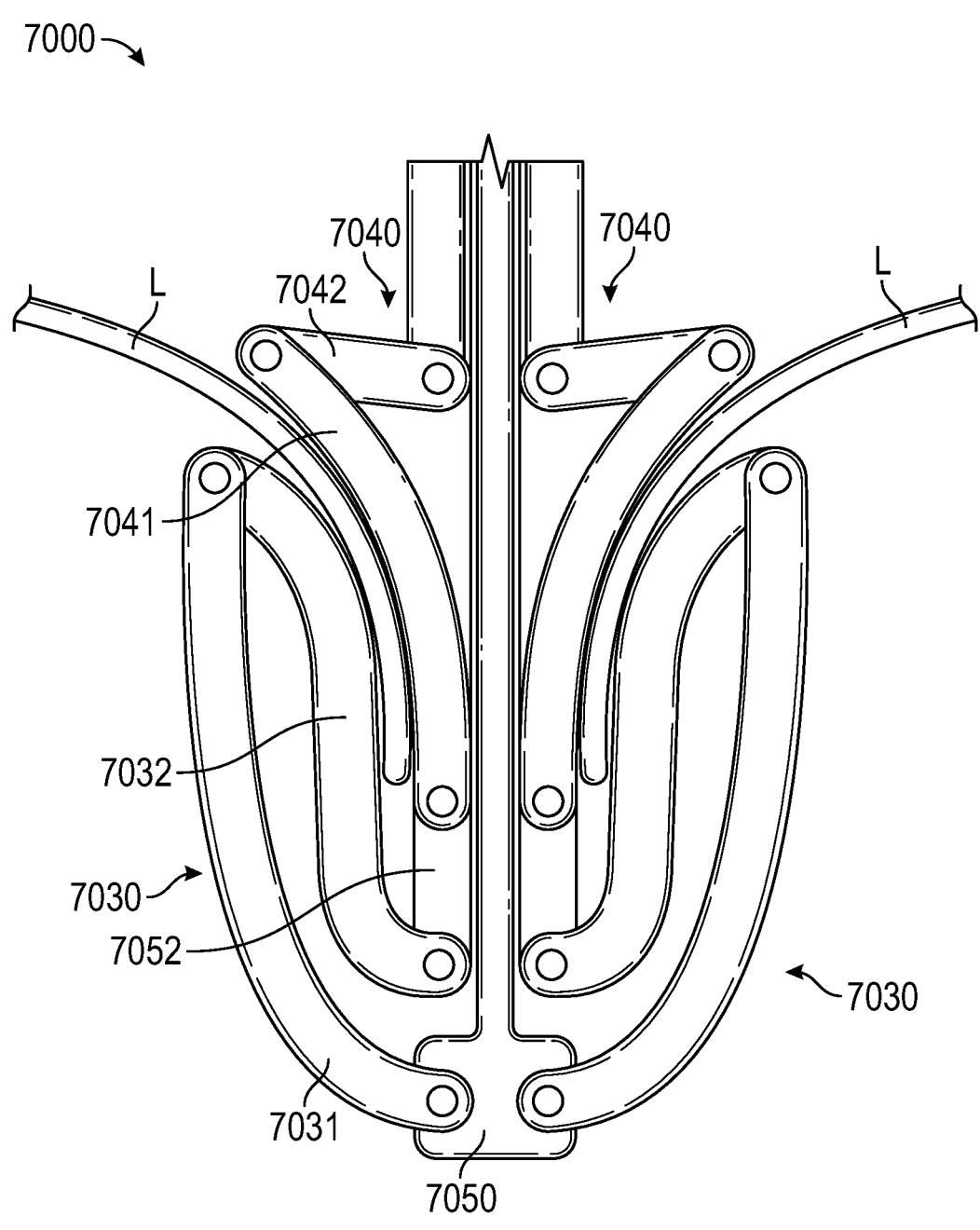

FIG. 70B is a side view of the valve repair device of FIG. 70A in a deployed configuration and implanted at a cardiac valve in accordance with embodiments of the present technology.

DETAILED DESCRIPTION

The present technology is directed to cardiac valve repair devices and associated systems and methods. In some embodiments, for example, a cardiac valve repair device (also referred to herein as a "valve repair device," "coaptation assist device," "implant device," and iterations thereof) includes features that anchor to native anatomy of a heart of a patient, such as one or more of the native leaflets of the mitral valve or the tricuspid valve of a human patient. For example, the cardiac valve repair device can include (i) a coaptation member (also referred to as a "coaptation structure," "space filler," "filler," "baffle," "intravalvular body," "intermediate structure," and iterations thereof) positioned at least partially between the native leaflets, and (ii) one or more clip mechanisms that secure the coaptation member in position relative to the native leaflets. The coaptation member can at least partially fill a regurgitant orifice in the cardiac valve and provide a new coaptation surface for the native leaflets to seal around. The coaptation member can also push a portion of the native leaflets outward toward the ventricular wall, while reducing or minimizing disruption of the remaining portion of the native leaflets. The clip mechanisms can engage the ventricular and/or the atrial side of the native leaflets to secure the position of the coaptation member relative to the cardiac valve.

In some embodiments, a cardiac valve repair device in accordance with additional embodiments of the present technology can include (i) a coaptation member positioned between the native valve leaflets, and (ii) one or more anchors and/or brace members that secure the coaptation member to anatomy of the heart other than the native leaflets. For example, the anchors can be secured to an atrial wall, ventricular wall, valve annulus, ventricular outflow tract, and/or other portions of the cardiac anatomy of the patient.

In some embodiments a cardiac valve repair device in accordance with additional embodiments of the present technology includes an atrial member and a ventricular member configured to capture (e.g., "sandwich") one or more native leaflets therebetween. For example, the atrial and ventricular members can include multiple small clips, fingers, arms, or other features that interlock and waffle onto the native leaflets. The atrial and ventricular members can together at least partially fill a regurgitant orifice in the cardiac valve and, in some embodiments, the atrial and ventricular members can provide a coaptation surface for the native leaflets to seal around.

Figure 1A:
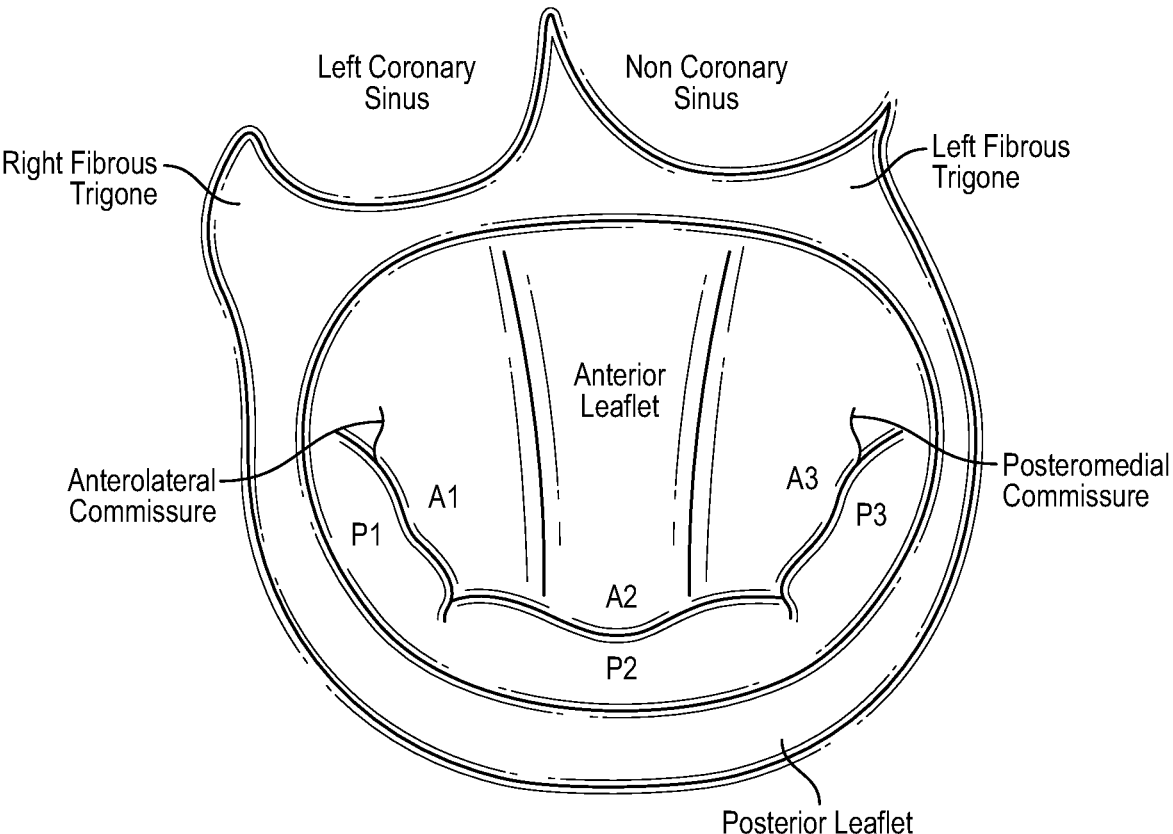
FIG. 1A is a diagram of a mitral valve and surrounding anatomy at which a cardiac valve repair device can be implanted in accordance with embodiments of the present technology.

Specific details of several embodiments of the present technology are described herein with reference to FIGS. 1A-70B. The present technology, however, can be practiced without some of these specific details. In some instances, well-known structures and techniques often associated with catheter-based delivery systems, prosthetic heart valves, and the like have not been shown in detail so as not to obscure the present technology. The terminology used in the description presented below is intended to be interpreted in its broadest reasonable manner, even though it is being used in conjunction with a detailed description of certain specific embodiments of the disclosure. Certain terms can even be emphasized below; however, any terminology intended to be interpreted in any restricted manner will be overtly and specifically defined as such in this Detailed Description section.

The accompanying Figures depict embodiments of the present technology and are not intended to be limiting of its scope. The sizes of various depicted elements are not necessarily drawn to scale, and these various elements can be arbitrarily enlarged to improve legibility. Component details can be abstracted in the Figures to exclude details such as position of components and certain precise connections between such components when such details are unnecessary for a complete understanding of how to make and use the present technology. Many of the details, dimensions, angles, and other features shown in the Figures are merely illustrative of particular embodiments of the disclosure. Accordingly, other embodiments can have other details, dimensions, angles, and features without departing from the spirit or scope of the present technology.

With regard to the terms "distal" and "proximal" within this description, unless otherwise specified, the terms can reference a relative position of the portions of a catheter subsystem with reference to an operator and/or a location in the vasculature. Also, as used herein, the designations "rearward," "forward," "upward," "downward," and the like are not meant to limit the referenced component to use in a specific orientation. It will be appreciated that such designations refer to the orientation of the referenced component as illustrated in the Figures, and the systems of the present technology can be used in any orientation suitable to the user.

The headings provided herein are for convenience only and should not be construed as limiting the subject matter disclosed.

Many of the embodiments of cardiac valve repair devices are described and illustrated herein in the context of one of the tricuspid valve or the mitral valve. However, it is to be understood that unless expressly stated otherwise, the cardiac valve repair devices of the present technology are not limited to their described/illustrated embodiments, and can be implanted at the tricuspid valve, the mitral valve, and/or other valves.

I. OVERVIEW

FIG. 1A is a diagram of a mitral valve and surrounding anatomy at which a cardiac valve repair device can be implanted in accordance with embodiments of the present technology. The anterior leaflet has a semicircular shape and attaches to approximately two-fifths of the annular circumference. The motion of the anterior leaflet defines an important boundary between the inflow (diastole) and outflow (systole) tracts of the left ventricle. The posterior leaflet of the mitral valve has a crescent shape and is attached to approximately three-fifths of the annular circumference. The posterior leaflet typically has two well-defined indentations which divide the leaflet into three individual scallops identified as P1 (lateral scallop), P2 (middle scallop), and P3 (medial scallop). The three corresponding segments of the anterior leaflet are identified as A1 (lateral segment), A2 (middle segment), and A3 (medial segment). The leaflet indentations aid in opening the posterior leaflet during diastole.

As shown in FIG. 1A, the mitral valve has anterolateral and posteromedial commissures which define a distinct area where the anterior and posterior leaflets come together at their insertion into the annulus. Sometimes the commissures exist as well-defined leaflet segments, but often this area is a subtle structure that can be identified using the following two anatomic landmarks: (a) the axis of corresponding papillary muscles, and (b) the commissural chordae, which have a specific fan-like configuration. Several millimeters of valvular tissue separate the free edge of the commissures from the annulus.

The mitral valve is an atrio-ventricular valve separating the left atrium from the left ventricle. The mitral annulus constitutes the anatomical junction between the left ventricle and the left atrium. The fixed ends of the leaflets are attached to the annulus. The anterior portion of the mitral annulus is attached to the fibrous trigones and is generally more developed than the posterior annulus. The right fibrous trigone is a dense junctional area between the mitral valve, tricuspid valve, non-coronary cusp of the aortic valve, and the membranous septum. The left fibrous trigone is situated at the junction of both left fibrous borders of the aortic valve and the mitral valve.

The mitral annulus is less well developed at the insertion site of the posterior leaflet. This segment is not attached to any fibrous structures, and the fibrous skeleton in this region is discontinuous. This posterior portion of the annulus is prone to increase its circumference when mitral regurgitation occurs in association with left atrial or left ventricular dilation. The mitral annulus is saddle-shaped, and during systole the commissural areas move proximally—that is, towards the roof of the atrium—while annular contraction also narrows the circumference. Both processes aid in achieving leaflet coaptation, which may be adversely affected by annular dilatation and calcification. The mitral annulus is surrounded by several important anatomic structures, including the aortic valve, the coronary sinus, and the circumflex artery. As a result, implanted cardiac devices at the mitral valve need to be positioned to accommodate the asymmetrical anatomy of the mitral valve without impacting the surrounding cardiac structures.

Figure 1B:
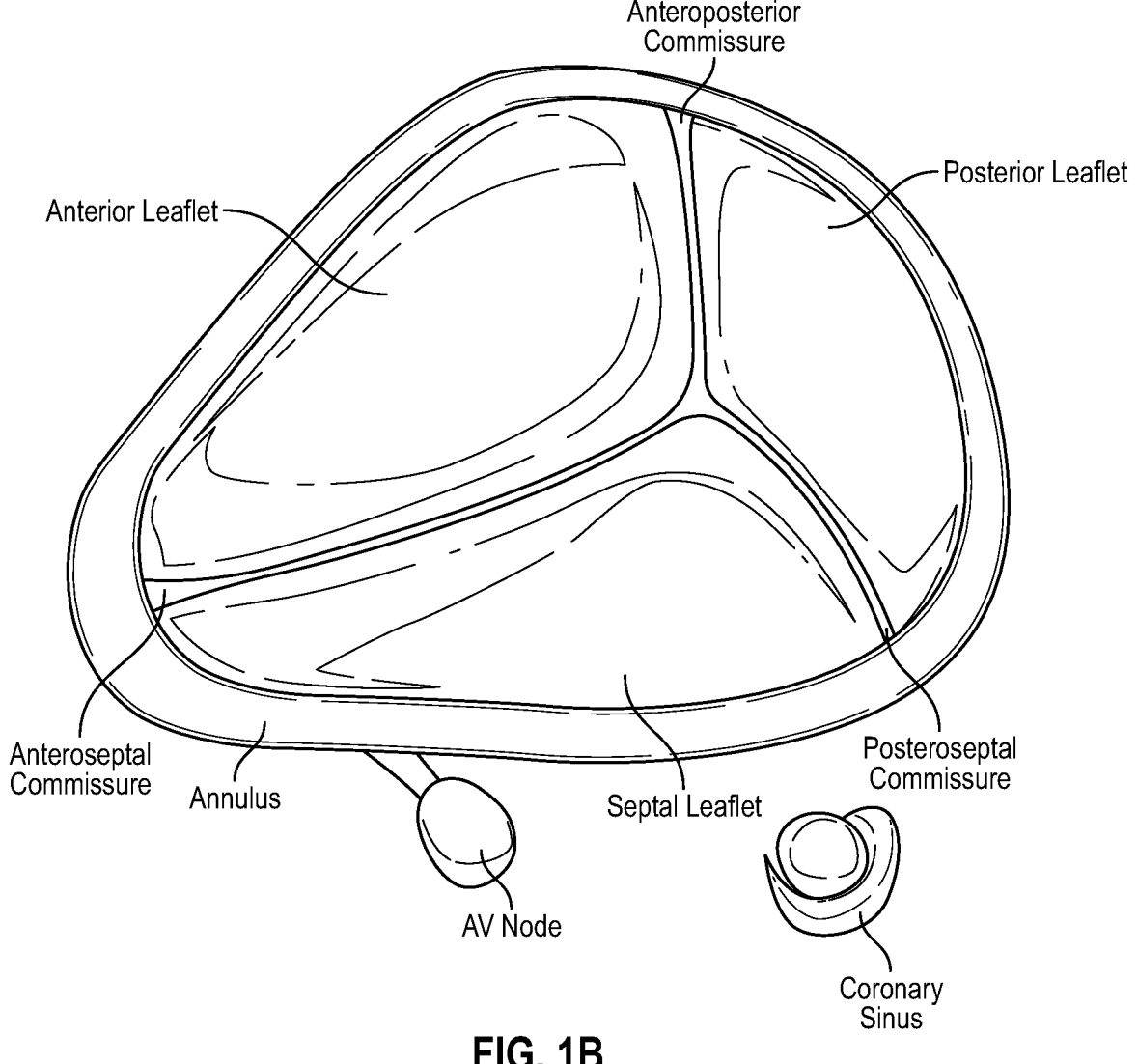
FIG. 1B is a diagram of a tricuspid valve and surrounding anatomy at which a cardiac valve repair device can be implanted in accordance with embodiments of the present technology.

FIG. 1B is a diagram of a tricuspid valve and surrounding anatomy at which a cardiac valve repair device can be implanted in accordance with embodiments of the present technology. The tricuspid valve is an atrio-ventricular valve separating the right atrium from the right ventricle, and is placed in a more apical position than the mitral valve. The tricuspid valve lies within the right trigone of the fibrous skeleton of the heart. The tricuspid annulus (a fibrous or membranous structure) constitutes the anatomical junction between the right ventricle and the right atrium, and provides a firm support structure for the tricuspid valve. The annulus is less fibrous than other annuli and slightly larger than the mitral valve annulus.

The tricuspid valve has an ovoid shape and includes an anterior leaflet (also referred to as an infundibular or antero-superior leaflet), a septal leaflet (also referred to as a medial leaflet), and a posterior leaflet (also referred to as an inferior or marginal leaflet). The anterior and septal leaflets are larger than the posterior leaflet. The fixed ends of the leaflets are attached to the annulus. The tricuspid valve has (i) a posteroseptal commissure that defines a distinct area where the septal and posterior leaflets come together at their insertion into the annulus, a (ii) an anteroseptal commissure that defines a distinct area where the septal and anterior leaflets come together at their insertion into the annulus, and (iii) an anteroposterior commissure that defines a distinct area where the anterior and posterior leaflets come together at their insertion into the annulus. The commissures can appear more like indentations than true commissures, and several millimeters of valvular tissue separate the free edges of the commissures from the annulus.

The septal leaflet has more support from the fibrous trigone than the anterior or posterior leaflets. Therefore, tricuspid regurgitation from annular dilation often occurs due to the loss of coaptation between the anterior and posterior leaflets. In addition to annular dilation, leaflet coaptation can also be adversely affected by annular calcification. The tricuspid annulus is surrounded by several important anatomic structures, including the left pulmonary artery, the coronary sinus, and the AV node. As a result, implanted cardiac devices at the tricuspid valve need to be positioned to accommodate the asymmetrical anatomy of the tricuspid valve without impacting the surrounding cardiac structures.

FIGS. 2A-2D are a front view, a side view, a rear view, and a top view, respectively, of a tricuspid valve repair device 200 ("device" or "valve repair device") that can be implanted in a heart of a subject (e.g., a human patient) in accordance with embodiments of the present technology. Referring to FIGS. 2A-2D together, the device includes a coaptation member 210, a stabilization 220 member extending from the coaptation member 210, and a pair of clip mechanisms 230 (also referred to as "capture clips") movably (e.g., hingedly, pivotally, rotatably) coupled to the coaptation member 210. In some embodiments, the device 200 can include some features generally similar or identical to one or more of the implantable devices described in (i) U.S. patent application Ser. No. 16/044,447, titled "PROS-THETIC LEAFLET DEVICE," and filed Jul. 24, 2018; (ii) International Patent Application No. PCT/US2018/061126, titled "LEAFLET EXTENSION FOR CARDIAC VALVE LEAFLET," and filed Nov. 14, 2018; (iii) U.S. patent application Ser. No. 16/745,246, titled "IMPLANTABLE COAPTATION ASSIST DEVICES WITH SENSORS AND ASSOCIATED SYSTEMS AND METHODS," and filed Jan. 16, 2020; (iv) U.S. patent application Ser. No. 16/817, 464, titled "CARDIAC VALVE REPAIR DEVICES WITH ANNULOPLASTY FEATURES AND ASSOCIATED SYSTEMS AND METHODS," and filed Mar. 12, 2020;

and/or (v) U.S. patent application Ser. No. 17/027,681, titled "VALVE REPAIR DEVICES WITH COAPTATION STRUCTURES AND MULTIPLE LEAFLET CAPTURE CLIPS," and filed Sep. 21, 2020; each of which is incorporated herein by reference in its entirety. Any of the valve repair devices disclosed herein can be delivered to the tricuspid valve intravascularly (e.g., trans-septal delivery via the femoral or axial vein), percutaneously (e.g., transapically), and/or surgically.

In the illustrated embodiment, the coaptation member 210 is configured to (i) fill at least a portion of a regurgitant orifice between the native leaflets of a cardiac valve, (ii) displace at least a portion of one or more of the native leaflets, and/or (iii) provide a prosthetic coaptation surface for one or more of the native leaflets. The clip mechanisms 230 are configured to be positioned on the ventricular (e.g., sub-annular) side of the valve and to extend behind and grasp portions of one or more of the native leaflets to affix the leaflets to the coaptation member 210. The stabilization 220 member is configured to be positioned at least partially on the atrial (e.g., supra-annular) side of the valve and to contact the atrial sides of one or more of the native leaflets and/or other portions of the cardiac anatomy (e.g., the atrial wall) to stabilize and secure the position of the coaptation member 210 relative to the valve. The stabilization member 220 can also serve to inhibit or even prevent prolapse of the coaptation member 210 during ventricular systole. The stabilization member 220 can also serve to provide a platform for tissue ingrowth and long-term fixation. In the illustrated embodiment, the coaptation member 210 has a trapezoidal side-cross sectional shape and an almond-like transverse cross-sectional shape. The coaptation member 210 can further include a pair of recesses 211 (FIG. 2C) for receiving at least a portion of the clip mechanisms 230.

In the illustrated embodiment, the stabilization member 220 includes a frame 221 having an M-like shape covered by a covering 222. In other embodiments, the frame 221 can have other shapes such as, for example, circular, elliptical, polygonal, irregular, rectilinear, and so on. The frame 221 can be a wire form, braid, or laser-cut stent-like structure formed from a suitably strong biocompatible material such as, for example, stainless steel, nickel-titanium alloys (e.g., nitinol), and/or other suitable stent materials. In some aspects of the present technology, the M-like shape of the frame 221 can provide the stabilization member with lateral stiffness (e.g., from side to side along the stabilization member), while preserving torsional and front-to-back stability so as not to translate loads to/from the coaptation member 210. In some embodiments, the covering 222 (e.g., fabric, graft material) can extend over at least a portion of the frame 221 to at least partially enclose the frame 221 and provide a smooth, atraumatic surface for contacting with the atrium (e.g., right atrium or left atrium) and/or other portions of the cardiac anatomy while promoting ingrowth into the annulus and right atrium. In some embodiments, the stabilization member 220 can have frictional elements (not shown) which engage the supra-annular and annular tissue and provide additional fixation and stability.

In some embodiments, the coaptation member 210 can extend away from a downstream portion of the stabilization member 220 along a flow axis of the device 200, and at least a portion of the coaptation member 210 can extend radially inward from the stabilization member 220 to, for example, fill a portion of the native valve orifice. In the illustrated embodiment, the stabilization member 220 is angled or biased outwardly from the coaptation member 210 by an angle A (FIG. 2B) of between about 10°-75° (e.g., about 15°, about 45°, more than about 45°) to, for example, (i) provide stiffness and support for the coaptation member 210 and/or (ii) push a portion of an adjacent native leaflet back from the valve opening and approximate a closed position of the native leaflet when the device 200 is implanted at a cardiac valve. In some embodiments, the angle A can be selected to inhibit the coaptation member 210 from contacting the ventricular wall during the cardiac cycle and, in particular, during systole. In some embodiments, the coaptation member 210 is more centrally located within the valve orifice. The coaptation member 210 can be substantially stationary (e.g., little to no movement) during cardiac cycles such that the position of the coaptation member 210 relative to the stabilization member 220 is at least substantially fixed when the device 200 is deployed at a native valve. Thus, unlike native leaflets that move back and forth to open and close the native valve, the coaptation member 210 can remain stationary during diastole and systole. In some embodiments, the coaptation member 210 does undergo some movement during cardiac cycling.

An outer portion 212 of the coaptation member 210 may have a smooth, atraumatic surface (also referred to as a "coaptation surface") for coapting with at least a portion of one or more opposing native leaflets, whereas an opposing inner portion 213 of the coaptation member 210 adjacent the clip mechanisms 230 can displace and engage at least a portion of another native leaflet. In some embodiments, the inner portion 213 and/or the outer portion 212 may include friction elements that engage the native leaflets. The coaptation member 210 can include an inner expandable frame structure (obscured in FIGS. 2A-2D; e.g., a mesh structure, a laser-cut stent frame) made from a plurality of connected struts that define an at least partially hollow interior space when the device 200 is in the illustrated deployed state. Portions of the frame structure may be disconnected allowing portions of the struts to slide over one another and/or move apart from one another to facilitate a low profile in a delivery state and/or adjustability of the coaptation member 210 dimensions. In some embodiments, the coaptation member 210 or portions thereof can be integral with the stabilization member 220. In other embodiments, the coaptation member 210 is a separate structure that is connected to a portion of the stabilization member 220 during manufacturing using welding, rivets, adhesives, connectors, sutures and fabric, and/or other suitable connection mechanisms.

The coaptation member 210 can include one or more access openings 219, such as slits, valves, and/or holes that provide access to the interior of the coaptation member 210 and components therein during delivery and/or retrieval. For example, the access openings 219 can provide access to delivery system connectors that allow for manipulation of the coaptation member 210 and/or clip actuation mechanisms for opening and closing the clip mechanisms 230. Further, the cavity of the coaptation member 210 may house extension members, supplemental clips, and/or other components that may be optionally deployed during implant procedures.

Figure 2A:
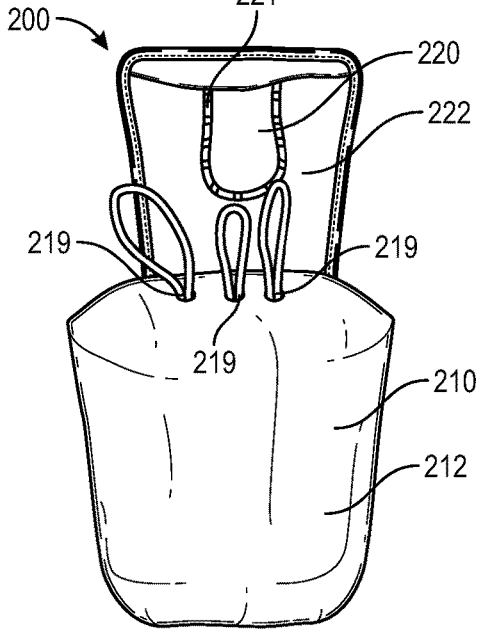
FIGS. 2A-2D are a front view, a side view, a rear view, and a top view, respectively, of a valve repair device that can be implanted in a heart of a subject in accordance with embodiments of the present technology.
Figure 2B:
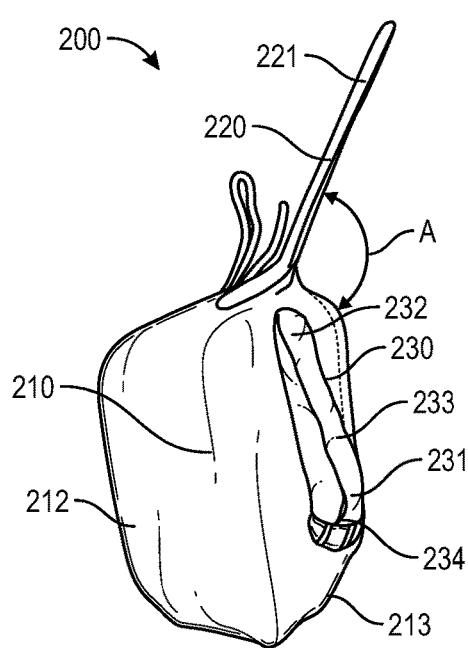
Figure 2C:
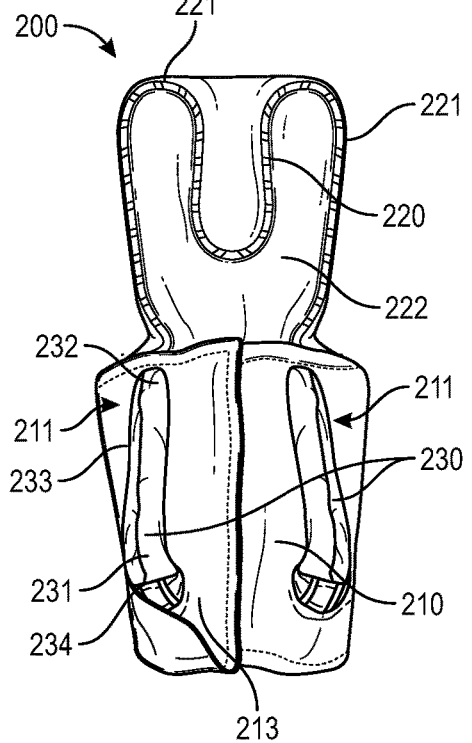
Figure 2D:
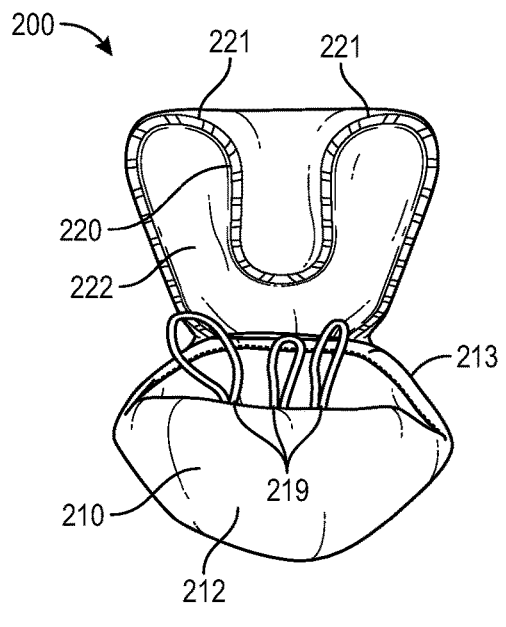
Figure 3A:
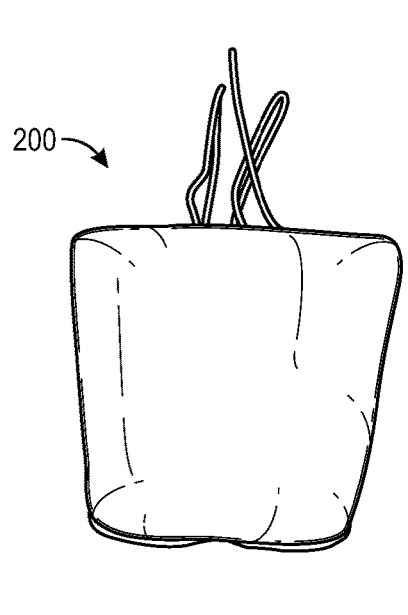
FIGS. 3A-3D are a front view, a side view, a rear view, and a top view, respectively, of a valve repair device without a stabilization member in accordance with embodiments of the present technology.
Figure 3B:
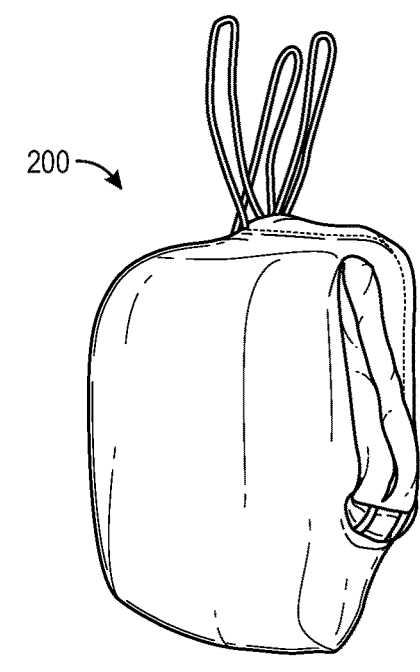
Figure 3C:
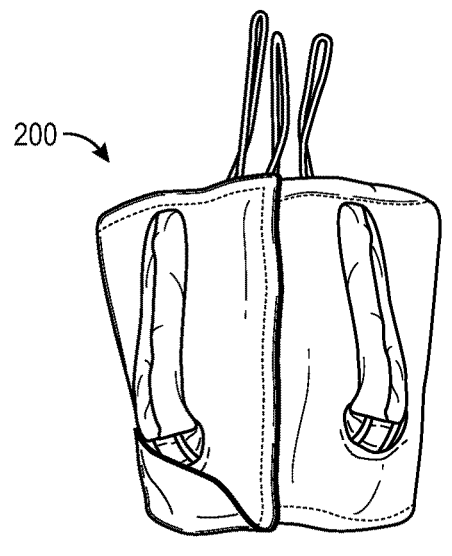
Figure 3D:
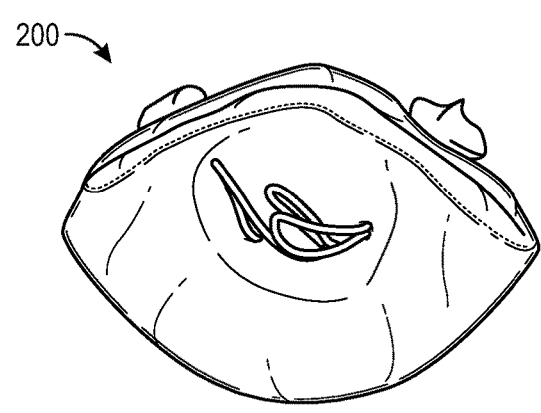
Figure 4A:
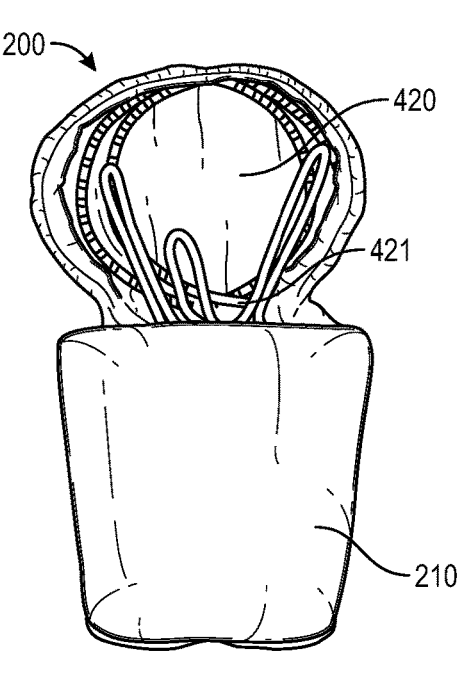
FIGS. 4A-4D are a front view, a side view, a rear view, and a top view, respectively, of a valve repair device including a flexible, generally-round stabilization member in accordance with embodiments of the present technology.
Figure 4B:
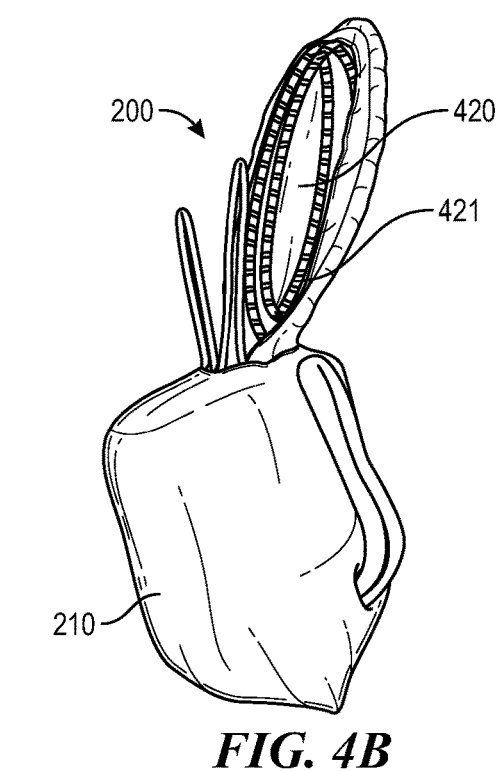
Figure 4C:
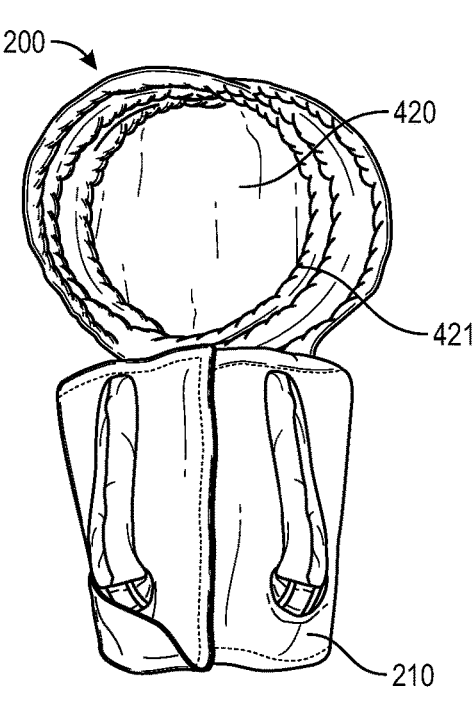
Figure 4D:
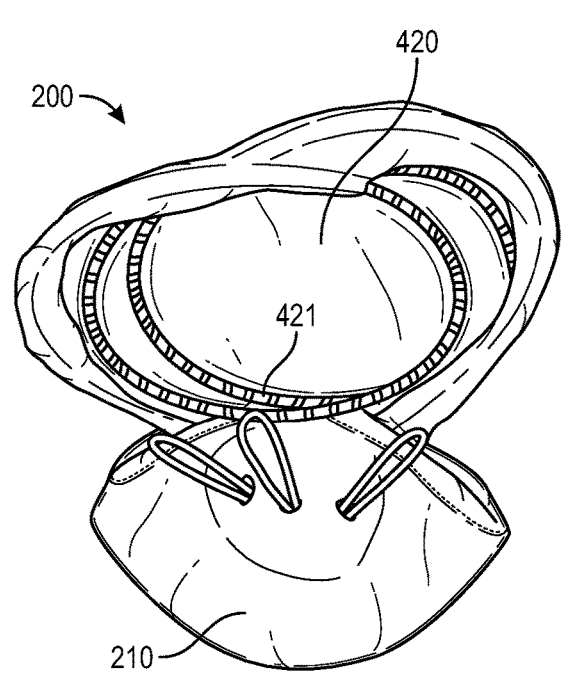

The clip mechanisms 230 extend from the coaptation member 210 (e.g., the inner portion 213 of the coaptation member) to allow the clip mechanisms 230 to extend behind and capture one or more native leaflets positioned on one or multiple sides of the coaptation member 210. With reference to FIGS. 2B and 2C, the clip mechanisms 230 can include a base portion 231 (also referred to as a "first portion") affixed to the coaptation member 210, a free end portion 232 (also referred to as a "second portion") unaffixed to the coaptation member 210, and an articulatable arm member 233 that extends from the base portion 231 and forms the free end portion 232. The base portion 231 can be attached to the coaptation member 210 by welding, riveting, adhesives, sutures, and/or other coupling mechanisms, or may be an extension of the coaptation member frame. The arm member 233 can extend from the base portion 231 in an upstream direction (e.g., toward the stabilization member 220) along a length of the coaptation member 210. For example, the arm member 233 can extend only partway up the coaptation member 210 and along the length of the coaptation member 210 to the downstream end of the stabilization member 220. In some embodiments, the arm member 233 may form an inverted U-like shape and flare outwardly to form a wider section where the arm member 233 clamps against the native leaflet. In other embodiments, the arm member 233 may have other suitable shapes for engaging leaflets and/or may include extensions at the distal-most end that engage sub-annular tissue for additional sub-annular stabilization and fixation.

The arm member 233 can be made from one or more wires, struts, and/or other semi-rigid/rigid structures with sufficient rigidity to clamp against a native leaflet and/or sub-annular tissue. In some embodiments, the arm member 233 includes a fabric covering, a biocompatible foam or other type of padding, and/or a coating on the rigid member to provide (i) a smooth surface at the arm root to reduce trauma to the leaflets and/or surrounding tissue, (ii) additional surface area for leaflet engagement, (iii) a platform for tissue ingrowth, and/or (iv) to provide additional friction to prevent leaflet slip-out. In some embodiments, the arm member 233 and/or other portions of the clip mechanism 230 can include spikes, tines, corrugations, or other frictional features (not shown) that enhance the stability and fixation to the native leaflet.

The clip mechanism 230 can further include an actuation mechanism 234, such as a spring-loaded lever, that acts on the arm member 233 to move it between a closed position (shown in FIGS. 2A-2D; also referred to as a "closed state," "closed configuration," or "first state") and an open position (also referred to as an "open state," "open configuration," or "second state"). In the closed state, the arm member 233 is positioned close to or against the surface of the coaptation member 210 in the corresponding recess 211, with at least a portion of the arm member 233 pressed against the surface of the coaptation member 210 to provide for leaflet engagement. In the open state, the articulatable arm member 233 extends away from the coaptation member 210 (e.g., forming a V-shape or L-shape with the surface of the coaptation member 210) to allow the free end portion 232 to extend behind a native leaflet and receive the native leaflet between the arm member 233 and the surface of the coaptation member 210. In some embodiments, the actuation mechanism 234 holds the clip mechanism 230 in a normally closed state (e.g., due to a spring force) such that (i) the clip mechanism 230 is in the closed state during device delivery and (ii) manipulation of the actuation mechanism 234 moves the clip mechanism 230 to the open state. In other embodiments, the clip mechanism 230 is arranged in a normally open state. The actuation mechanism 234 for the clip mechanism 230 can also have a locking mechanism to prevent clip actuation after deployment.

The actuation mechanism 234 can be a spring-loaded lever (e.g., a nitinol wire, laser cut nitinol or Co—Cr sheet) operably coupled to a portion of a delivery system (not shown) that can be manipulated to move the clip mechanism 230 between the open and closed positions. For example, a tendon (made of suture or nitinol wire) can be attached to the spring-loaded lever 234, extend alongside or through the body of the coaptation member 210 and through a delivery catheter to an external handle assembly. A clinician can pull on or otherwise apply tension to the tendon, which translates this force to the lever, thereby moving the arm member 233 between the closed and open positions. In other embodiments, the actuation mechanism 234 may have different actuation means, such as other springs, clamps, pulleys, interfacing threaded members, and/or further actuation mechanisms described in International Patent Application No. PCT/US2018/061126, filed Nov. 14, 2018. Further, because each clip mechanism 230 includes its own actuation mechanism 234, the clip mechanisms 230 can be independently actuated. As described in detail below, in some embodiments the device 200 can include more than two clip mechanisms 230 and/or one of the clip mechanisms 230 may be omitted.

Figure 5A:
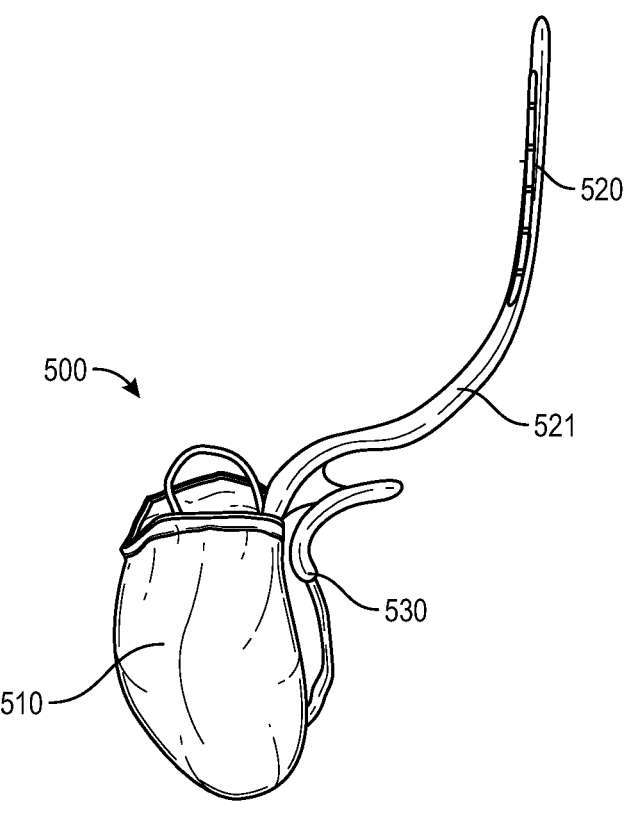
FIGS. 5A and 5B are a side view and a rear view, respectively, of a valve repair device including an elongate-curved stabilization member in accordance with embodiments of the present technology.
Figure 5B:
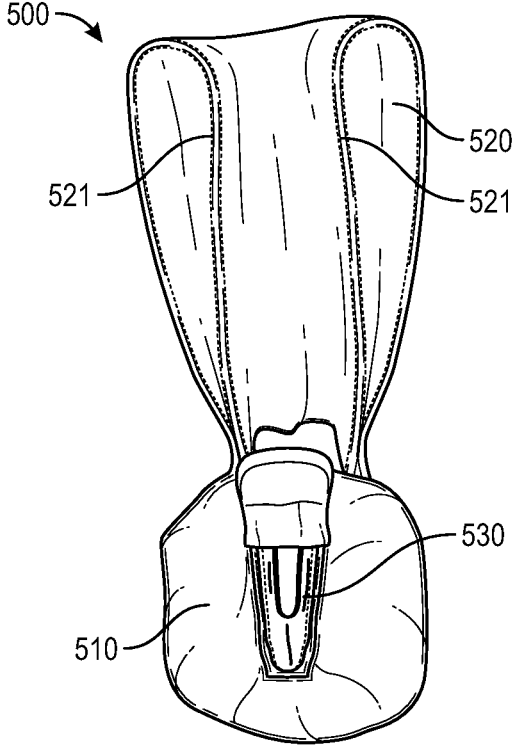

In some other embodiments, the valve repair device 200 can omit the stabilization member 220, the stabilization member 220 can have a different shape, and/or the number and position of the clip mechanisms 230 can be varied. For example, FIGS. 3A-3D are a front view, a side view, a rear view, and a top view, respectively, of the valve repair device 200 with the stabilization member 220 omitted in accordance with embodiments of the present technology. For example, FIGS. 4A-4D are a front view, a side view, a rear view, and a top view, respectively, of the valve repair device 200 including a flexible, generally-round stabilization member 420 in accordance with embodiments of the present technology. In the illustrated embodiment, the stabilization member 420 includes a frame 421 having a number of generally-circular rings attached to the coaptation member 210 at a portion of their perimeter to, for example, provide (i) radial flexibility while minimizing lateral flexibility and (ii) a target location for additional sequential fixation to stabilize the rings against the atrial wall. And, for example, FIGS. 5A and 5B are a side view and a rear view, respectively, of a valve repair device 500 including an elongate-curved stabilization member 520 extending from a coaptation member 510 in accordance with embodiments of the present technology. In the illustrated embodiment, the stabilization member 520 includes a frame 521 having two tall wire form or laser cut structures that curve to, for example, track the shape of and brace against an atrial wall. Further, the coaptation member 510 includes only a single, centrally-located clip mechanism 530 depending therefrom.

Figures 6A, 6B, 6C:
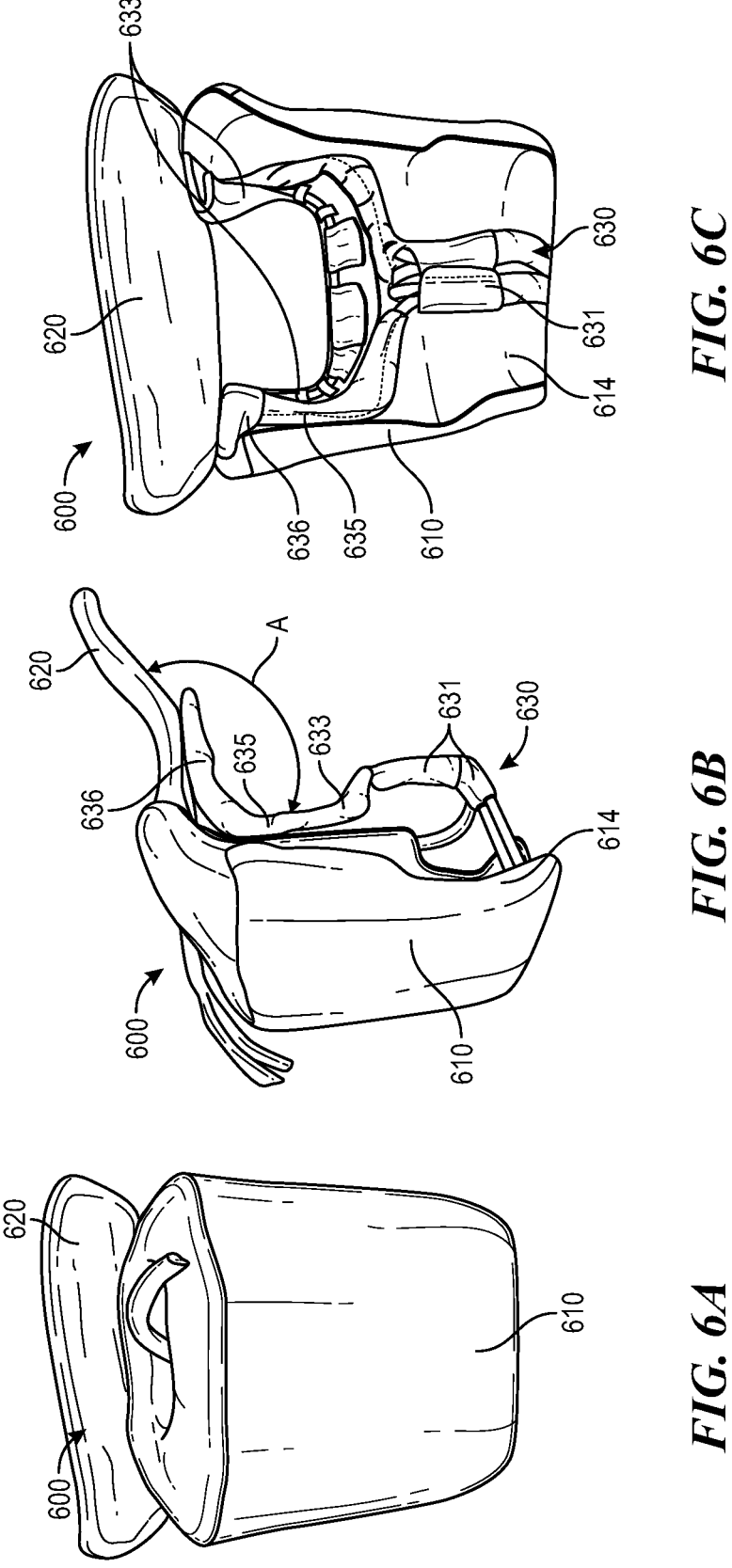
FIGS. 6A-6C are a front view, a side view, and a rear view, respectively, of a valve repair device in accordance with embodiments of the present technology.

FIGS. 6A-6C are a front view, a side view, and a rear view, respectively, of a valve repair device 600 configured in accordance with embodiments of the present technology. Referring to FIGS. 6A-6C together, the valve repair device 600 includes a coaptation member 610, a stabilization member 620 extending from the coaptation member 610, and a clip mechanism 630 movably coupled to the coaptation member. In some embodiments, the stabilization member 620 can extend at angle A (FIG. 6B) of between about 90°-130° (e.g., between about 95°-110°) relative to the coaptation member 610. The clip mechanism 630 can include a base 631 and a pair of arms or prongs 633 extending from the base 631. The prongs 633 can each include a first section 635 extending from the base 631 and a second section 636 extending from the first section 635. When the clip mechanism 630 is closed as shown in FIGS. 6A-6C, the first section 635 can extend generally parallel to the coaptation member 610, and the second section 636 can extend generally parallel to the stabilization member 620. In the illustrated embodiment, the coaptation member 610 has a jog or offset and/or a tapered shape in a direction from the top to the bottom of the coaptation member 610. That is, the coaptation member 610 can be wider/thicker toward the top than toward the bottom. In some aspects of the present technology, when the coaptation member 610 is implanted at a cardiac valve, this shape of the coaptation member 610 can help offset the coaptation member 610 from the cardiac anatomy and/or stabilize the valve repair device 600 against the ventricular wall while also maintaining the coaptation member 610 generally centrally positioned within the valve. In the illustrated embodiment, the coaptation member 610 further includes a curved portion 614 at the bottom thereof that can, for example reduce leaflet flail during systole.

Figure 7C:
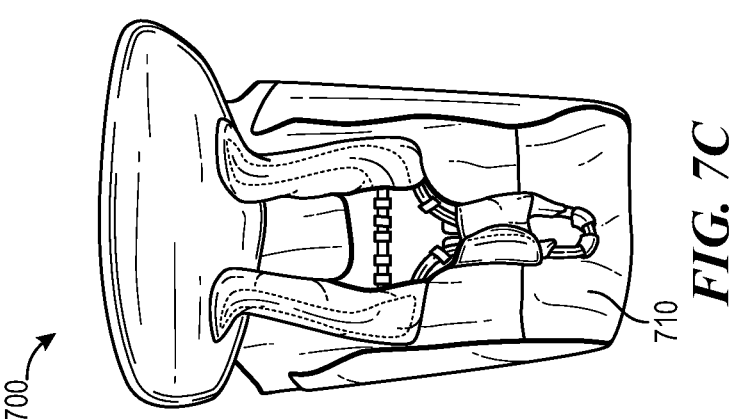
FIGS. 7A-7C are a front view, a side view, and a rear view, respectively, of a valve repair device in accordance with embodiments of the present technology.
Figure 7B:
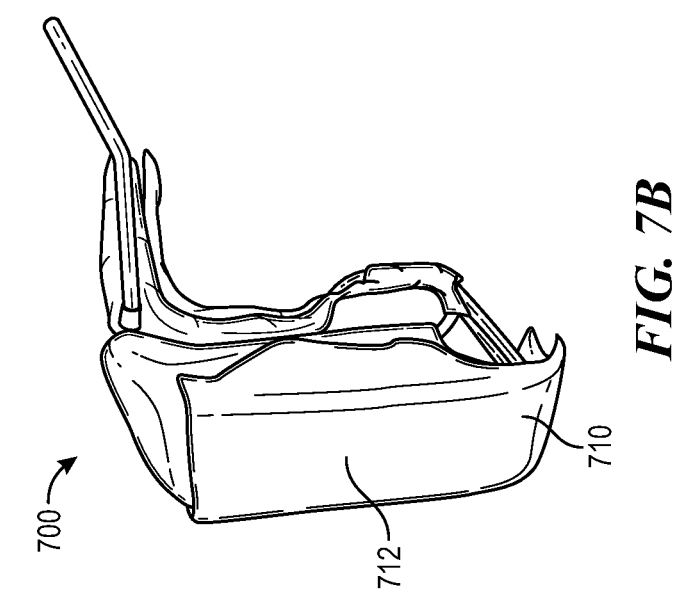
Figure 7A:
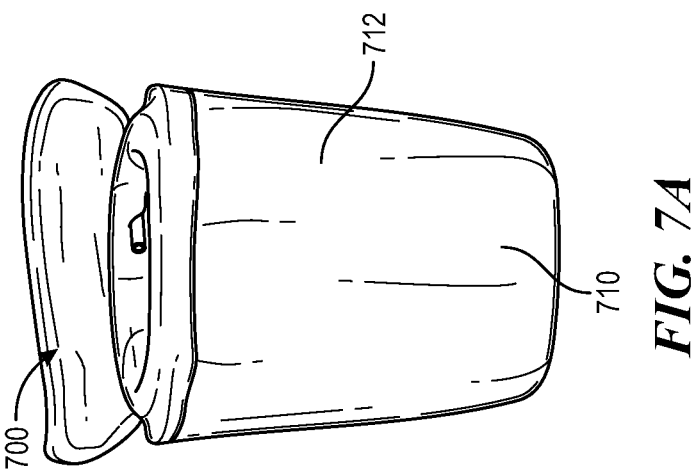
Figure 9A:
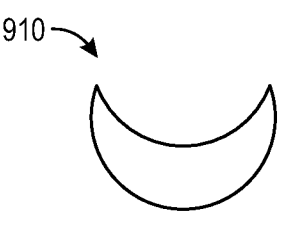
FIGS. 9A-9H are transverse cross-sectional views of various coaptation members in accordance with embodiments of the present technology.
Figure 9B:
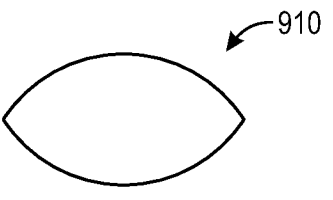
Figure 9C:
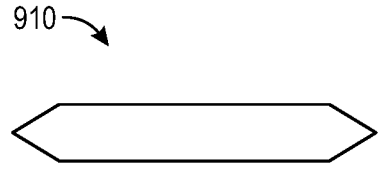
Figure 9D:
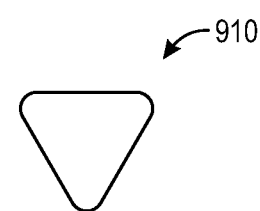
Figure 9E:
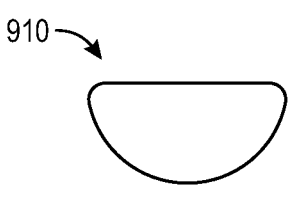
Figure 9F:
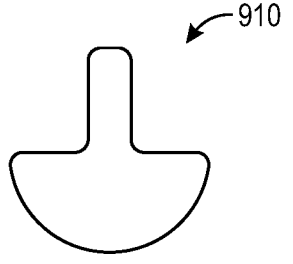
Figure 9G:
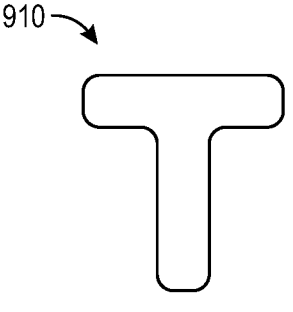
Figure 9H:
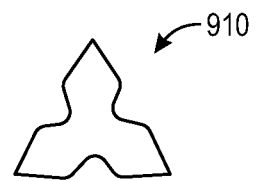
Figure 10:
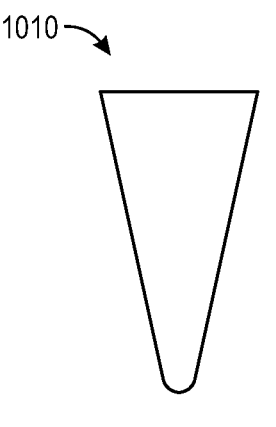
FIGS. 10A-10L are side cross-sectional views of various coaptation members in accordance with embodiments of the present technology.
Figure 10B:
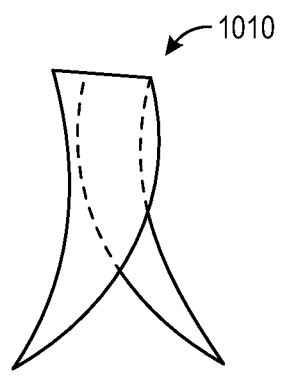
Figure 10C:
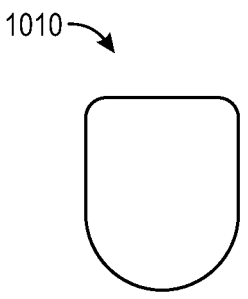
Figure 10D:
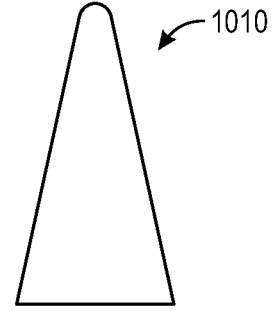
Figure 10E:
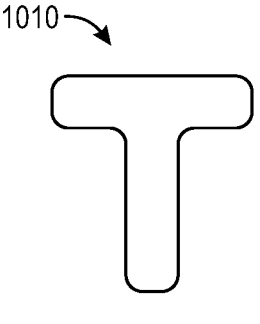
Figure 10F:
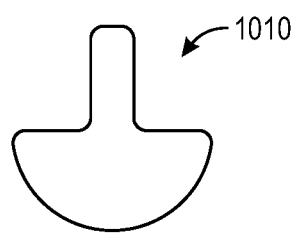

FIGS. 7A-7C are a front view, a side view, and a rear view, respectively, of a valve repair device 700 configured in accordance with embodiments of the present technology. Likewise, FIGS. 8A-8C are a front view, a side view, and a rear view, respectively, of a valve repair device 800 configured in accordance with embodiments of the present technology. The valve repair devices 700 and 800 of FIGS. 7A-7C and 8A-8C, respectively, can include some features that are at least generally similar in structure and function, or identical in structure and function, to the corresponding features of the valve repair device 600 of FIGS. 6A-6C and one another. For example, the valve repair device of FIGS. 7A-7C can include a coaptation member 710 that has a greater length (e.g., from top to bottom) than the coaptation member 610 of FIGS. 6A-6C, has a reduced profile (e.g., from front to back), and/or that has a generally flatter front face 712. The valve repair device 800 of FIGS. 8A-8C can include a pair of separate and individually actuatable clip mechanisms 830 and a coaptation member 810 that is shorter (reduced length from top to bottom) than the coaptation member 610 of FIGS. 6A-6C.

II. SELECTED EMBODIMENTS OF CARDIAC VALVE REPAIR DEVICES INCLUDING COAPTATION MEMBERS

In general, cardiac valve repair devices in accordance with the present technology can include a coaptation member having a shape (e.g., transverse cross-sectional shape, side cross-sectional shape, three-dimensional volumetric shape) and size (e.g., volume, area, cross-sectional dimension) selected to correspond with the natural shape of a coaptation line of a cardiac valve to, for example, fill a leak between and/or provide a coaptation surface for one more native leaflets of the cardiac valve. For example, all or a portion of the coaptation member can be positioned (e.g., centrally positioned) between the leaflets, or positioned with a bias toward one or more of the leaflets and/or the annulus of the cardiac valve. The coaptation member can be positioned to primarily displace one or more of the leaflets and/or primarily to fill a commissural gap between two or more of the leaflets. The shape of the coaptation member can be selected to encourage leaflet coaptation, fill areas of regurgitation, fixate leaflets into clip mechanisms, provide a coaptation surface, facilitate native coaptation in areas not in contact with the implant device, minimize coaptation member movement/deflection during the cardiac cycle, and/or suppress native leaflet flail. For example, shapes that narrow in the coaptation zone may pull the leaflets together, increasing coaptation depth along the coaptation line and creating an annuloplasty effect. Conversely, shapes that widen along the coaptation zone can uniquely fill regurgitation spaces (e.g., clefts) in the distended anatomy, further create coaptation redundancies, and/or fill space left by the native leaflets. In some embodiments, the slight annuloplasty effect of approximating the leaflets can combine with the coaptation redundancy of the coaptation member to create an overall more competent valve. In some embodiments, the size and/or orientation of the coaptation member can be adjusted by a delivery system used to deliver the cardiac valve repair device before the delivery system is removed.

In some embodiments, the coaptation member can be shaped with an atrial to ventricular gradient—such as a taper or twist—configured to direct forward flow, minimize trans-valvular gradient, maximize pressure recovery, promote native leaflet closure, and/or mimic the natural eddies of blood flow throughout the cardiac cycle. The coaptation member can be covered by a fabric covering that facilitates ingrowth into the leaflets to provide robust long-term fixation, while also providing an atraumatic surface for coapting with the native leaflets. In some embodiments, the coaptation member can include foam under the fabric covering to provide for further atraumatic coaptation of leaflets against the coaptation member. The coaptation member can be supported by braided wire, nitinol wire forms superelastic nitinol stent-like frames, expanding sponge-like materials, polymer balloons, and/or other support structures.

More specifically, for example, FIGS. 9A-9H are transverse cross-sectional views (e.g., top or atrial views, bottom or ventricular views) of various coaptation members 910 in accordance with embodiments of the present technology. As shown in FIGS. 9A-9H, respectively, the coaptation member 910 can have a crescent shape, oval shape, elongated polygonal shape, triangular or asymmetrical hexagonal shape, semicircular shape, mushroom-like or umbrella-like shape, T-shape, and/or star shape (e.g., having three or more points). Similarly, FIGS. 10A-10L are side cross-sectional views (e.g., anterior-posterior views and/or commissure-commissure views) of various coaptation members 1010 in accordance with embodiments of the present technology. As shown in FIGS. 10A-10L, respectively, the coaptation member 1010 can have a triangular shape (e.g., isosceles triangular shape), curved or fin-like shape, oval shape, inverted-triangular shape, elongated T-shape, inverted umbrella-like shape, trapezoidal shape, semicircular shape, laterally-elongated T-shape, square shape, circular shape, or bow-tie-like shape (e.g., including a pair of trapezoidal portions extending from a central member). The various transverse cross-sectional and side cross-sectional shapes of the coaptation members 910, 1010 can be combined to form coaptation members of different shapes and sizes. Likewise, in other embodiments, coaptation members in accordance with the present technology can have other shapes.

Figures 11A, 11B, 11C, 11D:
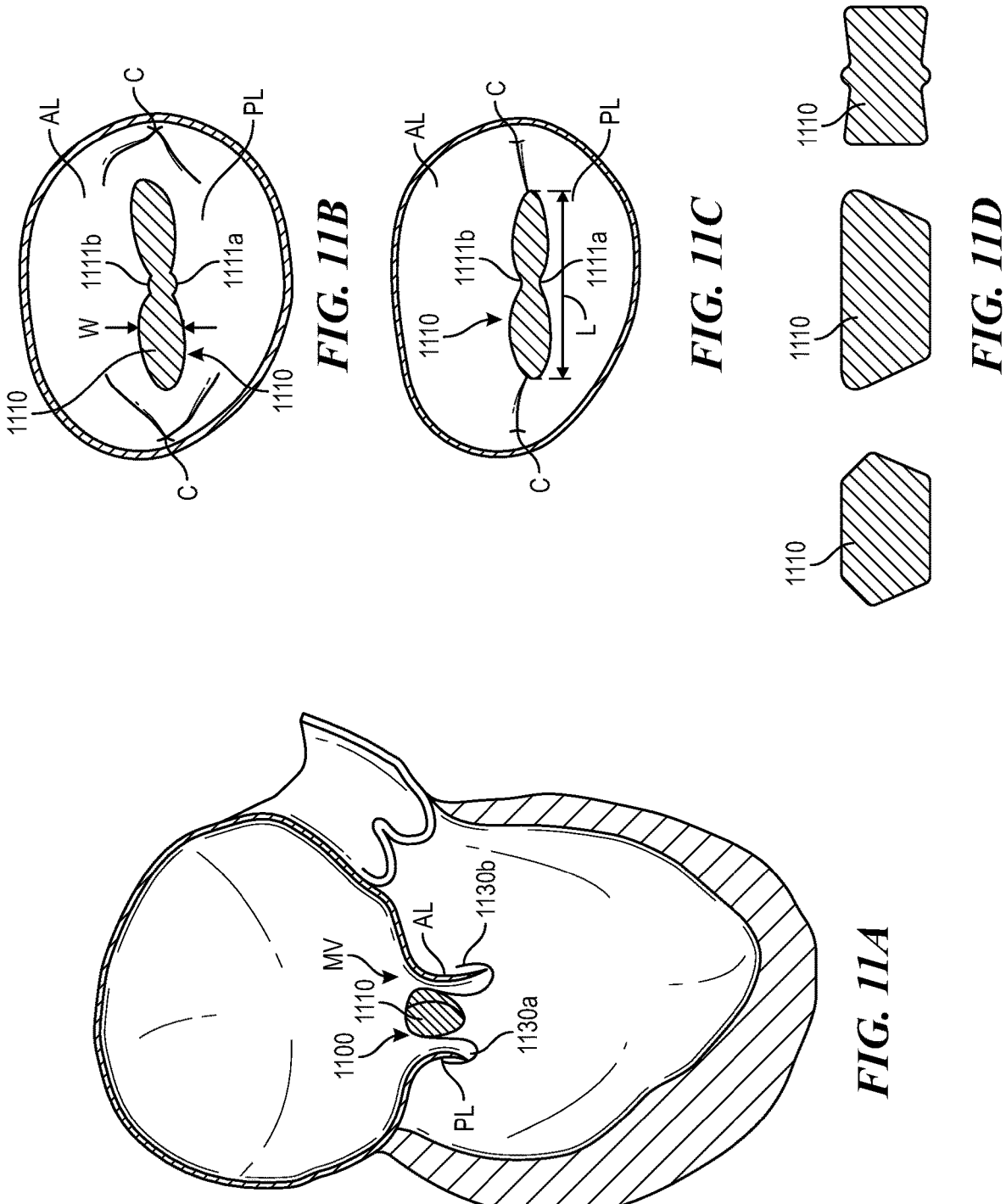
FIG. 11A is a side cross-sectional view of a valve repair device implanted at a mitral valve in accordance with embodiments of the present technology.
FIGS. 11B and 11C are transverse cross-sectional views of the valve repair device of FIG. 11A during diastole and systole, respectively, in accordance with embodiments of the present technology.
FIG. 11D illustrates various representative side views of the coaptation member shown in FIGS. 11B and 11C as viewed from a commissure-to-commissure perspective in accordance with embodiments of the present technology.

The various coaptation member shapes illustrated in FIGS. 9A-10L can be combined and/or modified based on, for example, the particular anatomy and/or abnormality of a cardiac valve at which the cardiac valve repair device is to be implanted. For example, FIG. 11A is a side cross-sectional view of a valve repair device 1100 implanted at a mitral valve MV in accordance with embodiments of the present technology. FIGS. 11B and 11C are transverse cross-sectional views of the valve repair device 1100 of FIG. 11A during diastole and systole, respectively, in accordance with embodiments of the present technology. Referring to FIGS. 11A-11C together, the valve repair device 1100 includes a coaptation member 1110 having a circular or oval side cross-sectional shape and an elongated-hourglass-like or peanut-like transverse cross-sectional shape. More specifically, the coaptation member 1110 can have a first elongate side portion 1111a and a second elongate side portion 1111b configured to be positioned adjacent the posterior leaflet PL and the anterior leaflet AL, respectively. The coaptation member 1110 can further include (i) a width W (FIG. 11B) extending between the first and second side portions 1111*a-b* and perpendicular to an axis extending between commissures C between the anterior leaflet AL and the posterior leaflet PL (e.g., in a direction between the leaflets), and (ii) a length L (FIG. 11C) generally orthogonal to the width W and extending along the axis between commissures C. The length L can be greater than the width W such that the coaptation member has the elongate transverse cross-sectional shape. The shape of the coaptation member 1110 can facilitate the coaptation of the anterior leaflet AL or the posterior leaflet PL of the mitral valve MV against the surface thereof, as shown in FIG. 11C. In other embodiments, the coaptation member 1110 of the valve repair device 1100 can have any of the side cross-sectional shapes shown in FIG. 11D including, for example, a pentagonal, trapezoidal, or bow-tie-like shape.

In the illustrated embodiment, the valve repair device 1100 includes clip mechanisms 1130 (including an individually identified first clip mechanism 1130*a* and a second clip mechanism 1130*b* shown in FIG. 11A) configured to secure the valve repair device 1100 to one or both of the anterior leaflet AL or the posterior leaflet PL of the mitral valve MV. More specifically, the first clip mechanism 1130*a* can extend from the first elongate side portion 1111*a* to capture the posterior leaflet PL to at least partially secure the posterior leaflet PL against the coaptation member 1110, and the second clip mechanism 1130*b* can extend from the second elongate side portion 1111*b* and capture the anterior leaflet AL to at least partially secure the anterior leaflet AL at against the coaptation member 1110.

FIG. 12A is a side cross-sectional view of a valve repair device 1200 implanted at the mitral valve MV in accordance with embodiments of the present technology. FIGS. 12B and 12C are transverse cross-sectional views of the valve repair device 1200 of FIG. 12A during diastole and systole, respectively, in accordance with embodiments of the present technology. Referring to FIGS. 12A-12C together, the valve repair device 1200 includes a coaptation member 1210 having (i) a dual-finned cross-sectional shape including, for example, a first fin portion 1215 (FIG. 12A) having a concave surface facing the posterior leaflet PL and a second fin portion 1216 (FIG. 12A) having a concave surface facing the anterior leaflet AL and (ii) an elongate oval or skewed-hourglass transverse cross-sectional shape. In some embodiments, the coaptation member 1210 can flex between the skewed-hourglass shape shown in FIG. 12B to the oval shape of FIG. 12C to facilitate the coaptation of the anterior leaflet AL or the posterior leaflet PL of the mitral valve MV against the surface thereof, as shown in FIG. 12C. In other embodiments, the coaptation member 1210 has a constant shape during both diastole and systole. In yet other embodiments, the coaptation member 1210 of the valve repair device 1200 can have any of the side cross-sectional shapes shown in FIG. 12D including, for example, a trapezoidal, flared- or curved-rectangular, or rectangular shape. The valve repair device 1200 can be secured in position relative to the mitral valve MV via one or more clip mechanisms, lock mechanisms, anchors, and/or other securing features described herein (not shown).

Figures 13A, 13B, 13C:
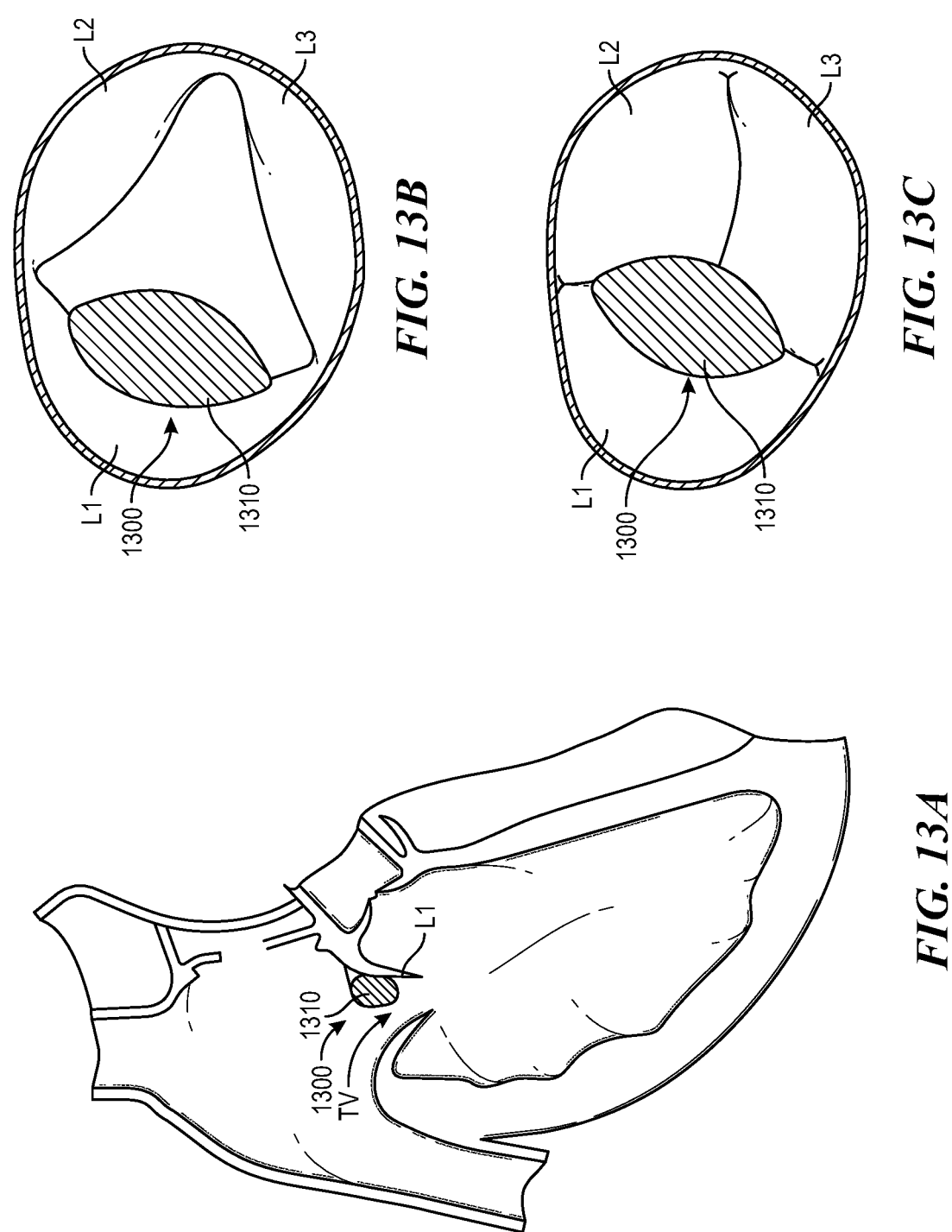
FIG. 13A is a side cross-sectional view of a valve repair device implanted at a tricuspid valve in accordance with embodiments of the present technology.
FIGS. 13B and 13C are transverse cross-sectional views of the valve repair device of FIG. 13A during diastole and systole, respectively, in accordance with embodiments of the present technology.

FIG. 13A is a side cross-sectional view of a valve repair device 1300 implanted at a tricuspid valve TV in accordance with embodiments of the present technology. FIGS. 13B and 13C are transverse cross-sectional views of the valve repair device 1300 of FIG. 13A during diastole and systole, respectively, in accordance with embodiments of the present technology. Referring to FIGS. 13A-13C together, the valve repair device 1300 includes a coaptation member 1310 having a generally circular side cross-sectional shape and an oval transverse cross-sectional shape. In the illustrated embodiment, the coaptation member 1310 can be secured to and/or against a first leaflet L1 of the tricuspid valve TV, such as the posterior leaflet, via one or more clip mechanisms, anchors, and/or other securing features described herein (not shown). In other embodiments, the coaptation member 1310 can additionally or alternatively be secured to and/or against a second leaflet L2 (e.g., the anterior leaflet) and/or a third leaflet L3 (e.g., the septal leaflet). The coaptation member 1310 provides a coaptation surface for the first and second leaflets L2 and L3 as shown in, for example, FIG. 13C.

Figures 14A, 14B, 14C, 14D:
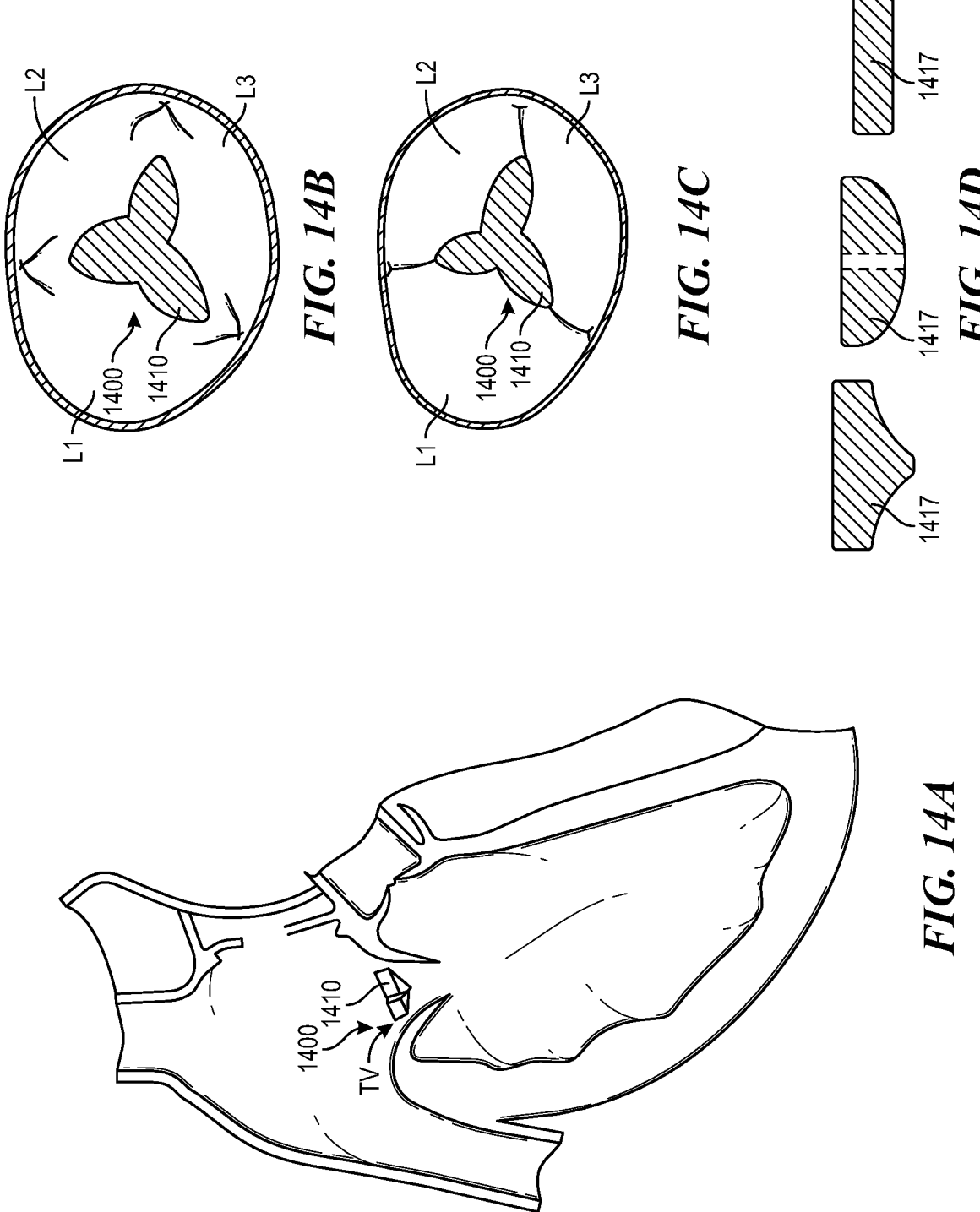
FIG. 14A is a side cross-sectional view of a valve repair device implanted at the tricuspid valve in accordance with embodiments of the present technology.
FIGS. 14B and 14C are transverse cross-sectional views of the valve repair device of FIG. 14A during diastole and systole, respectively, in accordance with embodiments of the present technology.
FIG. 14D illustrates various representative side views of the coaptation member shown in FIGS. 14B and 14C in accordance with embodiments of the present technology.

FIG. 14A is a side cross-sectional view of a valve repair device 1400 implanted at the tricuspid valve TV in accordance with embodiments of the present technology. FIGS. 14B and 14C are transverse cross-sectional views of the valve repair device of FIG. 14A during diastole and systole, respectively, in accordance with embodiments of the present technology. Referring to FIGS. 14A-14C together, the valve repair device 1400 includes a coaptation member 1410 having a generally pentagonal side cross-sectional shape and a three-pointed-star-like transverse cross-sectional shape. In the illustrated embodiment, the valve repair device 1400 can be secured between the leaflets L1-L3 of the tricuspid valve TV via one or more clip mechanisms, lock mechanisms, anchors, and/or other securing features described herein (not shown). As best seen in FIGS. 14B and 14C, the star-like transverse cross-sectional shape of the coaptation member 1410 can be oriented such that each of the points of the star generally points toward a corresponding one of the commissures between the leaflets L1-L3 to, for example, facilitate the coaptation of the leaflets L1-L3 against the surface of the coaptation member 1410. In other embodiments, the coaptation member 1410 of the valve repair device 1400 can have any of the side cross-sectional shapes shown in FIG. 14D including, for example, a curved-pentagonal, squared-semicircular, or rectangular shape. In addition, the relative size of the coaptation features may be varied to meet user needs though features within the coaptation surface and actuated through the delivery system as described herein.

Figure 15A:
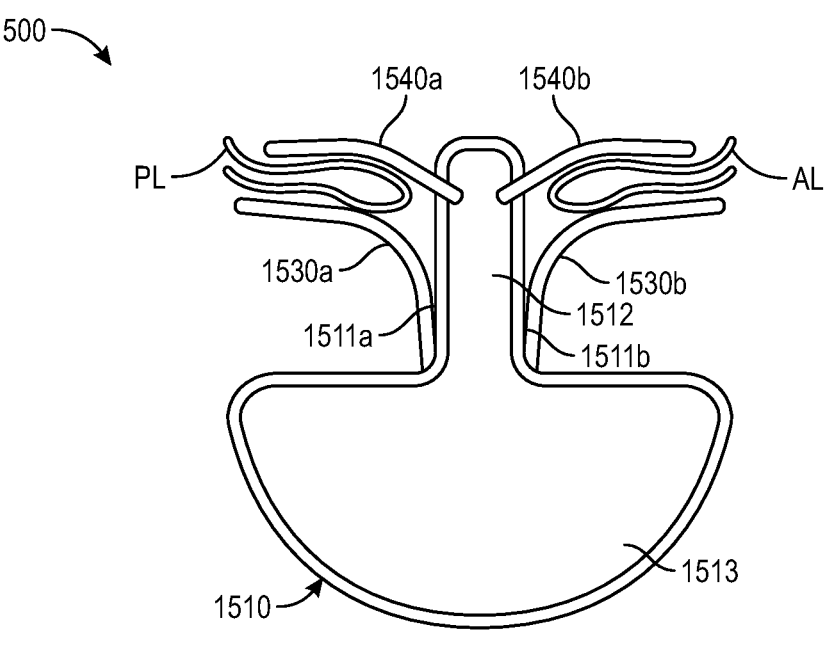
FIGS. 15A and 15B are a front view and a side view, respectively, of a valve repair device implanted at a mitral valve in accordance with embodiments of the present technology.
Figure 15B:
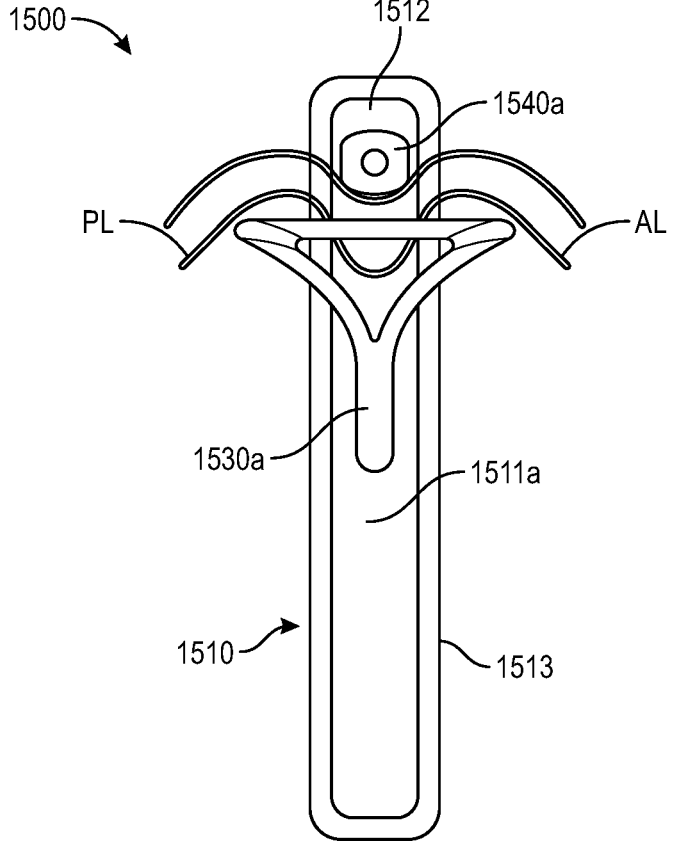

FIGS. 15A and 15B are a front view and a side view, respectively, of a valve repair device 1500 implanted at a mitral valve in accordance with embodiments of the present technology. FIG. 15C is a side cross-sectional view of the valve repair device 1500 of FIGS. 15A and 15B implanted at the mitral valve MV in accordance with embodiments of the present technology. FIGS. 15D and 15E are transverse cross-sectional views of the valve repair device 1500 of FIGS. 15A-15C during diastole and systole, respectively, in accordance with embodiments of the present technology. Referring to FIGS. 15A-15E together, the valve repair device 1500 includes a coaptation member 1510 having an inverted umbrella-like side cross-sectional shape and elongate curved-rectangular or oval-like transverse cross-sectional shape. In the illustrated embodiment, the coaptation member 1510 is narrow at the coaptation line and widens beneath the mitral valve MV within the anterior-posterior (AP) chord-free window. More specifically, the coaptation member 1510 can include a lower portion 1513 having a semicircular cross-sectional shape, an upper portion 1512 having a rectangular or cylindrical cross-sectional shape, a first side portion 1511*a* configured to be positioned adjacent to (e.g., face) the posterior leaflet PL, and a second side portion 1511*b* configured to be positioned adjacent to (e.g., face) the anterior leaflet AL.

In the illustrated embodiment, the valve repair device 1500 includes clip mechanisms 1530 (identified individually as a first clip mechanism 1530*a* and a second clip mechanism 1530*b*) and lock mechanisms 1540 (identified individually as a first lock mechanism 1540*a* and a second lock mechanism 1540*b*) extending from the coaptation member 1510. The clip mechanisms 1530 are configured to be positioned on the ventricular side of the mitral valve MV and to capture the posterior leaflet PL and the anterior leaflet AL for securing the leaflets against the coaptation member 1510. As described in greater detail below with reference to FIGS. 31A-40D, for example, the lock mechanisms 1540 (which can also be referred to as "locking clips," "stabilization members," "stabilization features," and iterations thereof) can be generally similar to the clip mechanisms 1530 but are configured to be positioned on the atrial side of the mitral valve MV (or another cardiac valve) and to engage the atrial side of the posterior leaflet PL, anterior leaflet AL, and/or other portions of the cardiac anatomy to, for example, help secure the coaptation member 1510 in a selected position relative to the mitral valve MV. In the illustrated embodiment, the first clip mechanism 1530*a* and the second clip mechanism 1530*b* extend from the first and second side portions 1511-*a*-*b*, respectively, of the upper portion 1512. Likewise, the first lock mechanism 1540*a* and the second lock mechanism 1540*b* extend from the first and second side portions 1511-*a*-*b*, respectively, of the upper portion 1512. In some embodiments, the lock mechanisms 1540 can be generally aligned over the clip mechanisms 1530 and can nest within the clip mechanisms 1530, causing the anterior and posterior leaflets AL and PL to plicate around the interlocking features of the device 1500. In some embodiments, after capturing the leaflets with the clip mechanisms 1530, the lock mechanisms 1540 can be simultaneously released (e.g., actuated) to align with the clip mechanisms 1530 and press onto the atrial side of the leaflets to provide further leaflet fixation.

FIG. 16A is a side cross-sectional view of a valve repair device 1600 implanted at the mitral valve MV in accordance with embodiments of the present technology. FIGS. 16B and 16C are transverse cross-sectional views of the valve repair device 1600 of FIGS. 16A and 16B during diastole and systole, respectively, in accordance with embodiments of the present technology. Referring to FIGS. 16A-16C together, the valve repair device 1600 includes features generally similar to the valve repair device of FIGS. 15A-15E including, for example, a coaptation member 1610, clip mechanisms 1630, and lock mechanisms 1640. In the illustrated embodiment, however, the coaptation member 1610 has a generally trapezoidal or rectilinear side cross-sectional shape. As shown in FIGS. 16B and 16C, in some embodiments the clip mechanisms 1630 and the lock mechanisms 1640 can cooperate to plicate the valve leaflets (e.g., the anterior and posterior leaflets AL and PL) independent of the shape of the coaptation member 1610.

Figure 17A:
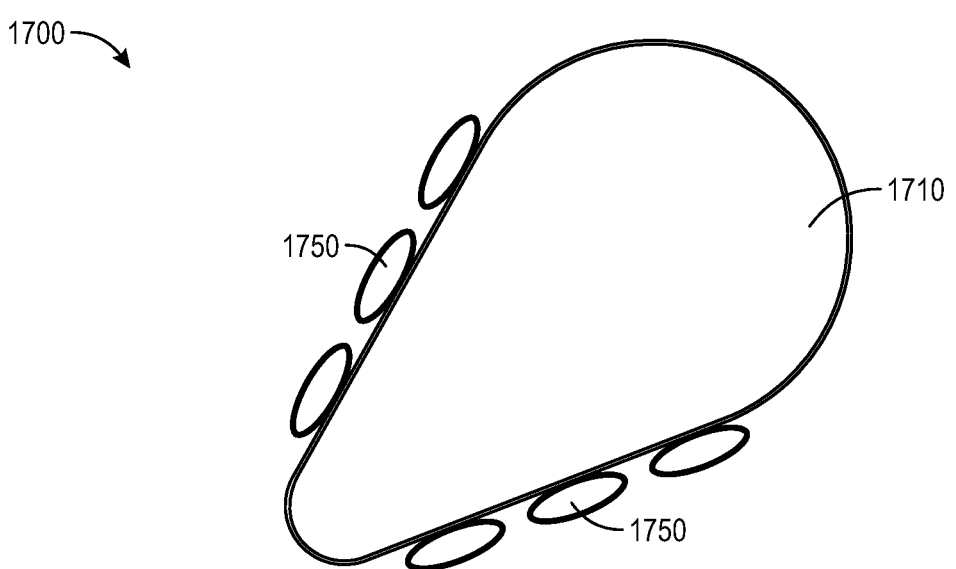
FIG. 17A is a top view of a valve repair device in accordance with embodiments of the present technology.
Figures 17B, 17C, 17D:
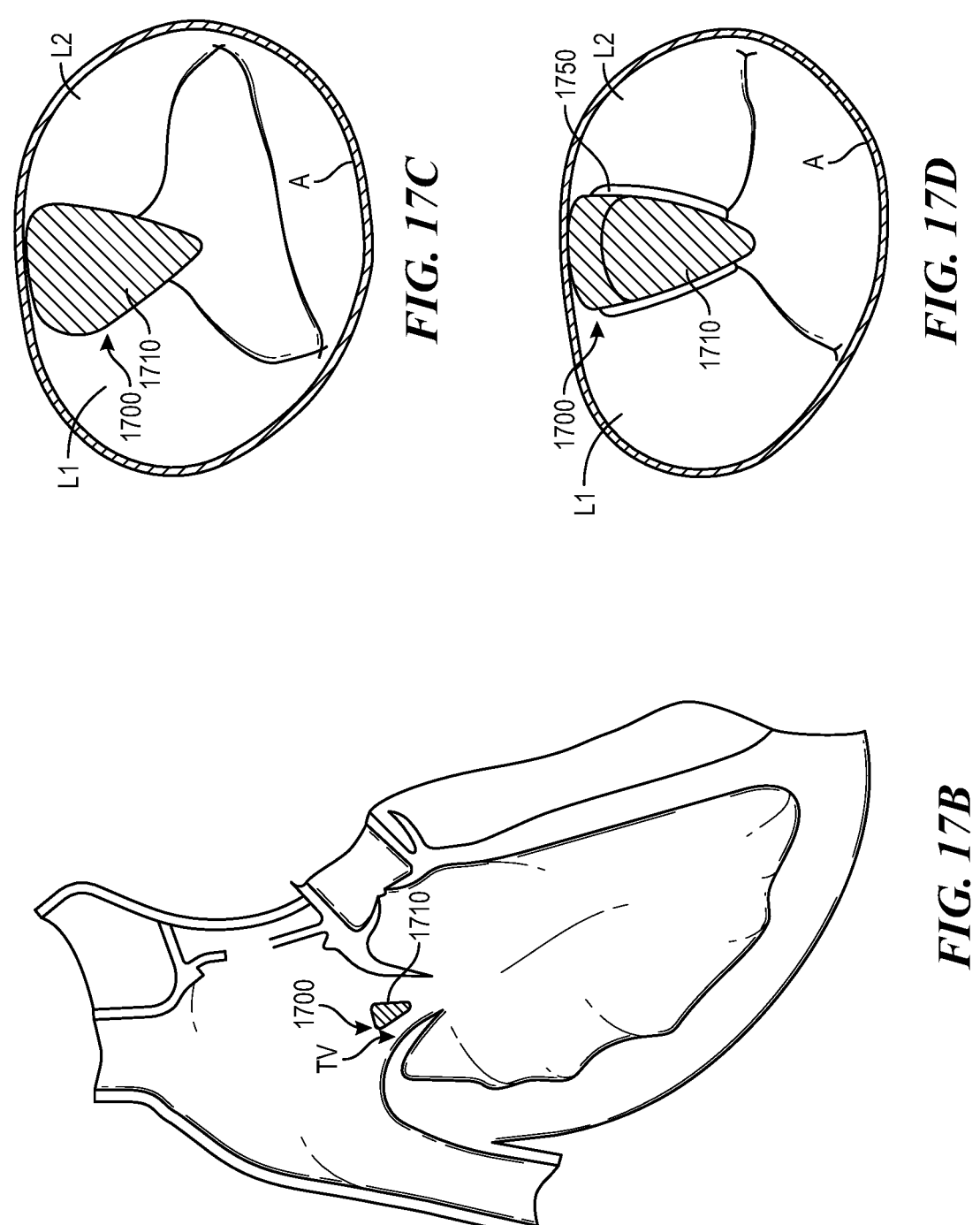
FIG. 17B is a side cross-sectional view of the valve repair device of FIGS. 17A implanted at the tricuspid valve in accordance with embodiments of the present technology.
FIGS. 17C and 17D are transverse cross-sectional views of the valve repair device of FIGS. 17A-17B during diastole and systole, respectively, in accordance with embodiments of the present technology.

FIG. 17A is a top view of a valve repair device 1700 in accordance with embodiments of the present technology. FIG. 17B is a side cross-sectional view of the valve repair device 1700 of FIG. 17A implanted at the tricuspid valve TV in accordance with embodiments of the present technology. FIGS. 17C and 17D are transverse cross-sectional views of the valve repair device of FIGS. 17A and 17B during diastole and systole, respectively, in accordance with embodiments of the present technology. Referring to FIGS.

17A-17D together, the valve repair device 1700 includes a coaptation member 1710 with generally triangular (e.g., teardrop-shaped, ovoid-shaped, guitar-pick-shaped) side and transverse cross-sectional shapes. The valve repair device 1700 further includes a fixation mechanism 1750 extending from one or more edges of coaptation member 1710 and configured to secure the coaptation member 1710 to two or more of the leaflets of the tricuspid valve, such as the leaflets L1 and L2 of the tricuspid valve TV. In some embodiments, the fixation mechanism 1750 can be generally similar or identical to any of the atrial and ventricular "sandwich" members described in detail below with reference to FIGS. 42A-60B. In other embodiments, the fixation mechanism 1750 can include one or more clip mechanisms, lock mechanisms, anchors, and/or other securing features described herein for fixating the device onto the leaflets of the valve. Accordingly, the coaptation member 1710 can (i) be positioned in the commissure between the leaflets, (ii) extend into the center of the tricuspid valve TV, and (iii) be shaped to fill a regurgitant orifice and prevent regurgitation. In some embodiments, the coaptation member 1710 can be biased toward an annulus A of the tricuspid valve TV to help fill a regurgitant space in the valve.

Figures 18A, 18B, 18C:
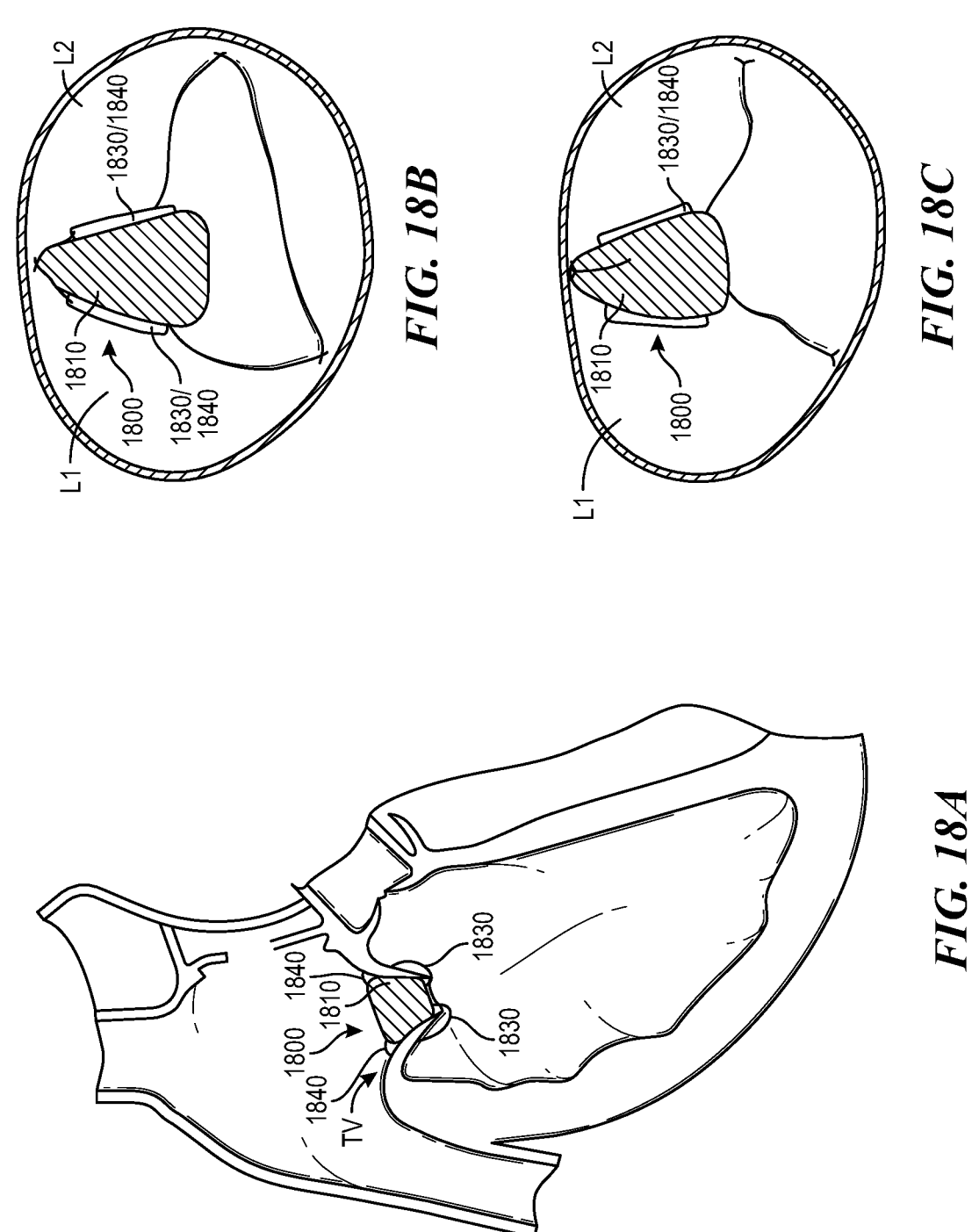
FIG. 18A is a side cross-sectional view of a valve repair device implanted at the tricuspid valve in accordance with additional embodiments of the present technology.
FIGS. 18B and 18C are transverse cross-sectional views of the valve repair device of FIGS. 18A during diastole and systole, respectively, in accordance with embodiments of the present technology.

FIG. 18A is a side cross-sectional view of a valve repair device 1800 implanted at the tricuspid valve TV in accordance with embodiments of the present technology. FIGS. 18B and 18C are transverse cross-sectional views of the valve repair device 1800 of FIG. 18A during diastole and systole, respectively, in accordance with embodiments of the present technology. Referring to FIGS. 18A-18C together, the valve repair device includes features generally similar to the valve repair device 1700 of FIGS. 17A-17D including, for example, a coaptation member 1810 secured to the leaflets L1 and L2. In the illustrated embodiment, however, the coaptation member 1810 has a fixation mechanism including (i) clip mechanisms 1830 configured to engage the ventricular sides of the leaflets L1 and L2 and (ii) lock mechanisms 1840 configured to engage the atrial side of the leaflets L1 and L2. In addition, the coaptation member 1810 orientation has been reversed from the valve repair devices 1700 of FIGS. 17A-17D with the narrow portion of the surface of the coaptation member 1810 oriented towards the commissure between the leaflets. Accordingly, in some aspects of the present technology the coaptation member 1810 can be oriented and/or placed in versatile manner between the leaflets. In general, the various coaptation members of the present technology can be optionally placed in different orientations depending on the specific application of the valve and valve repair device.

In some embodiments, the coaptation member 1810 is expandable. For example, the coaptation member 1810 can include an inflatable bladder or means for mechanically expanding the coaptation member 1810. In some aspects of the present technology, the coaptation member 1810 can be expanded further into the orifice of the tricuspid valve TV. For example, the coaptation member 1810 can be selectively expanded by a physician or other operator until regurgitation of the tricuspid valve TV is sufficiently reduced.

Figure 19:
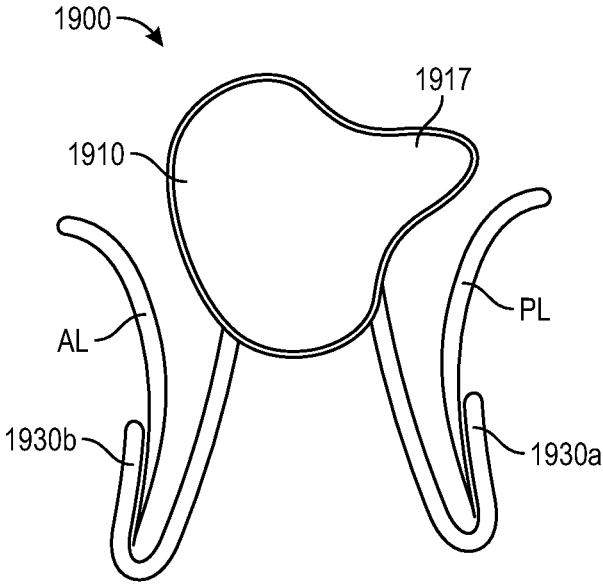
FIG. 19 is a side view of a valve repair device configured to be implanted at, for example, a mitral valve in accordance with embodiments of the present technology.

FIG. 19 is a side view of a valve repair device 1900 configured to be implanted at, for example, a mitral valve in accordance with embodiments of the present technology. In the illustrated embodiment, the valve repair device 1900 includes a posterior clip 1930*a* and an anterior clip 1930*b* for fixing the coaptation member 1910 (e.g., baffle) to the posterior leaflet PL and the anterior leaflet AL of the mitral valve, respectively. The coaptation member 1910 can include a protrusion or point 1917 configured (e.g., shaped, sized) to engage the anterior leaflet above the anterior clip 1930*b*.

Figures 20, 21:
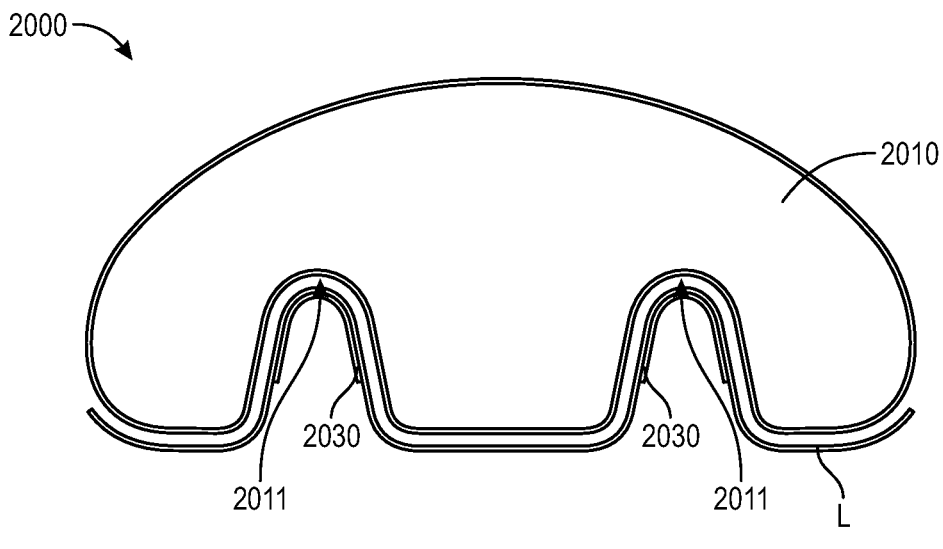
FIG. 20 is a top cross-sectional view of a valve repair device implanted at a cardiac valve in accordance with embodiments of the present technology.
FIG. 21 is a top cross-sectional view of a valve repair device configured in accordance with embodiments of the present technology.

FIG. 20 is a top cross-sectional view of a valve repair device 2000 implanted at a cardiac valve in accordance with embodiments of the present technology. In the illustrated embodiment, the valve repair device 2000 includes a coaptation member 2010 having a rear surface defining a pair of recesses 2011 each configured to receive a corresponding clip mechanism 2030 or corresponding portion of the clip mechanism 2030. The clip mechanisms 2030 can secure the coaptation member 2010 to a leaflet L of the cardiac valve. In some aspects of the present technology, positioning the clip mechanisms 2030 in the recesses 2011 can increase waffling of the leaflet L between the clip mechanisms 2030 and the coaptation member 2010. That is, for example, the valve repair device 2000 can be configured to cause the leaflet to traverse a more tortuous path against the coaptation member 2010 to improve the stability (e.g., by inhibiting or even preventing excessive deflection of the coaptation member 2010) and securement of the valve repair device 2000 at the cardiac valve.

FIG. 21 is a top cross-sectional view of a valve repair device 2100 configured in accordance with embodiments of the present technology. In the illustrated embodiment, the valve repair device 2100 includes a coaptation member 2110 having a bean-like shape (e.g., curved in a crescent shape) including a recess 2111 located at a rear surface thereof. Similar to the embodiment illustrated in FIG. 21, one or more clip mechanisms (not shown) can be positioned in the recess 2111 to, for example, increase waffling of a leaflet of a cardiac valve (not shown) between the clip mechanism(s) and the coaptation member 2110.

FIG. 22 is a table including images of valve repair devices having coaptation members of various shapes in accordance with embodiments of the present technology.

III. SELECTED EMBODIMENTS OF CARDIAC VALVE REPAIR DEVICES INCLUDING COAPTATION MEMBERS CONFIGURED TO MOVE AND/OR EXPAND

In some embodiments, cardiac valve repair devices in accordance with the present technology can include a coaptation member configured to pivot, expand, or otherwise move to, for example, facilitate positioning of the coaptation member at and/or in a desired position relative to a cardiac valve.

Figure 23A:
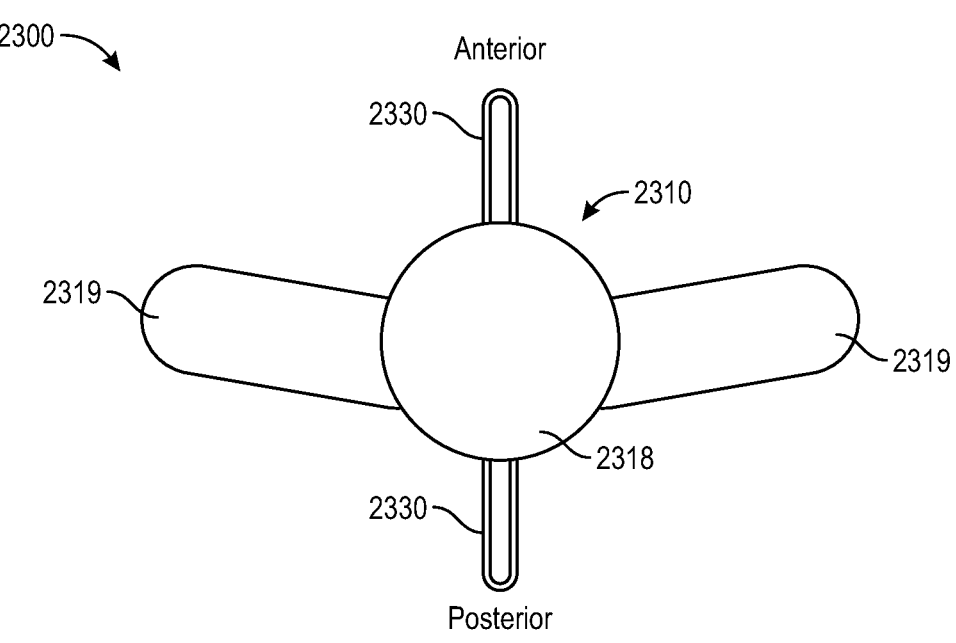
FIGS. 23A and 23B are a top view and a side perspective view, respectively, of a valve repair device including a an expandable coaptation member in accordance with embodiments of the present technology.
Figure 23B:
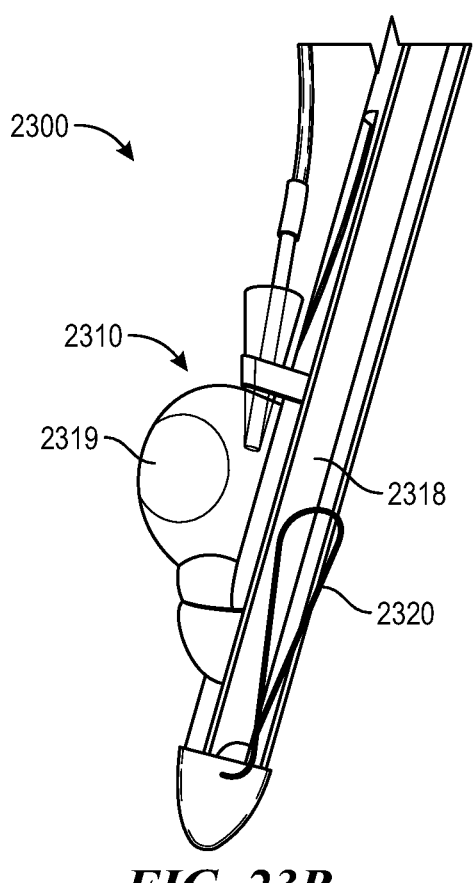
Figures 23C, 23D, 23E:
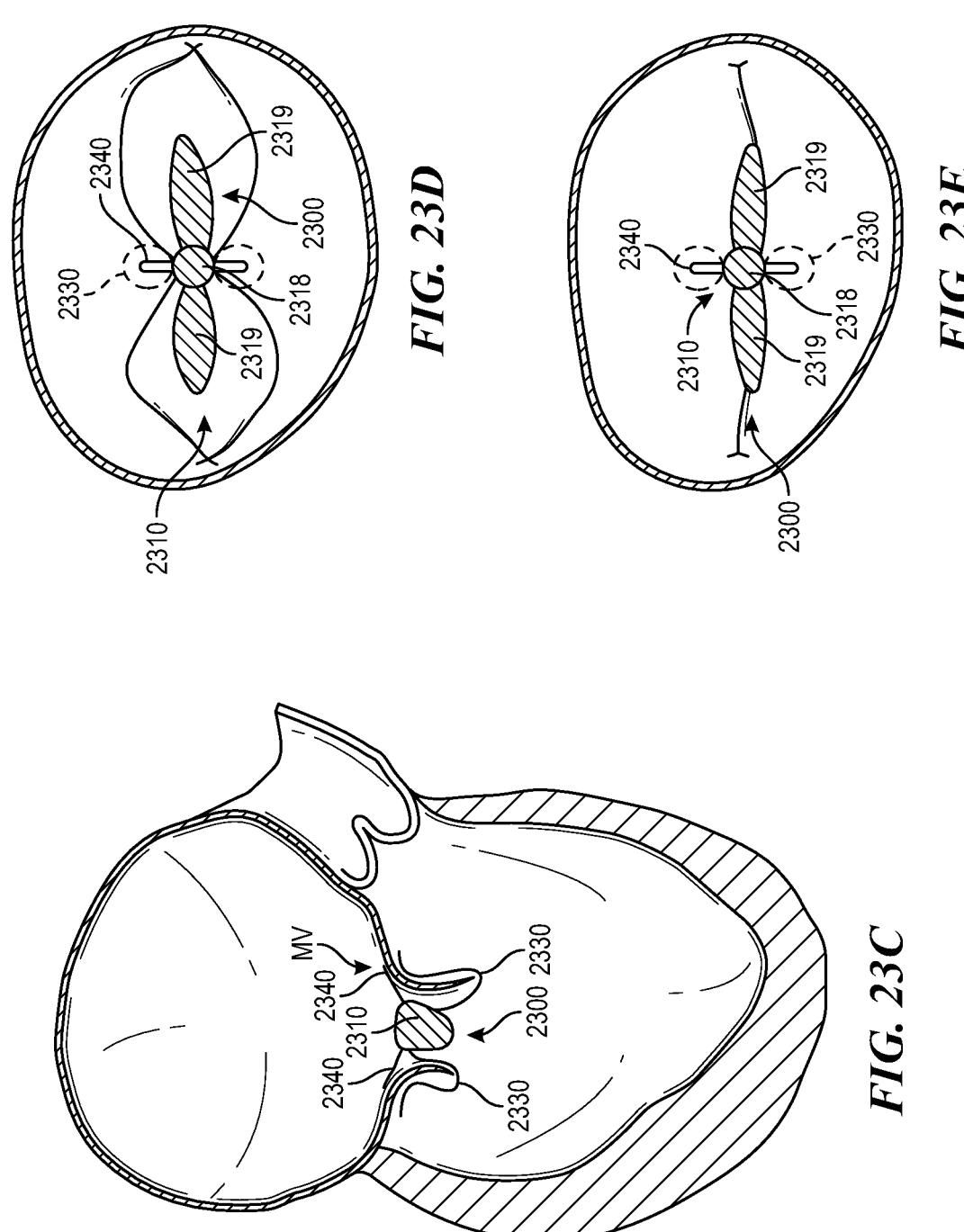
FIG. 23C is a side cross-sectional view of the valve repair device of FIGS. 23A and 23B implanted at the mitral valve in accordance with embodiments of the present technology.
FIGS. 23D and 23E are transverse cross-sectional views of the valve repair device of FIG. 23A-23C during diastole and systole, respectively, in accordance with embodiments of the present technology.

For example, FIGS. 23A and 23B are a top view and a side perspective view, respectively, of a valve repair device 2300 including an expandable coaptation member 2310 in accordance with embodiments of the present technology. FIG. 23C is a side cross-sectional view of the valve repair device 2300 of FIGS. 23A and 23B implanted at the mitral valve MV in accordance with embodiments of the present technology. FIGS. 23D and 23E are transverse cross-sectional views of the valve repair device 2300 of FIG. 23A-23C during diastole and systole, respectively, in accordance with embodiments of the present technology. Referring to FIGS. 23A-23E together, the coaptation member 2310 includes a static central portion 2318 and a pair of expandable side portions 2319 extending from (e.g., coupled to, integrally formed with) the central portion 2318. In the illustrated embodiment, the expandable side portions 2319 protrude into the commissure-commissure (C-C) direction from the central portion 2318. The expandable side portions 2319 can include stent-like structures, balloons, and/or other expandable structures. In some embodiments, the protrusion of the side portions 2319 in the C-C direction can be adjusted (e.g., fine-tuned) by, for example, controlling the amount of expansion of the side portions 2319. For example, the side portions 2319 can expand independently from each side of the static central portion 2318. In some embodiments, the side portions 2319 can be covered with a fabric (e.g., a non-woven fabric), such as expanded polytetrafluoroethylene (ePTFE) to allow for atraumatic coaptation of the native leaflets against the side portions 2319. The valve repair device 2300 can include a pair of clip mechanisms 2330 for capturing the leaflets of the valve. In some embodiments, the valve repair device 2300 can further include lock mechanisms 2340 configured to engage the atrial side of the leaflets above the clip mechanisms 2330.

Figure 24A:
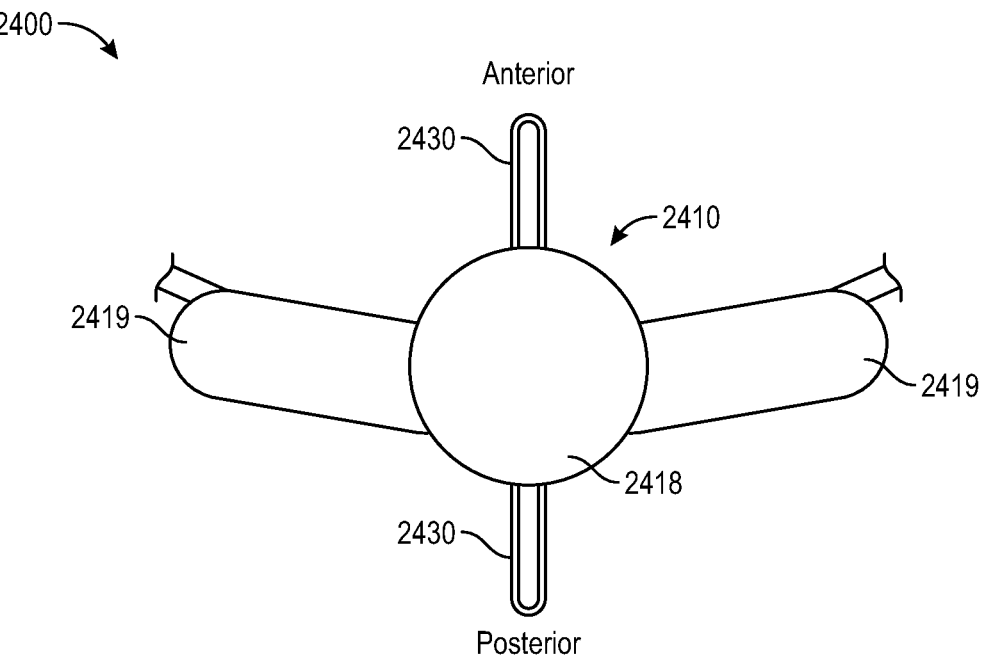
FIGS. 24A and 24B are top views of a valve repair device in a first adjusted position and a second adjusted position, respectively, in accordance with embodiments of the present technology.
Figure 24B:
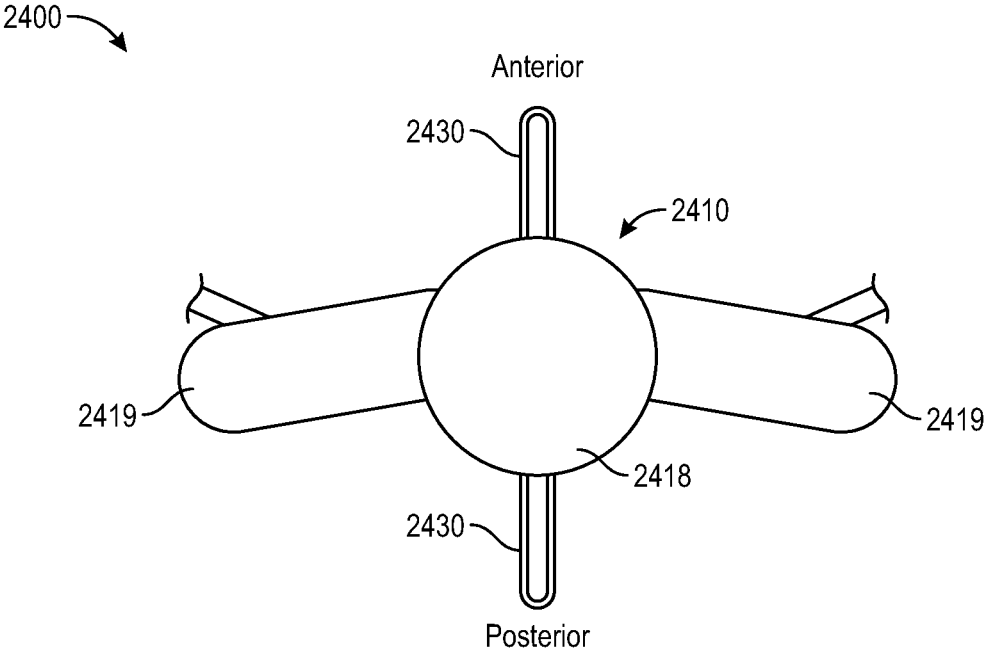
Figures 24C, 24D, 24E:
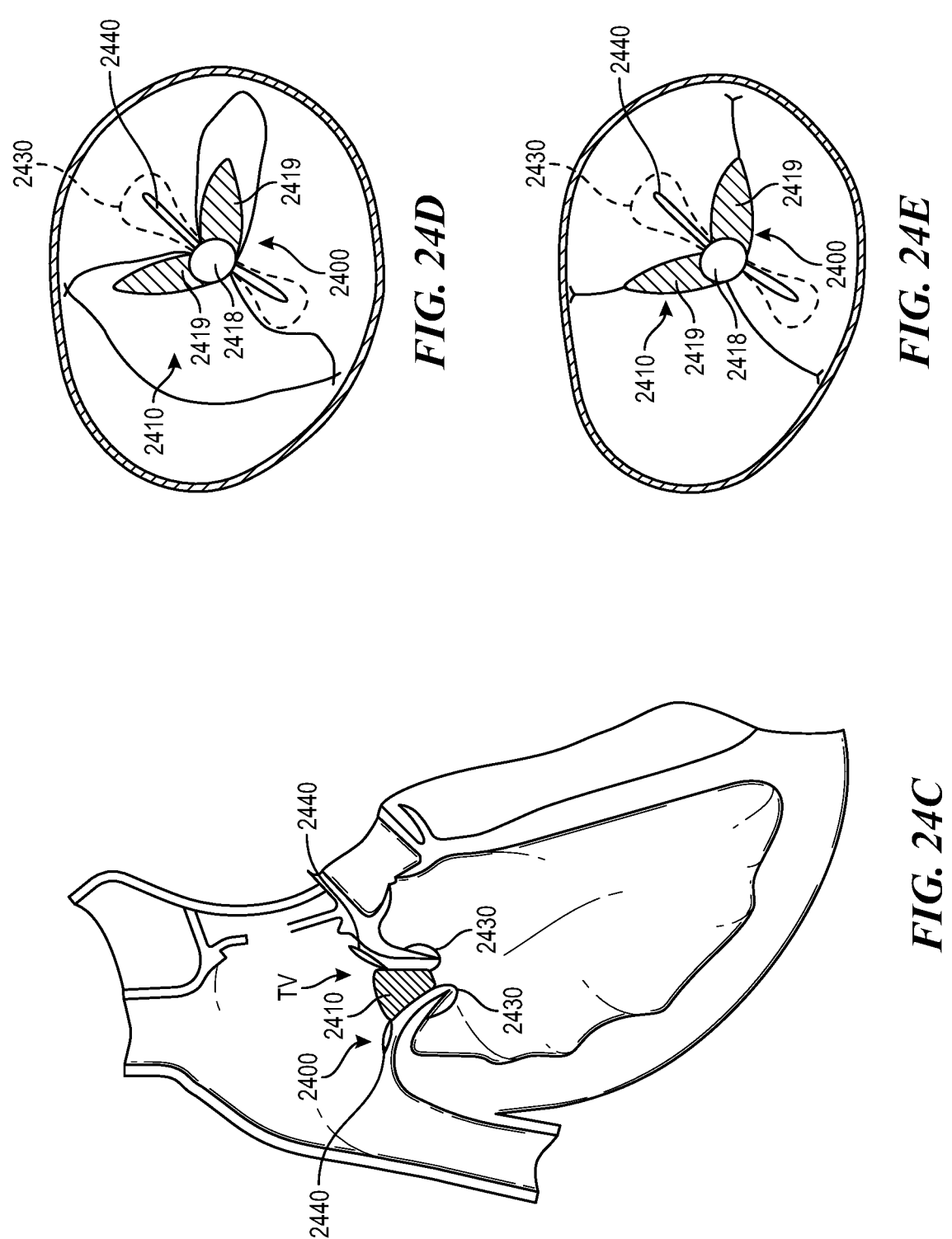

FIGS. 24A and 24B are top views of a valve repair device 2400 in a first position (e.g., first configuration, initial position) and a second position (e.g., second configuration, deployed position), respectively, in accordance with embodiments of the present technology. FIGS. 24C and 24F are side cross-sectional views of the valve repair device 2400 of FIGS. 24A and 24B implanted at the tricuspid valve TV and the mitral valve MV, respectively, in accordance with embodiments of the present technology. FIGS. 24D and 24E are transverse cross-sectional views of the valve repair device 2400 of FIGS. 24A and 24B implanted at the tricuspid valve TV during diastole and systole, respectively, in accordance with embodiments of the present technology. FIGS. 24G and 24H are transverse cross-sectional views of the valve repair device 2400 of FIGS. 24A and 24B implanted at the mitral valve MV during diastole and systole, respectively, in accordance with embodiments of the present technology. Referring to FIGS. 24A-24H together, the valve repair device includes features generally similar to the valve repair device of FIGS. 23-23E including, for example, a coaptation member 2410 including a central portion 2418 and a pair of expandable side portions 2419, and clip mechanisms 2430 and lock mechanisms 2440 coupled to the coaptation member 2410. In the illustrated embodiment, however, the side portions 2419 are movable (e.g., rotatable, pivotable) relative to the central portion 2418 and the clip mechanisms 2430 and the lock mechanisms 2440. Accordingly, the side portions 2419 can be rotated relative to, for example, the anterior and posterior positions of the clip mechanisms 2430 to treat non-central valve regurgitation. That is, the side portions 2419 can be selectively rotated to fill areas of valve regurgitation. In some embodiments, the rotation or pivoting of the side portions 2419 can be actively controlled by a physician or other operator via a mechanism of an associated delivery system. In other embodiments, the side portions 2419 are configured to passively rotate to align with the line of coaptation of the native leaflets. In some embodiments, the side portions 2419 and/or other portions of the coaptation member 2410 can be modular to allow for their placement after initial clipping of the native valve leaflets (e.g., the anterior leaflet AL and the posterior leaflet PL of the mitral valve MV).

Figure 25A:
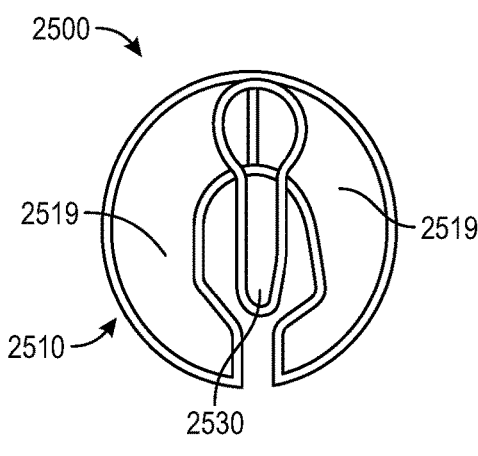
FIGS. 25A and 25B are a side view and a top view, respectively, of a valve repair device in an unexpanded position in accordance with embodiments of the present technology.
Figure 25B:
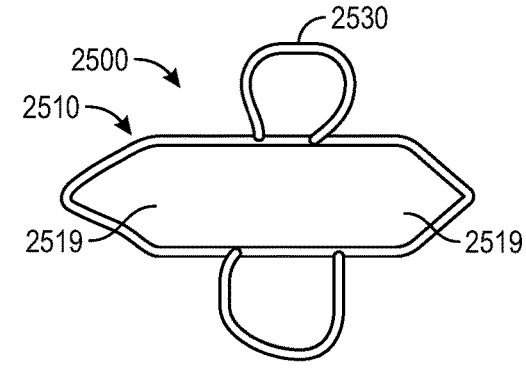
Figure 25C:
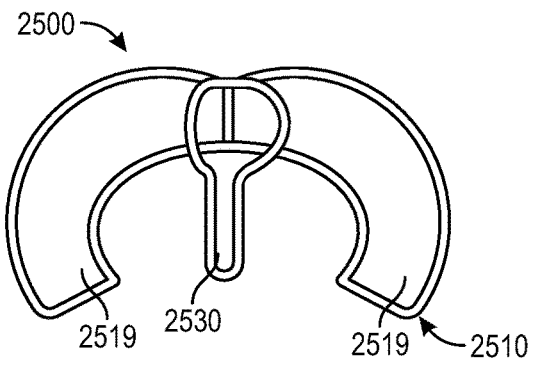
FIGS. 25C and 25D are a side view and a top view, respectively, of the valve repair device of FIGS. 25A and 25B in an expanded in accordance with embodiments of the present technology.
Figure 25D:
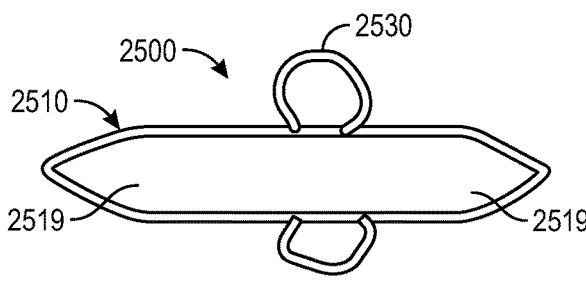
Figures 25H, 25I, 25J:
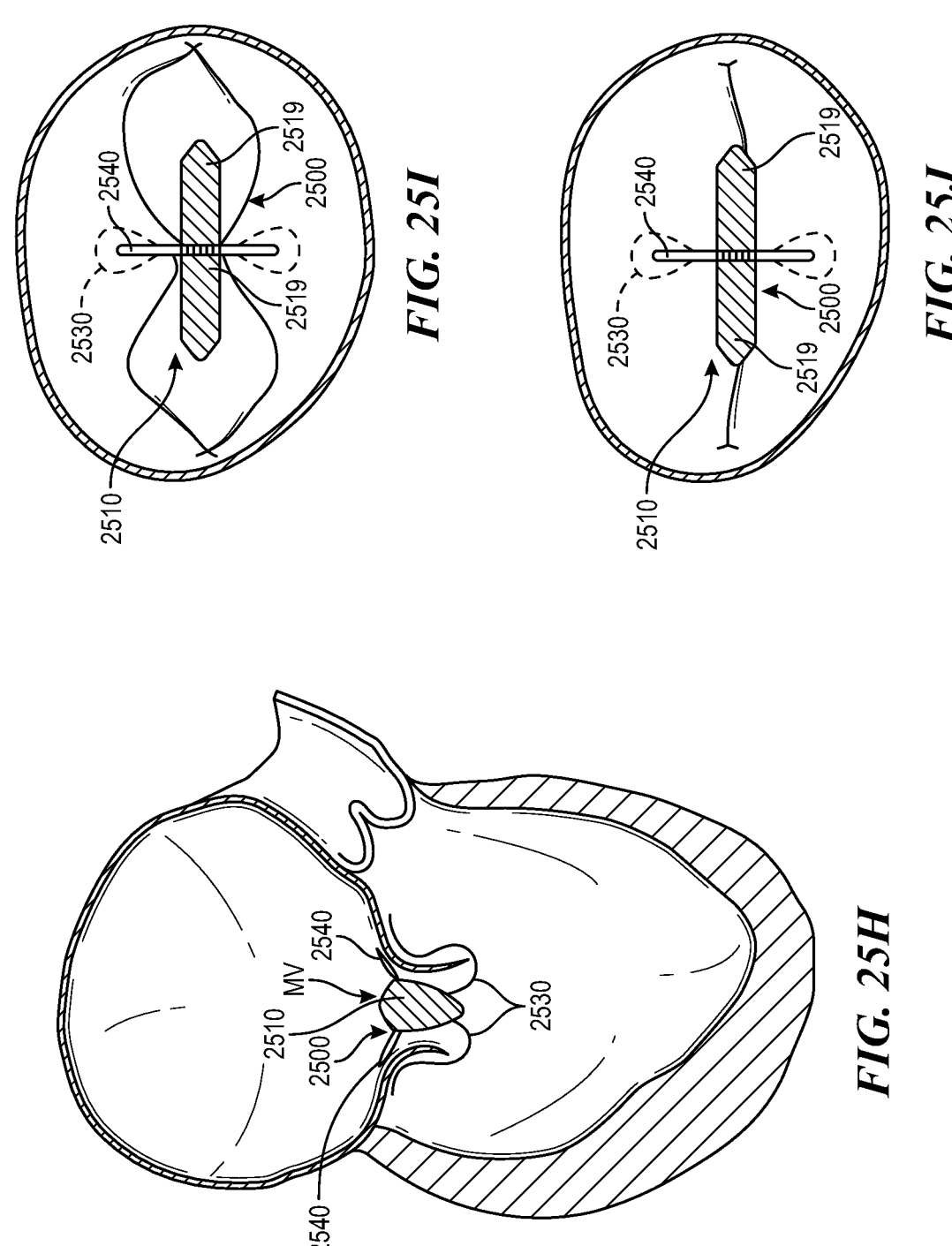

FIGS. 25A and 25B are a side view and a top view, respectively, of a valve repair device 2500 in an unexpanded position (e.g., first position, first configuration, initial position) in accordance with embodiments of the present technology. FIGS. 25C and 25D are a side view and a top view, respectively, of the valve repair device 2500 of FIGS. 25A and 25B in an expanded position (e.g., second position, second configuration, deployed position) in accordance with embodiments of the present technology. FIGS. 25E and 25H are side cross-sectional views of the valve repair device 2500 of FIGS. 25A-25D implanted at the mitral valve MV in the unexpanded position and the expanded position, respectively, in accordance with embodiments of the present technology. FIGS. 25F and 25G are transverse cross-sectional views of the valve repair device 2500 of FIGS. 25A-25D implanted at the mitral valve MV in the unexpanded position during diastole and systole, respectively, in accordance with embodiments of the present technology. FIGS. 25I and 25J are transverse cross-sectional views of the valve repair device 2500 of FIGS. 25A-25D implanted at the mitral valve MV in the expanded position during diastole and systole, respectively, in accordance with embodiments of the present technology.

Referring to FIGS. 25A-25J together, the valve repair device 2500 includes a coaptation member 2510 having a pair of hinged side portions 2519 that facilitate the expansion of the coaptation member 2510 in, for example, the C-C direction. That is, the coaptation member 2510 can open from the unexpanded position to the expanded position to increase the C-C width of the device 2500. In some embodiments, the side portions 2519 are semi-circular and include a pointed spine that extends into the C-C direction, allowing for a tapered surface to interface with a coaptation surface of the device 2500. The amount of C-C expansion can be binary (e.g., expanded or unexpanded), or the device 2500 can include features configured to facilitate a gradual expansion of the side portions 2519, such as corset like strings (not shown) coupled to the side portions 2519. The valve repair device 2500 can be secured in position relative to the native valve via one or more clip mechanisms 2530, lock mechanisms 2540, anchors, and/or other securing features described herein.

Figure 26A:
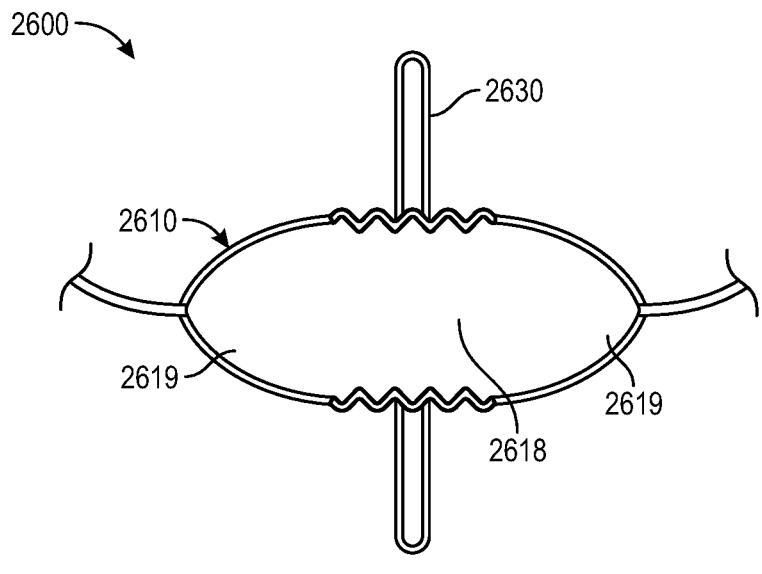
FIGS. 26A and 26B are top views of a valve repair device in an unexpanded position and an expanded position, respectively, in accordance with embodiments of the present technology.
Figure 26B:
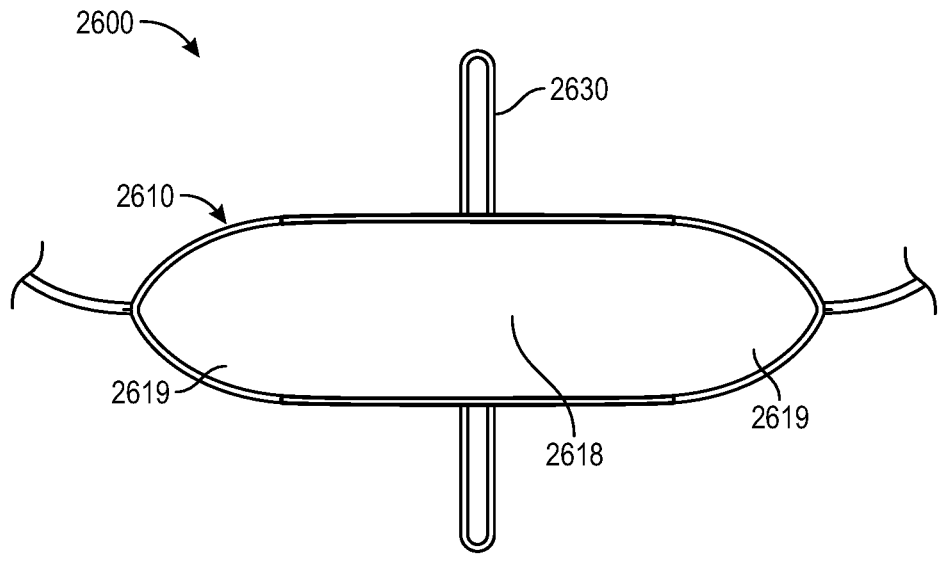
Figures 26F, 26G, 26H:
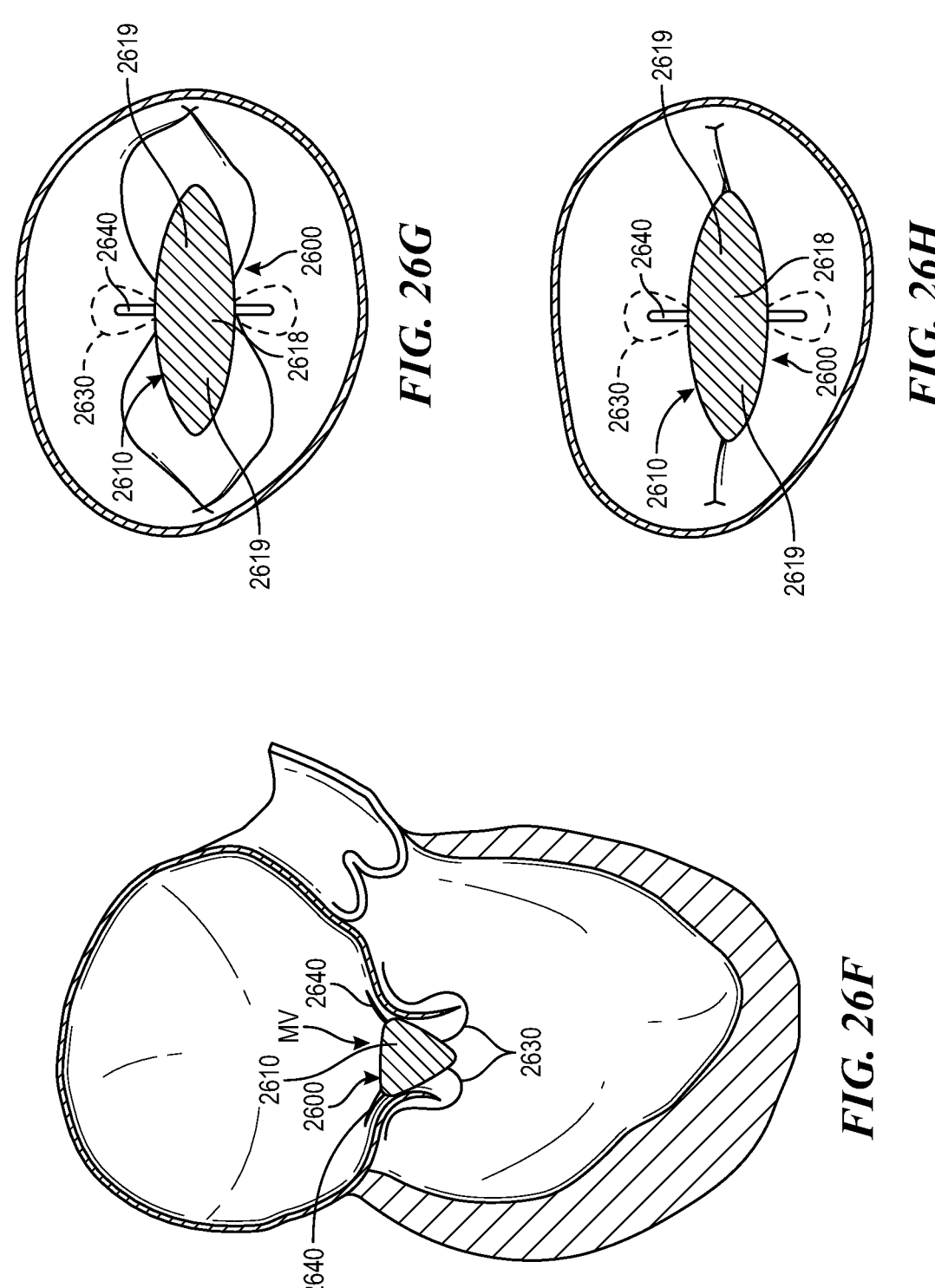

FIGS. 26A and 26B are top views of a valve repair device 2600 in an unexpanded position and an expanded position, respectively, in accordance with embodiments of the present technology. FIGS. 26C and 26F are side cross-sectional views of the valve repair device 2600 of FIGS. 26A and 26B implanted at the mitral valve MV in the unexpanded position and the expanded position, respectively, in accordance with embodiments of the present technology. FIGS. 26D and 26E are transverse cross-sectional views of the valve repair device 2600 of FIGS. 26A and 26B implanted at the mitral valve MV in the unexpanded position during diastole and systole, respectively, in accordance with embodiments of the present technology. FIGS. 26G and 26H are transverse cross-sectional views of the valve repair device 2600 of FIGS. 26A and 26B implanted at the mitral valve MV in the expanded position during diastole and systole, respectively, in accordance with embodiments of the present technology.

Referring to FIGS. 26A-26H together, the valve repair device 2600 includes a coaptation member 2610 having an expandable central portion 2618 and tapered side portions 2619 extending from the central portion 2618. The central portion 2618 can have parallel sides configured to expand in the C-C direction. Accordingly, the expansion can come from the central portion 2618, maintaining the C-C-most shape. In some embodiments, the valve repair device 2600 includes a pair of clip mechanisms 2630 aligned with the central portion 2618. In some embodiments, the central portion 2618 can further expand in other directions, such as the anterior-posterior (A-P) dimension, further filling a coaptation distance and increasing the force with which the clip mechanisms 2630 are engaged with the central portion 2618. That is, the expansion of the central portion 2618 can be in two directions or all four (elliptical vs. circular), further filling any distance between native leaflet coaptation. In some embodiments, the valve repair device 2600 can include more than two of the clip mechanisms 2630 to ensure adequate fixation of the coaptation member 2610, such as when the coaptation member 2610 is wider.

Figure 27A:
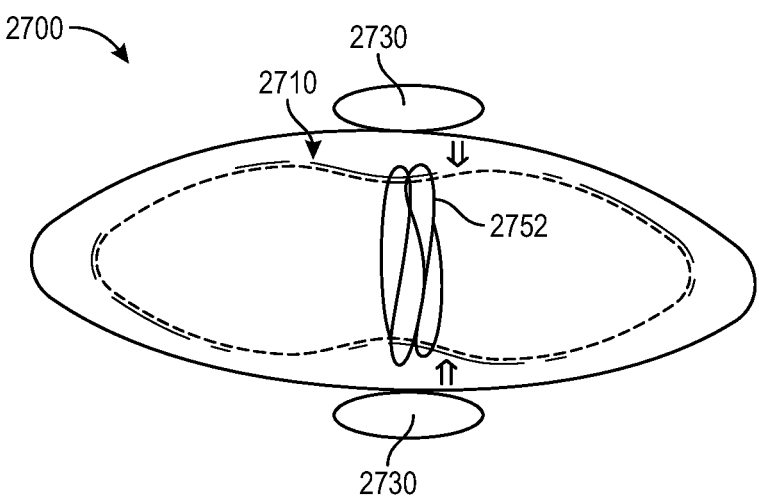
FIG. 27A is a top view of a valve repair device in an unexpanded position in accordance with embodiments of the present technology.

FIG. 27A is a top view of a valve repair device 2700 in an unexpanded position in accordance with embodiments of the present technology. FIGS. 27B and 27E are side cross-sectional views of the valve repair device 2700 of FIG. 27A implanted at the mitral valve MV in the unexpanded position and an expanded position, respectively, in accordance with embodiments of the present technology. FIGS. 27C and 27D are transverse cross-sectional views of the valve repair device 2700 of FIG. 27A implanted at the mitral valve MV in the unexpanded position during diastole and systole, respectively, in accordance with embodiments of the present technology. FIGS. 27F and 27G are transverse cross-sectional views of the valve repair device 2700 of FIG. 27A implanted at the mitral valve MV in the expanded position during diastole and systole, respectively, in accordance with embodiments of the present technology.

Referring to FIGS. 27A-27G together, the valve repair device 2700 includes a coaptation member 2710 configured to extend in the C-C direction and clip mechanisms 2730 and/or lock mechanisms 2740 extending from the coaptation member 2710 for fixating native valve leaflets (e.g., the anterior leaflet A1 and posterior leaflet PL) against the coaptation member 2710. In the illustrated embodiment, the valve repair device 2700 includes a corset-type feature 2752 that is actuatable to (i) reduce the width of the coaptation member 2710 (e.g., an A-P distance), (ii) increase the length of the coaptation member 2710 in the C-C dimension, and/or (iii) increase the bulk of the coaptation member 2710 in the A1/P1 and A3/P3 directions. That is, the corset-type feature 2752 can reduce the distance between the clip mechanisms 2730, increasing the length in the coaptation dimension and increasing the width parallel to the clip mechanisms 2730. In some embodiments, the coaptation member 2710 can have a stent form or braided form and may be covered by atraumatic coaptation materials described herein.

Figure 28A:
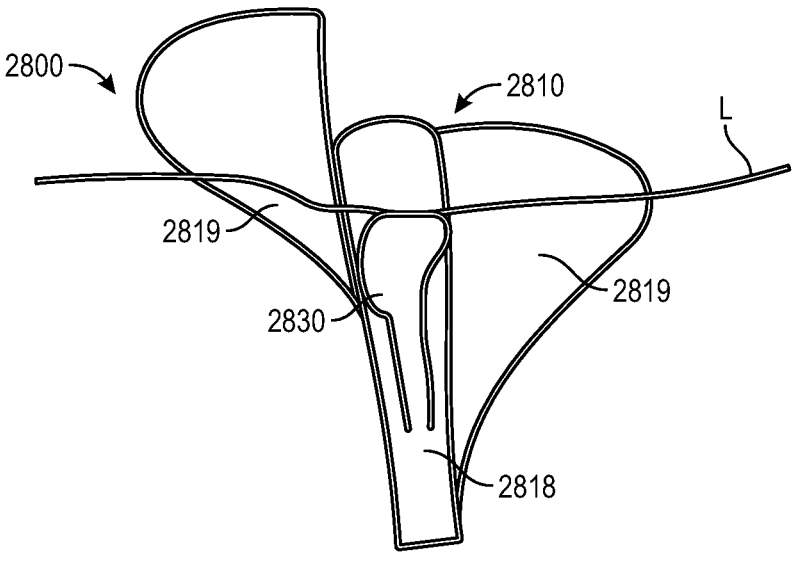
FIGS. 28A and 28B are a side view and top view, respectively, of a valve repair device in accordance with embodiments of the present technology.
Figure 28B:
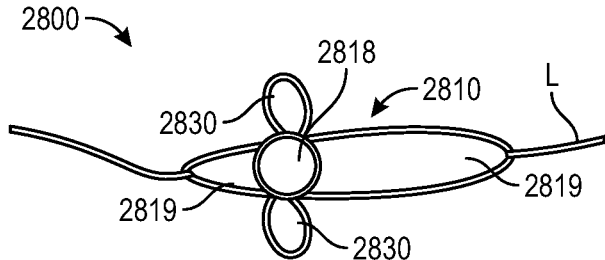

FIGS. 28A and 28B are a side view and top view, respectively, of a valve repair device 2800 in accordance with embodiments of the present technology. FIG. 28C is a side cross-sectional view of the valve repair device 2800 of FIGS. 28A and 28B implanted at the mitral valve MV in accordance with embodiments of the present technology. FIGS. 28D and 28E are transverse cross-sectional views of the valve repair device 2800 of FIGS. 28A-28C during diastole and systole, respectively, in accordance with embodiments of the present technology. Referring to FIGS. 28A-28E together, the valve repair device 2800 includes a coaptation member 2810 having a central portion 2818 and a pair of tapered side portions 2819 extending from the central portion 2818 in the C-C direction. The valve repair device 2800 can further include clip mechanisms 2830 and lock mechanisms 2840 for securing one or more leaflets L of the mitral valve MV against the coaptation member 2810 (e.g., against the central portion 2818). In some embodiments, the tapered side portions 2819 are configured to be individually raised or lowered in the atrial-ventricular direction to increase or decrease the amount of the coaptation member 2810 (e.g., filler) in the C-C direction. In some embodiments, the valve repair device 2800 can also include features to lock the tapered side portions 2819 in place to prevent movement of the side portions of the coaptation member 2610 after deployment.

In some embodiments, a coaptation member of a cardiac valve device (and/or another atrial portion of the device) can include a flexible (e.g., nitinol) frame cut from a tube with multiple struts connected on both the atrial-most and ventricular-most ends. The frame can include a central thread or locking nut cut and shaped into the frame. A delivery system can be configured to compress the atrial portion of the frame, reducing the overall height while increasing the diameter of the struts, thereby increasing the diameter of the coaptation surface filling an existing coaptation gap. The device may be shaped asymmetrically to expand in an elliptical or otherwise non-circular fashion, or may include multiple central adjustable components for localized height changes and increases in diameter.

IV. SELECTED EMBODIMENTS OF CARDIAC VALVE REPAIR DEVICES INCLUDING CLIP MECHANISMS AND/OR LOCK MECHANISMS FOR SECURING COAPTATION MEMBERS AT AND/OR PROXIMATE TO A CARDIAC VALVE

In some embodiments, cardiac valve repair devices in accordance with the present technology can include implant fixation mechanisms for securing the device into the local native anatomy of a cardiac valve via, for example, anchoring into or laying against the native atrial or ventricular wall, against the annulus, and/or onto the leaflets themselves. As described in detail above, the implant fixation mechanisms can include one or more clip mechanisms and one or more lock mechanisms. The clip mechanisms (also referred to as "clips," "capture clips," "capture mechanisms," and iterations thereof) are configured to be positioned on the ventricular side of the cardiac valve and to capture one or more leaflets of the valve for securing the leaflets against, for example, a coaptation member coupled to the clip mechanisms and lock mechanisms. The lock mechanisms (also referred to as "clips," "locking clips," "stabilization members," "stabilization features", and iterations thereof) can be generally similar to the clip mechanisms but are configured to be positioned on the atrial side of the cardiac valve and to engage the atrial side of the valve leaflets and/or other portions of the cardiac anatomy to, for example, help secure the coaptation member in a selected position relative to the valve and/or provide additional leaflet fixation. The clip and lock mechanisms may or may not require a specific orientation.

In some embodiments, the clip mechanisms can be on (i) opposing sides of the coaptation member, (ii) one side of the coaptation member, and/or (iii) a mating surface inferior to the coaptation member. In some embodiments, the clip mechanisms and/or the lock mechanisms can be movable, expandable, and/or otherwise adjustable. In some embodiments, the clip mechanisms can be narrow features configured to navigate chordae proximate to the valve and/or to minimize leaflet disruption during diastole (e.g., allowing forward flow), and the lock mechanisms can be wide features on the atrial side to minimize leaflet flail and provide additional flow resistance during systole. In some embodiments, the clip and lock mechanisms can operate independently from one another and can be repositionable. Further, the clip and lock mechanisms (e.g., arms thereof) can (i) have various shapes supporting the native leaflet shapes, (ii) be set at an angle to mimic the natural leaflet coaptation angle, and/or (iii) be configured to capture only the free edge of one or more of the leaflets.

In some embodiments, the implant fixation mechanisms can include features configured to enhance leaflet fixation, such as (i) interlocking components configured to increase leaflet plication, (ii) materials or features that increase surface area in contact with the leaflets, (iii) frictional elements (e.g., cleats, barbs, textures) that increase friction against the leaflets, (iv) features that puncture the leaflets, and/or (v) combinations thereof. For valve repair devices having clips on the atrial and ventricular sides of the device, features on the atrial side of the leaflet (e.g., lock mechanisms) may fit within the spacing of the sub-valvular features. Fixation features can be gear driven, hydraulic, super-elastic, or spring-loaded. Features that contact the leaflet can be widened to distribute the closing force across a wider area. Some stabilizing features can utilize flared, angled, or wide fixation mechanisms to add stability to the device and facilitate the natural coaptation angle of the native valve. In some embodiments, the clip mechanisms and/or the lock mechanisms can include a patent foramen ovale (PFO) closure device configured as an atrial anchor.

In some embodiments, the clip mechanisms and/or the lock mechanisms can be in the form of a hook so as to not tightly pull the leaflet up against the coaptation member but to just approximate it. This configuration can allow for a captured leaflet to open more during diastole thereby reducing pressure gradients. When multiple (e.g., two) ventricular clip mechanisms are in the form of hooks, atrial annular support and/or fixation members in the form of anchor, barbs or cleats, and/or the like can be included to inhibit migration of the device into the ventricle. In some embodiments, the clip mechanisms can include one or more clip expandable arms that work efficiently in treating a wide mitral regurgitation jet without the need for a coaptation member with a C-C protrusion.

FIG. 29A is a side cross-sectional view of a valve repair device 2900 implanted at the tricuspid valve TV in accordance with embodiments of the present technology. FIGS. 29B and 29C are transverse cross-sectional views of the valve repair device 2900 of FIG. 29A during diastole and systole, respectively, in accordance with embodiments of the present technology. Referring to FIGS. 29A-29C together, the valve repair device 2900 can include features generally similar to the valve repair device 2300 of FIGS. 23A-23E including, for example, a coaptation member 2910, and clip mechanisms 2930. In the illustrated embodiment, the valve repair device 2900 includes a coaptation member 2910 having three triangular portions 2919 (e.g., side portions) that together give the coaptation member 2910 a star-like transverse cross-sectional shape. In some embodiments, one or more of the triangular portions 2919 can be independently expandable from an unexpanded position (not shown). In the illustrated embodiment, the valve repair device 2900 is secured between the leaflets L1-L3 of the tricuspid valve TV via the clip mechanisms 2930 extending from the coaptation member 2910 and, for example, interspersed or interleaved between the triangular portions 2919 of the coaptation member 2910. As best seen in FIGS. 29B and 29C, each of the triangular portions 2919 can be oriented to project toward a corresponding one of the commissures between the leaflets L1-L3 to, for example, facilitate the coaptation of the leaflets L1-L3 against the surface of the coaptation member 2910. In some embodiments, the valve repair device 2900 can further include lock mechanisms (not shown) configured to further secure the valve repair device 2900 at the tricuspid valve TV.

Figure 30:
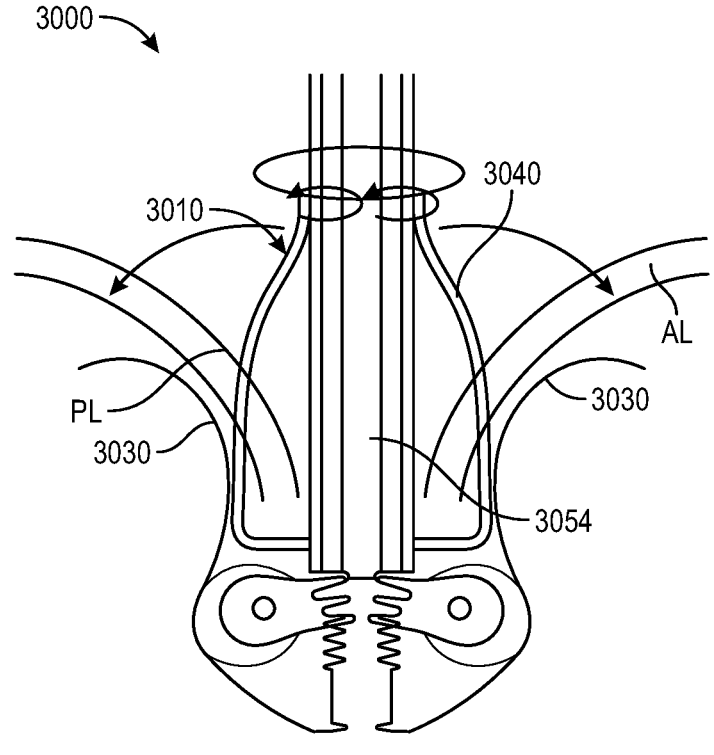
FIG. 30 is a side view of a valve repair device in accordance with embodiments of the present technology.

FIG. 30 is a side view of a valve repair device 3000 in accordance with embodiments of the present technology. In the illustrated embodiment, the valve repair device 3000 includes a central coaptation member 3010 configured to provide a coaptation surface for one or of the native leaflets of a cardiac valve. The valve repair device 3000 further includes a pair of gear-driven clip-mechanisms 3030 configured to capture, for example, the middle scallop P2 of the posterior leaflet PL and the middle segment A2 of the anterior leaflet AL of the mitral valve MV. The clip mechanisms 3030 can be independently operated to facilitate optimization of an angle and amount of clip closure during capture of the anterior and posterior leaflets AL and PL. In some embodiments, the valve repair device 3000 further includes spring-loaded lock mechanisms 3040 that can, for example, also be gear driven.

In some embodiments, the clip mechanisms 3030 are maintained in proximity by a central rail 3054. The coaptation member 3010 can be inserted onto the rail 3054 and slid down into place—for example, into the space between the anterior and posterior leaflets AL and PL. In some embodiments, the coaptation member 3010 can be replaced if a larger size is required to plug a regurgitant leak. In some embodiments, after a selected coaptation member 3010 is installed during a delivery procedure, the lock mechanisms 3040 can be operated either simultaneously or independently to lock down onto the secured leaflets. In some embodiments, the coaptation member 3010 can be modular—having several segments to allow for segmental addition of posterior, anterior, medial, lateral, septal, and/or other segments to the coaptation member 3010 or to alter the level of coaptation along the ventricular axis.

FIG. 31A is a side cross-sectional view of a valve repair device 3100 implanted at the mitral valve MV in accordance with embodiments of the present technology. FIGS. 31B and 31C are transverse cross-sectional views of the valve repair device 3100 of FIG. 31A during diastole and systole, respectively, in accordance with embodiments of the present technology. Referring to FIGS. 31A-31C together, the valve repair device 3100 includes a rotatable coaptation member 3110, a pair of clip mechanisms 3130 (identified individually as an anterior clip mechanism 3130*a* and a posterior clip mechanism 3130*b*) extending from the coaptation member 3110, and a lock mechanism 3140 extending from the coaptation member 3110. In the illustrated embodiment, the coaptation member 3110 includes a posteriorly-biased protrusion 3151. The posterior clip mechanism 3130*b* is located under the posterior annulus and grasps the posterior leaflet PL. The anterior clip mechanism 3130*a* grabs the anterior leaflet AL from the ventricular side securing, for example, the A2 leaflet against the coaptation member 3110. The coaptation member 3110 can rotate, with a mating feature (e.g., the protrusion 3151) locking down onto the posterior clip mechanism 3130*b* and a mating feature (e.g., the lock mechanism 3140) on the anterior side furthering engagement with the anterior leaflet. Accordingly, in the illustrated embodiment the coaptation member 3110 is posteriorly-biased and doubles as a posterior lock mechanism. The anterior clip mechanism 3130*a* may nest within an anterior face of the coaptation member 3110 and its use may be optional. In other embodiments, the posterior clip mechanism 3130*b* can have a locking clip feature that falls on the atrial surface of the posterior leaflet before laying down the protrusion 3151 on the posterior leaflet.

Figure 32A:
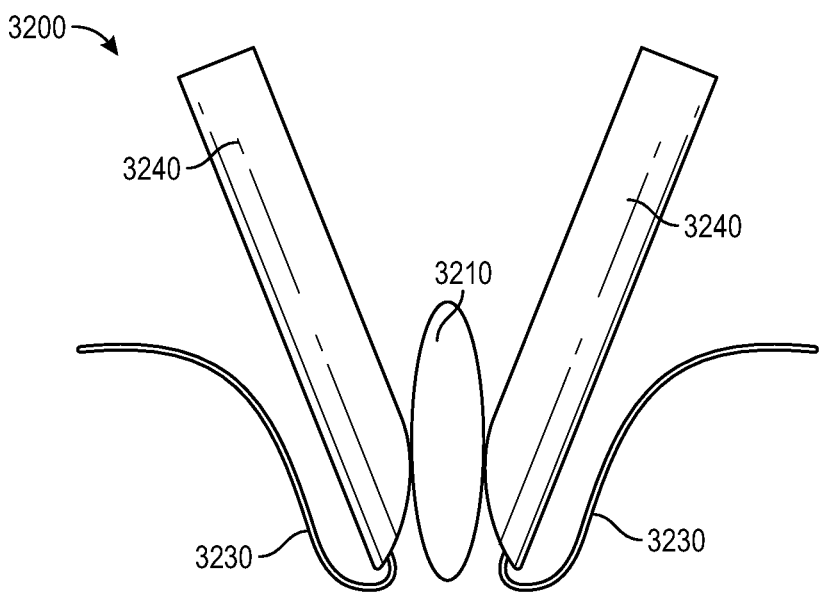
FIGS. 32A and 32B are side views of a valve repair device in a first position and a second position, respectively, in accordance with embodiments of the present technology.
Figure 32B:
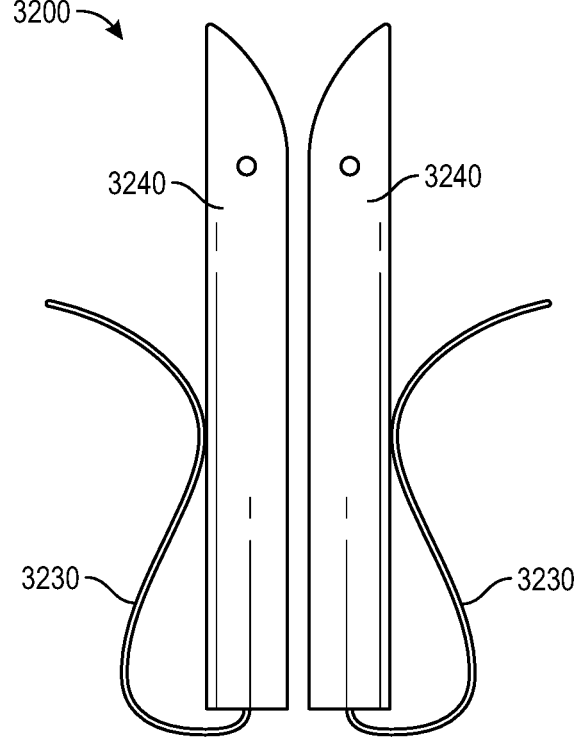

FIGS. 32A and 32B are side views of a valve repair device 3200 in a first position and a second position, respectively, in accordance with embodiments of the present technology. FIG. 32C is a side cross-sectional view of the valve repair device 3200 of FIGS. 32A and 32B implanted at the mitral valve MV in the first position accordance with embodiments of the present technology. FIGS. 32D and 32E are transverse cross-sectional views of the valve repair device 3200 of FIGS. 32A-32C during diastole and systole, respectively, in accordance with embodiments of the present technology. Referring to FIGS. 32A-32E together, the valve repair device 3200 includes an optional coaptation member 3210, a pair of clip mechanisms 3230 coupled to the coaptation member 3210, and a hinged lock mechanism 3240 coupled to the coaptation member 3210. The clip mechanisms 3230 separately capture and secure the anterior leaflet AL and the posterior leaflet PL. The lock mechanism 3240 on the atrial side of the leaflets is a locking clip that is hinged in the center of the A-P dimension. The hinge is located on the ventricular side of the central coaptation member 3210, creating a V shape. The angle of the V-opening of the lock mechanism 3240 is adjustable, allowing the angle of the clip mechanisms 3230 to be varied per user discretion. In some embodiments, the optional coaptation member 3210 can be adjusted in the anterior-posterior dimension, allowing the distance of the lock mechanism 3240 to be varied per user discretion while filling any residual gap in the coaptation surface. In some embodiments, the optional coaptation member 3210 can be adjusted in the C-C dimension (e.g., adjusted perpendicular to the clip mechanisms 3230 and/or to align with a head level of the clip mechanisms 3230) filling any residual gap in the coaptation surface or plane in the C-C direction.

Figure 33A:
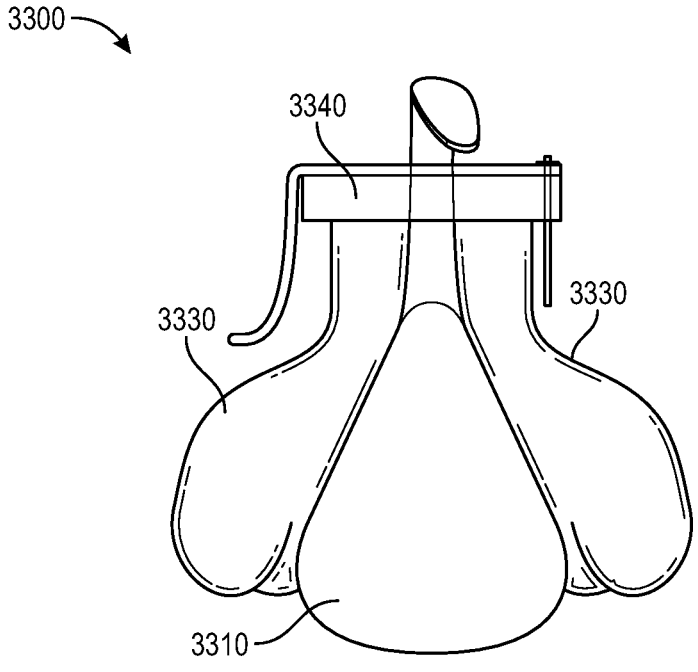
FIG. 33A is a side view of a valve repair device in accordance with embodiments of the present technology.

FIG. 33A is a side view of a valve repair device 3300 in accordance with embodiments of the present technology. FIG. 33B is a side cross-sectional view of the valve repair device 3300 of FIG. 33A implanted at the mitral valve MV in accordance with embodiments of the present technology. FIGS. 33C and 33D are transverse cross-sectional views of the valve repair device 3300 of FIGS. 33A and 33B during diastole and systole, respectively, in accordance with embodiments of the present technology. Referring to FIGS. 33A-33D together, the valve repair device 3300 includes a coaptation member 3310, a pair of clip mechanisms 3330 coupled to the coaptation member 3310, and a central lock mechanism 3340 coupled to the coaptation member 3310. The clip mechanisms 3330 separately capture and secure the anterior leaflet AL and the posterior leaflet PL. In the illustrated embodiment, the lock mechanism 3340 nests on top of the coaptation member 3310 and the clip mechanisms 3330 and is configured to further pull in the valve leaflets to provide a slight annuloplasty effect. In some embodiments, the central lock mechanism 3340 has a diameter that is greater than a distance between the clip mechanisms 3330. In the illustrated embodiment, the central lock mechanism 3340 has a generally elongate oval or rectangular shape. In other embodiments, the central lock mechanism can have other shapes. For example, FIG. 33E is a side cross-sectional view of the valve repair device 3300 of FIG. 33A implanted at the mitral valve MV and having a central lock mechanism 3340' having a generally circular shape in accordance with embodiments of the present technology. FIGS. 33F and 33G are transverse cross-sectional views of the valve repair device 3300 of FIG. 33E during diastole and systole, respectively, in accordance with embodiments of the present technology.

Figures 34A, 34B:
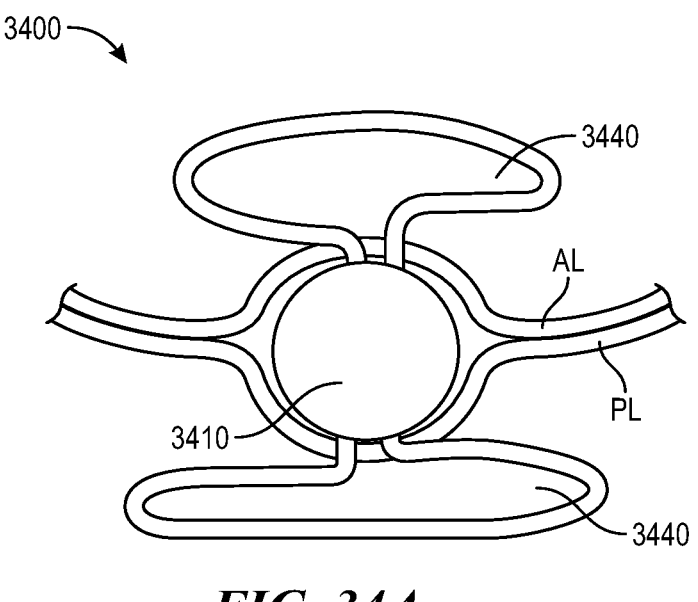
FIGS. 34A and 34B are a top view and a bottom view, respectively, of a valve repair device in accordance with embodiments of the present technology.

FIGS. 34A and 34B are a top view and a bottom view, respectively, of a valve repair device 3400 in accordance with embodiments of the present technology. FIG. 34C is a side cross-sectional view of the valve repair device 3400 of FIGS. 34A and 34B implanted at the mitral valve MV in accordance with embodiments of the present technology. FIGS. 34D and 34E are transverse cross-sectional views of the valve repair device 3400 of FIGS. 34A-34C during diastole and systole, respectively, in accordance with embodiments of the present technology. Referring to FIGS.

34A-34E together, the valve repair device 3400 includes a coaptation member 3410, a pair of clip mechanisms 3430 coupled to the coaptation member 3410, and a pair of lock mechanisms 3440 coupled to the coaptation member 3410. The clip mechanisms 3430 separately capture and secure the anterior leaflet AL and the posterior leaflet PL. The lock mechanisms 3440 engage the atrial side of the anterior and posterior leaflets AL and PL above the clip mechanisms 3430. In the illustrated embodiment, the clip mechanisms 3430 have a narrower profile (e.g., width) than the lock mechanisms 3440 that can help minimize leaflet disruption during diastole, allowing forward flow. The relatively wider geometry of the lock mechanisms 3440 can help minimize leaflet flail and provide additional flow resistance during systole.

In some embodiments, the valve repair device 3400 can include multiple narrow clip mechanisms 3430 extending below the corresponding lock mechanisms 3440. For example, FIG. 34F is a side cross-sectional view of another embodiment of the valve repair device 3400 of FIGS. 34A and 34B implanted at the mitral valve MV in accordance with embodiments of the present technology. FIGS. 34G and 34H are transverse cross-sectional views of the valve repair device 3400 of FIG. 34F during diastole and systole, respectively, in accordance with embodiments of the present technology. Referring to FIGS. 34F-34H together, the valve repair device 3400 can include two pairs of clip mechanisms 3430—each pair extending from opposite sides of the coaptation member 3410 and aligned beneath the wider lock mechanisms 3440.

Figure 35A:
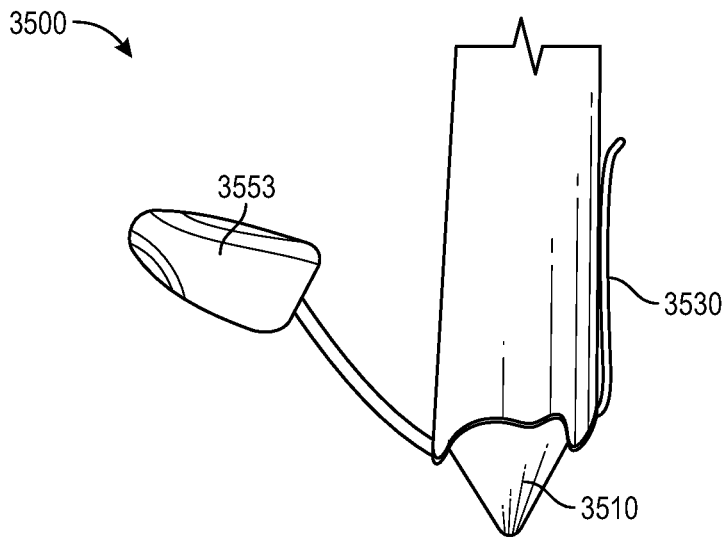
FIGS. 35A and 35B are side perspective views of a valve repair device in accordance with embodiments of the present technology.
Figure 35B:
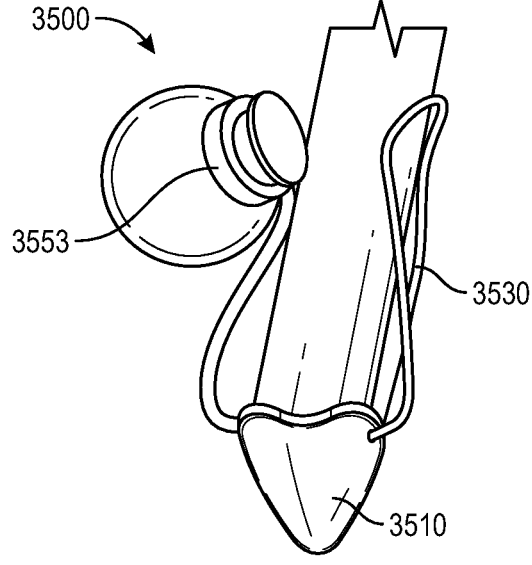

FIGS. 35A and 35B are side perspective views of a valve repair device 3500 in accordance with embodiments of the present technology. FIG. 35C is a side cross-sectional view of the valve repair device 3500 of FIGS. 35A and 35B implanted at the mitral valve MV in accordance with embodiments of the present technology. FIGS. 35D and 35E are transverse cross-sectional views of the valve repair device 3500 of FIGS. 35A-35C during diastole and systole, respectively, in accordance with embodiments of the present technology. Referring to FIGS. 35A-35E together, the valve repair device 3500 includes a coaptation member 3510, a clip mechanism 3530 and a lock mechanism 3540 extending from the coaptation member 3510, and an expandable support 3553 extending from the coaptation member 3510. The expandable support 3553 can extend beneath and support the posterior leaflet PL and can be made from a stent structure, braided structure, expandable balloon, and/or another expandable element. In some embodiments, the expandable support 3553 can be covered with a fabric to allow for ingrowth into the posterior sub annular space. In some embodiments, the expandable support 3553 can be held in place by a corresponding expandable locking clip on the atrial side of the leaflet (not shown) that, for example, extends toward the annulus within the P2 section of the posterior leaflet PL. The clip mechanism 3530 and the lock mechanism 3540 can align with one another and engage the ventricular and atrial sides of the anterior leaflet AL, respectively, to capture and close onto the anterior leaflet AL.

Figure 36A:
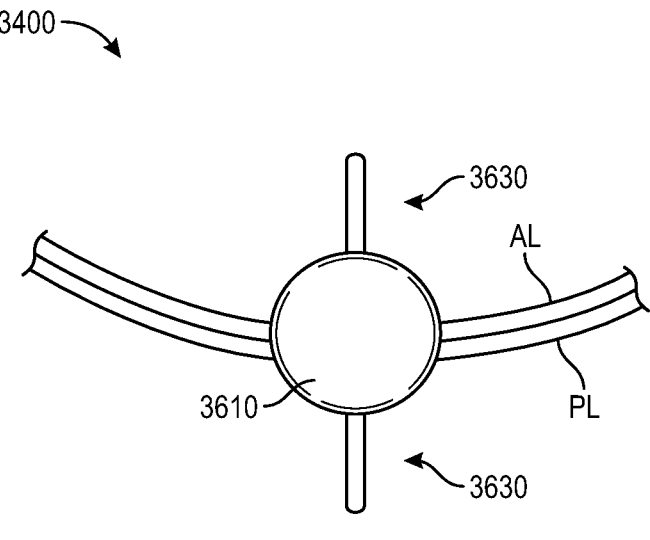
FIGS. 36A and 36B are top views of a valve repair device in an unexpanded position and an expanded position, respectively, in accordance with embodiments of the present technology.
Figure 36B:
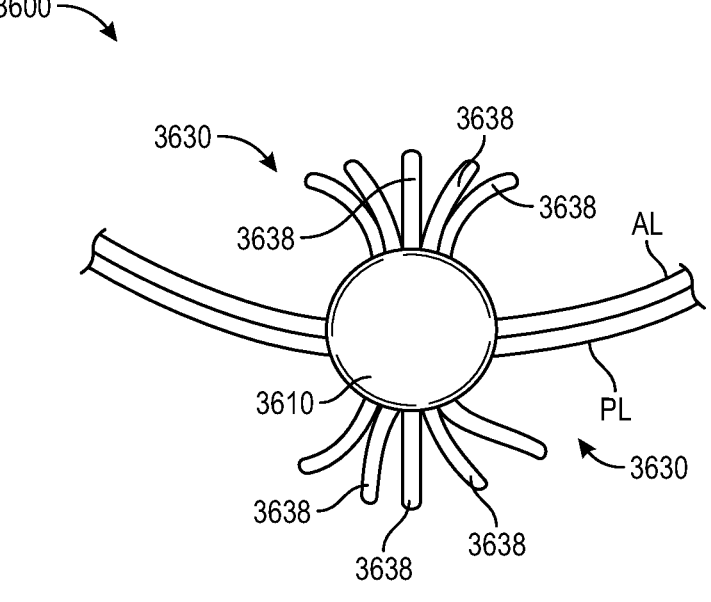

FIGS. 36A and 36B are top views of a valve repair device 3600 in an unexpanded position and an expanded position, respectively, in accordance with embodiments of the present technology. FIG. 36C is a side cross-sectional view of the valve repair device 3600 of FIGS. 36A and 36B implanted at the mitral valve MV in accordance with embodiments of the present technology. FIGS. 36D and 36E are transverse cross-sectional views of the valve repair device 3600 of FIGS. 36A-36C implanted at the mitral valve MV in the expanded position during diastole and systole, respectively, in accordance with embodiments of the present technology. Referring to FIGS. 36A-36E together, the valve repair device 3600 includes a coaptation member 3610, and clip mechanism 3630 and (optional) lock mechanisms 3640 extending from the coaptation member 3610 for engaging and capturing the anterior and posterior leaflets AL and PL. In the illustrated embodiment, the clip mechanisms 3630 each include a plurality of movable fingers 3638 that can be independently expanded to increase the amount of leaflet area captured. For example, the fingers 3638 can fan out in the second position shown in FIGS. 36B, 36D, and 36E to increase the amount of leaflet area captured. In some embodiments, the valve repair device 3600 can be delivered to the mitral valve MV with the clip mechanisms 3630 in the narrowed first position, and then released to fan out in one or both directions beneath the leaflets after placement at the mitral valve MV. In other embodiments, the coaptation member 3610 can be omitted and the expandable fingers 3638 can work efficiently in treating a wide mitral regurgitation jet without the need for the coaptation member with, for example, a C-C protrusion. In other embodiments, the expandable fingers 3638 may be separately actuated to eject from the coaptation member 3610 if additional fixation or leaflet stabilization is required.

Figure 37A:
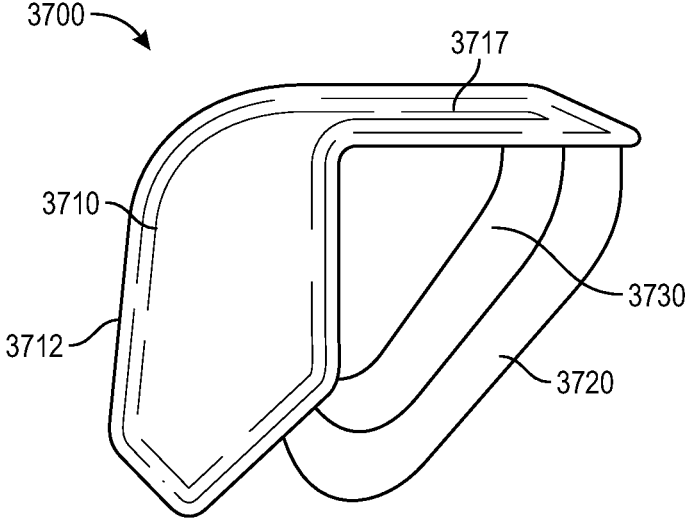
FIGS. 37A and 37B are side views of a valve repair device configured in accordance with embodiments of the present technology.
Figure 37B:
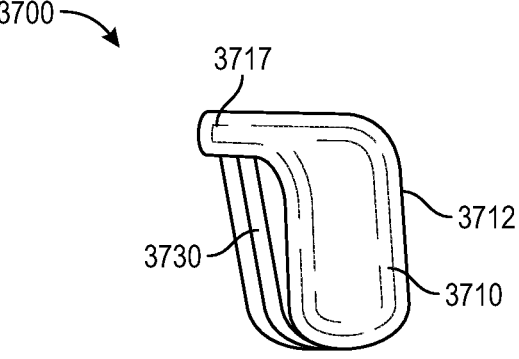
Figures 37C, 37D, 37E:
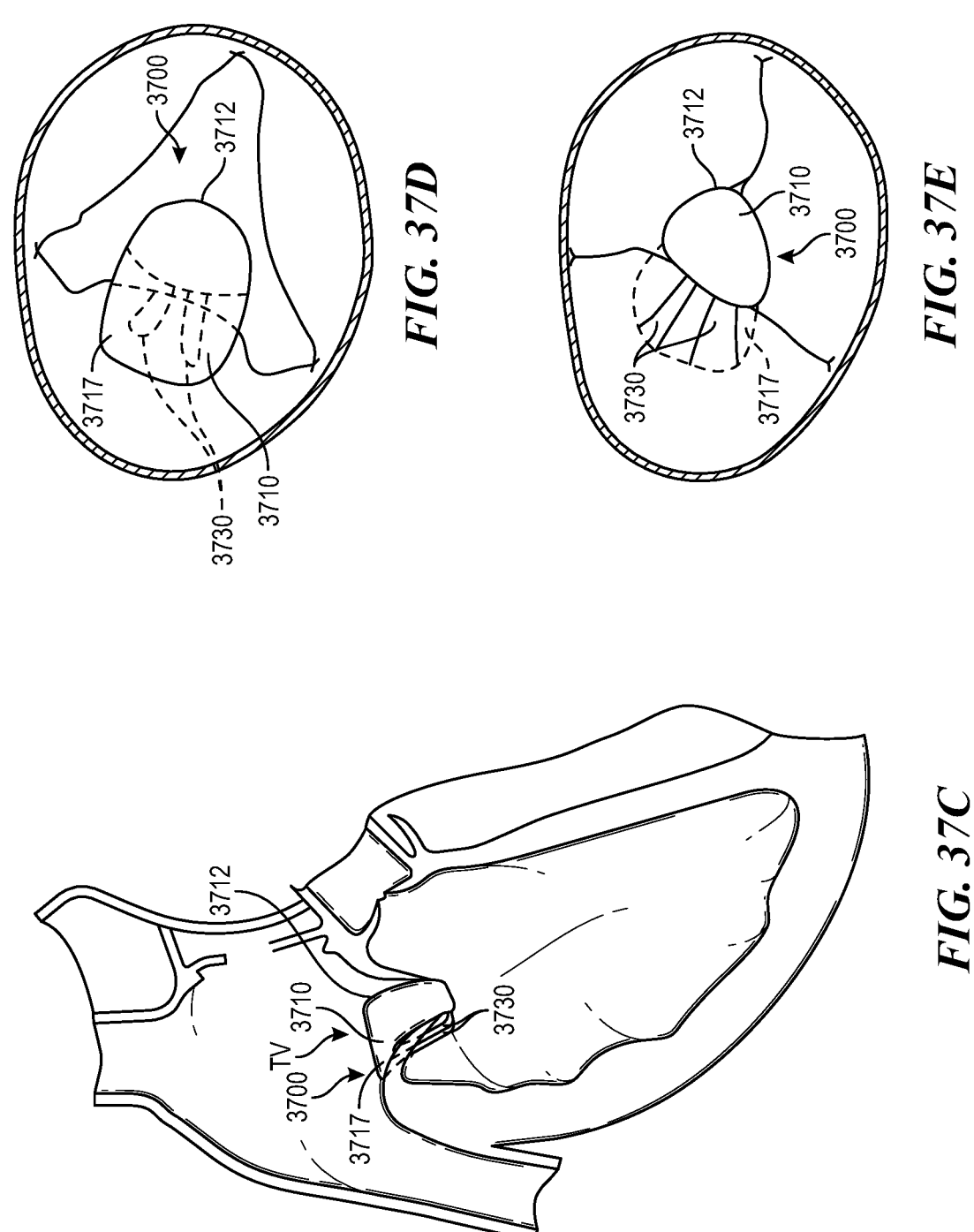
FIG. 37C is a side view of the valve repair device of FIGS. 37A and 37B implanted at the tricuspid valve in accordance with embodiments of the present technology.
FIG. 37D is a top view of the valve repair device of FIGS. 37A-37C during diastole.
FIG. 37E is a bottom view of the valve repair device of FIGS. 37A-37C during systole in accordance with embodiments of the present technology.

FIGS. 37A and 37B are side views of a valve repair device 3700 configured in accordance with embodiments of the present technology. FIG. 37C is a side view of the valve repair device 3700 of FIGS. 37A and 37B implanted at the tricuspid valve TV in accordance with embodiments of the present technology. FIG. 37D is a top view of the valve repair device 3700 of FIGS. 37A-37C during diastole, and FIG. 37E is a bottom view of the valve repair device 3700 of FIGS. 37A-37C during systole in accordance with embodiments of the present technology. Referring to FIGS. 37A-37E together, the valve repair device 3700 includes a coaptation member 3710 and one or more clip mechanisms 3730 coupled to the coaptation member 3710. The coaptation member 3710 includes an enlarged top portion 3717 configured to be positioned above the tricuspid valve TV (e.g., at the annulus and/or in the right atrium). The clip mechanisms 3730 extend behind the coaptation member 3710 and contact a portion of one or more leaflets of the tricuspid valve TV below the top portion 3717. Accordingly, the top portion 3717 of the coaptation member 3710 can serve as a surface against which the leaflets are pressed and held by the ventricularly-positioned clip mechanisms 3730. The clip mechanisms 3730 can capture one or multiple leaflets to orient a face 3712 of the coaptation face towards any free leaflet to extend leaflet functionality by filling a regurgitant leak space. In some embodiments, a surface of the coaptation member 3710 can be slightly rounded to accommodate a variety of positionings and displacements resulting from various systolic pressures.

FIG. 70A is a side view of a valve repair device 7000 in a delivery configuration (e.g., a compressed configuration) in accordance with embodiments of the present technology. FIG. 70B is a side view of the valve repair device 7000 of FIG. 70A in a deployed configuration (e.g., an expanded configuration) and implanted at a cardiac valve in accordance with embodiments of the present technology. Referring to FIGS. 70A and 70B together, the valve repair device 7000 includes a central member 7050, a pair of clip mechanisms 7030, and a pair of lock mechanisms 7040. In the deployed configuration, the clip mechanisms 7030 and the lock mechanisms 7040 can cooperate to capture one or more leaflets L of the cardiac valve therebetween. In the illustrated embodiment, (i) the clip mechanisms 7030 each include a first link 7031 and a second link 7032, (ii) the anchor mechanisms 7040 similarly include a third link 7041 and a fourth link 7042, and (iii) the valve repair device 7000 further includes a drive link 7052. The first link 7031 is hingedly coupled (e.g., at a first end portion) to the central member 7050 and hingedly coupled (e.g., at a second end portion) to the second link 7032 (e.g., to a first end portion of the second link 7032). The second link 7031 is further hingedly coupled (e.g., at a second end portion) to the drive link 7052. The third link 7031 is hingedly coupled (e.g., at a first end portion) to the drive link 7052 and hingedly coupled (e.g., at a second end portion) to the fourth link 7042 (e.g., to a first end portion of the second link 7032). In some embodiments, the fourth link 7042 is hingedly coupled (e.g., at a second end portion) to the central member 7050 and/or another component of the valve repair device 7000.

In the delivery configuration shown in FIG. 70A, the first link 7031, the second link 7032, the third link 7041, the fourth link 7042, and the drive link 7052 (collectively links 7031-7052) are folded longitudinally such that, for example, the links 7031-7052 extend generally parallel to the central member 7050. Thus, in the delivery configuration the clip mechanisms 7030 and the anchor mechanisms 7400 are radially compressed such that, for example, the valve repair device 7000 can be advanced through an associated delivery catheter. In the deployed configuration shown in FIG. 70B, the links 7031-7052 are folded radially outward such that the second link 7032 of each of the clip mechanisms 7030 and the third link 7041 of the associated anchor mechanism 7040 generally face each other to capture one of the leaflets L therebetween. More specifically, the second links 7032 can engage the ventricular sides of the leaflets L while the third links 7041 engage the atrial sides of the leaflets L to capture the leaflets L therebetween. In some aspects of the present technology, the links 7031-7052 provide a strong locking arrangement in the deployed configuration. To move the valve repair device 7000 between the delivery and deployed configurations, one or more of the links 7031-7052 can be actuated (e.g., driven longitudinally) to drive the various links 7031-7052 to pivot between the delivery and deployed configurations.

V. SELECTED EMBODIMENTS OF CARDIAC VALVE REPAIR DEVICES INCLUDING NON-CLIP AND/OR OTHER MECHANISMS FOR SECURING COAPTATION MEMBERS AT AND/OR PROXIMATE TO A CARDIAC VALVE

In some embodiments, cardiac valve repair devices in accordance with the present technology can include implant fixation mechanisms for securing the device into the cardiac anatomy other than clip and/or lock mechanisms. In some embodiments, the implant fixation mechanisms can include brace (e.g., support) members for securing a coaptation member at a cardiac valve such that the coaptation member is "floating" within the valve between the native leaflets. For example, the implant fixation mechanisms can include coil or cone-shaped forms anchored in the atrium, right ventricle, right atrium, right ventricular outflow tract, coronary sinus, atrial appendage, and/or other areas of anatomy not directly proximal to the device.

Figures 38A, 38B, 38C:
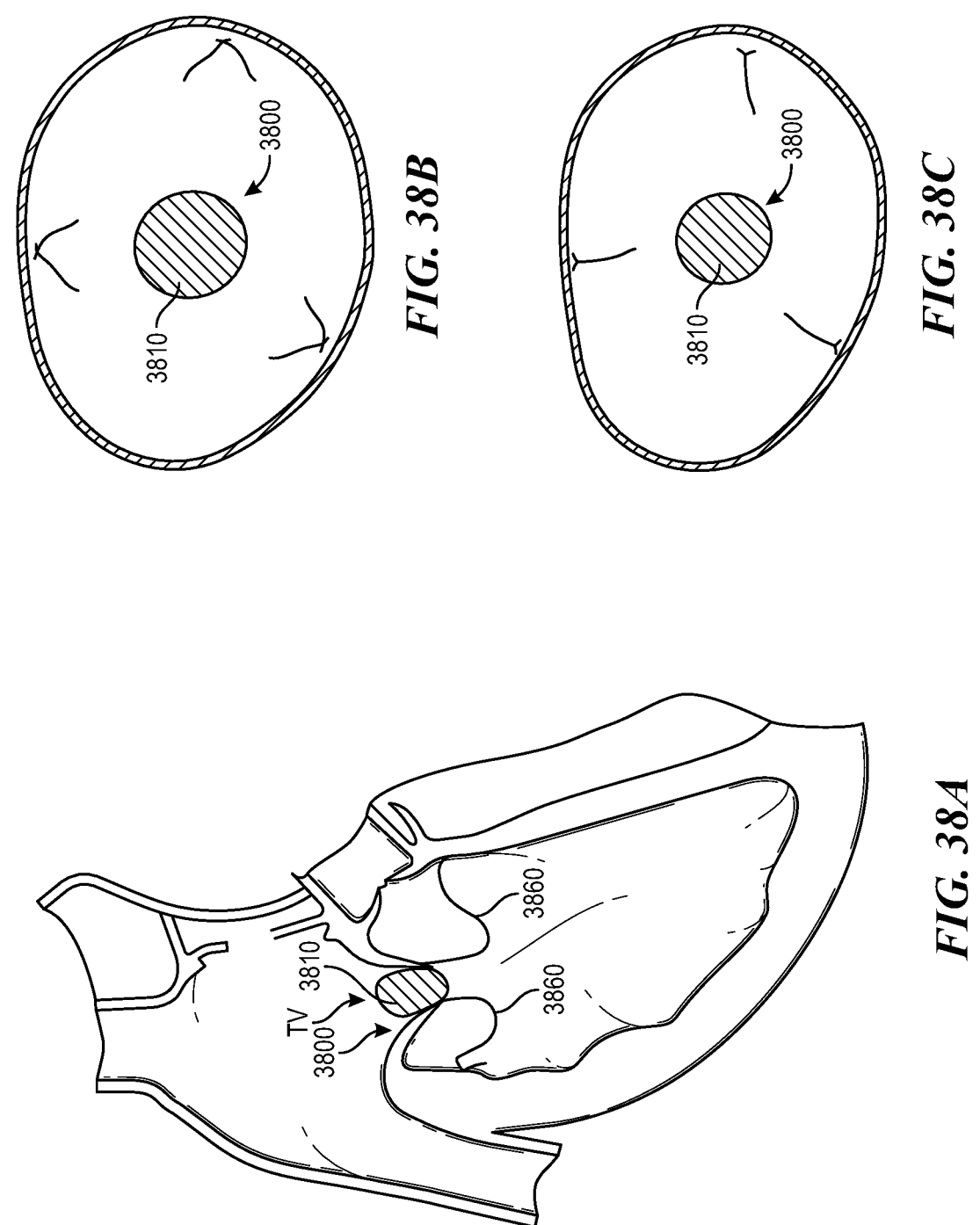
FIG. 38A is a side cross-sectional view of a valve repair device implanted at the tricuspid valve in accordance with embodiments of the present technology.
FIGS. 38B and 38C are transverse cross-sectional views of the valve repair device of FIG. 38A during diastole and systole, respectively, in accordance with embodiments of the present technology.

FIG. 38A is a side cross-sectional view of a valve repair device 3800 implanted at the tricuspid valve TV in accordance with embodiments of the present technology. FIGS. 38B and 38C are transverse cross-sectional views of the valve repair device 3800 of FIG. 38A during diastole and systole, respectively, in accordance with embodiments of the present technology. Referring to FIGS. 38A-38C together, the valve repair device 3800 includes a coaptation member 3810 and sub-valvular brace members 3860 configured to engage and apply an outward force to the ventricle (e.g., the ventricular wall) to support the coaptation member 3810 at the valve between the native leaflets. In some embodiments, the device 3800 can optionally include one or more leaflet clips (not shown) configured to fixate a leaflet onto the coaptation member 3810 for additional stability, to reduce regurgitation, and/or to provide an annuloplasty effect. In other embodiments, the brace members 3860 can be positioned in the atrium to engage the atrial wall to support the coaptation member 3810. In some embodiments, such an atrial bracing member can support sub-valvular leaflet clips. The brace members 2860 can be made of a superelastic material, such as nitinol.

Figures 39A, 39B, 39C:
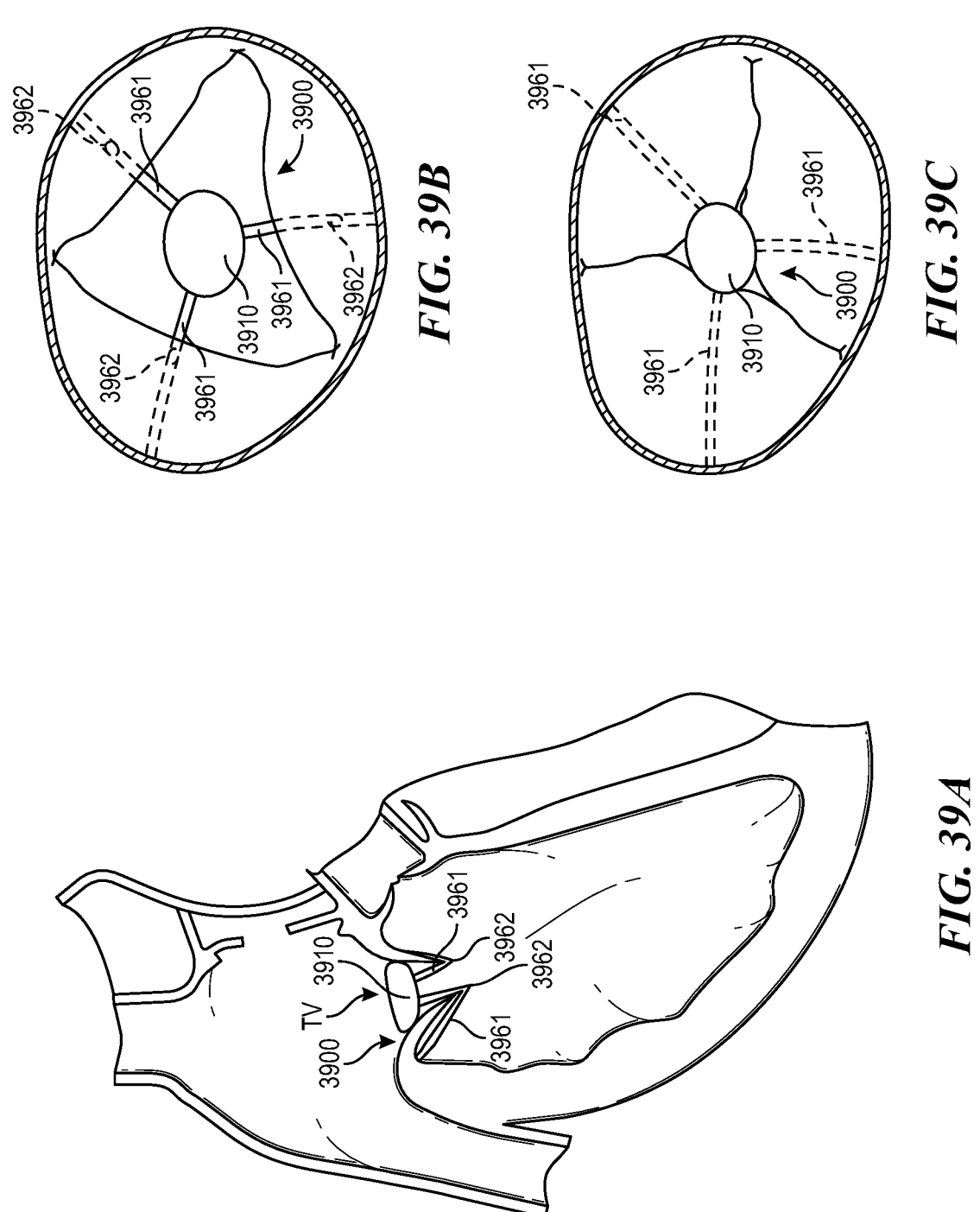
FIG. 39A is a side view of a valve repair device implanted at the tricuspid valve in accordance with embodiments of the present technology.
FIGS. 39B and 39C are top views of the valve repair device of FIG. 39A during diastole and systole, respectively, in accordance with embodiments of the present technology.

FIG. 39A is a side cross-sectional view of a valve repair device 3900 implanted at the tricuspid valve TV in accordance with embodiments of the present technology. FIGS. 39B and 39C are top views of the valve repair device 3900 of FIG. 39A during diastole and systole, respectively, in accordance with embodiments of the present technology. Referring to FIGS. 39A-39C together, the valve repair device 3900 includes a coaptation member 3910 and multiple fingers or anchors (e.g., three anchors) 3961 that extend ventricularly below the leaflets to engage the annulus of the tricuspid valve TV to secure (e.g., anchor, affix) the coaptation member 3910 between the leaflets of the tricuspid valve TV. In some embodiments, the anchors 3961 can be hinged at hinges 3962 such that the anchors 3961 extend downward below the leaflets into the ventricle and then upward to the annulus. The hinges 3962 can be moving or fixed.

Figure 40:
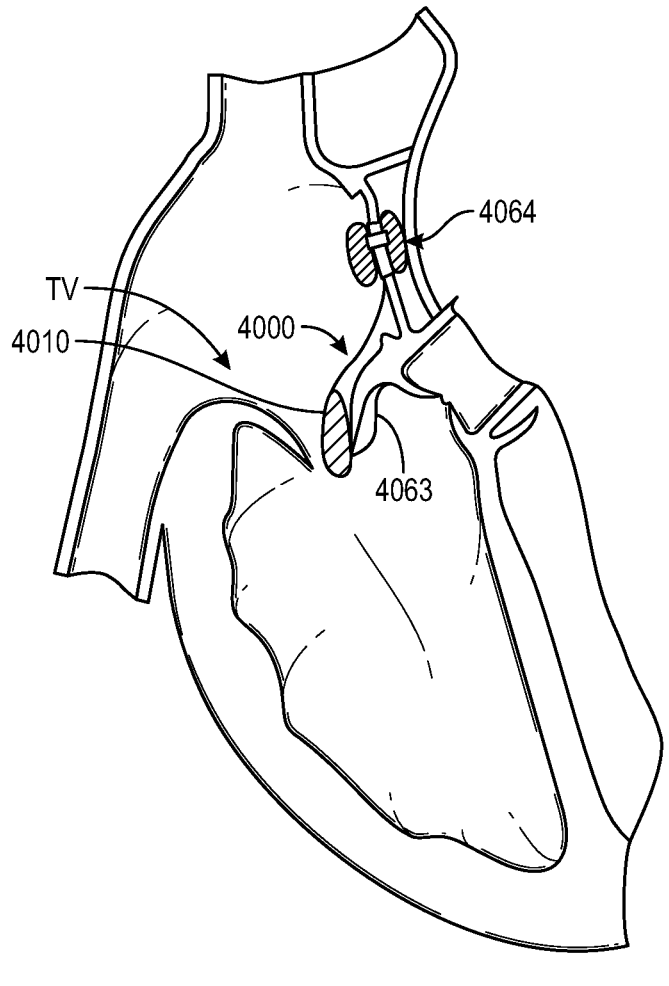
FIG. 40 is a side cross-sectional view of a valve repair device implanted at the tricuspid valve in accordance with embodiments of the present technology.

FIG. 40 is a side cross-sectional view of a valve repair device 4000 implanted at the tricuspid valve TV in accordance with embodiments of the present technology. In the illustrated embodiment, the valve repair device 4000 includes a coaptation member 4010 movably secured to one or more native leaflets via a hook 4063 and an anchor 4064. More specifically, (i) the anchor 4064 can extend from the coaptation member 4010 to the septum or another portion of the cardiac anatomy (e.g., supra-valvular cardiac anatomy) and (ii) the hook 4063 can extend from the coaptation member 4010 around the ventricular side of the one or more leaflets. The hook and anchor system can allow the one or more leaflets to still move during the cardiac cycle while, for example, inhibiting upward motion of the one or more leaflets, thereby inhibiting leaflet flail and regurgitation. The anchor 4064 can be delivered supplementally after placement of the coaptation member 4010.

VI. SELECTED EMBODIMENTS OF CARDIAC VALVE REPAIR DEVICES INCLUDING MECHANISMS FOR MOVABLY SECURING COAPTATION MEMBERS AT A CARDIAC VALVE

Figure 41A:
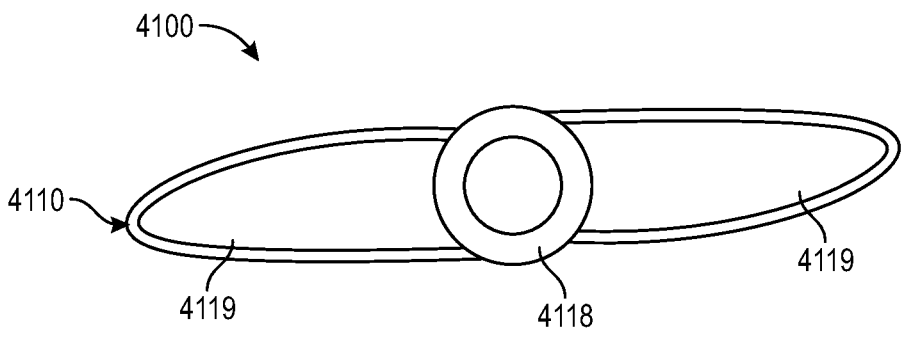
FIGS. 41A-41C are a top view during systole, a top view during diastole, and side view during diastole, respectively, of a valve repair device in accordance with embodiments of the present technology.
Figure 41B:
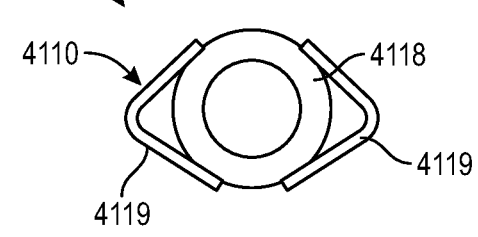
Figure 41C:
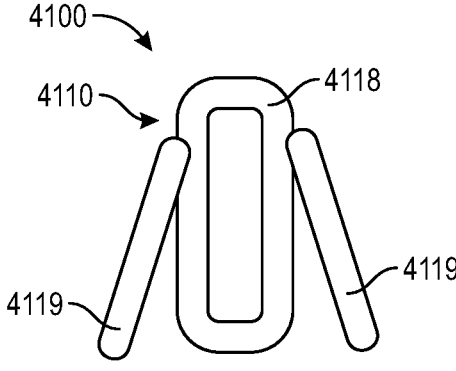
Figures 41D, 41E, 41F:
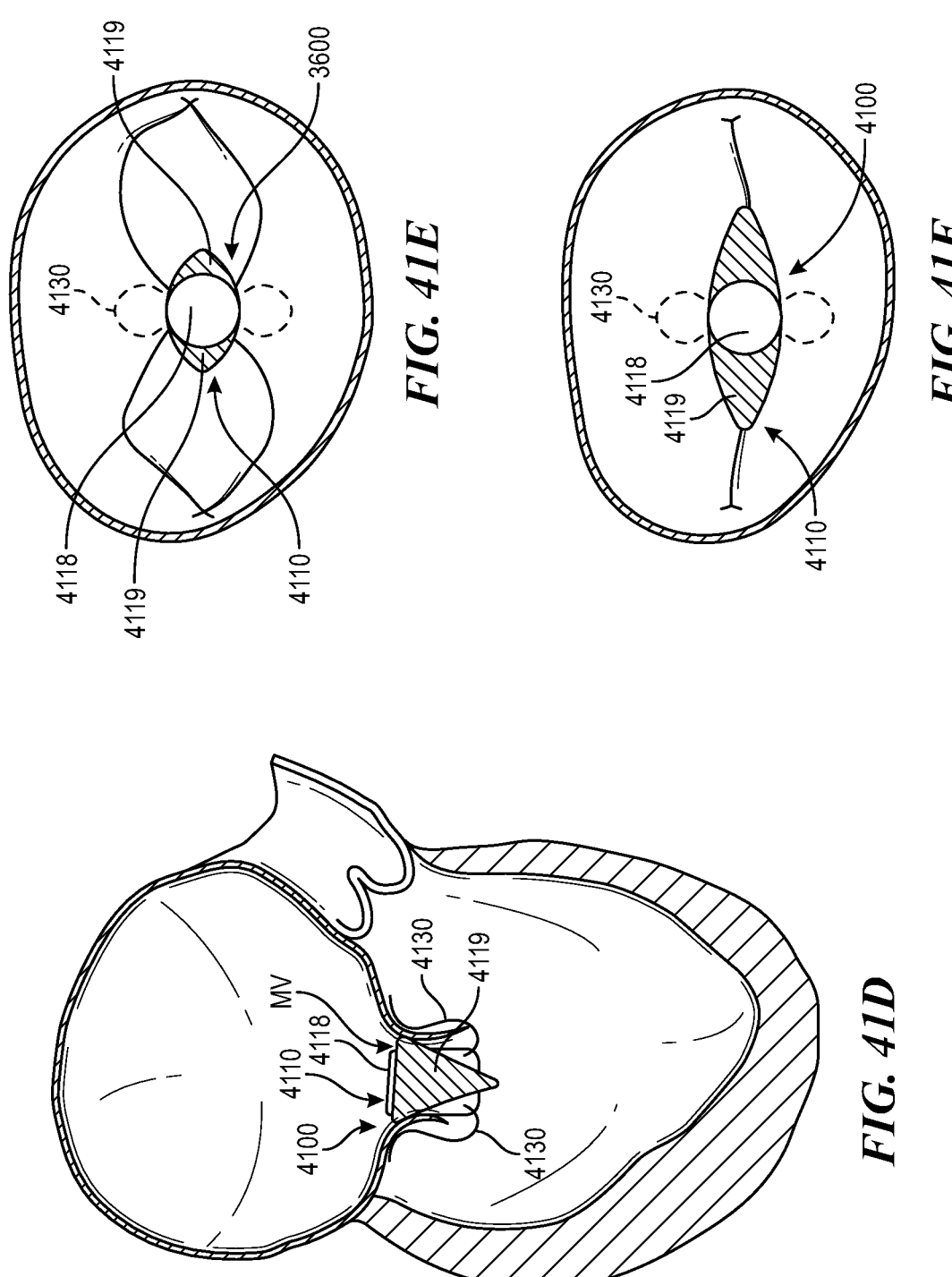
FIG. 41D is a side cross-sectional view of the valve repair device of FIGS. 41A-41C implanted at the mitral valve in accordance with embodiments of the present technology.
FIGS. 41E and 41F are transverse cross-sectional views of the valve repair device of FIGS. 41A-41D during diastole and systole, respectively, in accordance with embodiments of the present technology.

In some embodiments, cardiac valve repair devices in accordance with the present technology can be movably secured at or proximate to a cardiac valve to, for example, facilitate selective movement of the device during the cardiac cycle. For example, FIGS. 41A-41C are a top view during systole, a top view during diastole, and side view during diastole, respectively, of a valve repair device 4100 in accordance with embodiments of the present technology. FIG. 41D is a side cross-sectional view of the valve repair device 4100 of FIGS. 41A-41C implanted at the mitral valve MV in accordance with embodiments of the present technology. FIGS. 41E and 41F are transverse cross-sectional views of the valve repair device 4100 of FIGS. 41A-41D during diastole and systole, respectively, in accordance with embodiments of the present technology. Referring to FIGS. 41A-41F together, the valve repair device 4100 includes a coaptation member 4110 including a central portion 4118 and a pair of hinge portions 4119 extending from the central portion 4118. The valve repair device 4100 further includes a pair of clip mechanisms 4130 for securing the coaptation member 4110 to one or more leaflets of the mitral valve MV, as described in detail above with reference to, for example, FIGS. 29A-37E. The hinge portions 4119 are hingedly (e.g., movably, pivotably, rotatably) coupled to the central portion 4118 and configured to be (i) opened by the systolic flow in the C-C direction to occlude flow and (ii) pushed closed during diastole. In some embodiments, one or both of the hinge portions 4119 can include piezoelectric or other electrical generation components configured to harness and repurpose the mechanical motion generated by the blood flow.

VII. SELECTED EMBODIMENTS OF CARDIAC VALVE REPAIR DEVICES INCLUDING ATRIAL AND VENTRICULAR MEMBERS CONFIGURED TO CAPTURE ONE OR MORE VALVE LEAFLETS THEREBETWEEN

In some embodiments, cardiac valve repair devices in accordance with the present technology can include an atrial member and a ventricular member configured to capture (e.g., "sandwich") one or more native leaflets therebetween. For example, the atrial and ventricular members can include multiple small clips or other features that interlock and waffle onto the native leaflets. The atrial and ventricular members can together at least partially fill a regurgitant orifice in a leaking cardiac valve (e.g., the mitral valve or the tricuspid valve). In some embodiments, the atrial and ventricular members can provide a coaptation surface for the native leaflets to seal around. The ventricular members can be designed such that they are tolerant to one leaflet not being captured. In such embodiments, the ventricular members can be designed to allow for coaptation against the non-captured leaflet.

Figures 42A, 42B, 42C:
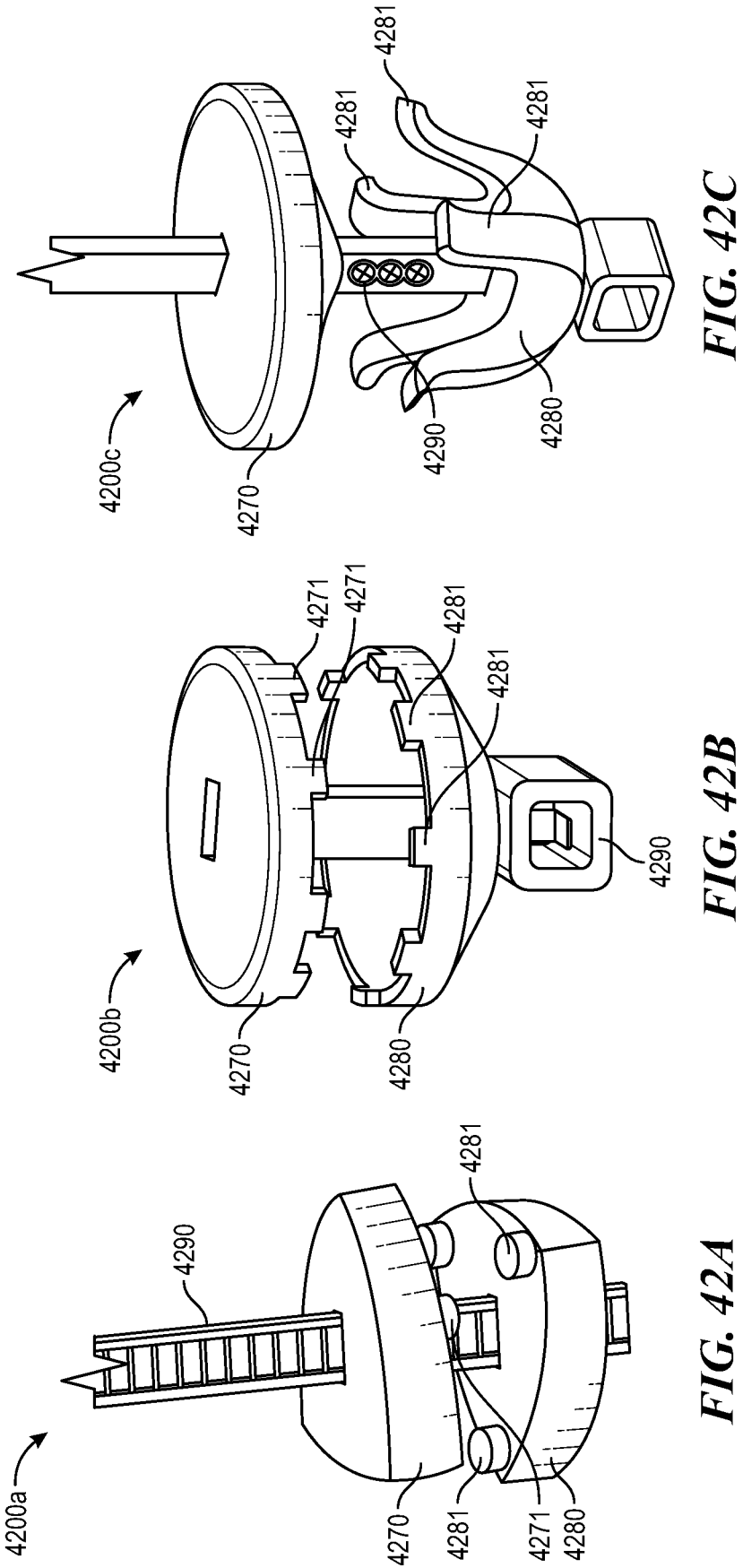
FIGS. 42A-42C are perspective side views of various valve repair devices in accordance with embodiments of the present technology.

FIGS. 42A-42C are perspective side views of various valve repair devices 4200a-4200c, respectively, (collectively valve repair devices 4200) in accordance with embodiments of the present technology. Referring to FIGS. 42A-42C together, the valve repair devices 4200 can include generally similar features including, for example, an atrial member 4270 (also referred to as an "upper member," "first member," "supra-valvular member," "atrial disc," "atrial half," "top plate," and iterations thereof) and a ventricular member 4280 (also referred to as a "lower member," "second member," "sub-valvular member," "ventricular disc," "ventricular half," and iterations thereof). One or both of the atrial and ventricular members 4270, 4280 can be slidably coupled to a central member 4290 (e.g., an elongate central member) and configured to be pressed together (e.g., slid toward each other along the central member, "sandwiched" together, compressed) to capture one or more native leaflets therebetween. That is, one or both of the atrial and ventricular members 4270, 4280 can be moved toward one another along the central member 4290 to reduce a distance between the atrial and ventricular members 4270, 4280 to thereby capture one of more native leaflets therebetween. In some embodiments, the atrial member 4270 can include atrial engagement features 4271 and/or the ventricular member 4280 can include ventricular engagement features 4281. The engagement features 4271, 4281 can comprise clips, fingers, and/or securing features and can be positioned around edges of the atrial member 4270 and/or the ventricular member 4280. The engagement features 4271, 4281 can interlock with one another and waffle onto leaflets at the line of coaptation, and/or the atrial and ventricular members 4270, 4280 can be locked in place by the central member 4290 that runs through each of the atrial and ventricular members 4270, 4280 (e.g., similar to a button snap). That is, the atrial member 4270 can nest within the ventricular member 4280. More generally, the atrial member 4270 can reside within, between, or on top of the ventricular engagement features 4281 of the ventricular member. In some embodiments, the ventricular member 4280 can have a claw-like or multi-pronged shape to navigate through chordae surrounding the valve and secure one or more leaflets to the atrial member 4270 while providing space for chordae motion.

When engaged together, the atrial and ventricular members 4270, 4280 can be shaped to suppress flail and fill coaptation gaps in the cardiac valve. In some embodiments, the atrial and ventricular members 4270, 4280 can be generally circular (e.g., rendering them agnostic to a particular alignment with the valve) while, in other embodiments, the atrial and ventricular members 4270, 4280 can have other shapes. In some embodiments, the atrial and ventricular members 4270, 4280 can provide a coaptation surface for one or more native valve leaflets. In some embodiments, the atrial and ventricular members 4270, 4280 can be angled to mimic the natural coaptation angle of the leaflets. In some embodiments, the atrial member 4270 may be expanded or contracted in the radial direction after the ventricular member 4280 is attached—which can pull more leaflet in and provide an optional annuloplasty effect.

In some embodiments, the devices 4200 can be deployed sequentially to provide a reduced delivery profile and to aid in the verification of leak resolution before fully deployment. For example, the atrial member 4270 can be deployed before the ventricular member 4280, allowing the resolution of the leak to be verified before the ventricular member 4280 is deployed and locked into the atrial member 4270. In other embodiments, a balloon may be deployed into the area of leakage to verify placement before the device 4200 is deployed.

Figure 43A:
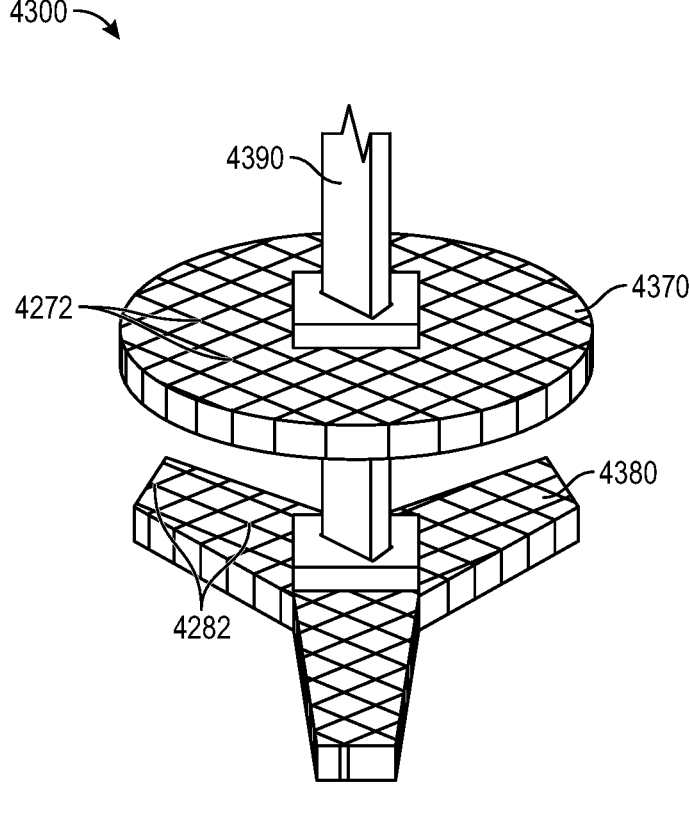
FIGS. 43A and 43B are a side perspective view and enlarged side cross-sectional view, respectively, of a valve repair device in accordance with embodiments of the present technology.
Figure 43B:
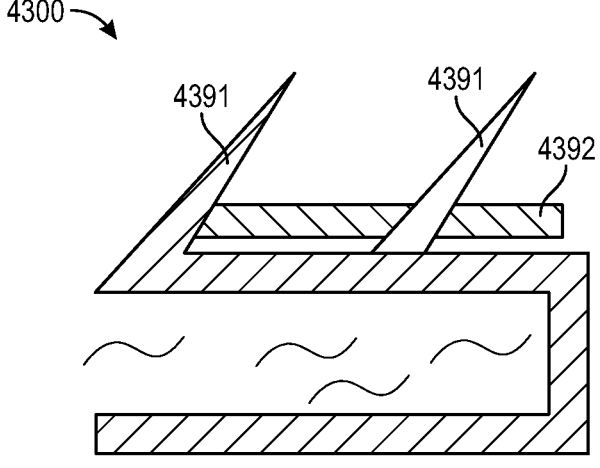

FIGS. 43A and 43B are a side perspective view and enlarged side cross-sectional view, respectively, of a valve repair device 4300 in accordance with embodiments of the present technology. Referring first to FIG. 43A, the valve repair device 4300 includes an atrial member 4370 and a ventricular member 4380 (i) coupled together via a central member 4290 and (ii) configured to be pressed together to sandwich one or more valve leaflets therebetween. In the illustrated embodiment, the atrial member 4370 comprises a plurality of interconnected struts 4372 and the ventricular member 4380 also comprises a plurality of interconnected struts 4382. The struts 4372, 4382 can enable the valve repair device 4300 to be collapsed/expanded to facilitate sheathing, delivery, and/or recapture. The struts 4372, 4382 can be formed from stainless steel, nickel-titanium alloy (e.g., nitinol), and/or other suitable biocompatible materials, and can be a laser-cut pattern or wire form. The valve repair device 4300 can be centrally located relative to a valve or biased along one or more coaptation lines. In some aspects of the present technology, the atrial and ventricular members 4370, 4380 act as a two-piece space filler between the native leaflets and the double-layered structure of the device 4300 can provide strength and sealing and, in some embodiments, house clotting provisions. Referring to FIG. 43B, the valve repair device 4300 can include cleats 4391 or other engagement features for anchoring onto the leaflets. In some embodiments, the outside of the atrial and ventricular members 4370, 4380 can include a material 4392, such as knit or woven polyester to promote bio-incorporation into the leaflets. In some embodiments, the material 4392 can further include PTFE or ePTFE to help provide an atraumatic surface for coaptation to occur against.

Figure 44:
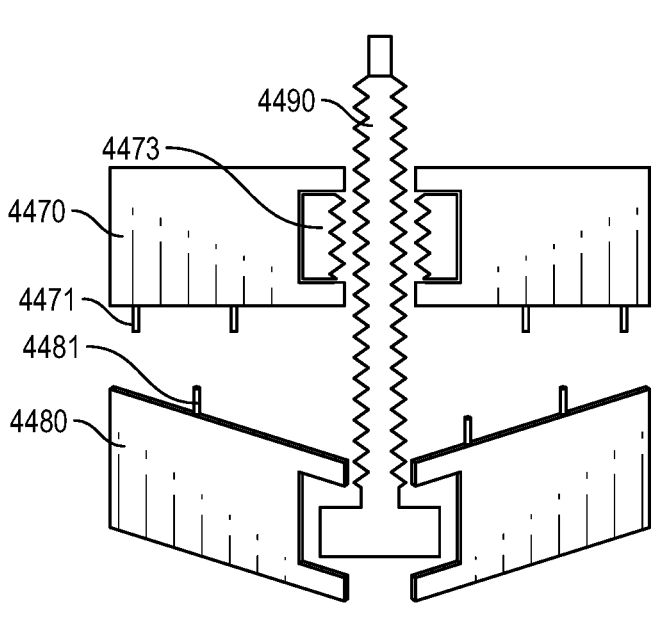
FIG. 44 is a side cross-sectional view of a valve repair device and lock mechanism in accordance with embodiments of the present technology.

FIG. 44 is a side cross-sectional view of a valve repair device 4480 in accordance with embodiments of the present technology. In the illustrated embodiment, the valve repair device 4480 includes an atrial member 4470 and a ventricular member 4480 (*i*) coupled together via a central threaded member 4490 (e.g., a threaded stud) and (ii) configured to be pressed together to sandwich one or more valve leaflets therebetween. More specifically, the atrial member 4470 can be threadably coupled to the threaded member 4490 via a captive nut 4473, while the ventricular member 4480 is fixedly (e.g., non-rotatably) coupled to the threaded member 4490. Accordingly, rotation of the threaded member 4490 can move (e.g., translate) the atrial member 4470 toward or away from the ventricular member 4480. The threaded member 4490 can be rotated by a torque shaft or other component of an associated delivery system. In some aspects of the present technology, the valve repair device 4400 allows for the leaflets to be released after capture (e.g., if it is determined that the leaflet capture is inadequate) via the movement of the atrial member 4470 away from the ventricular member 4480 along the threaded member 4490. In some embodiments, the atrial and/or ventricular members 4470, 4480 can include cleats or other engagement features 4471, 4481, respectively, (e.g., at edges thereof) for anchoring onto the leaflets.

Figures 45A, 45B:
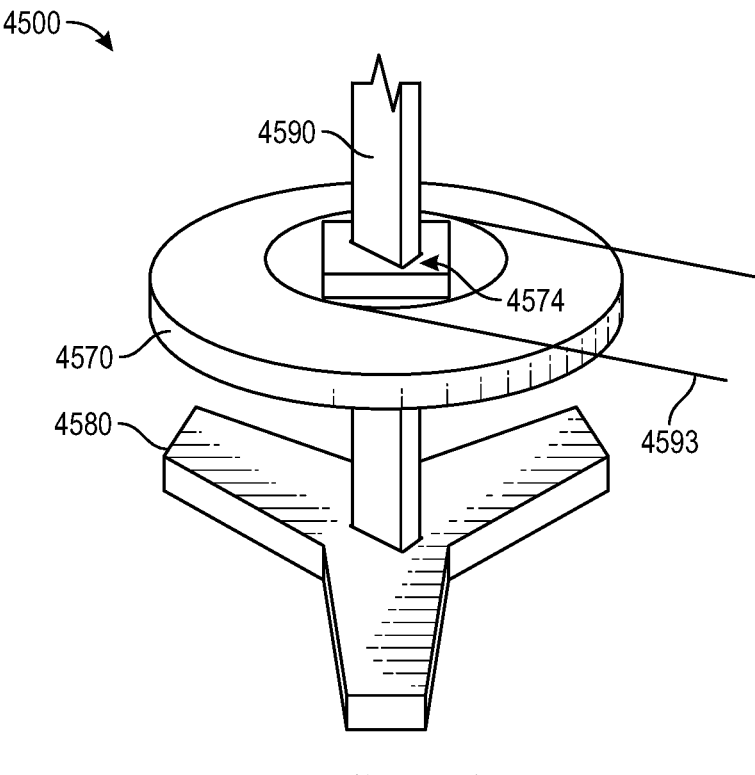
FIG. 45A is a side perspective view of a valve repair device in accordance with embodiments of the present technology.
FIGS. 45B-45D are enlarged side cross-sectional views of an unlock mechanism of the valve repair device of 45A in accordance with embodiments of the present technology.

FIG. 45A is a side perspective view of a valve repair device 4500 in accordance with embodiments of the present technology. In the illustrated embodiment, the valve repair device 4500 includes an atrial member 4570 and a ventricular member 4580 (*i*) coupled together via a central post member 4590 (e.g., a locking post) and (ii) configured to be pressed together to sandwich one or more valve leaflets therebetween. The atrial member 4570 can be movably coupled to the post member 4590 via, for example, an unlock mechanism 4574. FIG. 45B is an enlarged side cross-sectional view of the unlock member 4574 in accordance with embodiments of the present technology. Referring to FIGS. 45A and 45B together, an associated delivery system can be actuated to unlock the unlock mechanism 4574 move the atrial member 4570 toward the ventricular member 4580 along the post member 4590 to capture the one or more leaflets therebetween. In some embodiments, the delivery system can include an unlock cable 4593 that is actuatable to pull in a tooth 4575 of the unlock mechanism 4574 to unlock the atrial member 4570 from the post member 4590 and allow the atrial member 4570 to move freely. That is, the unlock mechanism 4574 can comprise a "ratcheting" mechanism. Accordingly, the unlock cable 4593 can be actuated to facilitate movement of the atrial member away 4570 from the ventricular member 4580, allowing the leaflets to be released from between the atrial and ventricular members 4570, 4580 if, for example, leaflet capture is determined to be inadequate.

Figure 45C:
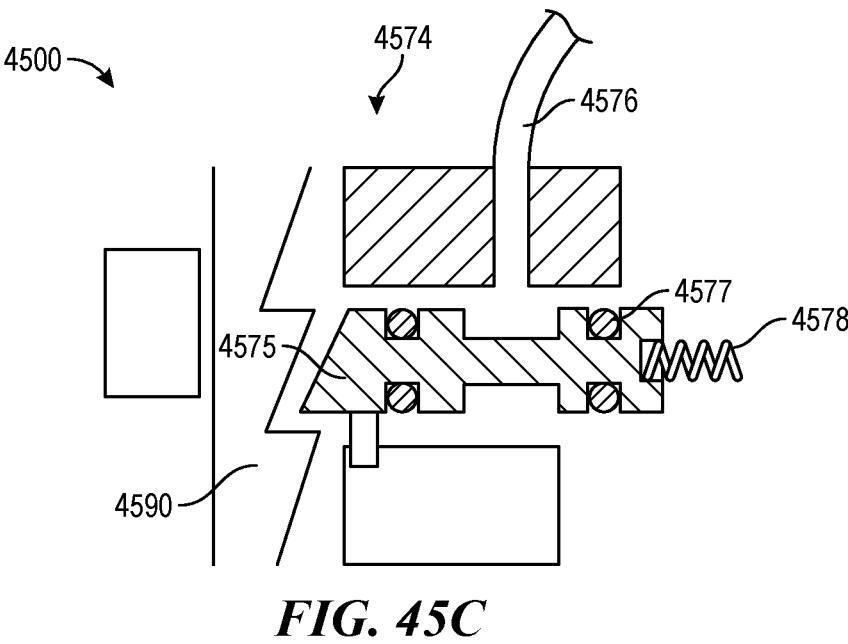
Figure 45D:
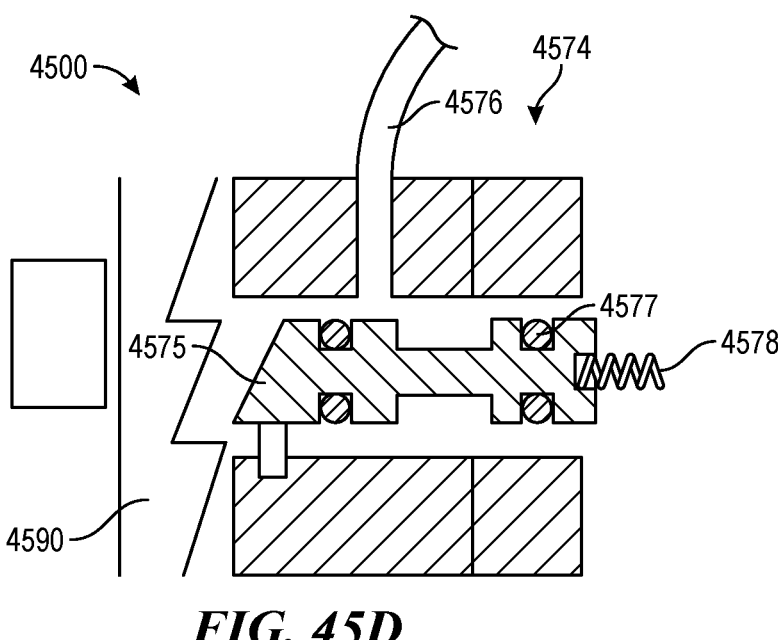

In other embodiments, the atrial member 4570 can be unlocked from the post member 4590 via other mechanisms aside from an unlock cable 4593. For example, FIGS. 45C and 45D are enlarged views of the valve repair device of FIG. 45A are enlarged side cross-sectional view of the unlock member 4574 in accordance with additional embodiments of the present technology. Referring to FIGS. 45A, 45C, and 45D together, the device 4500 can utilize a hydraulic line 4576, sealed piston 4577, and compression spring 4578 to facilitate unlocking of the atrial member 4570 from the post member 4590. More specifically, the compression spring 4579 can keep the tooth 4575 normally closed to allow for the tooth 4575 to ratchet on the post member 4590—facilitating advancement of the atrial member 4570 toward the ventricular member 4580. The unlock mechanism 4574 can be pressurized to overcome the biasing force of the compression spring 4578—pulling the tooth 4575 inward and allowing the atrial member 4570 to move freely along the post member 4590.

FIG. 46A is a side cross-sectional view of a valve repair device 5700 in accordance with embodiments of the present technology. FIGS. 46B-46E are side views of the valve repair device 5700 during delivery and deployment in accordance with embodiments of the present technology. Referring first to FIG. 46A, the valve repair device 4600 includes an atrial member 4670 and a ventricular member 4680 coupled to a threaded post 4690. Similar to the embodiments described in detail above with reference to FIGS. 44-46D, the atrial member 4670 can be movably coupled to the threaded post 4690 (e.g., via a captive nut 4673) while the ventricular member 4680 can be fixedly attached to the threaded post 4690 such that rotation of the post 4690 moves the atrial member 4670 relative to the ventricular member 4680. In the illustrated embodiment, the atrial and ventricular members 4670, 4680 each comprise two or more hinged flaps (identified as atrial flaps 4679 and ventricular flaps 4689). With additional reference to FIGS. 46B-46E, the flaps 4679, 4689 can be pivoted toward one another and the threaded member 4490 to, for example, facilitate sheathing (e.g., a compact delivery position) within a delivery catheter C (FIGS. 46B and 46C). After unsheathing, the flaps 4679, 4689 can be toggled open as shown in FIGS. 46C and 46E and the atrial member 4670 can be moved toward the ventricular member 4680 (e.g., via rotation of a torque shaft coupled to the post 4690) to capture one or more leaflets L therebetween.

Figures 47A, 47B, 47C:
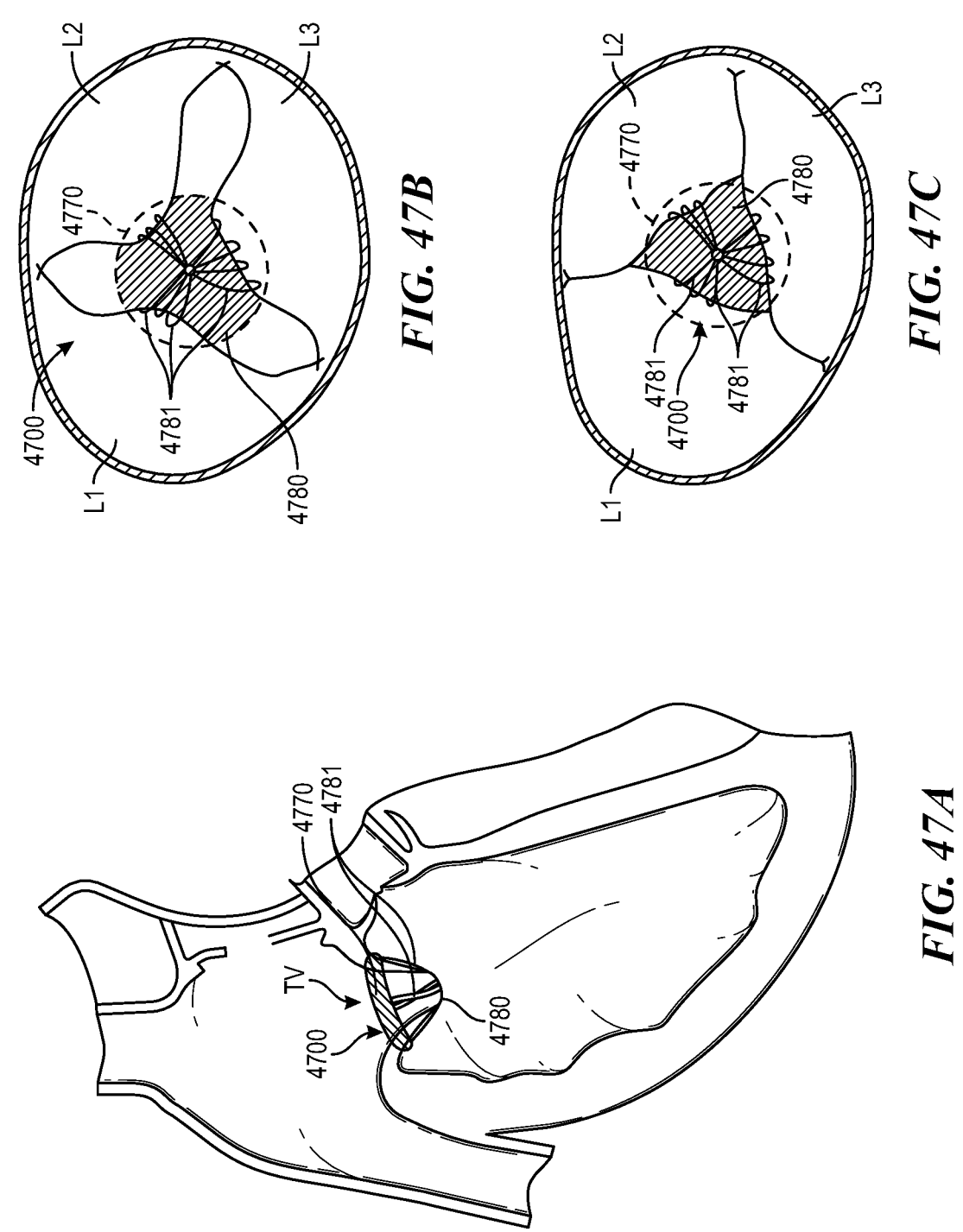
FIG. 47A is a side cross-sectional view of the valve repair device implanted at the tricuspid valve in accordance with embodiments of the present technology.
FIGS. 47B and 47C are transverse cross-sectional views of the valve repair device of FIG. 47A during diastole and systole, respectively, in accordance with embodiments of the present technology.

FIG. 47A is a side cross-sectional view of the valve repair device 4700 implanted at the tricuspid valve TV in accordance with embodiments of the present technology. FIGS. 47B and 47C are transverse cross-sectional views of the valve repair device 4700 of FIG. 47A during diastole and systole, respectively, in accordance with embodiments of the present technology. Referring to FIGS. 47A-47C together, the valve repair device 4700 includes a ventricular member 4780 and an atrial member 4770 configured to sandwich two or more of the leaflets of the tricuspid valve TV therebetween (e.g., each of the leaflets L1-L3). In the illustrated embodiment, the ventricular member 4780 includes a plurality of narrow fingers 4781 (e.g., engagement features) configured to rotate around a central axis of the device 4700, allowing the fingers 4781 to navigate through chordae and bunch together where paths allow, collectively creating wider points of contact when met with the atrial member 4770. When sandwiched together, the atrial and ventricular members 4770, 4780 act as a space filler between the leaflets L1-L3. The device 4700 can be centrally positioned within the valve as shown in FIGS. 47A-47C, or can be biased toward one side of the valve.

Figure 48A:
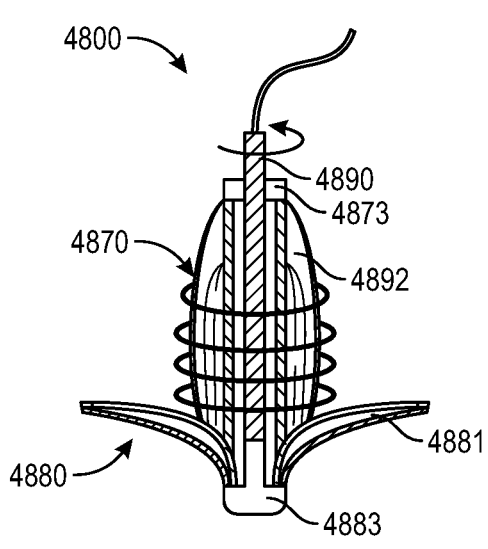
FIGS. 48A and 48B are a side view and an enlarged side view, respectively, of a valve repair device in a partially-deployed position in accordance with embodiments of the present technology.
Figure 48B:
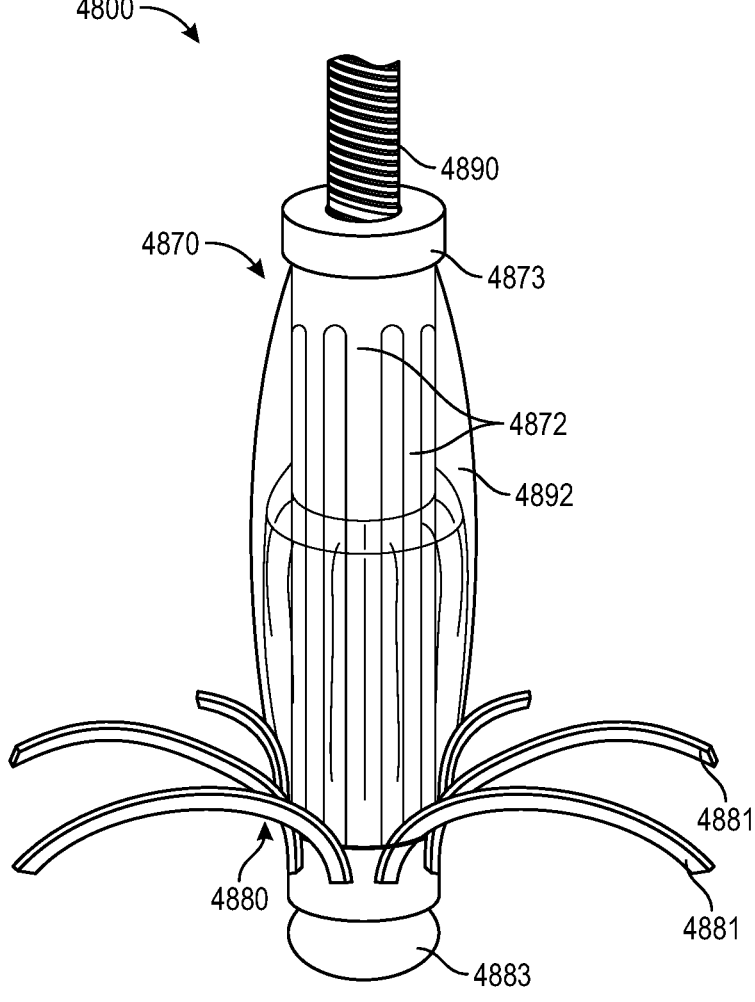
Figure 48C:
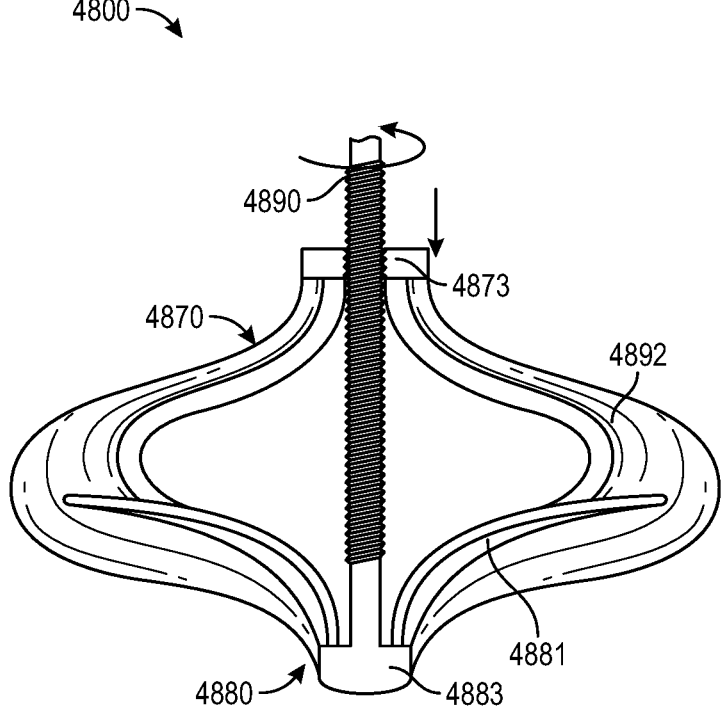
FIG. 48C is a side view of the valve repair device of FIGS. 48A and 48B in a fully-deployed position in accordance with embodiments of the present technology.

FIGS. 48A and 48B are a side view and an enlarged side view, respectively, of a valve repair device 4800 in a partially-deployed position in accordance with embodiments of the present technology. FIG. 48C is a side view of the valve repair device 4800 of FIGS. 48A and 48B in a fully-deployed position in accordance with embodiments of the present technology. Referring to FIGS. 48A-48C together, the valve repair device 4800 includes a ventricular member 4880 and an atrial member 4870 configured to sandwich one or more valve leaflets therebetween. In the illustrated embodiment, the ventricular member 4880 includes a plurality of fingers 4881 (also referred to as "arms"; e.g., six, evenly spaced fingers), connected by a circular base 4883 and that are configured to navigate through chordae around the valve. The atrial member 4870 is flexible and can be formed of, for example, an ePTFE-covered foam 4892 that can fill in and between the fingers 4881 of the ventricular member 4880 when the atrial and ventricular members 4870, 4880 are sandwiched together-thereby pulling in the leaflets while also bulging through the fingers 4881 of the ventricular member 4880. Accordingly, the flexible atrial member 4870 secures the native leaflets in place after they are captured by the fingers 4881. The atrial member 4870 can also function as a space filler between the leaflets and, in some embodiments, provides a prosthetic coaptation surface for one or more of the leaflets, especially if not all leaflets are captured.

In some embodiments, the underlying device structure is a stent-like structure cut from a single tube (e.g., a nitinol tube) and/or from nitinol wire forms. The ventricular fingers 4881 can be shaped in the deployed configuration and covered with ePTFE or another atraumatic material which also promotes tissue ingrowth. As best seen in FIG. 48B, the atrial member can include a plurality of vertical struts 4872 cut from the same tube as the ventricular fingers 4881 and shaped in a flattened configuration such that the struts protrude at least up to or past the ventricular surface of the ventricular fingers 4881 when deployed. The struts 4872 can be covered with the highly compressible foam 4892 which is further covered with an atraumatic ePTFE layer. In the deployed state (FIG. 48C), the ventricular fingers 4881 and the atrial member 4870 together clamp the leaflets and secure the device 4800 in place. If no leaflet is captured around part of the circumference of the device 4800, the ventricular fingers 4881 can sink into the foam 4892 of the atrial member 4870 and provide a relatively contiguous, atraumatic coaptation surface for the leaflet(s) that was not captured.

To deliver the device 4800 to, for example, the tricuspid valve, the device 4800 can be positioned centrally over the tricuspid valve in the right atrium and then advanced into the right ventricle. The ventricular fingers 4881 can then be deployed (e.g., unsheathed from a catheter or uncinched) when the device 4800 is positioned in the right ventricle below the leading edge of the leaflets. Next, the device 4800 can be retracted to capture some or all leaflets of the tricuspid valve. When some or all of the leaflets are captured, the atrial member 4870 can be deployed by first uncinching or unsheathing the ePTFE/foam covering 4892, then compressing or flattening the underlying vertical struts 4872 using a threaded rod 4890 running through a nut 4873 attached to the proximal end of the underlying device structure. In other embodiments, the atrial member 4870 can be deployed by releasing a pin which holds it in the elongated configuration or by releasing the same cinching sutures that hold the ePTFE/foam covering 4892 in place during leaflet grasping. In yet other embodiments, the vertical struts 4872 can be replaced by a braided or laser cut structure (e.g., as described in detail with reference to FIGS.

62A and 62B). Alternatively, the atrial member 4870 can consist of a balloon or a foam-filled balloon instead of a metallic structure. In some embodiments, the ePTFE covering and foam of the atrial member 4870 can have slits that align with the ventricular fingers 4881 such that the fingers 4881 sink into the foam 4892 completely if no leaflet is captured.

Figure 49A:
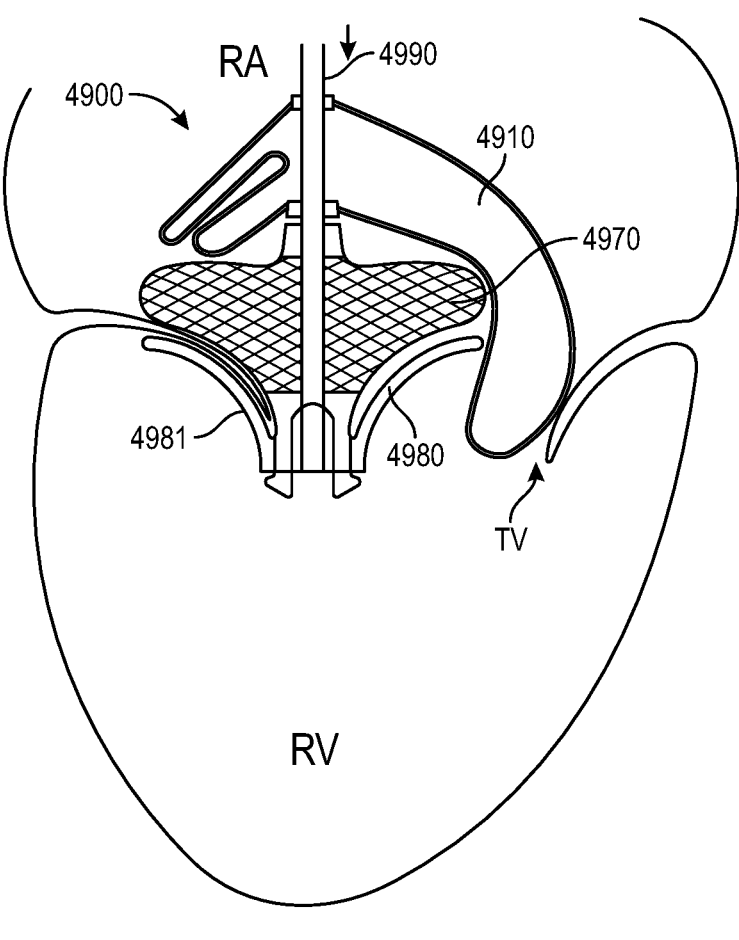
FIGS. 49A and 49B are a side cross-sectional view and a transverse cross-sectional view, respectively, of a valve repair device implanted at the tricuspid valve in accordance with embodiments of the present technology.
Figure 49B:
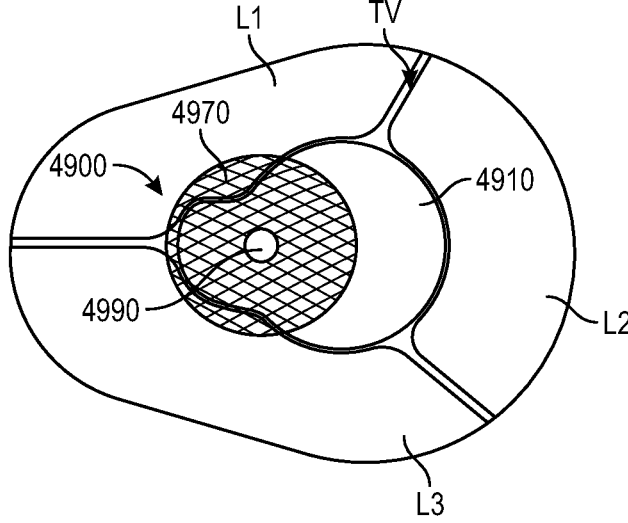

FIGS. 49A and 49B are a side cross-sectional view and a transverse cross-sectional view, respectively, of a valve repair device 4900 implanted at the tricuspid valve TV in accordance with embodiments of the present technology. Referring to FIGS. 49A and 49B together, the valve repair device 4900 includes a ventricular member 4980 including fingers 4981 and an atrial member 4970 formed from a braided structure. The atrial and ventricular members 4970, 4980 are configured to sandwich one or more leaflets of the tricuspid valve TV (e.g., the leaflets L1 and L3) therebetween. In the illustrated embodiment, the device 4900 further includes a coaptation member 4910 coupled to the atrial member 4970 and/or the ventricular member 4980 and configured to provide a smooth coaptation surface around the edge of the device 4900 for any leaflets not captured during deployment of the ventricular fingers 4981 and the atrial member 4970 (e.g., the uncaptured leaflet L2). In some embodiments, the coaptation member 4910 can include a foam/ePTFE-covered stent structure, braided structure, and/or balloon. In some embodiments, the coaptation member 4910 can be pre-shaped to wrap around the edge of the deployed atrial and/or ventricular members 4970, 4980, as best seen in FIG. 49A. The shape of the coaptation member 4910 can be selected based on, for example, the native anatomy and the extent of leaflet(s) not captured. In some embodiments, prior to deployment, the coaptation member 4910 is elongated, sheathed, and fed over the central delivery shaft 4990 with the delivery shaft 4990 still attached to the device 4900. The coaptation member 4910 can then be rotationally aligned based on echocardiographic or other imaging, and unsheathed and deployed either with a screw mechanism or pusher (not shown). In some embodiments, the deployment mechanism can be utilized to compress the coaptation member 4910, further increasing the width and covering of the atrial member 4970, thereby further filling residual coaptation gaps and providing a coaptation surface for any uncaptured leaflet.

Figures 50A, 50B, 50C:
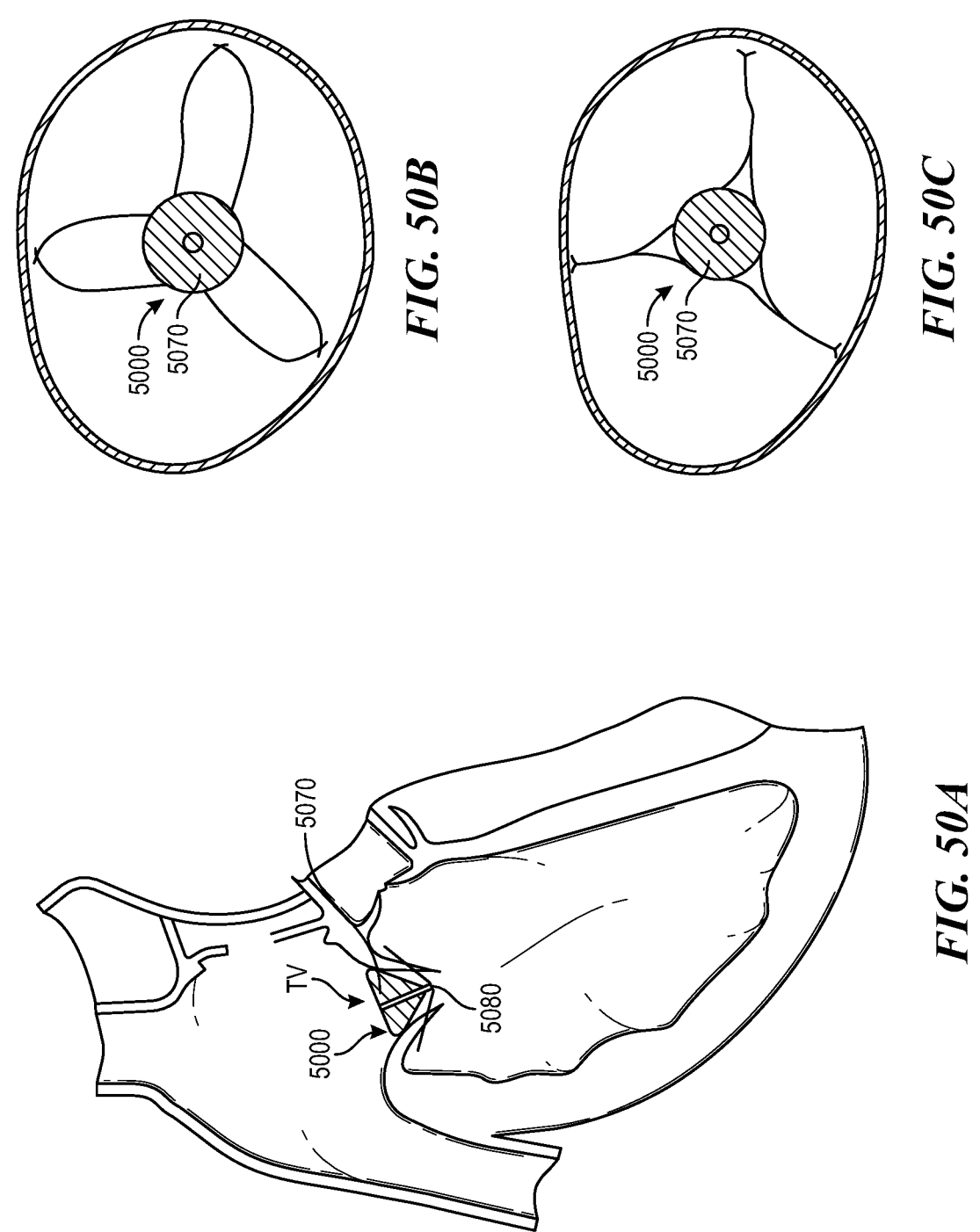
FIGS. 50A and 50D are side cross-sectional views of a valve repair device implanted at the tricuspid valve in an unexpanded position and an expanded position, respectively, in accordance with embodiments of the present technology.
FIGS. 50B and 50C are transverse cross-sectional views of the valve repair device in the unexpanded position of FIG. 50A during diastole and systole, respectively, in accordance with embodiments of the present technology.
Figures 50D, 50E, 50F:
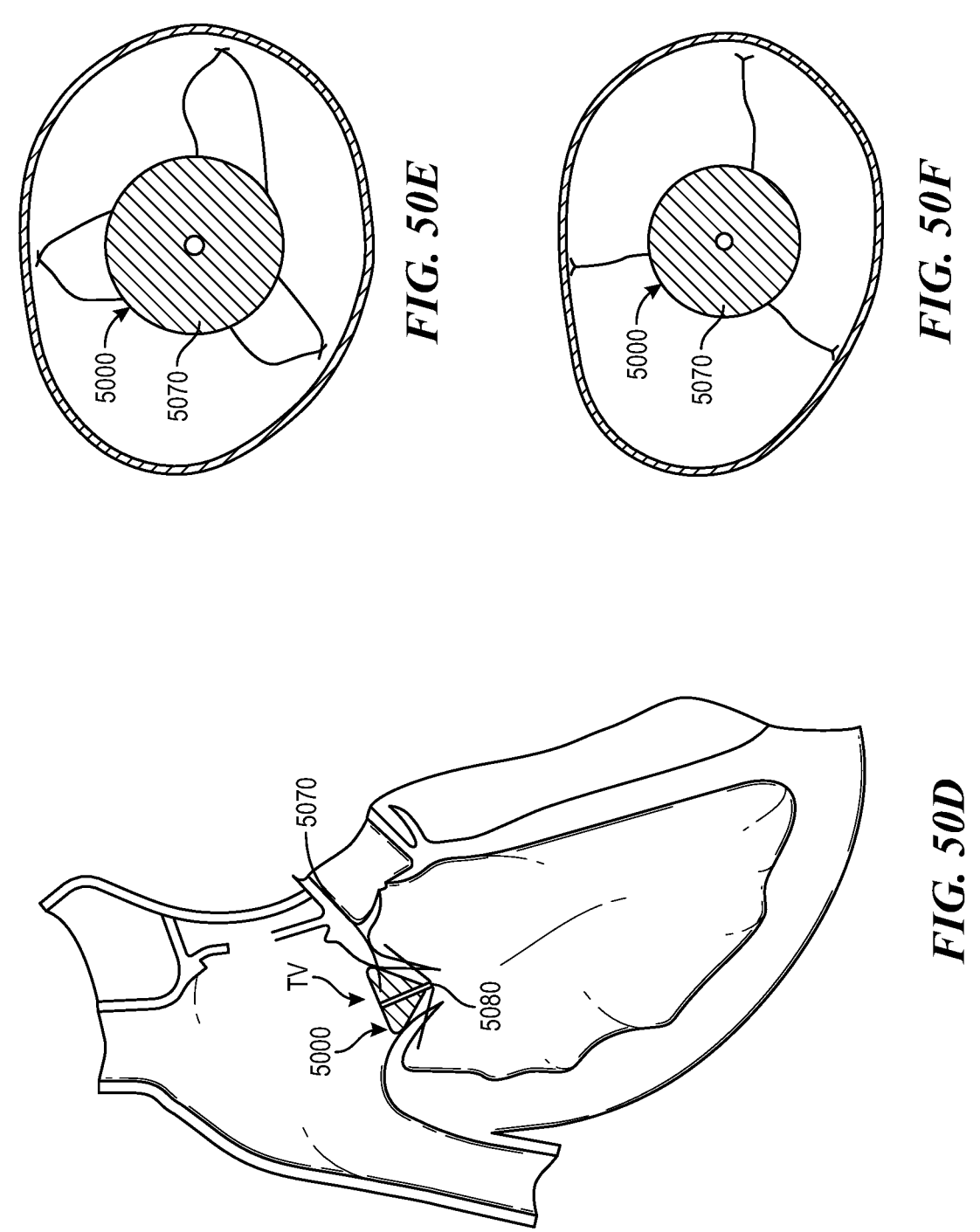
FIGS. 50E and 50F are transverse cross-sectional views of the valve repair device in the expanded position of FIG. 50D during diastole and systole, respectively, in accordance with embodiments of the present technology.

FIGS. 50A and 50D are side cross-sectional views of a valve repair device 5000 implanted at the tricuspid valve TV in an unexpanded position and an expanded position, respectively, in accordance with embodiments of the present technology. FIGS. 50B and 50C are transverse cross-sectional views of the valve repair device 5000 in the unexpanded position of FIG. 50A during diastole and systole, respectively, in accordance with embodiments of the present technology. FIGS. 50E and 50F are transverse cross-sectional views of the valve repair device 5000 in the expanded position of FIG. 50D during diastole and systole, respectively, in accordance with embodiments of the present technology. Referring to FIGS. 50A-50F together, the valve repair device 5000 includes an atrial member 5070 and a ventricular member 5080 configured to be sandwiched together to capture one or more leaflets of the tricuspid valve TV. In the illustrated embodiment, the atrial member 5070 is expandable between, for example, the unexpanded and expanded positions. Accordingly, the atrial member 5070 can be expanded to fill and plug any residual leaks that may exist before expansion of the atrial member 5070. For example, the atrial member 5070 can be expanded during a delivery procedure after determining that leakage through the tricuspid valve TV remains after initially positioning the device 5000 with the atrial member 5070 in the unexpanded position.

Figure 51E:
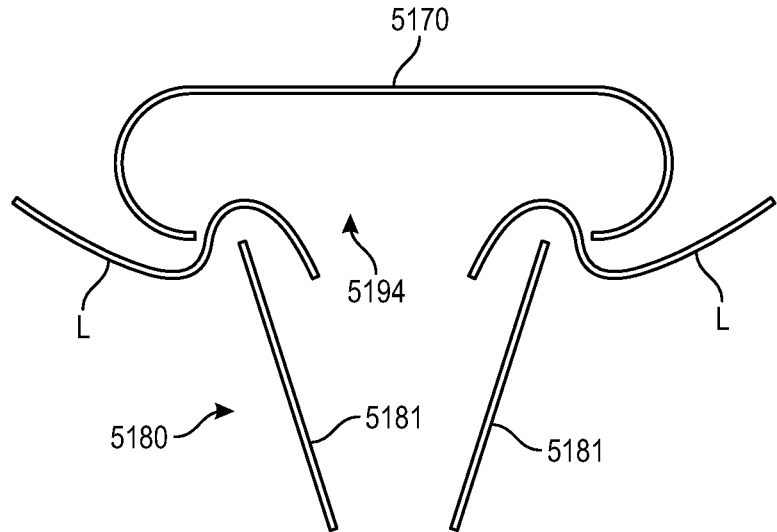
FIG. 51E is an enlarged cross-sectional view of the valve repair device of FIGS. 51A-51D secured to a pair of valve leaflets in accordance with embodiments of the present technology.

FIG. 51A is a perspective side view of a valve repair device 5100 in a first position in accordance with embodiments of the present technology. FIGS. 51B-51D are a perspective top view, perspective side view, and an enlarged perspective side view of the valve repair device 5100 of FIG. 51A in a second position in accordance with embodiments of the present technology. FIG. 51E is an enlarged cross-sectional view of the valve repair device 5100 of FIGS. 51A-51D secured to a pair of valve leaflets L in accordance with embodiments of the present technology. Referring to FIGS. 51A-51E together, the valve repair device 5100 includes an atrial member 5170 and a ventricular member 5180 coupled together via a central member 5190 and configured to be sandwiched together. In the illustrated embodiment, the ventricular member 5180 includes a plurality of fingers 5181, and the atrial member 5170 defines a recess 5194 configured to receive one or more of the fingers 5181 in the second position. That is, the fingers 5181 can nest with and be secured within the recess 5194 of the atrial member 5170. As best seen in FIG. 51E, the device 5100 is configured to capture the leaflets between the atrial and ventricular members 5170, 5180 such that the leaflets L curve around the top ends of the fingers 5181 and into the recess 5194 of the atrial member 5170, providing radial plication of the leaflets L for enhanced fixation.

FIG. 52A is a perspective side view of a valve repair device 5200 in a first position in accordance with embodiments of the present technology. FIGS. 52B and 52C are a perspective top view and a perspective side view of the valve repair device 5200 of FIG. 52A in a second position in accordance with embodiments of the present technology. FIG. 52D is an enlarged cross-sectional view of the valve repair device 5200 of FIGS. 52A-52C secured to a pair of valve leaflets L in accordance with embodiments of the present technology. Referring to FIGS. 52A-52D together, the valve repair device 5200 includes an atrial member 5270 and a ventricular member 5280 coupled together via a central member 5290 and configured to be sandwiched together. In the illustrated embodiment, the ventricular member 5280 includes a plurality of fingers 5281, and the atrial member 5270 has a trapezoidal or tapered shape configured to be received within an inner space defined between the fingers 5281. That is, all or a portion of the atrial member 5270 can nest with and be secured between the fingers 5281. As best seen in FIG. 52D, the device 5200 is configured to capture the leaflets L between the atrial and ventricular members 5270, 5280 such that the leaflets L extend around the lower surface of the atrial member 5270 (e.g., a curved or sloped lower surface) such that the leaflets L maintain a generally natural coaptation angle.

Figures 53A, 53B, 53C, 53D, 53E, 53F:
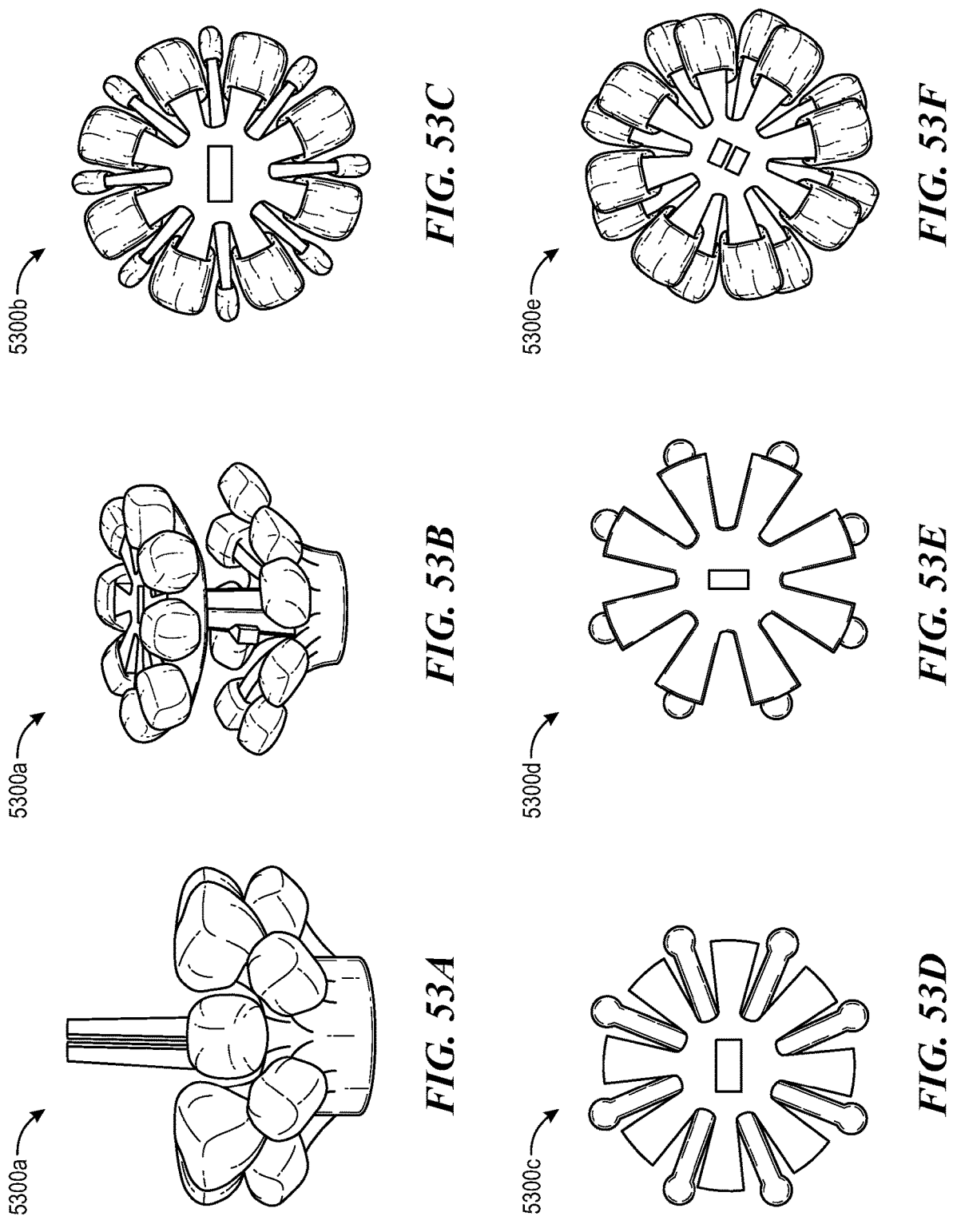
FIGS. 53A and 53B are perspective side views of a valve repair device including an atrial member and a ventricular member configured to sandwich together and in a closed and open position, respectively, in accordance with embodiments of the present technology.
FIGS. 53C-53F are perspective top views of various valve repair devices including an atrial member and a ventricular member configured to sandwich together in accordance with additional embodiments of the present technology.
Figure 55A:
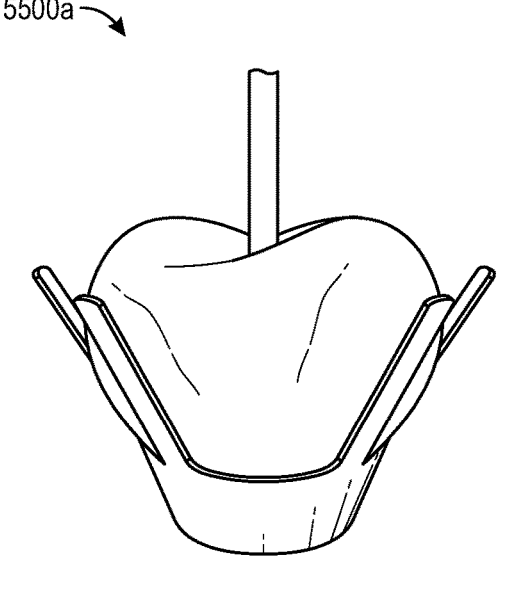
Figure 55B:
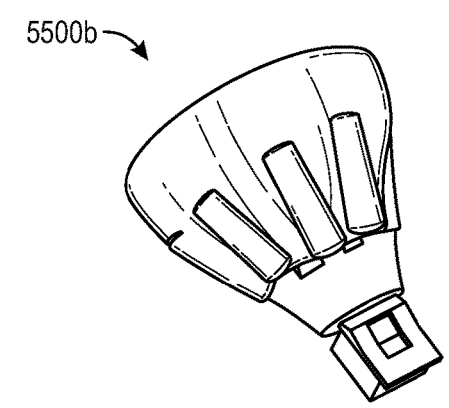
Figure 55C:
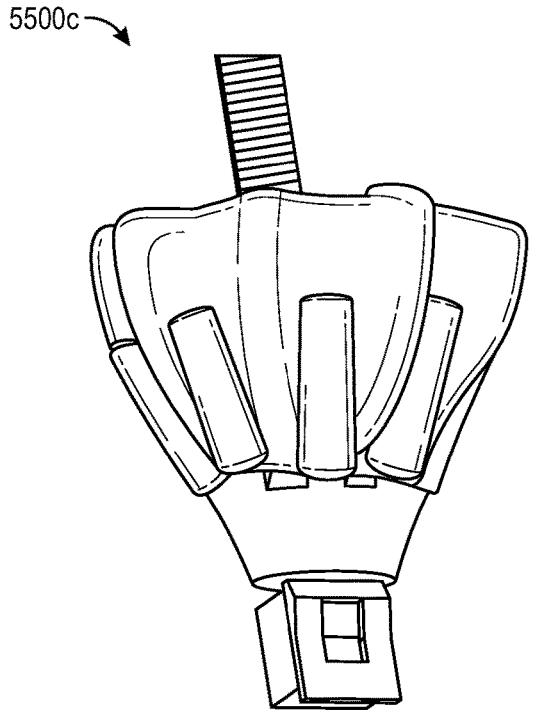
Figure 55D:
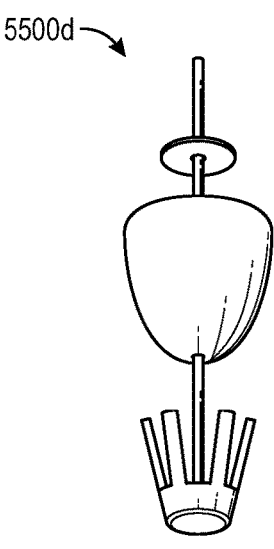
Figure 55E:
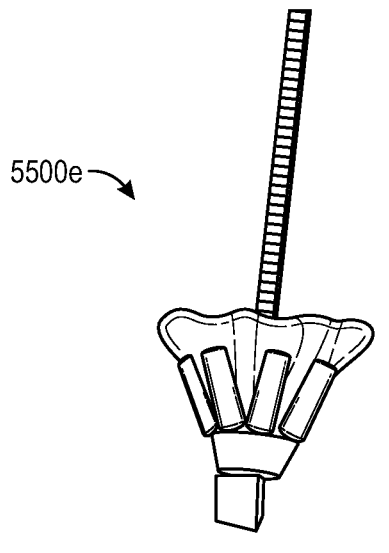
Figure 55F:
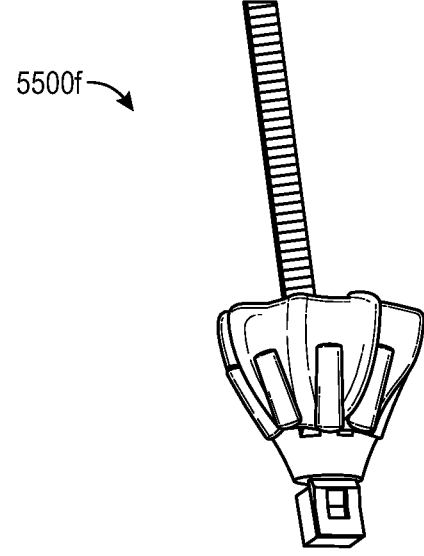
Figure 55G:
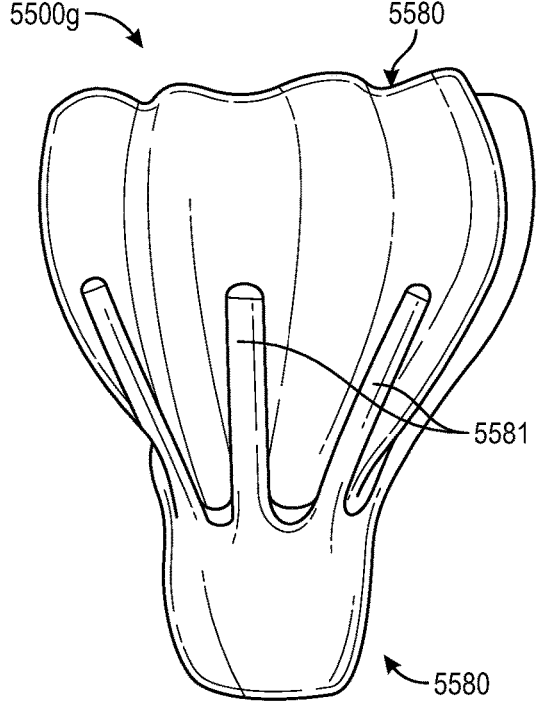
Figure 55H:
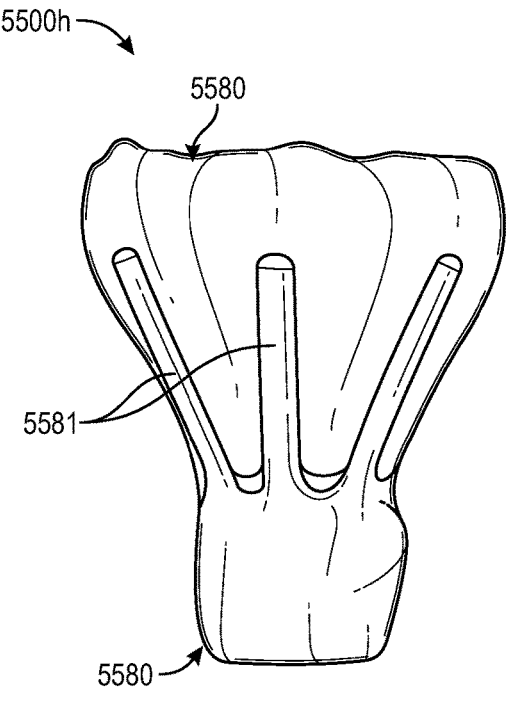

FIGS. 53A and 53B are perspective side views of a valve repair device 5300a including an atrial member and a ventricular member configured to sandwich together and in a closed and open position, respectively, in accordance with embodiments of the present technology. FIGS. 53C-53F are perspective top views of various valve repair devices 5300b-5300e, respectively, including an atrial member and a ventricular member configured to sandwich together in accordance with additional embodiments of the present technology. In the illustrated embodiments, the atrial members and the ventricular members of each of the valve repair devices 5300a-e each include a plurality of fingers that may be interleaved or interdigitated when sandwiched together to, for example, (i) plicate leaflets captured thereby, (ii)

provide a uniform coaptation surface for an uncaptured leaflet, and/or (iii) pinch the leaflets with a desired capture force.

FIGS. 54A-54E are perspective side views, and FIG. 54F is a perspective top view of various valve repair devices 5400a-5400f, respectively, each including an atrial member and a ventricular member configured to sandwich together in accordance with embodiments of the present technology. In the illustrated embodiments, the ventricular members include a plurality of fingers, and the atrial members are configured to reside within, between, and/or atop the ventricular fingers.

FIGS. 55A-55H are perspective side views of various valve repair devices 5500a-5500f, respectively, each including an atrial member 5570 (FIGS. 55G and 55H) and a ventricular member 5580 (FIGS. 55G and 55H) configured to sandwich together in accordance with embodiments of the present technology. In the illustrated embodiments, the ventricular members 5580 include a plurality of fingers 5581, and the atrial members 5570 include a foam or other flexible material configured to be positioned within and protrude through the fingers 5581. The use of a foam or other flexible material can help gather leaflets into the base provided by the ventricular fingers 5581, and the protrusion of the foam through the fingers 5581 can provide a smooth coaptation surface for uncaptured leaflets along the length of the devices 5500a-h. In some embodiments, the atrial members 5570 comprise a flexible frame (e.g., formed of nitinol) that is covered with foam and ePTFE to provide a recess for the ventricular fingers 5581 as well as an atraumatic coaptation surface for uncaptured leaflets. The recess for the ventricular fingers 5581 can enhance leaflet fixation.

FIGS. 56A and 56B are perspective side and bottom views, respectively, of a ventricular member 5680 of a valve repair device in a first (e.g., relaxed) position in accordance with embodiments of the present technology. FIGS. 56C and 56D are perspective side and bottom views, respectively, of the ventricular member 5680 of FIGS. 56A and 56B in a second (e.g., compressed, expanded) position in accordance with embodiments of the present technology. Referring to FIGS. 56A-56D together, the ventricular member 5680 is configured to lock to (e.g., be sandwiched to) an atrial member as described in detail above with reference to, for example, FIGS. 42A-55H. The ventricular member 5680 can be formed of a flexible material (e.g., nitinol) and can include multiple fingers 5681 extending from a base 5683. The base 5683 can have a chevron-like pattern of interconnected struts that allows the base 5683 to flex radially inward from the first position to the second position-thereby driving the fingers 5681 at the atrial end portion of the ventricular member 5680 radially outward. More specifically, in the illustrated embodiment the base 5683 includes a plurality of eyelets 5684 at least partially around a circumference thereof and configured to receive a suture 5695 (FIGS. 56A and 56B; e.g., of a delivery system) therethrough. The eyelets 5684 are positioned at or proximate to a ventricular end portion of the ventricular member 5680 such that pulling (e.g., gathering, tensioning, tightening) of the suture 5695 compresses the ventricular end portion of the base 5683 to drive (e.g., flare) the fingers 5681 radially outward. In some embodiments, the suture 5695 can be released to assist with leaflet capture and fixation, or the suture 5695 can be fixed to and/or within the valve repair device to lock the ventricular member 5680 in the second position.

Figure 57A:
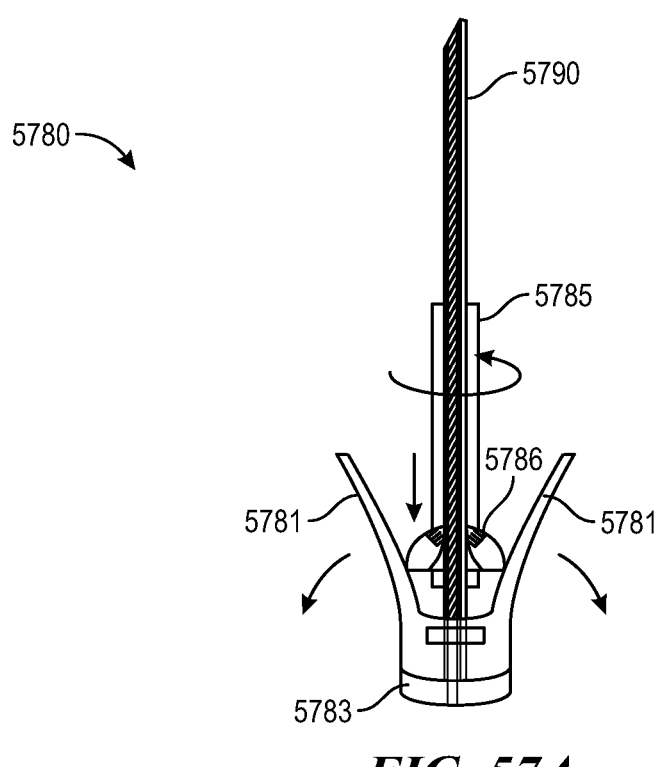
Figure 57B:
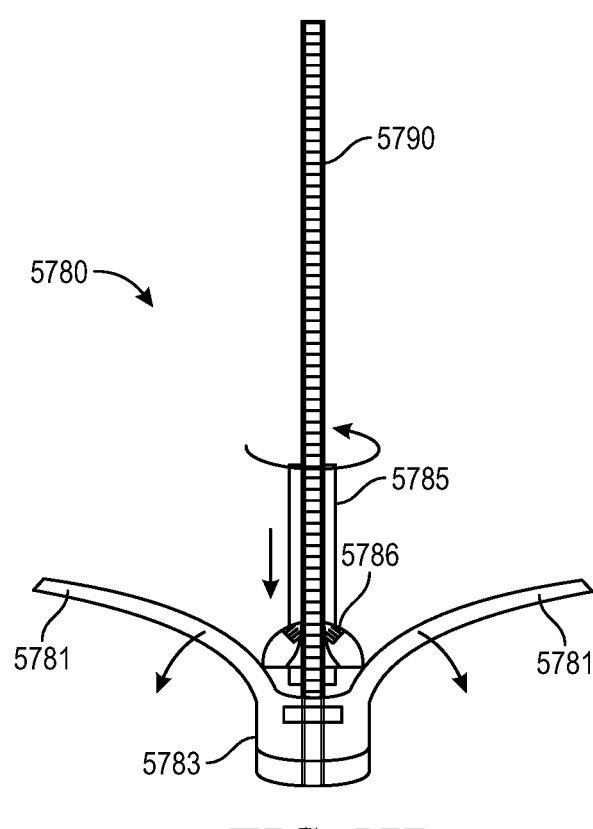

FIGS. 57A and 57B are side views of a ventricular member 5780 of a valve repair device in a first (e.g., compressed) position and a second (e.g., expanded) position, respectively, in accordance with embodiments of the present technology. Referring to FIGS. 57A and 57B together, the ventricular member 5780 is configured to lock to (e.g., be sandwiched to) an atrial member as described in detail above with reference to, for example, FIGS. 42A-55H. The ventricular member 5780 can include a central support rod 5790 coupled to (i) a hollow threaded rod 5785 and (ii) a base 5783 having a plurality of fingers 5781 (also referred to as "arms") extending therefrom. A cam 5786 is rotatably coupled to the threaded rod 5785 such that rotation of the rod 5785 advances the cam 5786 toward the base 5783 (e.g., between the fingers 5781) or away from the base 5783. In operation, the threaded rod 5785 can be rotated to move the cam 5786 toward the base 5783 to advance the cam 5786 between the fingers 5781 to push against the fingers 5781 (e.g., lower portions thereof), thereby spreading the fingers 5781 wider from the first position to the second position as the cam 5786 advances toward the base 5783.

Figures 58A, 58B, 58C:
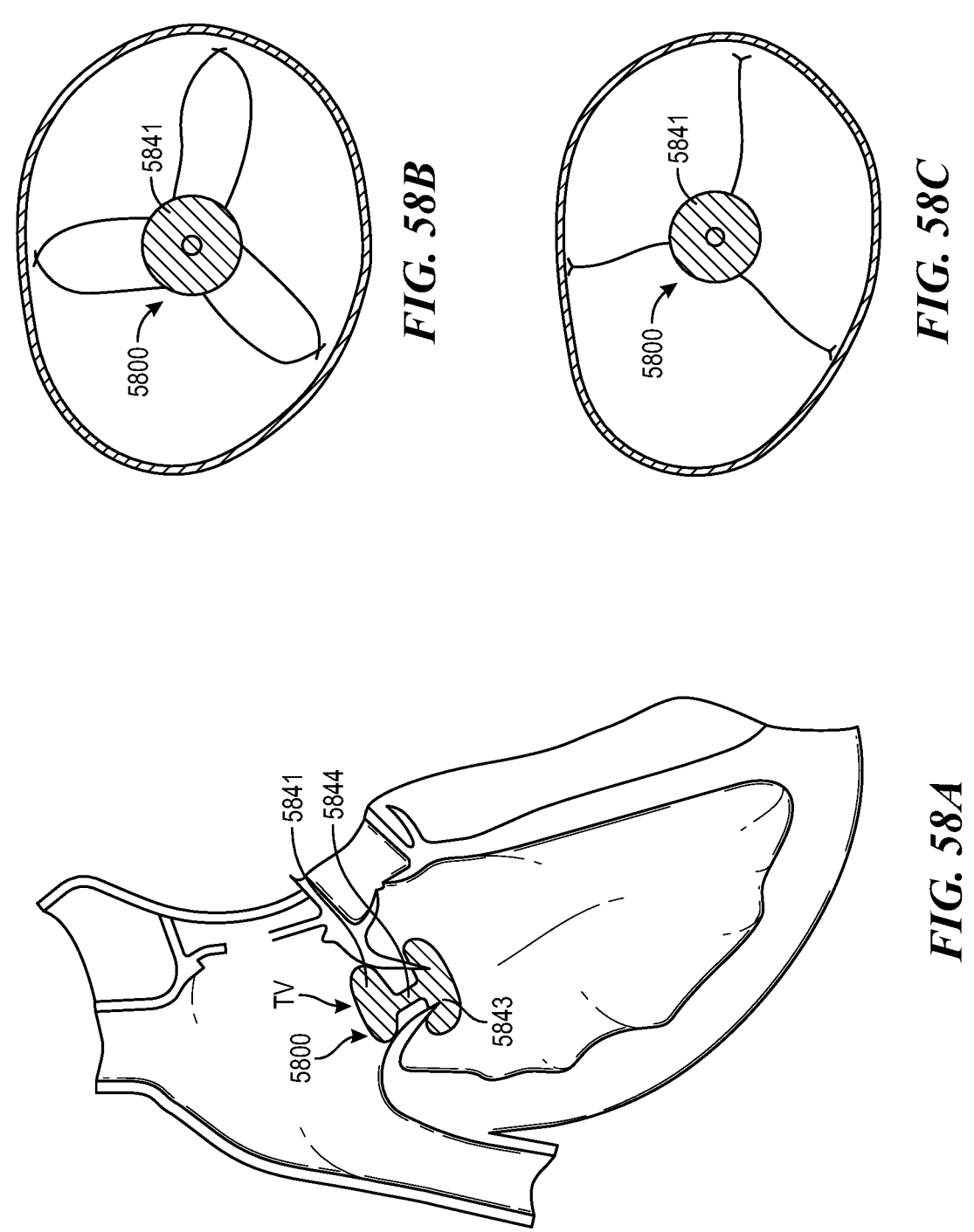

FIG. 58A is a side cross-sectional view of a valve repair device 5800 implanted at the tricuspid valve TV in accordance with embodiments of the present technology. FIGS. 58B and 58C are transverse cross-sectional views of the valve repair device 5800 of FIG. 58A during diastole and systole, respectively, in accordance with embodiments of the present technology. Referring to FIGS. 58A-58C together, the valve repair device 5800 comprises a braided mesh 5842, such as an Amplatzer-style braided mesh or filter. In other embodiments, a stent-like structure or other structure can be used instead of a braided mesh. In the illustrated embodiment, the braided mesh includes an upper (e.g., first, atrial) disc or lobe portion 5841, a lower (e.g., second, ventricular) disc or lobe portion 5843, and a connecting portion 5844 (e.g., waist) extending between the upper and lower disc portions 5841, 5843. In some embodiments, the upper and lower disc portions 5841, 5843 can each have an oval side cross-sectional shape and circular transverse cross-sectional shape, and the connecting portion 5844 can have a generally cylindrical shape. The shape of the braided mesh can pull the native leaflets together and facilitate improved coaptation between the native leaflets. In some embodiments, the braided mesh can be entirely or partially covered with a non-porous fabric (e.g., including polytetrafluorethylene (PTFE) and/or expanded PTFE (ePTFE)) for plugging a regurgitant jet between the native leaflets. The braided mesh (e.g., the connecting portion 5844) can be centrally positioned along the coaptation lines of the native leaflets or biased along one or more of the coaptation lines. In some embodiments, the braided mesh can include additional frictional elements, clip mechanisms, and/or lock mechanisms (not shown) configured to increase the fixation of the device 5800 to the native leaflets and/or another anatomy around the tricuspid valve TV.

Figures 59A, 59B, 59C:
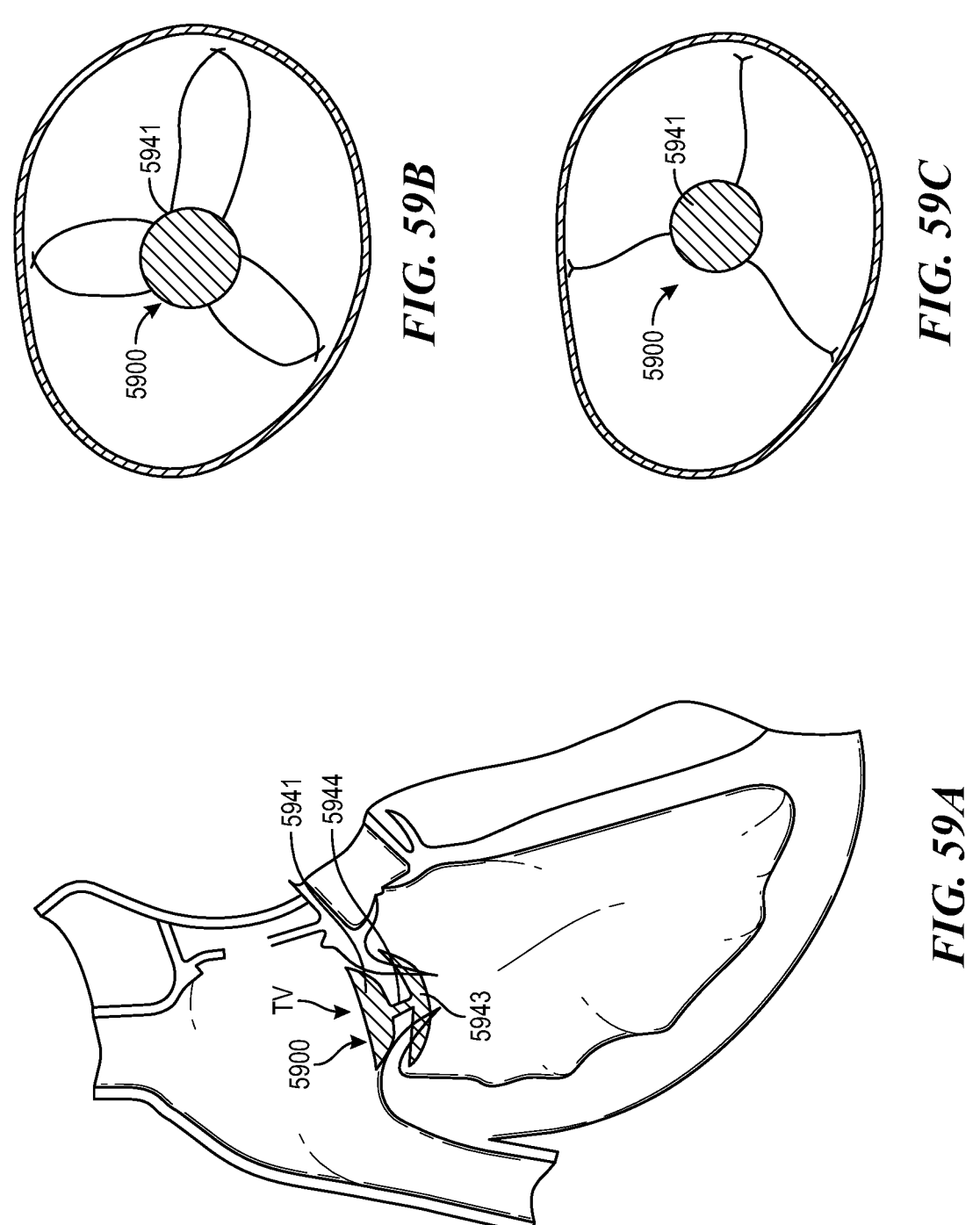

In other embodiments, the braided mesh can have different shapes and/or sizes. For example, FIG. 59A is a side cross-sectional view of a valve repair device 5900 implanted at the tricuspid valve TV in accordance with additional embodiments of the present technology. FIGS. 59B and 59C are transverse cross-sectional views of the valve repair device 5900 of FIG. 59A during diastole and systole, respectively, in accordance with embodiments of the present technology. Referring to FIGS. 59A-59C together, the valve repair device 5900 includes a braided mesh having an upper disc portion 5941 and a lower disc portion 5943 each having a curved (e.g., concave-up) side cross-sectional shape and a circular transverse cross-sectional shape. The braided mesh can further include a connecting portion 5944 between the upper and lower disc portions 5941, 5943 having a generally cylindrical shape.

FIGS. 60A and 60B are an isometric view and a side view, respectively, of a valve repair device 6000 in accordance with embodiments of the present technology. Referring to FIGS. 60A and 60B together, the valve repair device 6000 can include a ventricular member 6080 having a plurality of ventricular fingers 6081 and an atrial member 6070 (obscured in FIG. 60B) having a plurality of atrial fingers 6071. In the illustrated embodiment, the atrial and ventricular fingers 6071, 6081 can be coupled together via a joining member 6096. The joining member 6096 can include a biasing member (e.g., a helical spring), a band or ring, or the like. In other embodiments, the atrial and ventricular fingers 6071, 6081 can be integrally formed. The atrial and ventricular fingers 6071, 6081 can be formed of a flexible and/or shape memory material, such as nitinol. In the illustrated embodiment, the ventricular fingers 6081 are configured to extend ventricularly from the joining member 6096 before bending upward in an atrial direction back toward the atrial fingers 6071. As described in greater detail below with reference to FIGS. 65A-65P, the ventricular fingers 6081 can initially be unbent (e.g., elongated, straightened) in a delivery state within a delivery catheter before being deployed from the delivery catheter and, during deployment, can bend back toward the atrial member 6070 to capture one or more leaflets therebetween. In some embodiments, the valve repair device 6000 can further include a coaptation member 6010 (e.g., a "topper;" omitted in FIG. 60A for clarity) that can be positioned between the atrial fingers 6071. In the illustrated embodiment, the coaptation member 6010 includes grooves 6097 configured to receive one or more of the ventricular fingers 6081 therein (e.g., ones of the fingers 6081 that are not used to engage the leaflets). In some embodiments, the valve repair device 6000 can further include a central spine (not shown) that allows for compression between the components, locking the valve repair device 6000 in a wider profile to further plug a regurgitant leak.

VIII. SELECTED EMBODIMENTS OF METHODS OF DELIVERING AND/OR RECOVERING CARDIAC VALVE REPAIR DEVICES

In some embodiments, valve repair devices in accordance with the present technology can include features configured to enable the device to be sequentially delivered to a target valve and/or to make the process of leaflet capture reversible. For example, in the event leaflet capture is deemed inadequate, an unlock feature in the device and/or associated delivery system can facilitate multiple capture attempts and/or full recapture of the device.

Figures 61D, 61E, 61F:
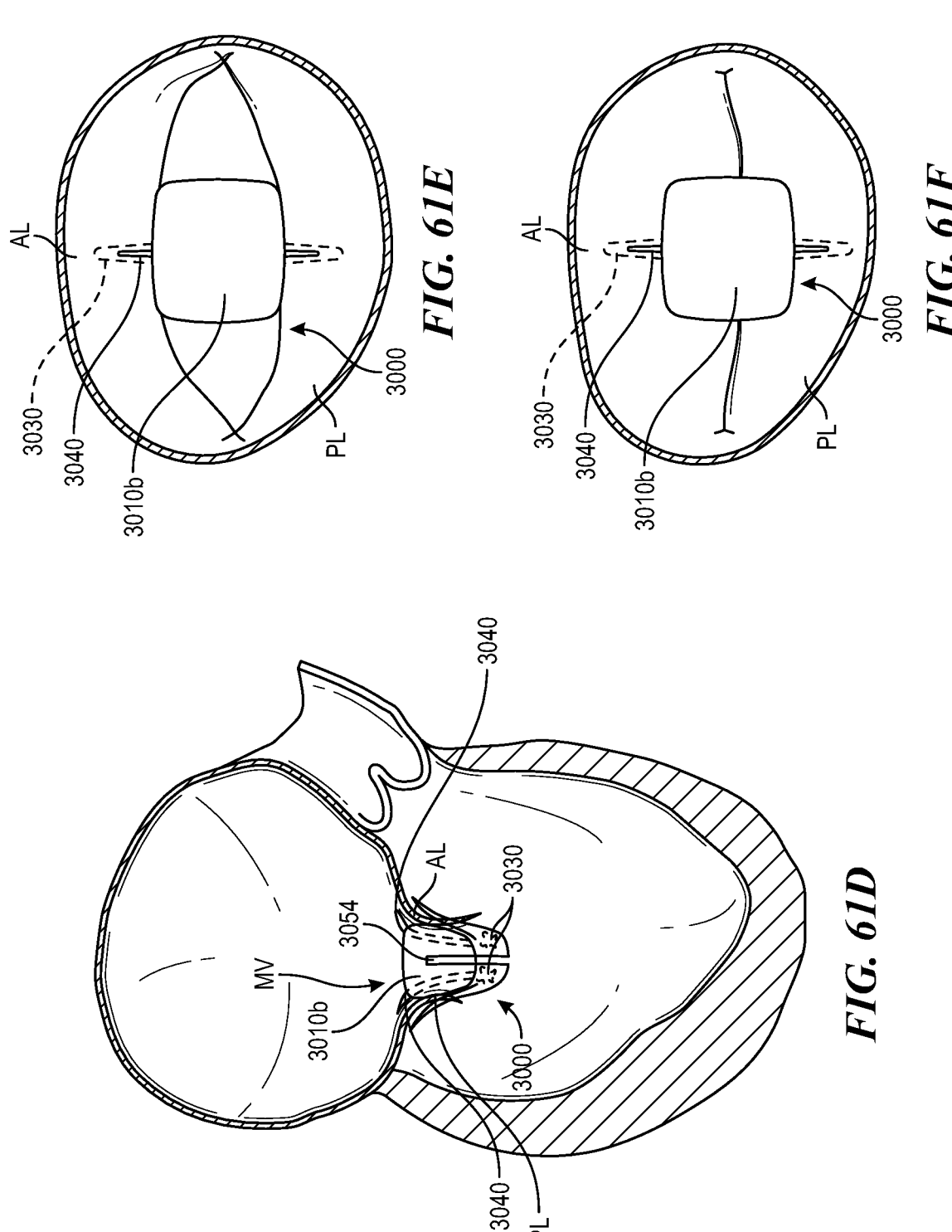

For example, FIGS. 61A and 61D are side views of the valve repair device 3000 of FIG. 30 during a first delivery stage (e.g., an initial stage) and a second delivery stage (e.g., a subsequent stage) to the mitral valve MV, respectively, in accordance with embodiments of the present technology. FIGS. 61B and 61C are transverse cross-sectional views of the valve repair device 3000 during the first delivery stage of FIG. 61A and during diastole and systole, respectively, in accordance with embodiments of the present technology. FIGS. 61E and 61F are transverse cross-sectional views of the valve repair device 3000 during the second delivery stage of FIG. 61D and during diastole and systole, respectively, in accordance with embodiments of the present technology. Referring first to FIGS. 61A-61C together, the valve repair device 3000 can initially be positioned at the mitral valve MV and the gear-driven clip mechanisms 3030 can capture the anterior leaflet AL and the posterior leaflet PL. In some embodiments, the clip mechanisms 3030 can be independently operated to optimize an angle of the central coaptation member 3010a relative to the anterior and posterior leaflets AL and PL. At this stage, the lock mechanisms 3040 have not been deployed.

In some embodiments, after positioning the valve repair device 3000 at the mitral valve MV, an operator can determine that a residual leak remains as shown in FIG. 61C. In some such embodiments, the operator can modularly deliver another coaptation member 3010b having a larger size to, for example, facilitate better coaptation and sealing of the anterior and posterior leaflets AL and PL therewith. The additional coaptation member 3010b can be slid into place along (i) a delivery rail 6102 (FIG. 61A) and (ii) the central rail 3054 of the device, and can be used in addition or instead of the smaller coaptation member 3010a. That is, the smaller coaptation member 3010a can be removed from the rail 3054 prior to positioning the larger coaptation member 3010b, or the larger coaptation member 3010b can be slid over the smaller coaptation member 3010a. In other embodiments, the initial coaptation member 3010a can replaced with a smaller coaptation member, a coaptation member of different shape, and so on.

Referring next to FIGS. 61D-61F, at the second stage the lock mechanisms 3040 are deployed to help lock the position of the coaptation member 3010b relative to the posterior and anterior leaflets AL and PL. The delivery rail (FIG. 61A-) and any other components of the delivery system can be removed after finally positioning the coaptation member 3010b and deploying the lock mechanisms 3040 as shown in FIGS. 61D-61F.

FIG. 62A is a side view of a valve repair device 6200 that can be sequentially delivered to a cardiac valve in accordance with embodiments of the present technology. FIG. 62B is a side view of the valve repair device 6200 of FIG. 62A at the mitral valve MV with an optional additional coaptation member 6210 on a central delivery rail 6202 in accordance with embodiments of the present technology. FIGS. 62C and 62D are side views of the valve repair device 6200 of FIG. 62B with the optional additional coaptation member 6210 added and during diastole and systole, respectively, in accordance with embodiments of the present technology. Referring to FIGS. 62A-62D together, in the illustrated embodiment the valve repair device 6200 includes (i) a first clip assembly 6244a including a first clip mechanism 6230a and a first lock mechanism 6240a coupled to a first elongate member 6245a and (ii) a second clip assembly 6244b including a second clip mechanism 6230b and a second lock mechanism 6240b coupled to a second elongate member 6245b. The valve repair device 6200 can further include the optional coaptation member 6210 that can be coupled to the first and/or second clip assemblies 6244a-b by, for example, sliding the coaptation member 6210 along the first and/or second elongate members 6245a-b.

FIGS. 62E, 62H, 62K, and 62N are side views of the valve repair device 6200 of FIG. 62A during first through fourth delivery stages to the tricuspid valve TV, respectively, in accordance with embodiments of the present technology. FIGS. 62F and 62G are transverse cross-sectional views of the valve repair device 6200 during the first delivery stage of FIG. 62E and during diastole and systole, respectively, in accordance with embodiments of the present technology.

FIGS. 62I and 62J are transverse cross-sectional views of the valve repair device 6200 during the second delivery stage of FIG. 62H and during diastole and systole, respectively, in accordance with embodiments of the present technology. FIGS. 62L and 62M are transverse cross-sectional views of the valve repair device 6200 during a third delivery stage of FIG. 62L and during diastole and systole, respectively, in accordance with embodiments of the present technology. FIGS. 62O and 62P are transverse cross-sectional views of the valve repair device 6200 during an alternate third delivery stage of FIG. 62N and during diastole and systole, respectively, in accordance with embodiments of the present technology.

Referring first to FIGS. 62E-62G together, at the first delivery stage the first clip assembly 6244a can be advanced through a delivery catheter 6204 (and/or another component of an associated delivery system) and used to capture a first leaflet of the tricuspid valve TV (e.g., the leaflet L1) between the first clip mechanism 6230a and the first lock mechanism 6240a. Referring next to FIGS. 62H-62J together, at the second delivery stage the second clip assembly 6244b can be advanced through the delivery catheter 6204 and used to capture a second leaflet of the tricuspid valve TV (e.g., the leaflet L3) between the second clip mechanism 6230b and second lock mechanism 6240b. Referring next to FIGS. 62K-62M together, at the third delivery stage the coaptation member 6210 can optionally be delivered to the tricuspid valve TV by, for example, advancing the coaptation member 6210 over the first and second elongate members 6245a-b to between the first and second clip assemblies 6244a-b (e.g., as illustrated in FIGS. 62B-62D). The size and shape of the coaptation member 6210 can be selected to fill a space between the leaflets and the position of the coaptation member 6210 can be adjusted in the A-P and or C-C to plug any leaks. In some embodiments, the coaptation member 6210 can be delivered together with the second clip assembly 6244b in a single delivery stage. Referring next to FIGS. 62N-62P together, instead of or in addition to deploying the coaptation member 6210, the alternate third delivery stage can include bringing the first and second clip assemblies 6244a-b into apposition or near apposition to narrow the gap between the first and third leaflets L1 and L3. That is, the operator can selectively adjust the space between the first and second clip assemblies 6244a-b.

Accordingly, in some aspects of the present technology the leaflet clip assemblies are deployed sequentially, capturing one leaflet within a dual-sided clip before steering the delivery system to the opposing leaflet for capture within a second dual-sided clip. The sequential deployment and capture can allow for a narrow delivery profile. Alternatively, the leaflet capture may not require direct apposition of the capture clip pairs to one another, allowing the user to dictate the necessary space between the clip assemblies.

FIGS. 63A, 63D, and 63G are side views of a valve repair device of any of, for example, FIGS. 42A-45D or 52A-54F during first through third delivery stages to the tricuspid valve TV, respectively, in accordance with embodiments of the present technology. FIGS. 63B and 63C are transverse cross-sectional views of the valve repair device during the first delivery stage of FIG. 63A and during diastole and systole, respectively, in accordance with embodiments of the present technology. FIGS. 63E and 63F are transverse cross-sectional views of the valve repair device during the second delivery stage of FIG. 63D and during diastole and systole, respectively, in accordance with embodiments of the present technology. FIGS. 63H and 63I are transverse cross-sectional views of the valve repair device during the third delivery stage of FIG. 63G and during diastole and systole, respectively, in accordance with embodiments of the present technology.

Referring first to FIGS. 63A-63C together, at the first delivery stage a central member 6390 and a coupled ventricular member 6380 including fingers 6381 of the valve repair device can be advanced from a delivery catheter 6304 (and/or another component of an associated delivery system) from within the right atrium RA, past the tricuspid valve TV, and into the right ventricle RV. In some embodiments, an atrial member 6370 of the valve repair device can remain compressed within the delivery catheter 6304 during advancement of the ventricular member 6380 at the first delivery stage. Referring next to FIGS. 63D-63F together, at the second delivery stage the ventricular member 6380 can be retracted proximally toward the leaflets of the tricuspid valve TV to, for example, gather one or more of the leaflets (e.g., each of the leaflets L1-L3) within the fingers 6381. Next, referring to FIGS. 63G-63I together, the atrial member 6370 can be advanced distally from the delivery catheter 6304 (FIGS. 63A and 63D) toward the ventricular member 6380 along the central member 6390 to secure (e.g., sandwich) the leaflets between the fingers 6381 of the ventricular member 6380 and an outer surface of the atrial member 6370. As best seen in FIG. 63I, the atrial member 6370 and/or the ventricular member 6380 can provide a smooth coaptation surface for one or more of the native leaflets L1-L3.

FIGS. 64A, 64D, 64G, and 64J are side views of a valve repair device of any of, for example, FIGS. 42A-45D or 52A-54F during first through fourth delivery stages to the tricuspid valve TV, respectively, in accordance with embodiments of the present technology. FIGS. 64B and 64C are transverse cross-sectional views of the valve repair device during the first delivery stage of FIG. 64A and during diastole and systole, respectively, in accordance with embodiments of the present technology. FIGS. 64E and 64F are transverse cross-sectional views of the valve repair device during the second delivery stage of FIG. 64D and during diastole and systole, respectively, in accordance with embodiments of the present technology, positioned in the area of regurgitant leak. FIGS. 64H and 64I are transverse cross-sectional views of the valve repair device during the third delivery stage of FIG. 64G and during diastole and systole, respectively, in accordance with embodiments of the present technology. FIGS. 64K and 64L are transverse cross-sectional views of the valve repair device during the fourth delivery stage of FIG. 64J and during diastole and systole, respectively, in accordance with embodiments of the present technology.

Referring first to FIGS. 64A-64C together, at the first delivery stage a ventricular member 6480 of the valve repair device can be constrained (e.g., compressed) within a first delivery catheter 6404, and the first delivery catheter 6404 can be advanced from a second delivery catheter 6405 from within the right atrium RA, past the tricuspid valve TV, and into the right ventricle RV. Referring next to FIGS. 64D-64F together, an atrial member 6470 of the valve repair device can be advanced through the second delivery catheter 6405 and over the first delivery catheter 6404 to the atrial side of the tricuspid valve TV. Next, referring to FIGS. 64G-64I together, at the third delivery stage the ventricular member 6480 can be (i) released from within the first delivery catheter 6404 allowing fingers 6481 of the ventricular member 6480 to expand and then (ii) retracted proximally toward the leaflets of the tricuspid valve TV and the atrial member 6470 to, for example, gather one or more of the leaflets (e.g., each of the leaflets L1-L3) within the fingers 6481. Finally, referring to FIGS. 64J-64L together, at the fourth delivery stage the ventricular member 6480 can be retracted along a central member 6490 of the valve repair device to secure (e.g., sandwich) the leaflets between the fingers 6481 of the ventricular member 6480 and an outer surface of the atrial member 6470.

FIGS. 65A, 65D, 65G, 65J, and 65M are side views of a valve repair device 6000 of, for example, FIGS. 60A and 60B, during first through fifth delivery stages to the tricuspid valve TV, respectively, in accordance with embodiments of the present technology. FIGS. 65B and 65C are transverse cross-sectional views of the valve repair device 6000 during the first delivery stage of FIG. 65A during diastole and systole, respectively, in accordance with embodiments of the present technology. FIGS. 65E and 65F are transverse cross-sectional views of the valve repair device 6000 during the second delivery stage of FIG. 65D during diastole and systole, respectively, in accordance with embodiments of the present technology. FIGS. 65H and 65I are transverse cross-sectional views of the valve repair device 6000 during the third delivery stage of FIG. 65G during diastole and systole, respectively, in accordance with embodiments of the present technology. FIGS. 65K and 65L are transverse cross-sectional views of the valve repair device 6000 during the fourth delivery stage of FIG. 65J during diastole and systole, respectively, in accordance with embodiments of the present technology. FIGS. 65N and 65O are transverse cross-sectional views of the valve repair device 6000 during the fifth delivery stage of FIG. 65M during diastole and systole, respectively, in accordance with embodiments of the present technology.

Referring first to FIGS. 65A-65C together, at the first delivery stage the valve repair device 6000 can be constrained (e.g., compressed) within a delivery catheter 6504, and the delivery catheter 6504 can be advanced at last partially from within the right atrium RA, through the annulus of the tricuspid valve TV, and at least partially into the right ventricle RV. In the constrained position, the ventricular fingers 6081 can be straightened/elongated within the delivery catheter 6504.

Referring next to FIGS. 65D-65F together, the valve repair device 6000 can be distally advanced through the delivery catheter 6504 to first expose the ventricular fingers 6081 within the right ventricle RV, thereby allowing the ventricular fingers 6081 to expand and bend (e.g., curve) in an atrial direction below the leaflets. In some embodiments, as shown FIGS. 65G-65I, the delivery catheter 6504 can be retracted proximally toward the tricuspid valve TV after expansion of the ventricular fingers 6081 to capture one or more of the leaflets. In some embodiments, the ventricular fingers 6081 may deploy parallel to the annulus and thread through chordae, or deploy in a slight arc shape to gather chordae and leaflets within the ventricular fingers 6081.

FIGS. 65J-65L illustrate the deployment of the joining member 6096 from the delivery catheter 6504. In the illustrated embodiment, the joining member 6096 is a helical spring that can be elongated when constrained within the delivery catheter 6504 to facilitate the separate (e.g., sequential) deployment of the ventricular member 6080 and the atrial member 6070. FIGS. 65M-65O illustrate the continued deployment of the atrial fingers 6071 (obscured in FIGS. 65M-65O) within the right atrium RA and the deployment of the coaptation member 6010 between and/or around the atrial fingers 6071. In some embodiments, the atrial and ventricular members 6070, 6080 can compress one or more of the leaflets therebetween to secure the coaptation member

6010 between the leaflets. In some embodiments, the joining member 6096 can further exert a biasing force against the atrial and ventricular members 6070, 6080 to pull the atrial and ventricular members 6070, 6080 toward one another to compress the leaflets therebetween.

FIGS. 66A-66C are side views of a valve repair device of any of, for example, FIGS. 42A-45D or 52A-54F during first through third recovery stages of recovering (e.g., removing) the valve repair device from an implantation procedure at the tricuspid valve TV, respectively, in accordance with embodiments of the present technology. Referring first to FIG. 66A, at the first recovery stage a ventricular member 6680 of the valve repair device is positioned in the right ventricle and unconstrained from a first delivery catheter 6604. The first delivery catheter 6604 can be advanced through a second delivery catheter 6605, and an atrial member 6670 of the valve repair device can be constrained within the first delivery catheter 6604. In the illustrated embodiment, the valve repair device includes one or more restraint features 6698 (e.g., a tether, a suture, a lasso) that gather fingers 6681 of the ventricular member 6680 together. More specifically, the restraint feature 6698 can extend through (e.g., be looped through) eyelets 6684 formed at atrial end portions of the fingers 6681. Referring next to FIG. 66B, (i) the restraint feature 6698 can be pulled (e.g., tightened, tensioned) to radially collapse the fingers 6681 and (ii) the first delivery catheter 6604 (and/or another component of an associated delivery system) can be advanced toward the ventricular member 6680. In the illustrated embodiment, the ventricular member 6680 is collapsed into a compressed position or narrow-profile position while positioned in the right ventricle RV. In some aspects of the present technology, collapsing the ventricular member 6680 in the right ventricle RV can help minimize interaction of the ventricular member 6680 with the chordae of the tricuspid valve TV. In other embodiments, the ventricular member 6680 can be collapsed in the right atrium RA. Finally, referring to FIG. 66C, the first delivery catheter 6604 can be advanced fully over the ventricular member 6680, and the first delivery catheter 6604 and the captured ventricular member 6680 can be withdrawn through the second delivery catheter 6605.

In some embodiments, an atrial member 6670 of the valve repair device (shown compressed within the second delivery catheter in FIG. 66A) can include features (e.g., eyelets) for receiving a corresponding restraint feature configured to narrow the profile of the atrial member 6670. In some embodiments, the restraint feature(s) can be used to narrow the atrial and/or ventricular members 6670, 6680 to facilitate repositioning of the valve repair device relative to the tricuspid valve TV. Similarly, when the valve repair device includes a coaptation member, the coaptation member, the atrial member 6670, and/or the ventricular member 6680 can include features configured to facilitate narrowing of the device to enable the device to be recovered and/or repositioned.

FIGS. 67A-67C are perspective side views of a ventricular member 6780 of a valve repair device positioned at a cardiac valve in a first position, a second position, and a third position, respectively, in accordance with embodiments of the present technology. FIGS. 67D-67F are top views of the ventricular member 6780 of FIGS. 67A-67C positioned at the cardiac valve in the first position, the second position, and the third position, respectively, in accordance with embodiments of the present technology. Referring to FIGS. 67A-67F together, the ventricular member 6780 is configured to lock to (e.g., be sandwiched to) an atrial member as described in detail above with reference to, for example, FIGS. 42A-60B. The ventricular member 6780 includes a plurality of fingers 6781 extending from a base 6783 (also referred to as a "hub"). In some embodiments, the ventricular member 6780 includes a chordae-clearing suture 6799 configured to facilitate the recovery and removal of the ventricular member 6780 from the cardiac valve before the valve repair device is finally released during a delivery procedure. In some embodiments, a tensioning suture 6798 (e.g., a separate suture or a portion of the chordae-clearing suture) can be coupled to the chordae-clearing suture 6799. In the illustrated embodiment, in the first position, the chordae-clearing suture 6799 extends (i) through an eyelet 6784 at a ventricular end of each of the fingers 6781 and (ii) down each of the fingers 6781 toward the base 6783 (e.g., toward a root of each of the fingers 6781), where the chordae-clearing suture 6799 is releasably held in place by a securement mechanism 6888 (obscured in FIGS. 67A-67F; shown in FIGS. 68A and 68B) coupled to the base 6783. Accordingly, in the first position, one or more chordae C around the cardiac valve can extend between the fingers 6781.

To recover the ventricular member 6780 from the cardiac valve, the securement mechanism 6888 (FIGS. 68A and 68B) can be actuated or otherwise moved to release the chordae-clearing suture 6799 from the base 6783. Releasing the chordae-clearing suture 6799 from the base 6783 allows the chordae-clearing suture 6799 to move outward away from the base 6783 to the second position shown in FIGS. 67B and 67E. To clear any of the chordae C from between the fingers 6781, the tensioning suture 6798 can be pulled to move the chordae-clearing suture 6799 to the third position shown in FIGS. 67C and 67F. As the chordae-clearing suture 6799 moves outward (e.g., straightens) from the base 6783, it pushes and clears the chordae C from between the fingers 6781. In some embodiments, further pulling the tensioning suture 6798 can radially collapse the fingers 6781 toward the base 6782 to allow the ventricular member 6780 to be pulled back into a delivery catheter (not shown). In some aspects of the present technology, removing the chordae C from between the fingers 6781 can inhibit or even prevent the chordae C from being tangled or captured between the fingers 6781 as the cardiac valve device is re-sheathed and removed.

FIGS. 68A and 68B are a side view and a top view, respectively, of the base 6783 of the ventricular member of FIGS. 67A-67F including the securement mechanism 6888 in accordance with embodiments of the present technology. Referring to FIGS. 67A-68B together, the securement mechanism 6888 can include (i) a movable sleeve 6846 and (ii) a plurality of U-shaped channels or grooves 6847 in the base 6783 corresponding to each of the fingers 6781 in which the chordae-clearing suture 6799 can seat. The chordae-clearing suture 6799 is held captive in the channels 6847 by the movable sleeve 6846, which can be actuated to allow the chordae-clearing suture 6799 to release and move outward to the third position shown in FIGS. 67C and 67F for device recovery.

FIG. 69A is a side view of the base of the ventricular member of FIGS. 67A-67F including a securement mechanism 6988 in accordance with additional embodiments of the present technology. FIG. 69B is an enlarged side view of a portion of the securement mechanism 6988 of FIG. 69A in accordance with embodiments of the present technology. Referring to FIGS. 67A-67F, 69A, and 69B together, the securement mechanism 6988 can include a plurality of posts 6907 coupled to, fixed to, and/or integrally formed with the base 6783 and corresponding to each of the fingers 6781. Each of the posts 6907 can include an eyelet 6908 extending therethrough. In the illustrated embodiment, the chordae-clearing suture 6799 is wrapped around each of the posts 6907 and held captive by pins, a suture, and/or other locking structure(s) 6909 extending through each of the eyelets 6908. When the locking structure 6909 is removed from the eyelets 6908, the chordae-clearing suture 6799 is free to slide off the posts 6907 and straighten to the third position shown in FIGS. 67C and 67F.

IX. ADDITIONAL EXAMPLES

The following examples are illustrative of several embodiments of the present technology:

1. A valve repair device for repairing a cardiac valve including a first native leaflet and a second native leaflet, the valve repair device comprising:
   a coaptation member configured to be positioned at least partially between the first native leaflet and the second native leaflet, wherein the coaptation member has a first portion configured to face the first native leaflet and a second portion configured to face the second native leaflet;
   a first clip mechanism extending from the first portion and configured to engage a ventricular side of the first native leaflet;
   a first anchor mechanism extending from the first portion and configured to engage an atrial side of the first native leaflet, wherein the first clip mechanism and the first anchor mechanism are configured to cooperate to at least partially secure a portion of the first native leaflet therebetween;
   a second clip mechanism extending from the second portion and configured to engage a ventricular side of the second native leaflet; and
   a second anchor mechanism extending from the second portion and configured to engage an atrial side of the second native leaflet, wherein the second clip mechanism and the second anchor mechanism are configured to cooperate to at least partially secure a portion of the second native leaflet therebetween.

2. The valve repair device of example 1 wherein the first clip mechanism is aligned over the first anchor mechanism.

3. The valve repair device of example 1 or example 2 wherein the first clip mechanism is aligned over the first anchor mechanism, and wherein the second clip mechanism is aligned over the second anchor mechanism.

4. The valve repair device of any one of examples 1-3 wherein the coaptation member includes an upper portion having a first shape and a lower portion having a second shape, wherein the first clip mechanism and the first anchor mechanism extend from the upper portion, and wherein the second clip mechanism and the second anchor mechanism extend from the upper portion.

5. The valve repair device of example 4 wherein the first shape is a cylindrical side cross-sectional shape, and wherein the second shape is a semicircular side cross-sectional shape.

6. The valve repair device of any one of examples 1-5 wherein the coaptation member has a generally trapezoidal side cross-sectional shape.

7. The valve repair device of any one of examples 1-5 wherein the coaptation member has a generally rectangular side cross-sectional shape.

8. The valve repair device of any one of examples 1-7 wherein the cardiac valve is a mitral valve, wherein the first native leaflet is a posterior leaflet of the mitral valve, and wherein the second native leaflet is an anterior leaflet of the mitral valve.

9. The valve repair device of any one of examples 1-8 wherein the first clip mechanism includes a locking mechanism configured to lock the first clip mechanism in a deployed position in which the first clip mechanism engages the ventricular side of the first native leaflet, and wherein the second clip mechanism includes a locking mechanism configured to lock the second clip mechanism in a deployed position in which second first clip mechanism engages the ventricular side of the second native leaflet.

10. The valve repair device of any one of examples 1-9 wherein
    the first clip mechanism and the first anchor mechanism are movable from a closed position in which the first clip mechanism and the first anchor mechanism cooperate to at least partially secure the portion of the first native leaflet therebetween, to an open position in which the first clip mechanism and the first anchor mechanism are configured to be spaced apart to release the portion of the first native leaflet; and
    the second clip mechanism and the second anchor mechanism are movable from a closed position in which the second clip mechanism and the second anchor mechanism cooperate to at least partially secure the portion of the second native leaflet therebetween, to an open position in which the second clip mechanism and the second anchor mechanism are configured to be spaced apart to release the portion of the second native leaflet.

11. The valve repair device of example 10 wherein the first clip mechanism and the first anchor mechanism are movable between the closed and open positions independently of the second clip mechanism and the second anchor mechanism, and wherein the second clip mechanism and the second anchor mechanism are movable between the closed and open positions independently of the first clip mechanism and the first anchor mechanism.

12. A method of repairing a cardiac valve including a first native leaflet and a second native leaflet, the method comprising:
    deploying a coaptation member of a valve repair device at least partially between the first native leaflet and the second native leaflet and such that a first portion of the valve repair devices faces the first native leaflet and a second portion of the valve repair device faces the second native leaflet;
    engaging a ventricular side of the first native leaflet with a first clip mechanism extending from the first portion of the valve repair device;
    engaging an atrial side of the first native leaflet with a first anchor mechanism extending from the first portion of the valve repair device to at least partially secure a portion of the first native leaflet between the first clip mechanism and the first anchor mechanism;
    engaging a ventricular side of the second native leaflet with a second clip mechanism extending from the second portion of the valve repair device; and engaging an atrial side of the second native leaflet with a second anchor mechanism extending from the second portion of the valve repair device to at least partially secure a portion of the second native leaflet between the second clip mechanism and the second anchor mechanism.

13. The method of example 12 wherein the cardiac valve has a regurgitant valve orifice, and wherein deploying the coaptation member at least partially between the first native leaflet and the second native leaflet includes deploying the coaptation member at least partially within the regurgitant valve orifice.

14. The method of example 12 or example 13 wherein the cardiac valve is a mitral valve, wherein the first native leaflet is a posterior leaflet of the mitral valve, and wherein the second native leaflet is an anterior leaflet of the mitral valve.

15. The method of any one of examples 12-14 wherein engaging the ventricular side of the first native leaflet with the first clip mechanism includes independently actuating the first clip mechanism relative to the first anchor mechanism, and wherein engaging the atrial side of the first native leaflet with the first anchor mechanism includes independently actuating the first anchor mechanism relative to the first clip mechanism.

16. The method of example 15 wherein engaging the ventricular side of the second native leaflet with the second clip mechanism includes independently actuating the second clip mechanism relative to the second anchor mechanism, and wherein engaging the atrial side of the second native leaflet with the second anchor mechanism includes independently actuating the second anchor mechanism relative to the second clip mechanism.

17. The method of any one of examples 12-16 wherein engaging the atrial side of the first native leaflet with the first anchor mechanism includes aligning the first anchor mechanism over the first clip mechanism to clamp the portion of the first native leaflet therebetween.

18. The method of example 17 wherein engaging the atrial side of the second native leaflet with the second anchor mechanism includes aligning the second anchor mechanism over the second clip mechanism to clamp the portion of the second native leaflet therebetween.

19. A valve repair device for repairing a cardiac valve including an annulus, a first native leaflet, and a second native leaflet, the valve repair device comprising:
   a coaptation member configured to be positioned between the first native leaflet and the second native leaflet, wherein the coaptation member has a first side portion configured to be positioned adjacent the first native leaflet and a second side portion configured to be positioned adjacent the second native leaflet, wherein the coaptation member has an elongate shape along a transverse cross-section of the annulus, wherein the elongate shape includes a width extending in a direction between the first and second side portions and a length extending generally orthogonal to the width, and wherein the length is longer than the width;
   a first clip mechanism extending from the first side portion and configured to engage the first native leaflet to at least partially secure the first native leaflet between the first clip mechanism and the coaptation member; and a second clip mechanism extending from the second side portion and configured to engage the second native leaflet to at least partially secure the second native leaflet between the second clip mechanism and the coaptation member.

20. The valve repair device of example 19 wherein the width varies along the length of the coaptation member such that the elongate shape is an elongate hourglass-like shape.

21. The valve repair device of example 19 or example 20 wherein the coaptation member has a pentagonal side cross-sectional shape.

22. The valve repair device of example 19 or example 20 wherein the coaptation member has a trapezoidal side cross-sectional shape.

23. The valve repair device of example 19 or example 20 wherein the coaptation member has a bow-tie-like side cross-sectional shape.

24. The valve repair device of any one of examples 19-23 wherein the cardiac valve is a mitral valve, wherein the first native leaflet is a posterior leaflet of the mitral valve, and wherein the second native leaflet is an anterior leaflet of the mitral valve.

25. The valve repair device of any one of examples 19-24 wherein the first clip mechanism and the second clip mechanism each comprise (a) a base portion coupled to the coaptation member, (b) a free end portion unaffixed to the coaptation member, and (c) an arm member extending between the base portion and the free end portion.

26. The valve repair device of example 25 wherein
   the arm member of the first clip mechanism is movable from a closed position in which the free end portion of the first clip mechanism is configured to be positioned proximate to a surface of the first side portion of the coaptation member, to an open position in which the free end portion of the first clip mechanism is positioned away from the surface of the first side portion of the coaptation member, and
   the arm member of the second clip mechanism is movable from a closed position in which the free end portion of the second clip mechanism is configured to be positioned proximate to a surface of the second side portion of the coaptation member, to an open position in which the free end portion of the second clip mechanism is positioned away from the surface of the second side portion of the coaptation member.

27. A valve repair device, comprising:
   a central member;
   an atrial member coupled to the central member and configured to engage an atrial side of at least one native leaflet of a cardiac valve; and
   a ventricular member coupled to the central member and configured to engage a ventricular side of the at least one native leaflet, wherein the atrial member and the ventricular member are configured to cooperate to at least partially secure a portion of the at least one native leaflet therebetween, and wherein at least one of the atrial member and the ventricular member is movable along the central member in a direction toward the at least one native leaflet.

28. The valve repair device of example 27 wherein the ventricular member includes a plurality of fingers extending upward toward the atrial member.

29. The valve repair device of example 27 or example 28 wherein the ventricular member is fixed to the central member, and wherein the atrial member is movable toward the ventricular member to clamp the portion of the at least one native leaflet therebetween.

30. The valve repair device of any one of examples 27-29 wherein the atrial member is formed of a flexible material.

31. The valve repair device of any one of examples 27-30 wherein the ventricular member includes a plurality of fingers extending upward toward the atrial member, and wherein the atrial member is formed of a flexible material configured to at least partially flex between the fingers of the ventricular member.

32. The valve repair device of any one of examples 27-31 wherein the ventricular member includes a plurality of fingers extending upward toward the atrial member, and wherein the atrial member includes a plurality of recesses each positioned to receive a corresponding one of the fingers.

33. The valve repair device of any one of examples 27-32 wherein the atrial and ventricular members are each formed from a plurality of interconnected struts.

34. The valve repair device of any one of examples 27-33 wherein the central member is threaded, wherein the atrial member is coupled to the central member via a nut, and wherein rotation of the nut is configured to move the atrial member along the central member toward the ventricular member.

35. The valve repair device of any one of examples 27-34 wherein the cardiac valve is a tricuspid valve.

36. The valve repair device of any one of examples 27-34 wherein the cardiac valve is a mitral valve.

37. The valve repair device of any one of examples 27-36 wherein the at least one native leaflet includes two native leaflets.

38. The valve repair device of any one of examples 27-37 wherein the atrial member has a coaptation surface configured to coapt with at least one other native leaflet of the cardiac valve.

39. The valve repair device of any one of examples 27-38 wherein the ventricular member has a coaptation surface configured to coapt with at least one other native leaflet of the cardiac valve.

40. The valve repair device of any one of examples 27-39 wherein the atrial member and the ventricular member together define a coaptation surface configured to coapt with at least one other native leaflet of the cardiac valve.

41. A method of repairing a cardiac valve having a regurgitant valve orifice, the method comprising:
    positioning a ventricular member of a valve repair device at least partially below the regurgitant valve orifice, wherein the ventricular member is coupled to a central member extending through the regurgitant valve orifice;
    positioning an atrial member of the valve repair device at least partially above the regurgitant valve orifice, wherein the atrial member is coupled to the central member; and
    advancing the atrial member, the ventricular member, or both the atrial member and ventricular member along the central member toward the regurgitant valve orifice to secure at least one native valve leaflet of the cardiac valve between the atrial and ventricular members.

42. The method of example 41 wherein the method comprises advancing the atrial member along the central member toward the ventricular member to secure the at least one native leaflet between the atrial and ventricular members.

43. The method of example 41 or example 42 wherein positioning the ventricular member includes advancing the ventricular member in a compressed state through a delivery catheter, and wherein positioning the atrial member includes advancing the atrial member in a compressed state through the delivery catheter.

44. The method of example 43 wherein the cardiac valve is a tricuspid valve, and wherein the method further includes advancing the delivery catheter into a right atrium above the tricuspid valve.

45. The method of example 43 or example 44 wherein the ventricular member includes a plurality of fingers, wherein the fingers are generally straightened within the delivery catheter in the compressed state, and wherein positioning the ventricular member includes advancing the ventricular member out of the delivery catheter below the regurgitant valve orifice to permit the fingers to bend back toward the regurgitant valve orifice.

46. The method of any one of examples 41-45 wherein the ventricular member includes a plurality of fingers, and wherein positioning the ventricular member includes releasing a suture coupled to the fingers to allow the fingers to expand from a compressed state to an expanded state.

47. The method of example 46 wherein the method further comprises, after releasing the suture, tightening the suture to move the fingers from the expanded state to the compressed state to facilitate repositioning of the ventricular member relative to the cardiac valve.

48. The method of any one of examples 41-47 wherein the atrial member comprises a flexible material, and wherein the ventricular member comprises a plurality of fingers.

49. The method of example 48 wherein the method comprises advancing the flexible material toward the fingers such that (a) the at least one native leaflet is captured between the flexible material and a portion of the fingers (b) the flexible material flexes between another portion of the fingers.

50. The method of any one of examples 41-49 wherein positioning the ventricular member includes advancing the ventricular member in a compressed state through a delivery catheter to outside the delivery catheter to allow the ventricular member to expand from the compressed state to a deployed state, and wherein the method further comprises—
    at least partially recapturing the ventricular member within the delivery catheter; and
    again advancing the ventricular member from the delivery catheter to reposition the ventricular member relative to the regurgitant valve orifice.

X. CONCLUSION

The above detailed description of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments can perform steps in a different order. The various embodiments described herein can also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms can also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications can be made without deviating from the technology. Further, while advantages associated with some embodiments of the technology have been described in the context of those embodiments, other embodiments can also exhibit such advantages, and not all embodiments need necessarily exhibit such advantages to fall within the scope of the technology. Accordingly, the disclosure and associated technology can encompass other embodiments not expressly shown or described herein.

We claim:

1. A valve repair device for repairing a cardiac valve including a first native leaflet and a second native leaflet, the valve repair device comprising:

a coaptation member configured to be positioned at least partially between the first native leaflet and the second native leaflet, wherein the coaptation member has a first portion configured to face the first native leaflet and a second portion configured to face the second native leaflet;

a clip mechanism extending from the first portion and configured to engage a ventricular side of the first native leaflet to at least partially secure the first native leaflet between the clip mechanism and the first portion of the coaptation member; and a stabilization member extending from the coaptation member at least partially upward from the coaptation member and laterally away from the first portion of the coaptation member, wherein the stabilization member comprises a frame and a covering at least partially enclosing the frame, the frame comprising at least one curved wire form shaped to match a shape of the atrial side of the first native leaflet and an atrial wall, and wherein the stabilization member is shaped to extend along and press against an atrial side of the first native leaflet and the atrial wall above the first native leaflet to substantially maintain the coaptation member in a substantially stationary position relative to the cardiac valve during cardiac cycles.

2. The valve repair device of claim 1 wherein the coaptation member has a generally trapezoidal side cross-sectional shape.

3. The valve repair device of claim 1 wherein the coaptation member has a generally rectangular side cross-sectional shape.

4. The valve repair device of claim 1 wherein the cardiac valve is a mitral valve, wherein the first native leaflet is a posterior leaflet of the mitral valve, and wherein the second native leaflet is an anterior leaflet of the mitral valve.

5. The valve repair device of claim 1 wherein the stabilization member extends away from the coaptation member at an angle of between 10-75 degrees.

6. The valve repair device of claim 1 wherein the stabilization member extends away from the coaptation member at angle of greater than about 45 degrees.

7. The valve repair device of claim 1 wherein the stabilization member extends away from the coaptation member at an angle selected to inhibit the coaptation member from contacting a ventricular wall below the first native leaflet during the cardiac cycles.

8. The valve repair device of claim 1 wherein the frame has an M-like shape.

9. The valve repair device of claim 1 wherein the covering fully encloses the frame.

10. The valve repair device of claim 1 wherein the frame comprises a wire form.

11. The valve repair device of claim 1 wherein the coaptation member has a generally trapezoidal side cross-sectional shape and a generally almond-like transverse cross-sectional shape.

12. The valve repair device of claim 1 wherein the frame has a generally circular shape.

13. The valve repair device of claim 1 wherein the frame comprises multiple generally-circular rings.

14. The valve repair device of claim 1 wherein the frame has an elongate curved shape.

15. The valve repair device of claim 1 wherein the frame comprises multiple curved wire forms each shaped to match a shape of the atrial side of the first native leaflet and the atrial wall.

16. The valve repair device of claim 1 wherein the coaptation member defines an interior volume and an opening to the interior volume, and wherein the clip mechanism is actuatable via a delivery component inserted through the opening in the coaptation member and into the interior volume of the coaptation member to move the clip mechanism between a closed position and an open position.

\* \* \* \* \*